United States Patent
Weng et al.

(10) Patent No.: US 7,894,650 B2
(45) Date of Patent: Feb. 22, 2011

(54) DISCOVER BIOLOGICAL FEATURES USING COMPOSITE IMAGES

(75) Inventors: Lee Weng, Bellevue, WA (US); Andrey Bondarenko, Bellevue, WA (US); Silvia C. Vega, Seattle, WA (US); Ernst S. Henle, Issaquah, WA (US); Brandon Hunt, Bothell, WA (US); Alexander Spiridonov, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 1136 days.

(21) Appl. No.: 11/599,184

(22) Filed: Nov. 13, 2006

(65) Prior Publication Data

US 2007/0211928 A1    Sep. 13, 2007

Related U.S. Application Data

(60) Provisional application No. 60/735,691, filed on Nov. 10, 2005.

(51) Int. Cl.
*G06K 9/00* (2006.01)

(52) U.S. Cl. .................................... 382/128

(58) Field of Classification Search ......... 382/128–132; 250/281; 436/173
See application file for complete search history.

(56) References Cited

U.S. PATENT DOCUMENTS

| | | | |
|---|---|---|---|
| 4,988,984 A | | 1/1991 | Gonzalez-Lopez |
| 5,221,518 A | * | 6/1993 | Mills ......................... 422/62 |
| 5,575,286 A | | 11/1996 | Weng |
| 6,219,440 B1 | * | 4/2001 | Schaff et al. ................. 382/128 |
| 6,787,761 B2 | | 9/2004 | Hastings |
| 6,835,927 B2 | | 12/2004 | Becker |
| 6,940,065 B2 | * | 9/2005 | Graber et al. ............... 250/282 |
| 2003/0040123 A1 | | 2/2003 | Hastings |
| 2003/0078739 A1 | | 4/2003 | Norton |
| 2004/0113062 A1 | | 6/2004 | Norton |
| 2004/0156854 A1 | * | 8/2004 | Mulligan et al. ......... 424/155.1 |

(Continued)

FOREIGN PATENT DOCUMENTS

EP    1 577 823    *    3/2004

(Continued)

OTHER PUBLICATIONS

Anderle, M., et al., "Quantifying Reproducibility for Differential Proteomics: Noise Analysis for Protein Liquid Chromatography-Mass Spectrometry of Human Serum," Bioinformatics vol. 20(18):3575-3582, Jul. 2004.

(Continued)

*Primary Examiner*—Vu Le
*Assistant Examiner*—Amara Abdi
(74) *Attorney, Agent, or Firm*—Klarquist Sparkman, LLP

(57) ABSTRACT

An image processing system extracts parts or characteristics of interest from prepared biological samples One suitable use of the image processing system is to find biomarkers. But many other suitable uses are possible. Some components of the system include image preprocessing (data interpolation, retention time alignment, image noise filtering, background estimation, and formation of a composite image); image feature extraction (peaks, isotope groups, and charge groups); and computation of feature characteristics and expression statistics, differential expression, and non-differential expression. Outputs of the system include a candidate list of parts or characteristic of interest for aiding further discovery.

17 Claims, 77 Drawing Sheets

U.S. PATENT DOCUMENTS

2005/0063864 A1* 3/2005 Sano et al. .................. 422/68.1
2005/0255606 A1* 11/2005 Ahmed et al. ................ 436/173

FOREIGN PATENT DOCUMENTS

| EP | 1 577 823 A1 | | 9/2005 |
|---|---|---|---|
| WO | WO 01/33573 | | 5/2001 |
| WO | 03/042774 A2 | | 5/2003 |
| WO | WO 03/038728 | * | 5/2003 |

OTHER PUBLICATIONS

Hendrickson, R.C., et al., "High Resolution Differential Mass Spectrometry (dMS) Reveals Markers of Alzheimer's Disease in Humans," 54th Annual ASMS Conference on Mass Spectometry, Seattle, May 28-Jun. 1, 2006, pp. 1-34.

Horn, D.M, et al., "Automated Reduction and Interpretation of High Resolution Electrospray Mass Spectra of Large Molecules," Journal of the American Society for Mass Spectrometry vol. 11(4):320-332, Apr. 2000.

Masselon, C., et al., "Targeted Comparative Proteomics by Liquid Chromatography-Tandem Fourier Ion Cyclotron Resonance Mass Spectrometry," Analytical Chemistry vol. 77(2):400-406, Jan. 2005.

Meng, F., et al., "Quantitative Analysis of Complex Peptide Mixtures Using FTMS and Differential Mass Spectrometry," Journal of the American Society for Mass Spectrometry vol. 18(2):226-233, Jan. 2007/ Epub Oct. 2006.

Senko, M.W., et al., "Automated Assignment of Charge States from Resolved Isotopic Peaks for Multiply Charged Ions," Journal of the American Society for Mass Spectrometry vol. 6(1):52-56, Jan. 1995.

Uomori, K., et al., "Automatic Image Stabilizing System by Full-Digital Signal Processing," IEEE Transactions on Consumer Electronics vol. 36(3):510-519, Aug. 1990.

Weng, L., et al., "Rosetta Error Model for Gene Expression Analysis," Bioinformatics vol. 22(9):1111-1121, Mar. 2006.

Wiener, M.C., et al., "Differential Mass Spectometry: A Label-Free LC-MS Method for Finding Significant Differences in Complex Peptide and Protein Mixtures," Analytical Chemistry vol. 76(20):6085-6096, Oct. 2004.

Yates, N.A., et al., "Identification of Peptidase Substrates in Human Plasma by FTMS Based Differential Mass Spectrometry," International Journal of Mass Spectrometry vol. 259(1-3):174-183, Oct. 2006.

Yergey, J.A., "A General Approach to Calculating Isotopic Distributions for Mass Spectrometry," International Journal of Mass Spectrometry and Ion Physics vol. 52:337-349, 1983.

Zhang, Z., and A.G. Marshall, "A Universal Algorithm for Fast and Automated Charge State Deconvolution of Electrospray Mass-to-Charge Ratio Spectra," Journal of the American Society for Mass Spectrometry vol. 9(3):225-233, Mar. 1998.

International Search Report and Written Opinion, from related PCT Application No. PCT/US06/44166, Feb. 7, 2008, 10 pages.

Reichenbach et al., "Image background removal in comprehensive two-dimensional gas chromatography," Journal of Chromatography A, 985 (2003) pp. 47-56.

Supplementary European Search Report, dated Dec. 21, 2009, received in co-pending European Application No. 06837548.4, 7 pages.

* cited by examiner

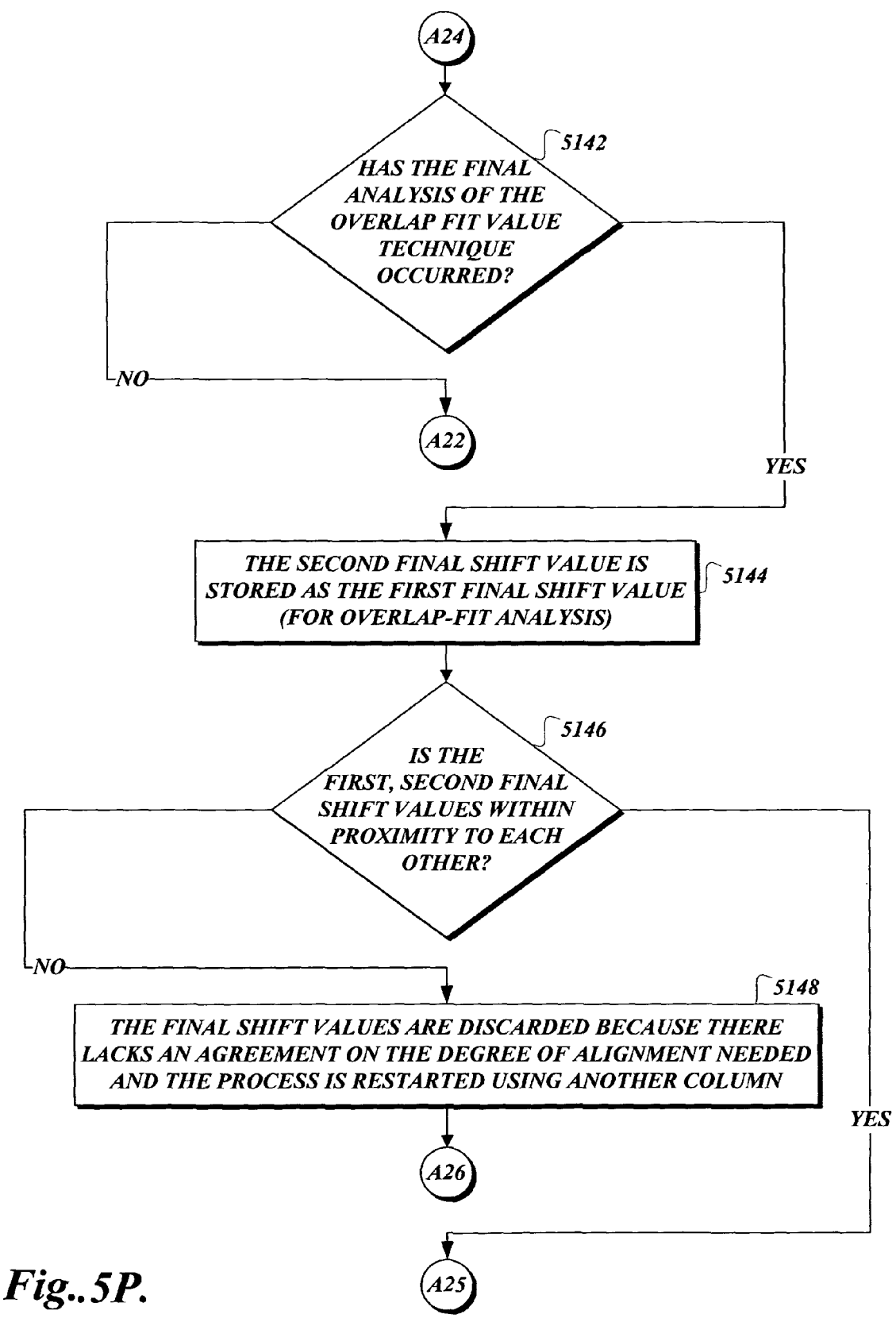
Fig..5P.

DISCOVER BIOLOGICAL FEATURES USING COMPOSITE IMAGES

CROSS-REFERENCE TO RELATED APPLICATION

This application claims the benefit of U.S. Provisional Application No. 60/735,691, filed Nov. 10, 2005, which is incorporated herein by reference.

TECHNICAL FIELD

The present invention relates generally to image processing, and more particularly, to analyzing images of prepared biological samples to discover features of interest for further analysis.

BACKGROUND

To improve the success rate of new drug developments, pharmaceutical companies have increasingly relied on the use of biomarkers. Biomarker is a term with many meanings, one of which may include one or more measurable quantities that can serve as indicators of biological processes, statuses, or outcomes of interest. For example, prostate-specific antigen is a commonly used diagnostic biomarker for prostate diseases. Ideal biomarkers may lead to better understanding of mechanism of drug treatments; better prediction and monitoring of therapeutic outcomes, and better management of risks associated with drug toxicities.

Ideal biomarkers should not only be sensitive and specific to biological conditions of interest, but ideal biomarkers should also be easy and convenient to detect and measure, preferably in body fluids, such as blood, urine, and cerebrospinal fluid. Although large-scale gene expression analysis by microarrays has helped to identify relevant biomarkers. Suitable biomarkers are often not genes, but proteins; protein fragments; metabolites; and others. One of the reasons this is the case is that tissue specific gene expression variation is not easily measurable in body fluids. Despite many technical challenges connected with protein identification and measurement, current efforts are focused on finding relevant protein biomarkers.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with this invention, an image processing pipeline, a system, a biological image preprocessor, and a method are provided. One computer-implementable image processing pipeline form of the invention includes a collector for collecting data from a process in which prepared biological samples are obtained from expression experiments of different treatment conditions. The pipeline further includes an image processor for processing the data from the collector and forming a composite image. The pipeline also includes an image feature extractor for extracting feature characteristics from the composite image, which include peaks, isotope groups, and charge groups.

In accordance with further aspects of this invention, a system form of the invention includes a collection of instruments for processing prepared biological samples to produce a set of images. The collection of instruments includes a liquid chromatography instrument and a mass spectrometer. The system further includes an image processor for processing a composite image, which is produced from the set of images. The image processing pipeline produces feature characteristics, expression profiles, and a candidate feature list.

In accordance with further aspects of this invention, a biological image preprocessor form of the invention includes an interpolator in combination with a data rasterizer for interpolating, rasterizing, and filtering raw LC/MS data to map to two-dimensional images. The preprocessor further includes a within-group replicates combiner in combination with a between-group image merger for combining and merging the two-dimensional images, which are indicative of different treatment groups, into a composite image.

In accordance with further aspects of this invention, a method form of the invention includes a method to remove inconsistency in chromatogram retention time among different images. The method comprises generating aligned two-dimensional LC/MS rasterized images by warping original raw data to reduce the total misalignment among all replicates. The method further comprises combining replicates within each treatment group to form combined images and merging the combined images from between treatment groups by taking the maximum pixel intensity to form a composite image.

In accordance with further aspects of this invention, a method form of the invention includes a method for extracting image features. The method comprises identifying isotope peaks from connected non-zero pixels on a composite image. The method further comprises splitting identified isotope peaks that are composed of two or more isotope peaks in a mass/charge direction, a retention time direction, or both.

In accordance with further aspects of this invention, a method form of the invention includes a method for extracting biological features. The method comprises processing images of different treatment conditions to form a composite image. The method further comprises finding isotope peaks from connected pixels in the composite image that have intensity above a background noise parameter which is selected from a group consisting of the mean, median, maximum, minimum, and the standard deviation at a particular location in the composite image.

In accordance with further aspects of this invention, a method form of the invention includes a method to split isotope peaks found in a composite image. The method comprises detecting an overlapped isotope peak by determining whether an isotope peak has a width that is wider than a width distribution of other isotope peaks. The method further comprises splitting the overlapped isotope peak in a retention time direction and in a mass/charge direction.

In accordance with further aspects of this invention, a method form of the invention includes a method to estimate a charge state for an isotope group. The method comprises constructing an MS continuum by weighted sum of individual continuaa around a retention time centroid of a peak from the top of a rank list. The method further comprises matching multiple ideal models for various charge states to the MS continuum and determining the ideal model that provides the best match. The charge state of the ideal model is the charge state of the isotope group.

In accordance with further aspects of this invention, a method form of the invention includes a method for aligning images representing replicates. The method comprises calculating correlation coefficients and overlap fit values, which measure the extent a target image aligns with a master image, to determine a first final shift value and a second final shift value in a set of overlaps. The method further comprises averaging the first and second final shift values to produce a final shift value for the time interval if the first and second final shift values are within proximity to each other. The method also comprises repeating the above steps to create multiple final shift values for multiple time intervals, each final shift value being a control point to create an interpolated function for rasterizing the images and aligning them.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
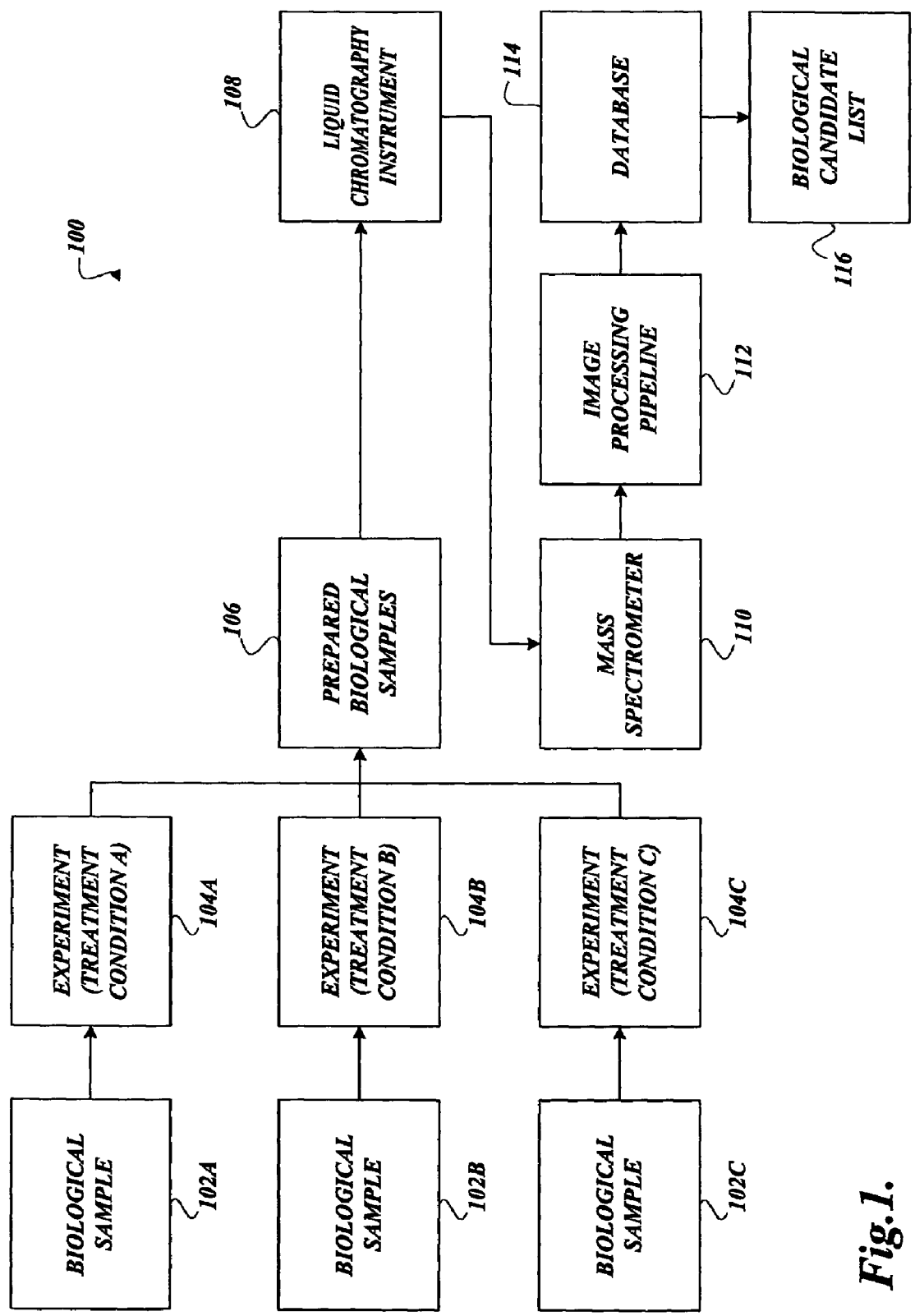
FIG. 1 is a block diagram illustrating an exemplary system including an exemplary image processing pipeline.

Various embodiments of an image processing pipeline 112 facilitate feature extraction and analysis, such as peptide feature extraction and differential expression analysis. See FIG. 1. One embodiment of the image processing pipeline is for use in protein biomarker discovery in the drug development process. Other embodiments of the image processing pipeline can be used for other types of discovery besides biomarkers. Input to the image processing pipeline 112 is a set of raw data 202 (See FIG. 2A) collected from a process in which prepared biological samples 106 are subjected to liquid chromatography instruments 108 and mass-spectrometers 110. The data is obtained from expression experiments 104A-104C of different phenotypical or treatment conditions 102A-102C, such as protein expressions under differential drug dosages. For each condition, measurement data from several biological replicates may be available. One embodiment of the image processing pipeline 112 facilitates the finding of those peptides or proteins that have their expression levels differ or not differ in various phenotypes or expression levels that are altered by the drug treatments. Other embodiments of the image processing pipeline facilitate the finding other biological features.

Some of the key elements of the image processing pipeline 112 include image preprocessing which is performed by a biological image preprocessor 204 (data interpolation, image alignment, image noise filtering, background correction, and forming a composite image); image feature extraction which is performed by an image feature extractor 208 (peaks, isotope groups, and charge groups); computing feature characteristics; and expression statistics which is performed by an expression statistics processor 212; and differential or non-differential expression analysis which is performed by an expression analysis processor 216. See FIG. 2A. Outputs of the image processing pipeline include (1) a list 210 of biological features and their characteristics (2) expression profiles 214 of all replicates in all conditions at three summarization levels (peak, isotope group, and charge group); and (3) a list 218 differentially or non-differentially expressed features for subsequent targeted identifications.

Liquid chromatography (LC) and mass spectrometry (MS) approaches have become a focus of gel-free protein expression profiling. Prepared biological samples (e.g., peptides from digested protein samples) are eluted from a chromatography column, ionized, and subsequently analyzed in the ion-trap. As will be appreciated by one skilled in the art, various embodiments of different methods are applicable to any type of spectroscopy or spectrometry. Mass spectrometry is a tool used for proteomics and metabolomics research because it provides for sensitive detection and identification of all types of proteins and metabolites over a large dynamic range. Given that the detected ion intensity may depend on factors in addition to sample component concentration, such as ionization efficiency, detector efficiency, sample size, and sample flow rate, other suitable quantification methods are employed. While protein and peptide ionization for mass spectrometry conventionally employ MALDI (matrix-assisted laser desorption ionization) or ESI (electrospray ionization), various embodiments of different methods can use any suitable current or future ionization method, as well as any suitable detection method, such as ion trap, time-of-flight, or quadrupole analyzers. Moreover, various embodiments of different methods can use data obtained from gas chromatography-mass spectrometry (GC-MS), particularly using electron-impact ionization (EI).

Different biological features, such as peptides, are separated in two dimensions (retention time and mass/charge). For a given retention time, a one-dimensional continuum can be obtained in the interested mass/charge range. Peptides are shown as peaks in the continuum although other biological features of interest may also shown as peaks. The peak intensity is assumed to be proportional to the abundance of the biological features of interest. Mass/charge continua are collected repeatedly at a defined sampling rate or a variable sampling rate. Conceptually, the sequentially collected one-dimensional mass-spectrometer continua form a two-dimensional data set. If intensity were a third dimension, various peaks appear as individual hills on a relief map.

One search made possible by various embodiments of the present invention is to find those peptides or proteins which expression intensities have changed or not changed among different experiment conditions. Other searches not connected to peptides or proteins are also possible. The peptides or proteins may become candidates for further validation to identify useful biomarkers. Some embodiments of the present invention focus on data processing between raw LC/MS data and differential or non-differential expression detections of peptide peaks or isotope groups. Those peaks, if not having been identified, can be sent to tandem mass spectrometry for identification of the peptide sequences.

FIG. 1 is a block diagram of a system 100 that includes the image processing pipeline 112. The input to the pipeline 112 is a set of raw LC/MS data, which are the prepared biological samples 106 from experiments 104A-104C under different treatment conditions or phenotypes. There are often several biological or technical replicates 102A-102C in each condition. Biological replicates 102A-102C are samples from different animals or cell lines and so on. Technical replicates are repeated LC/MS runs of the same animal sample. The output from the image processing pipeline includes feature characteristics, expression profiles, and differential or non-differential feature list. See collectively, biological candidate list 116.

Figure 3:
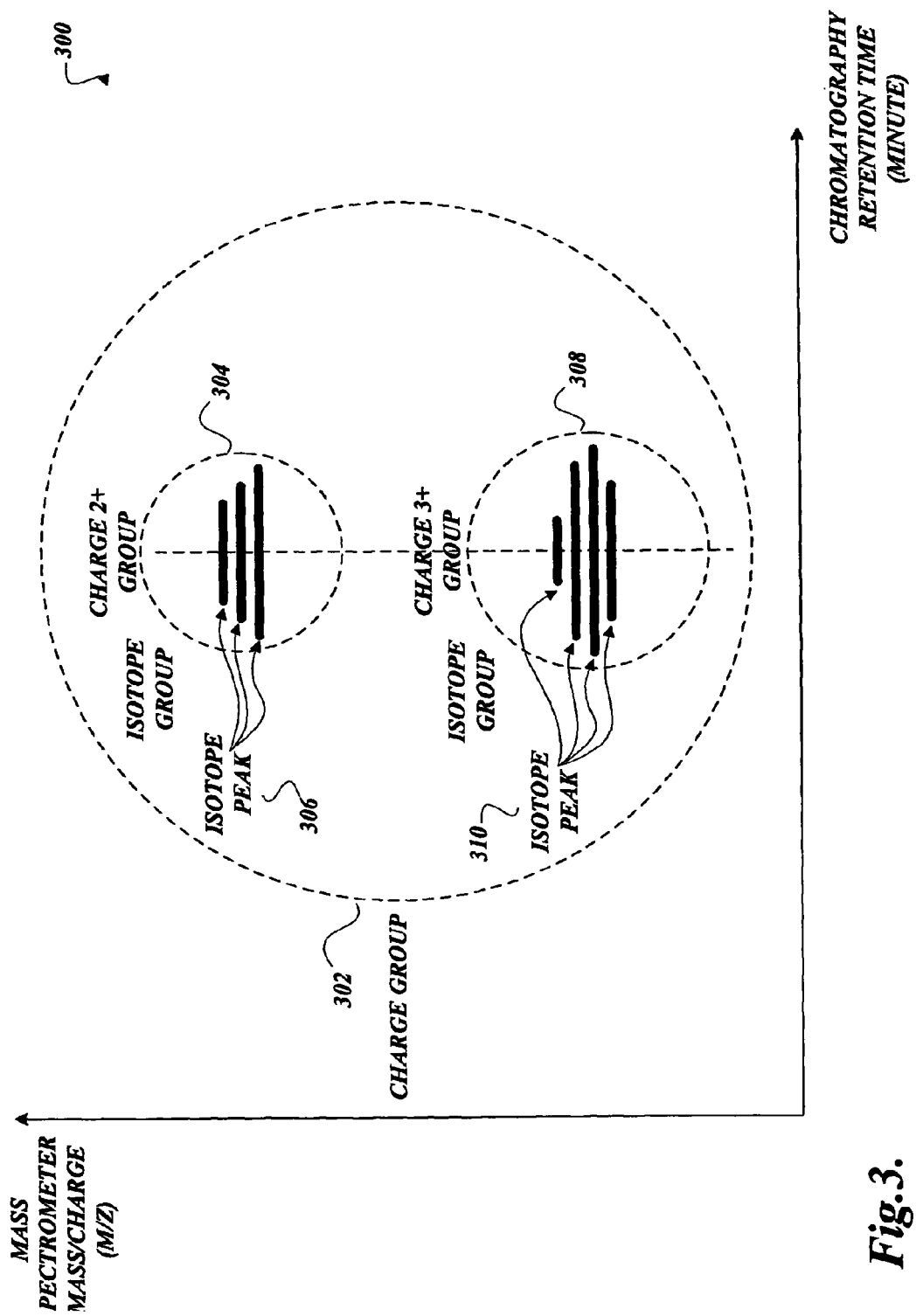
FIG. 3 is a pictorial diagram illustrating peaks, isotope groups, and charge groups, which are detected by various embodiments of the present invention.

The feature characteristics provide information about the biological feature 300 in three levels: peak, isotope group, and charge group. See FIG. 3. These characteristics include peak retention time start and end; peak mass/charge start and end; mass/charge centroid; charge state; mass; and so on. For a given peak, the characteristics apply to all data replicates in all conditions. FIG. 3 illustrates peaks 306-310, isotope groups 304-308, and a charge group 302. A peak is a two-dimensional LC/MS intensity hill defined by its contour at specific retention time range and m/z range. An isotope group is a group of isotopic peaks at the same charge state. The mass difference between two adjacent isotopic peaks is the result of one extra mass of a neutron acquired when one element is changed to another element. For one specific isotopic state, it is possible that there are more than one peak. This is particular true particularly for situations of low signal-to-noise ratios. Multiple isotope groups may be detected at different charge states. A charge group includes those isotope groups that belong together.

For each LC/MS run, expression profiles can be provided at three summarization levels: peak, isotope group, and charge group. Each profile includes intensity and other expression statistics from a particular run. For example, peak intensity is defined as the volume under the peak surface, which is a summation of intensity measurements of all non-zero pixels within the peak boundary contour. Expression profile is the quantitative foundation for all subsequent expression data analysis, such as differential expression detection. Differential feature list is a small set of features (peaks or isotope groups) that have been selected for peptide/protein identification by tandem mass spectrometry. This list can be the result of differential detection by statistical hypothesis tests, such as ANOVA, or the result of unsupervised learning (clustering) or supervised learning (classification) methods, or the combination of a few of them or all of them. After the peptide/protein identification, features in this list will be annotated by the peptide/protein sequence information. Expression profiles of annotated features can be used in subsequent analysis to understand the underlying biology. Of course, non-differential detection afforded by the various embodiments of the present invention can also be used to understand the underlying biology as well.

Figure 2A:
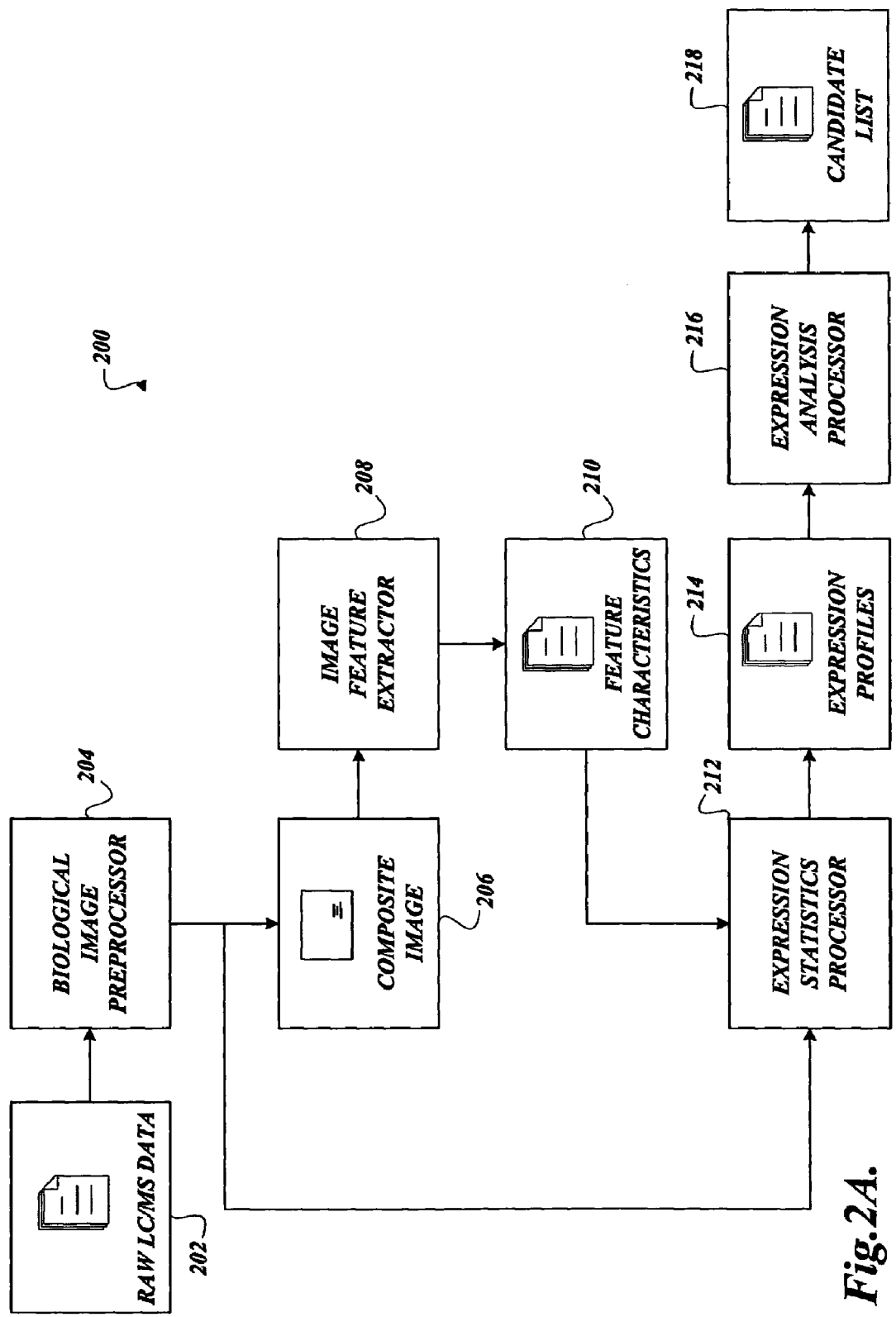
FIG. 2A is a block diagram illustrating an exemplary image processing pipeline for extracting biological candidates of interest for further discovery and analysis.
Figure 4A:
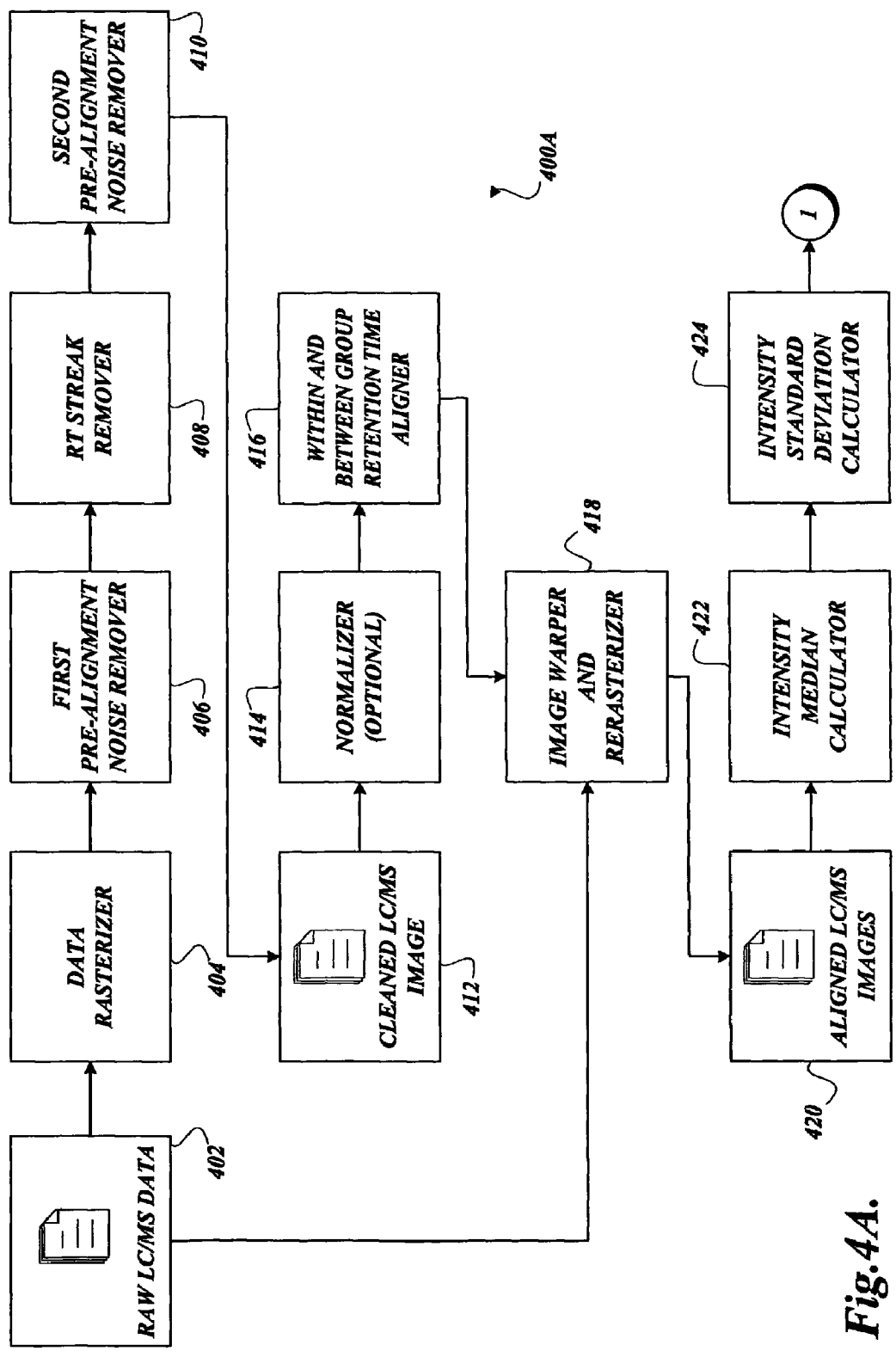
FIG. 4A is a block diagram illustrating an exemplary biological image preprocessor, which is a component of an exemplary image processing pipeline.
Figure 4B:
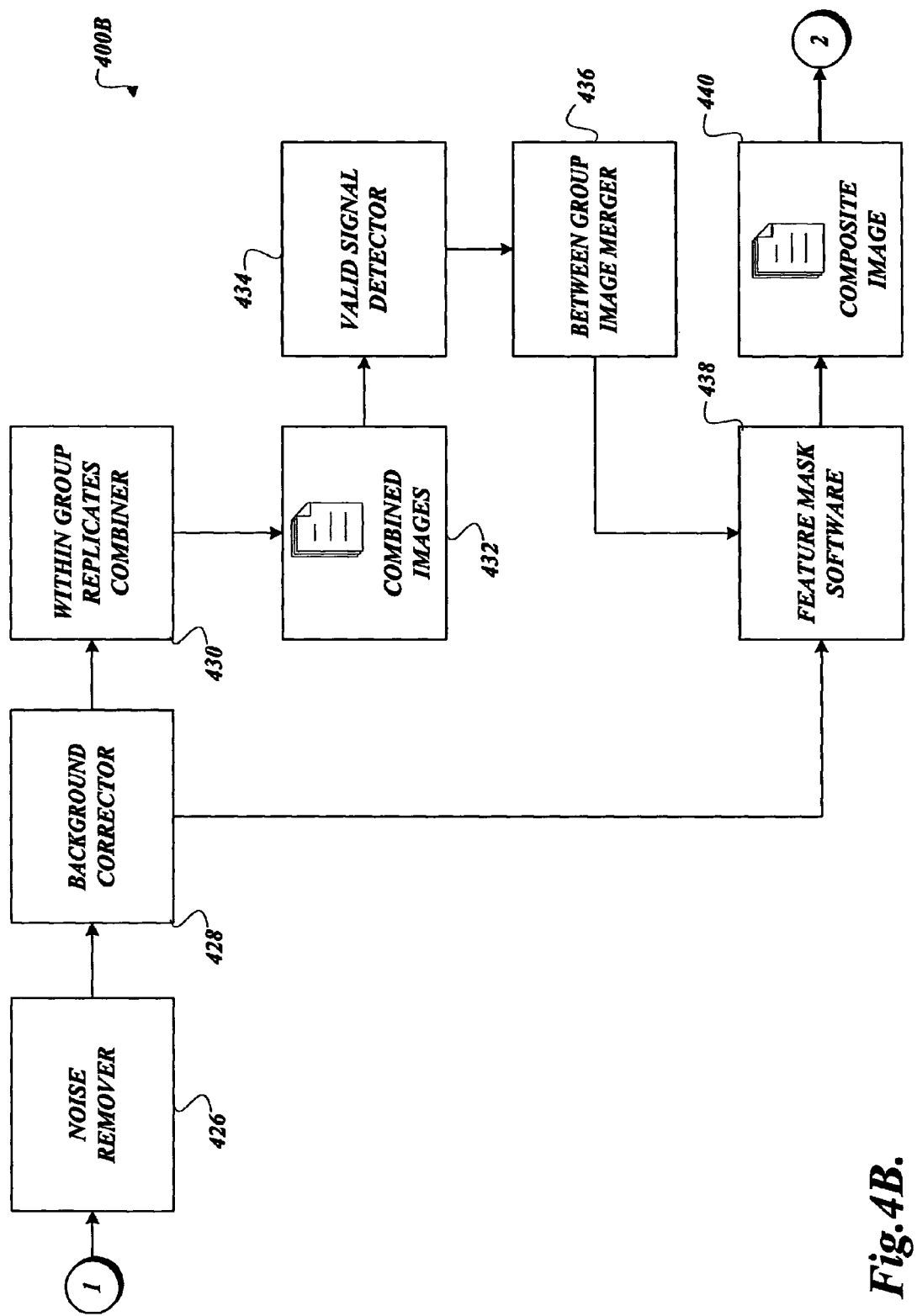
FIG. 4B is a block diagram illustrating another portion of an exemplary biological image preprocessor, which is a component of an exemplary image processing pipeline.
Figure 4C:
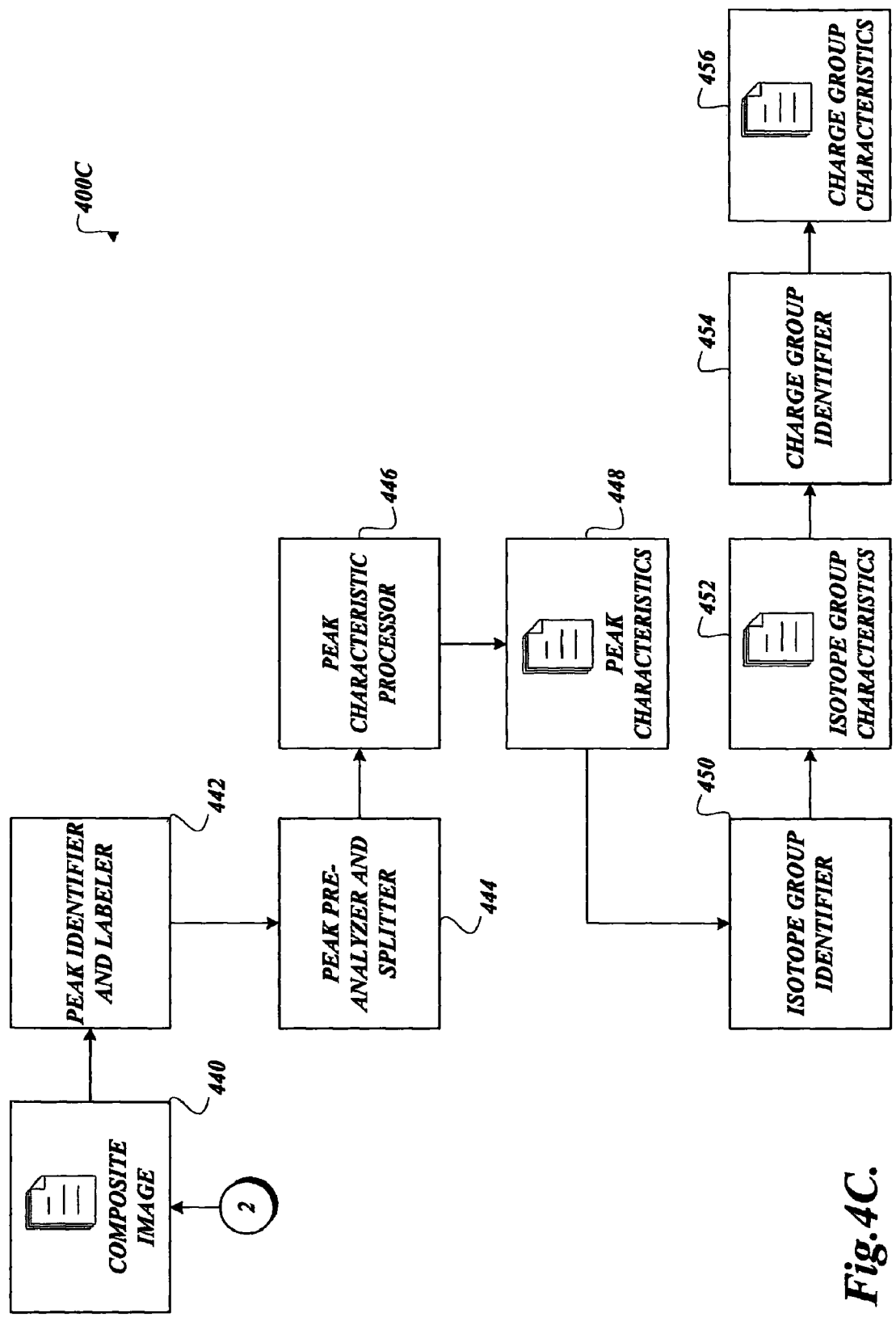
FIG. 4C is a block diagram illustrating an exemplary image feature extraction component of an exemplary image processing pipeline.

FIGS. 4A-4C are detailed block diagrams of the biological image preprocessor 400A-400B shown in FIG. 2A as element 204 and image feature extractor 400C shown in FIG. 2A as element 208. The input is a set of raw LC/MS data 402 that comes from protein samples of several differential treatment groups, within each of which there are several biological or technical replicates. Functions of this module include data rasterization performed by a data rasterizer 404; retention time alignment performed by an aligner 416 for within and between group retention time alignment as well as by an image warper and rerasterizer 418; image noise filtering performed by noise removers 406, 410, and 426; background corrector 428; retention time streak remover 408; a normalizer 414; intensity median calculator 422 and intensity standard deviation calculator 424; and forming one composite image 440 for feature extraction by peak identifier and labeler 442, peak pre-analyzer and splitter 444, peak characteristic processor 446, isotope group identifier 450, and charge group identifier 454. The rasterization function interpolates the raw LC/MS data 402 and maps all data to a common two-dimensional image grid for subsequent image processing. The time alignment function removes inconsistency in the chromatogram retention time among different LC/MS runs of replicates.

There are three steps in time alignment. See, for example, FIGS. 5B-5S. First, in one embodiment, the global time misalignment is estimated in the pre-alignment step before the initial data rasterization although in another embodiment, this step is optional. Then the local within-group misalignment and the local between-group misalignment are estimated in separate steps in one embodiment, but in another embodiment, both the local within-group misalignment an the local between-group misalignment are calculated in one step. The total misalignment is the combination of the three components. Aligned two-dimensional LC/MS rasterized images 420 are generated by warping the original raw data to reduce the total misalignment among all replicates. Spatial noises in the two-dimensional images are filtered at several locations in the preprocessor to ensure a reliable and robust image feature extraction. Replicates within each treatment group are combined into one image by pixel intensity averaging. One composite image 440 is generated by using a suitable technique, such as taking the maximum pixel intensity among all combined images. The composite image 440 is the information with which the image feature extractor 400C work to obtain various biological features of interest.

FIG. 4C is a detailed block diagram of the image feature extractor. Its input is the composite image 440 from the biological image preprocessor 400A-400B (illustrated in FIG. 2A as element 204). Initially, a peak is defined as connected non-zero pixels. Each peak is labeled with a unique index number. It is possible several real peaks are mistakenly identified as one big connected peak. In the image pre-analysis function, many of these connected peaks are identified and split in the m/z or the retention time directions. The total number of peaks is increased after the splitting. New peak index numbers are assigned to those newly split peaks. Peak characteristics are computed, such as peak m/z centroid and width; peak time centroid and width; and so on. In the isotope group identification function, those peaks that belong to the same isotope group are identified. Isotope group characteristics are estimated, such as charge state; mono-isotopic m/z; and the peptide mass; and so on. A unique isotope group index number is assigned to each isotope group. Many isotope groups may only include one peak. In this case, zero charge is assigned. (Zero charge is a way to label these isotope groups because the charge is unknown.) When identifying isotope groups, overlapped peaks are identified. In the overlapping case, it is possible one peak belongs to two isotope groups, if the peak is not splittable. In the subsequent isotope-group identification function, isotope groups having different charge states but having similar retention time and peptide mass are assigned to one charge group.

FIG. 2A includes the expression statistics processor 212 and the expression analysis processor 216. The expression statistics processor 212 estimates expression statistics, such as intensity, intensity error and present-call p-value, at three summarization levels: peak, isotope group, and charge group. At the peak level, based on the peak characteristics produced by the image feature extractor, peaks are identified in each of the aligned LC/MS images 420 to estimate the expression intensity, which is the pixel intensity summation within the peak contour boundary. Then a technology-specific error model is applied to estimate the intensity error. The result is a peak-level expression profile, one for each LC/MS image. At the isotope-group level, the input is the peak-level expression profile and the isotope group characteristics. Expression statistics of multiple peaks in one isotope group are "squeezed" together to obtain an expression estimation for the isotope group. The intensity of the isotope group is defined as the summation of the peak intensities included in this isotope group. The intensity error of the result isotope group intensity is also estimated. The output is the isotope group-level expression profile, one for each LC/MS image. At the isotope-group level, the input includes the isotope group expression profile and the isotope-group characteristics, and the output is the isotope-group expression profile.

Various embodiments of the present invention facilitate the finding of a list of signature peaks or isotope groups that closely relate to biological features of interest. These biological features, such as peptides/proteins, either demonstrate statistically significant differential or non-differential expressions among different drug treatments, or possibly, even lead to the prediction of a drug's efficacy or toxicity. The identity of the signature biological features of interest, such as peptide/protein, are likely to be discovered during the subsequent tandem mass spectrometry sequence identification although these biological features may also be discovered much earlier. In the expression analysis processor, the expression profiles can be used at all levels to derive a list of biological features of interest. Many suitable and different statistical and data-mining methods to obtain a list of many relevant biological features are possible. Commonly used differential expression detection methods include parametric hypothesis tests such as t-test and ANOVA, and non-parametric tests such as the Wilcoxon test and other rank or permutation based tests. Commonly used data-mining methods include unsupervised learning such as clustering algorithms and supervised learning such as classifiers.

Figure 5A:
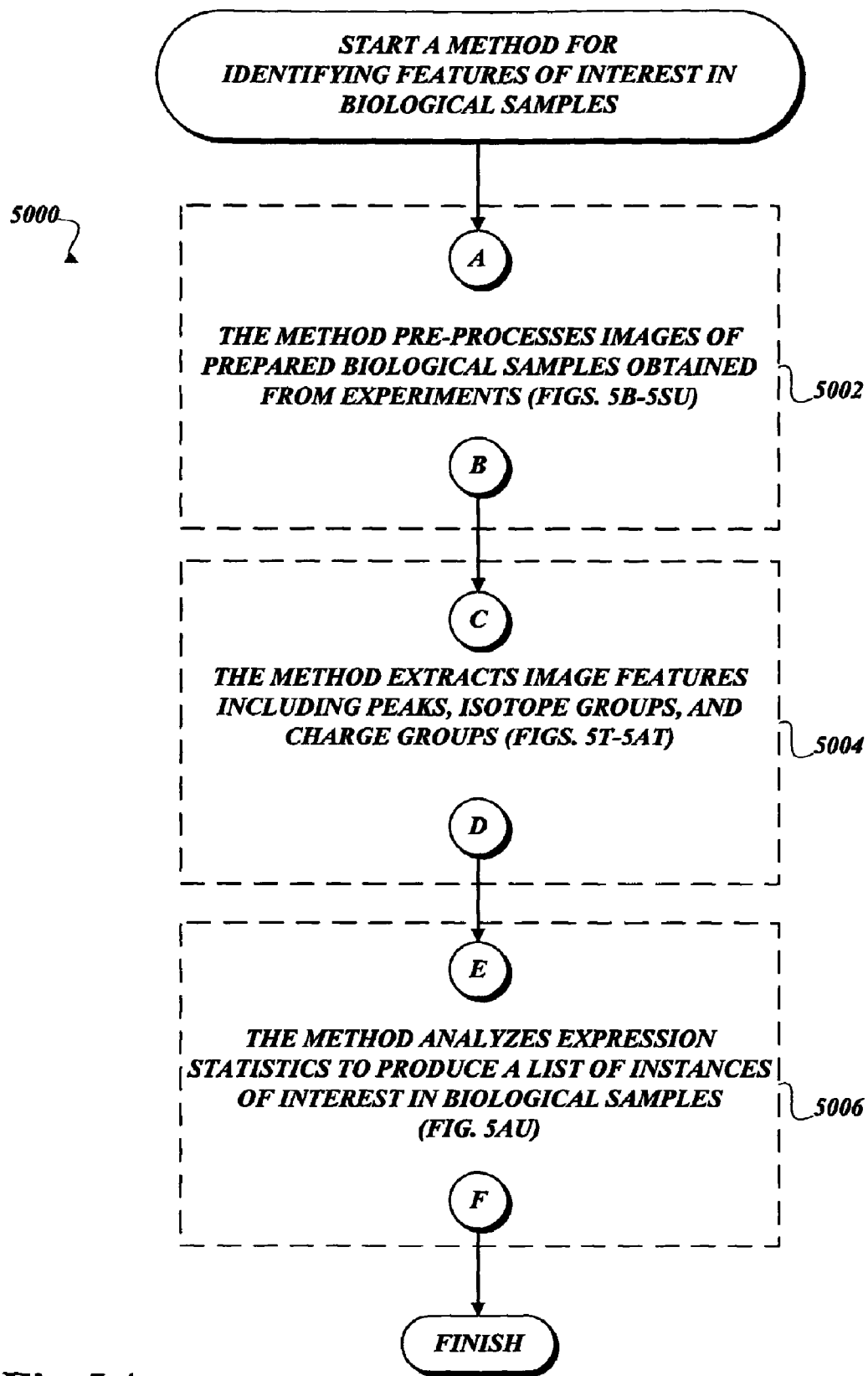
FIGS. 5A-5AU are process diagrams illustrating a method for identifying features of interest in biological samples.

The exemplary image processing pipeline of various embodiments of the present invention overcome or reduce limitations in sensitivity, accuracy and reproducibility of conventional analytical chemistry instruments. Hereinbelow, FIGS. 5A-5AU describes a method 5000 for identifying features of interest in biological samples. For the sake of simplicity in explanation, the description of the method 5000 illustrated by FIGS. 5A-5AU is broken into three parts. Initially, the method 5000 is discussed generally so as to allow a broader appreciation of various technical subject matters connected with the method 5000. Next, specific steps in the method 500 as illustrated by FIGS. 5A-5AU are described so that the flow of the method can be discerned. Finally, mathematical basis for various technical subject matters is discussed so as to allow a deeper apprehension of the techniques used for identifying features of interest in biological samples.

Figure 5B:
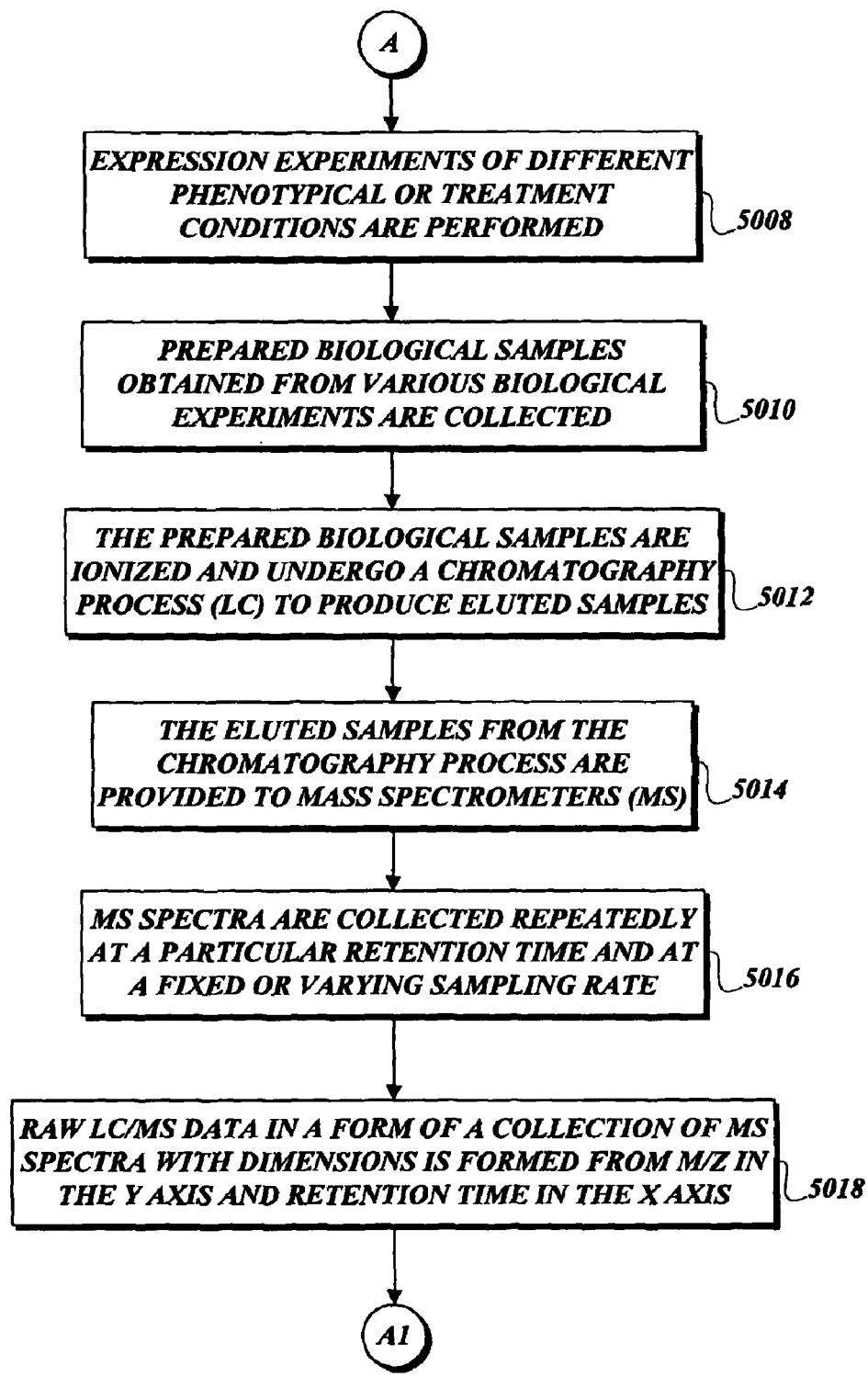
Figure 5C:
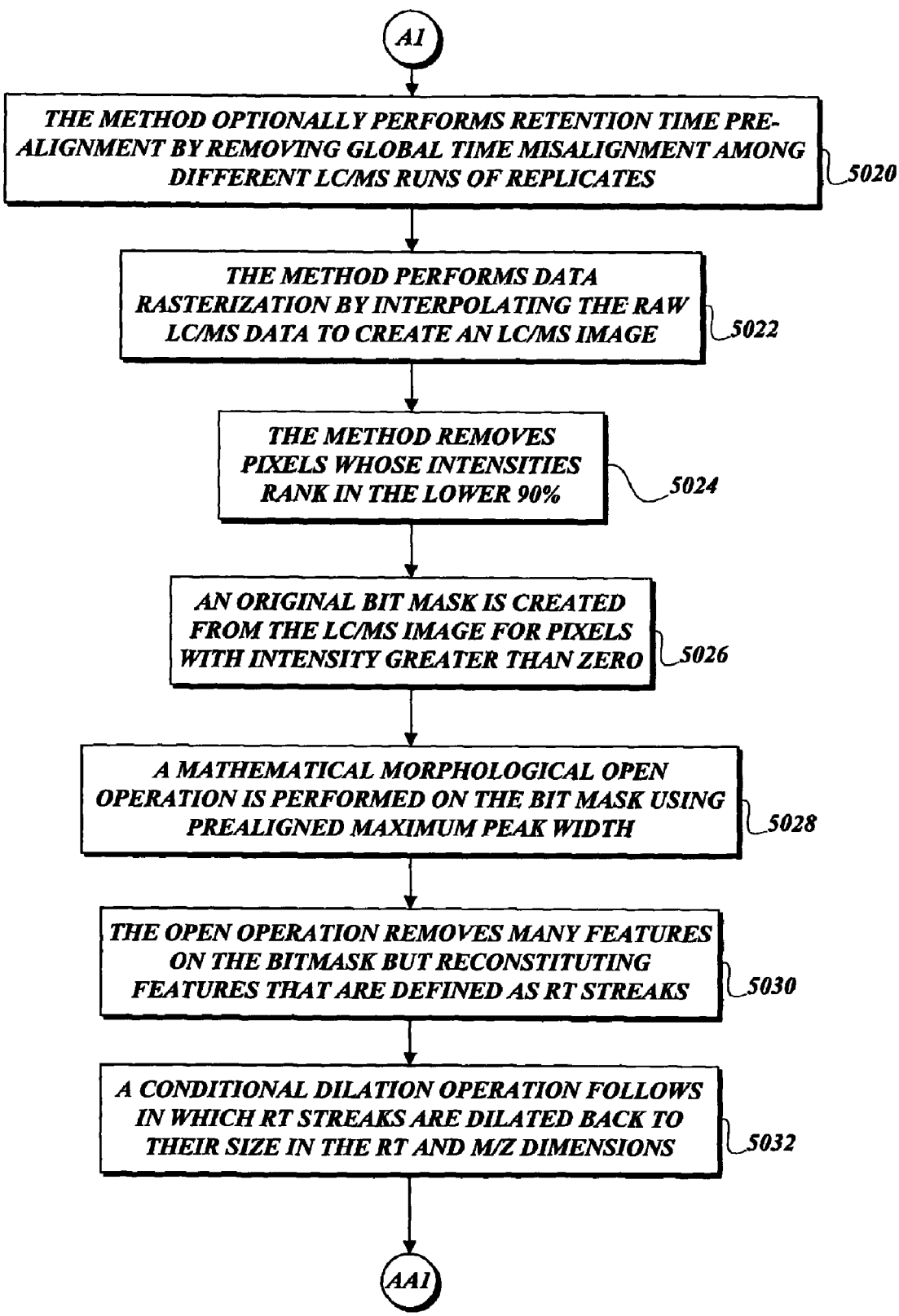
Figure 5C:
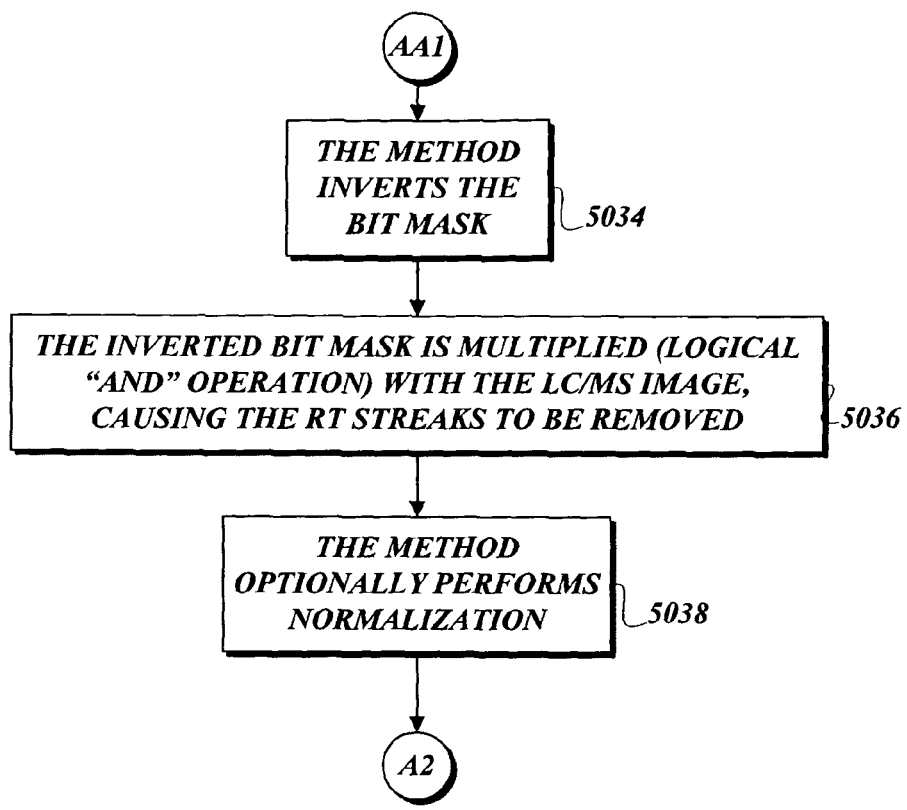
Figure 5D:
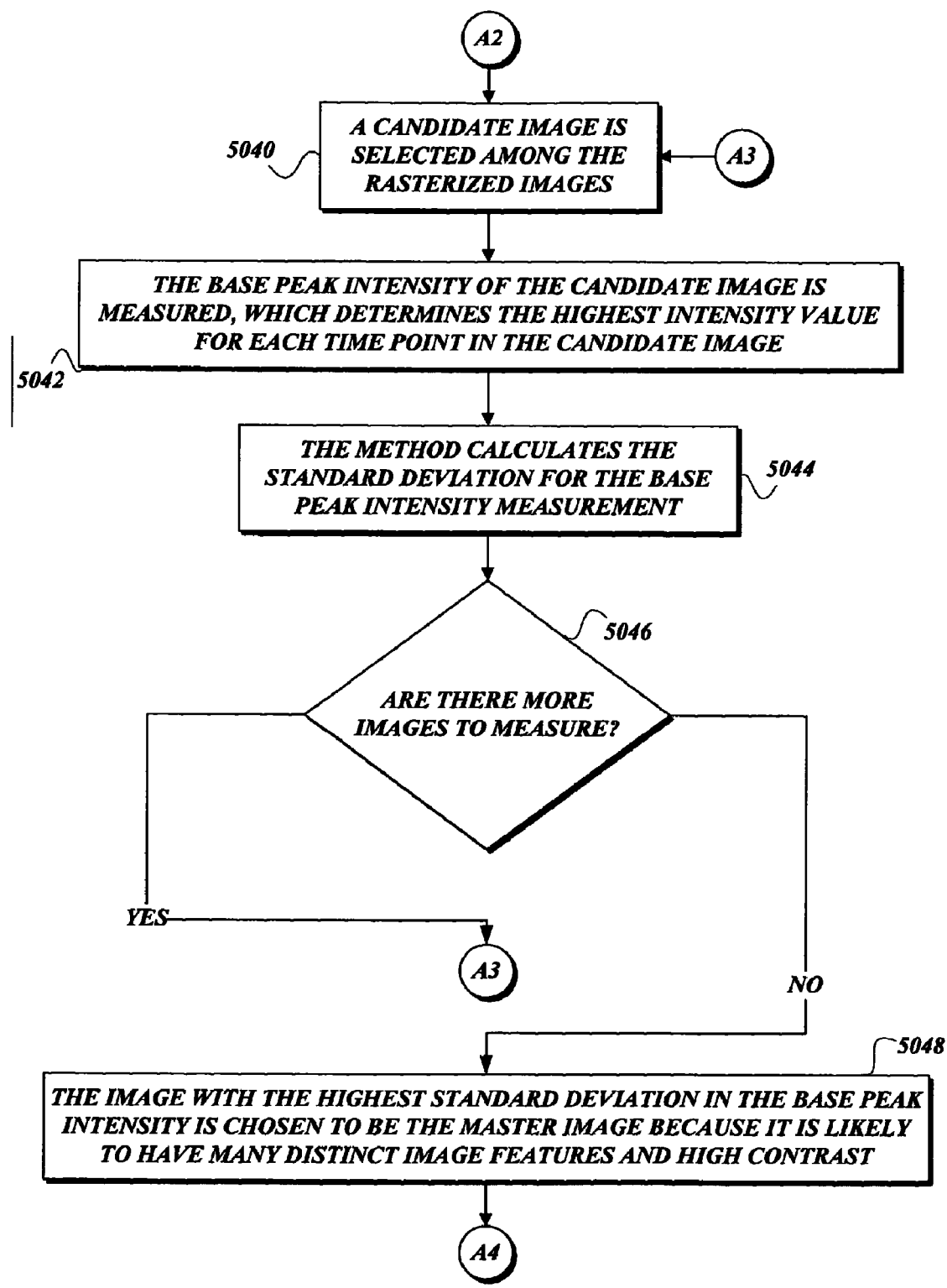
Figure 5E:
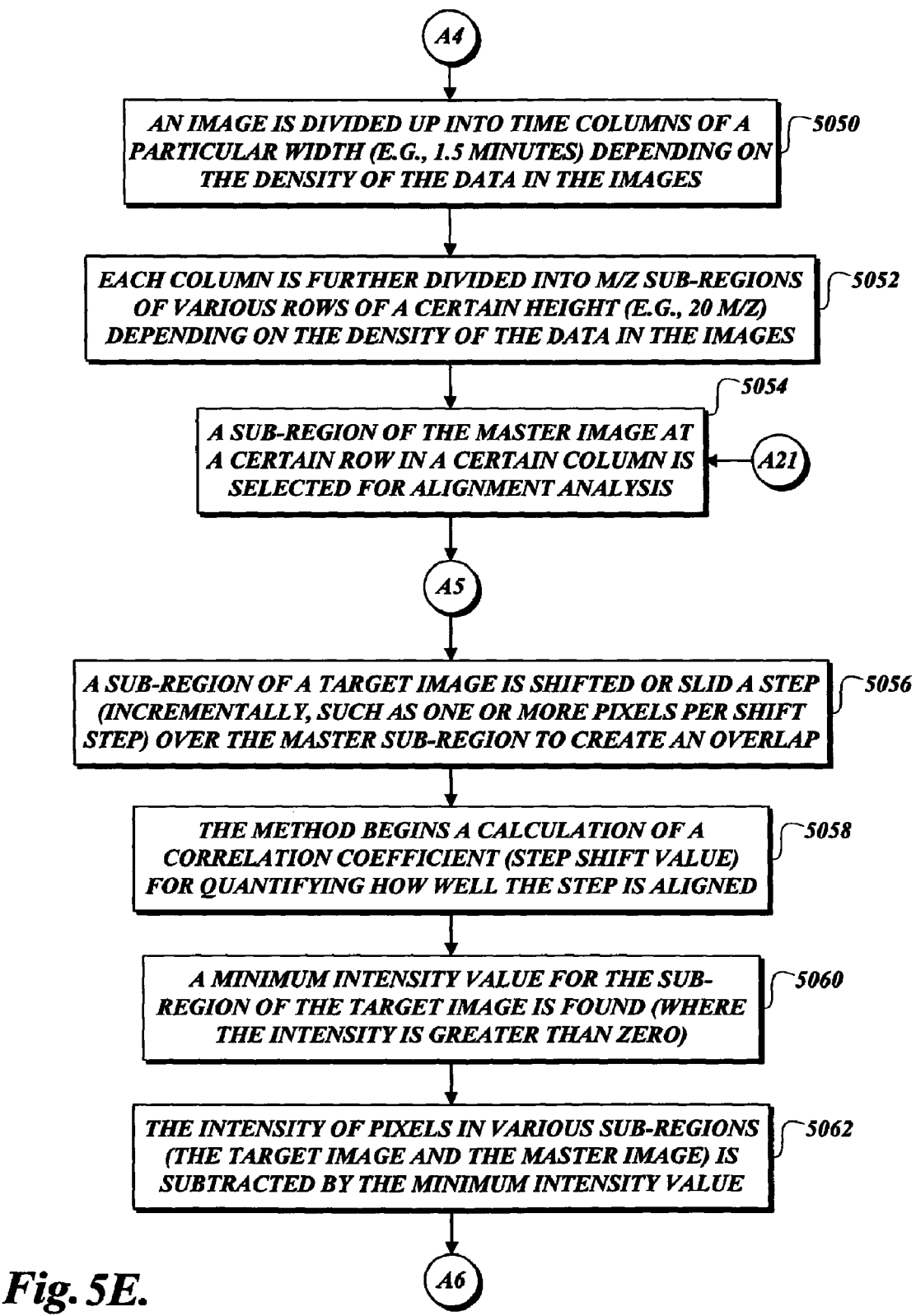
Figure 5F:
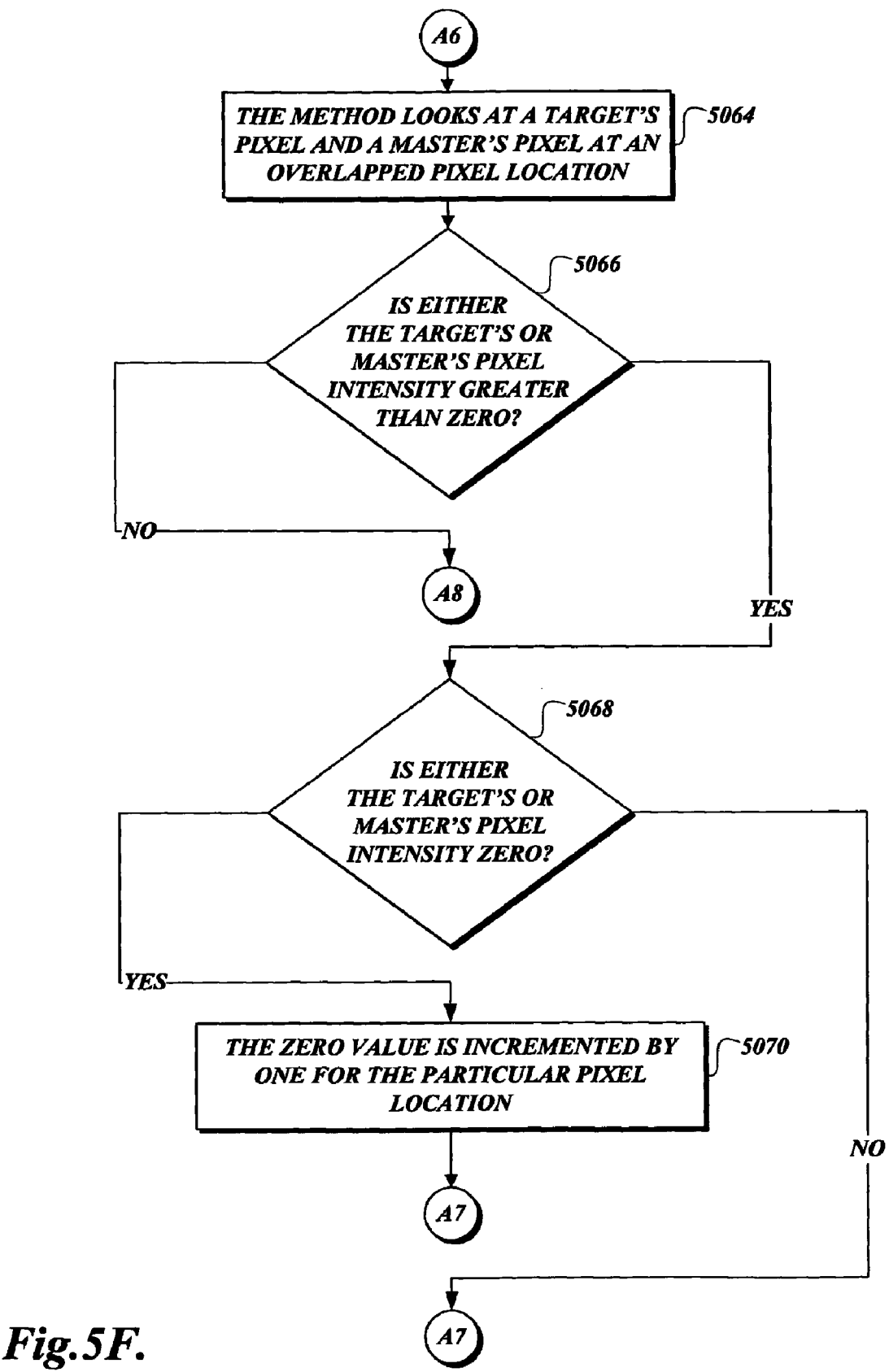
Figure 5G:
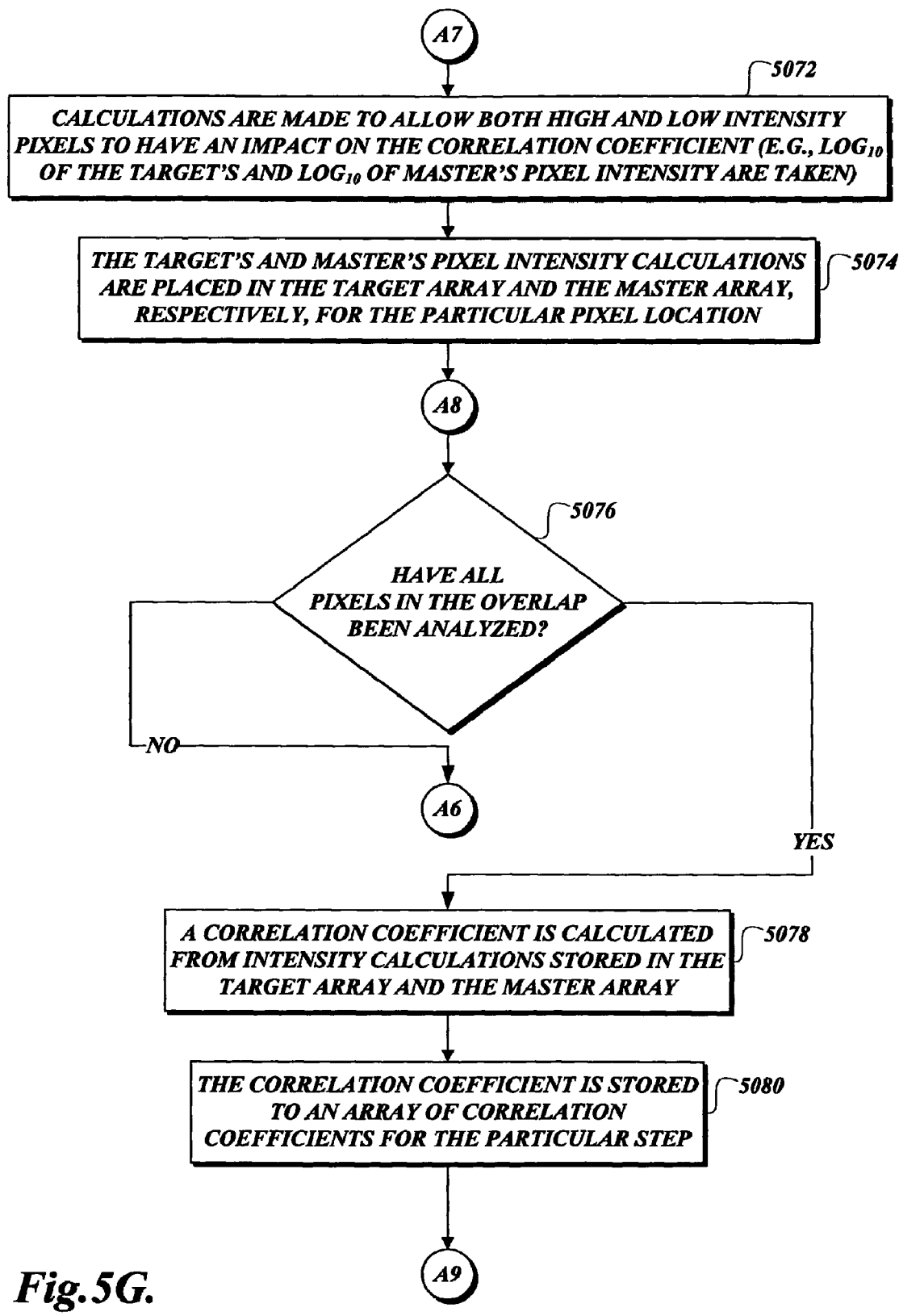
Figure 5H:
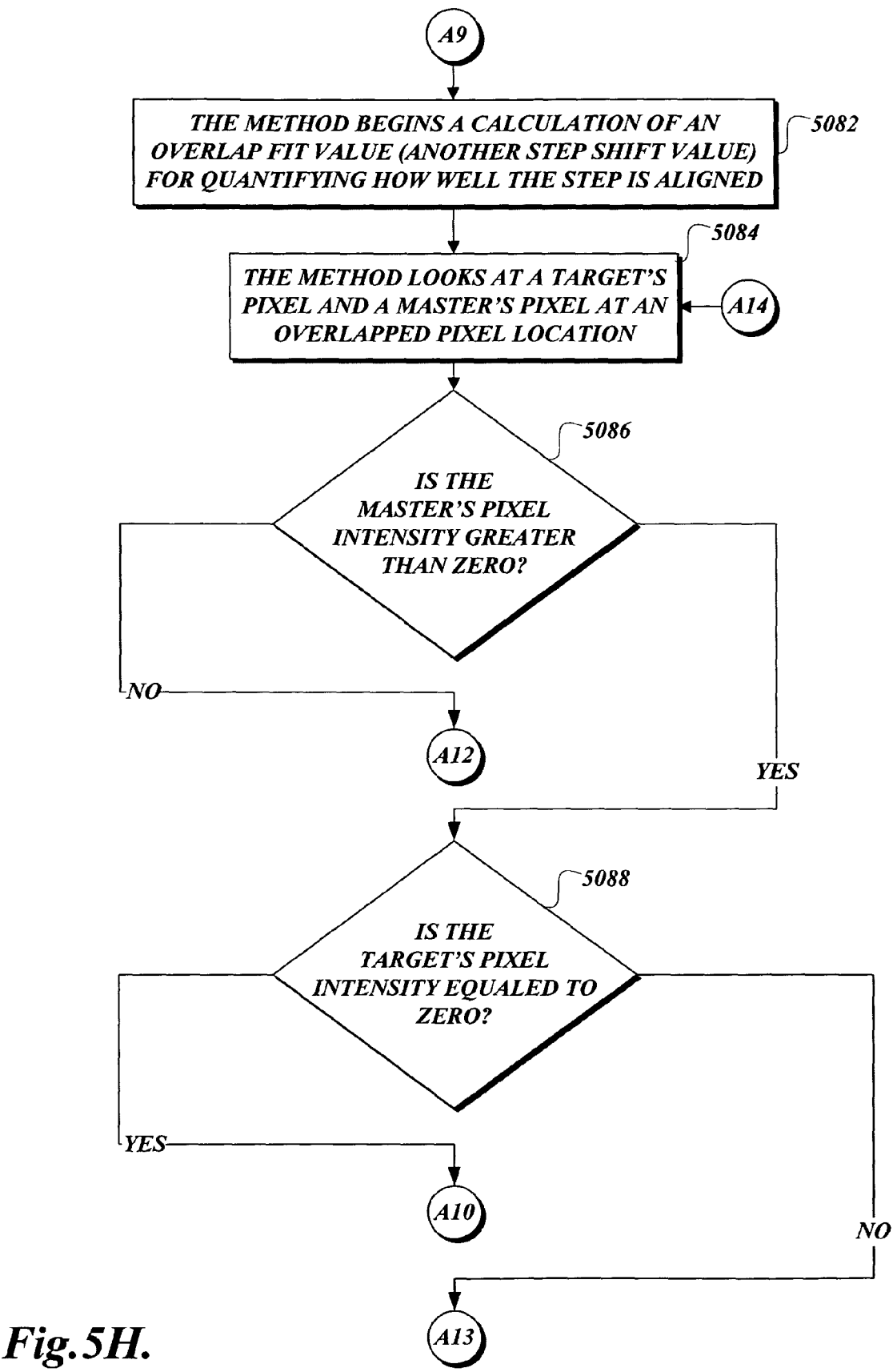
Figure 5I:
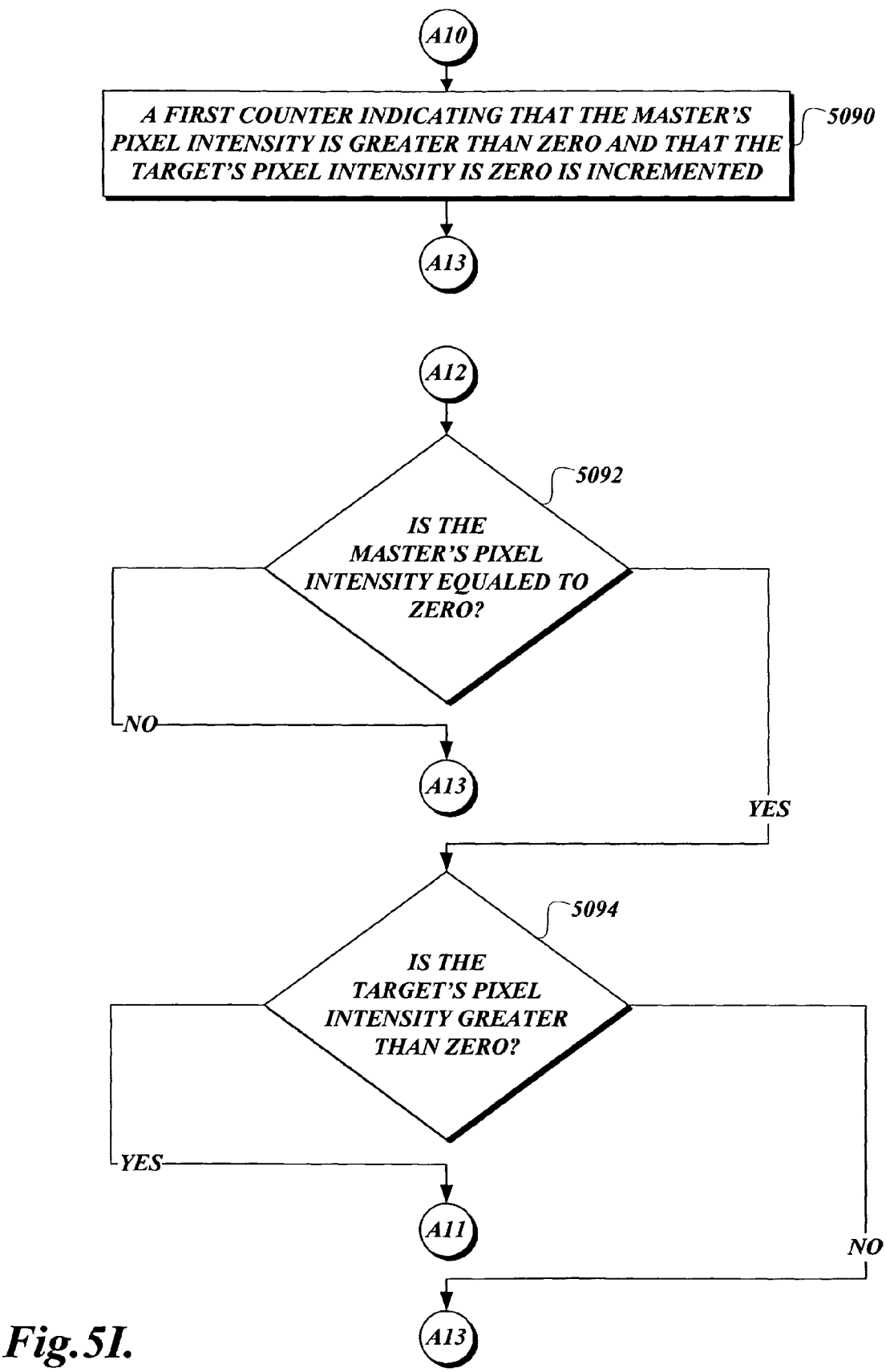
Figure 5J:
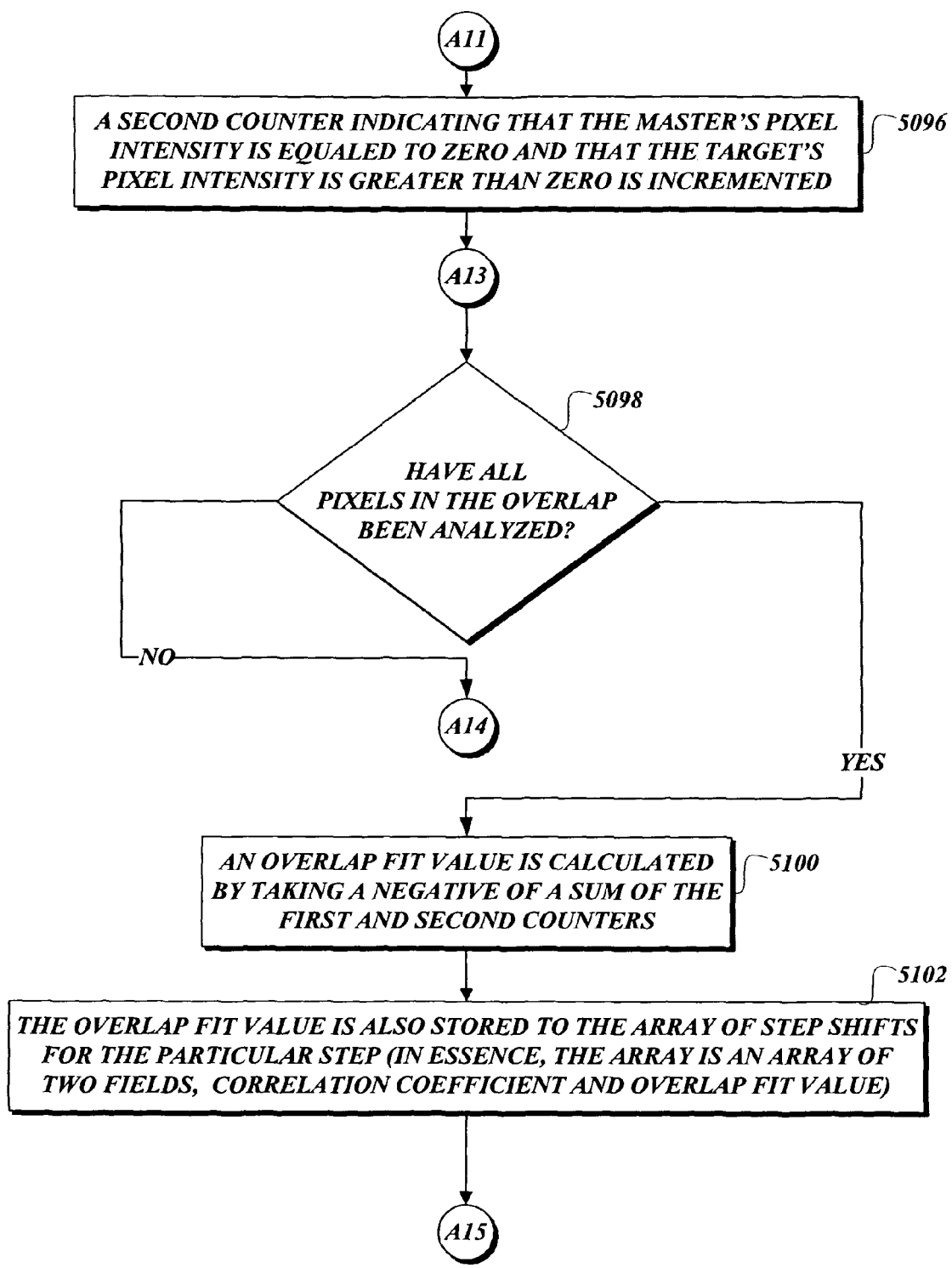
Figure 5K:
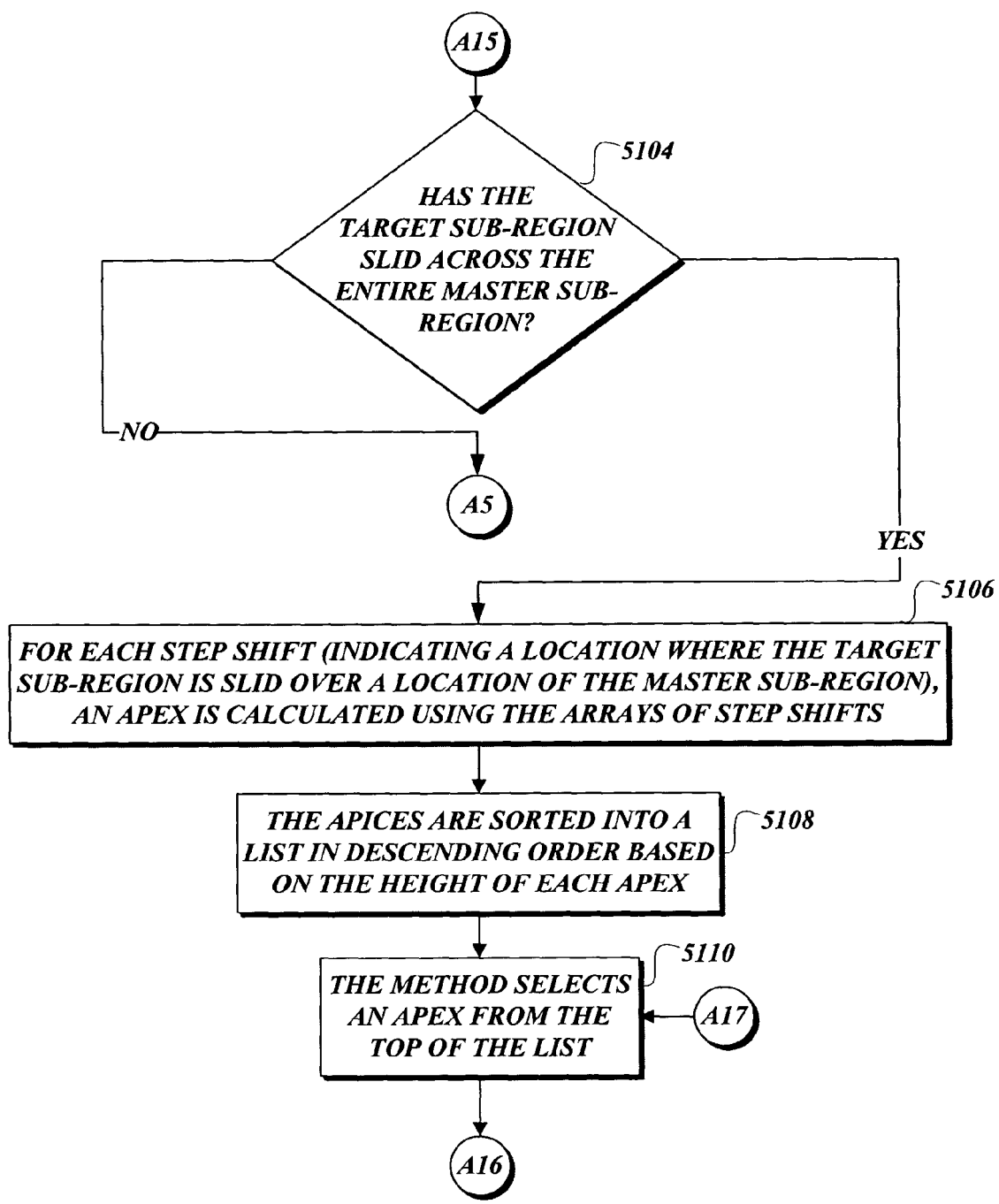
Figure 5L:
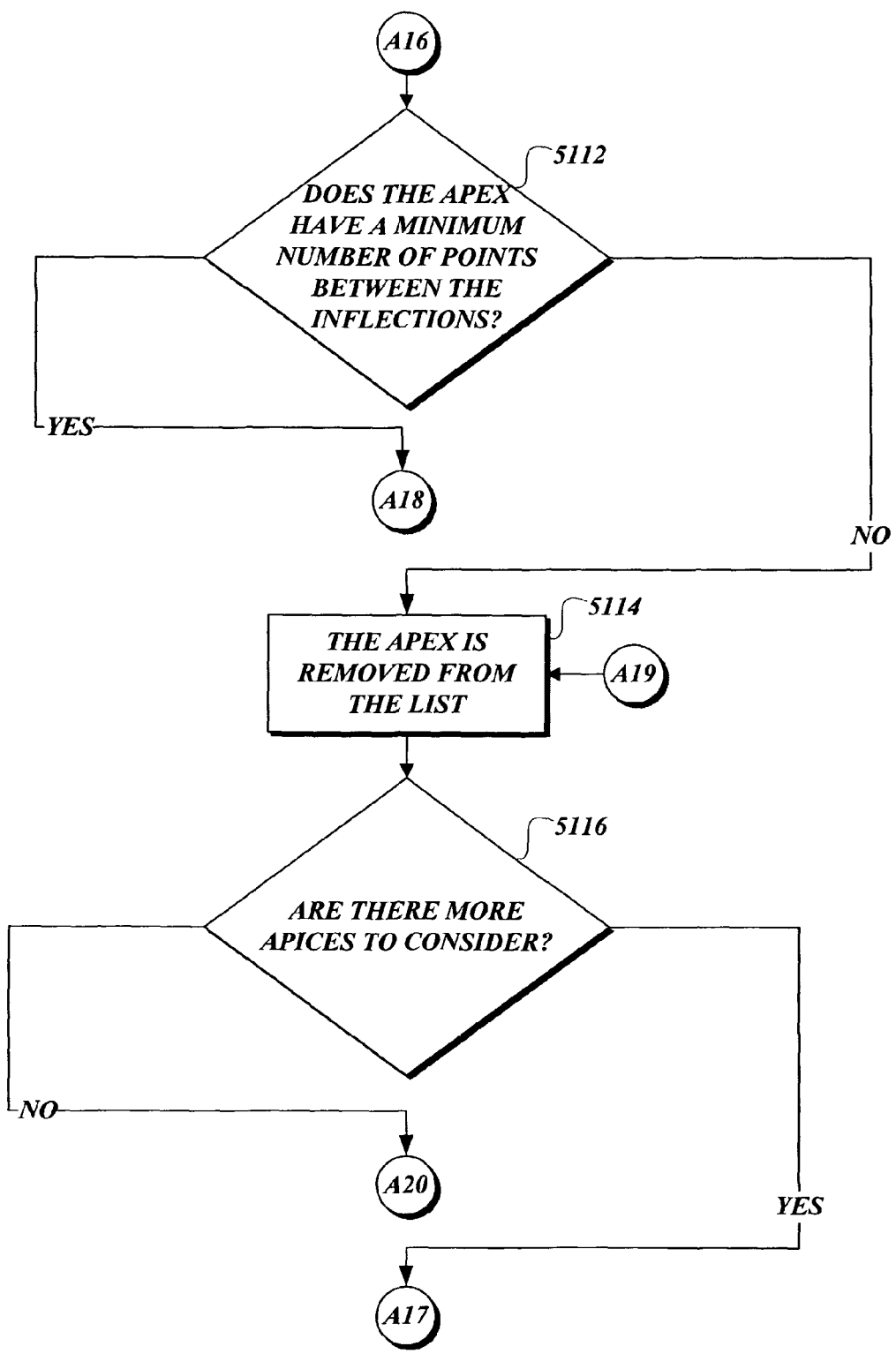
Figure 5M:
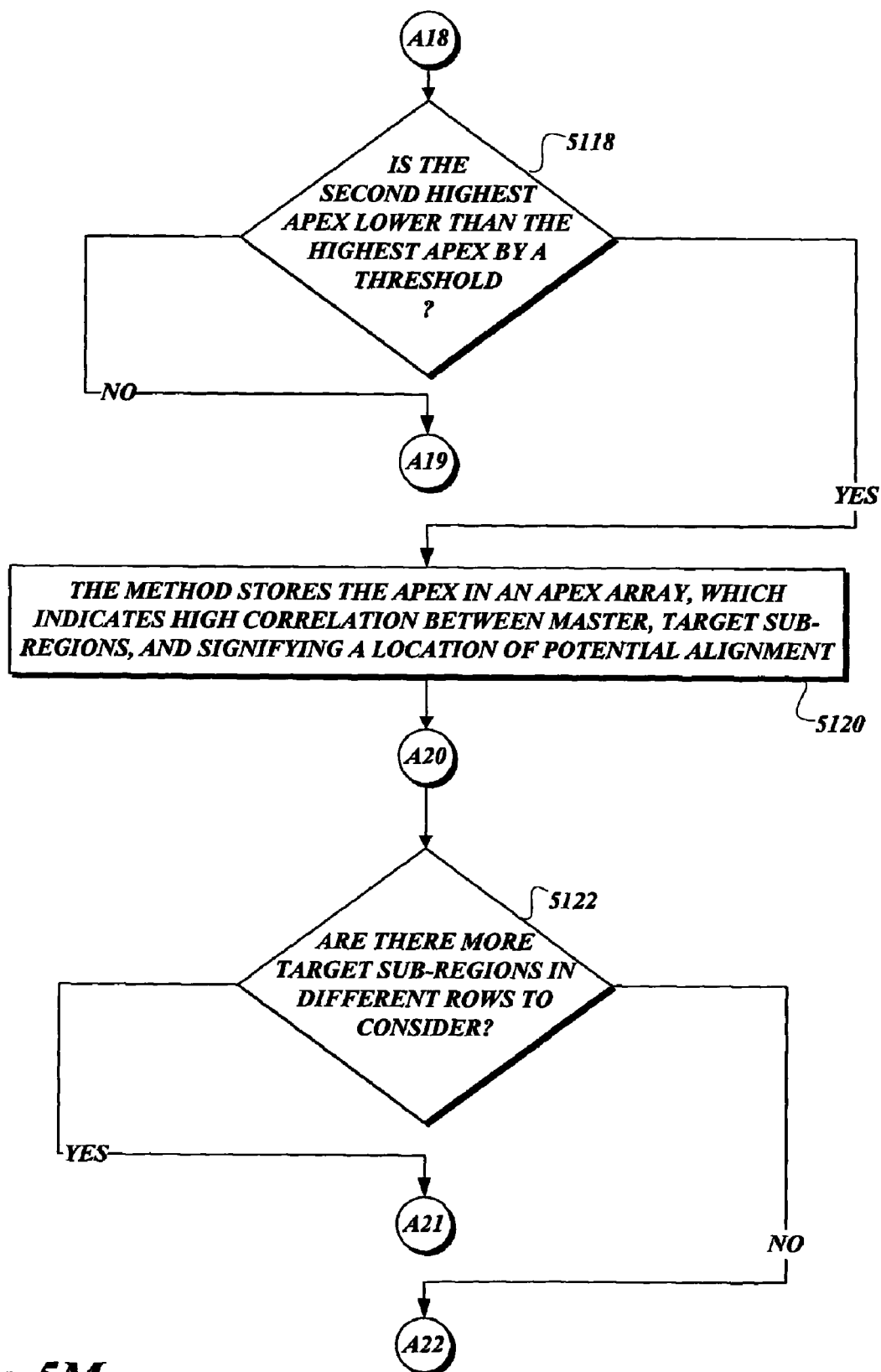
Figure 5N:
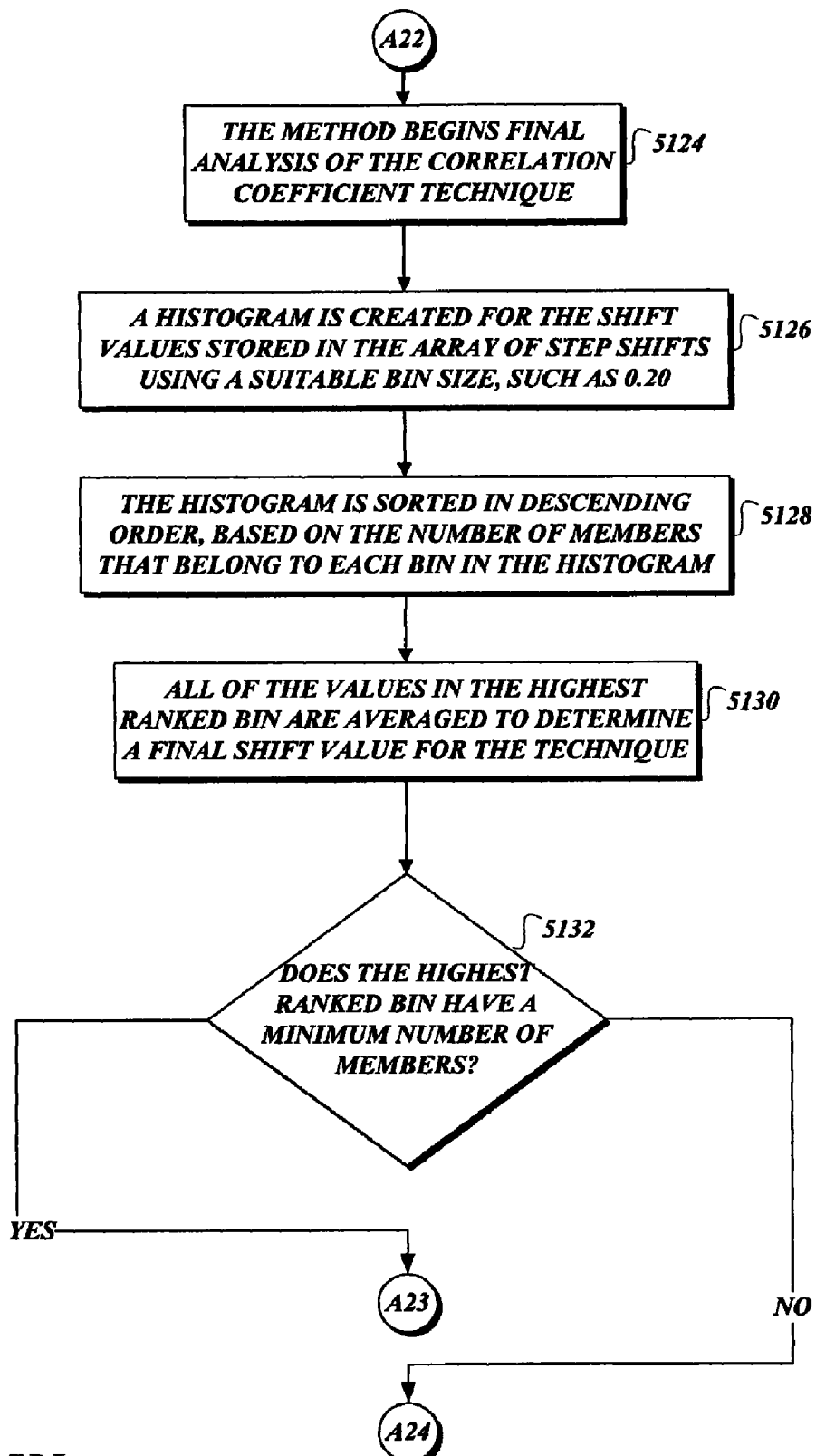
Figure 50:
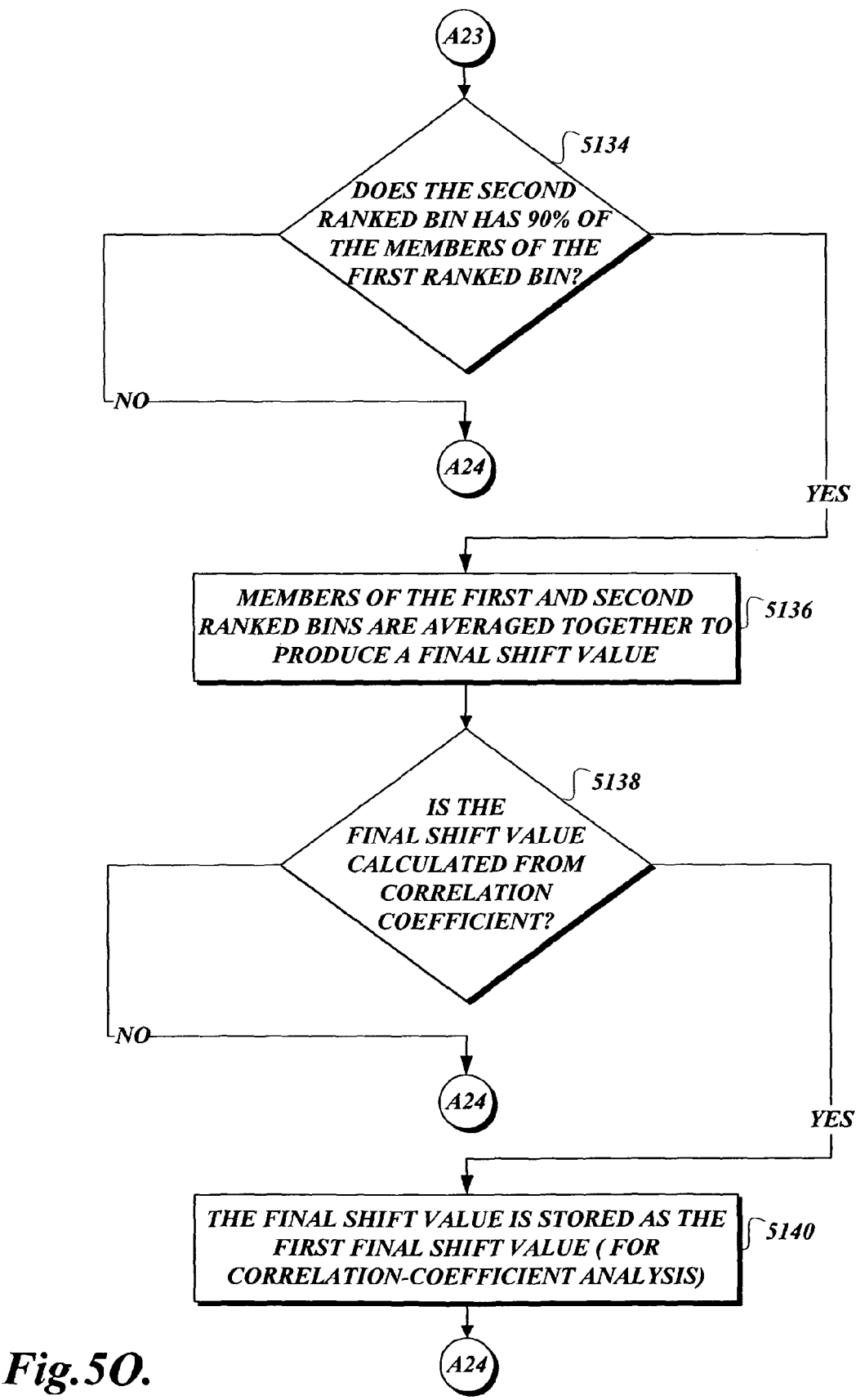
Figure 5Q:
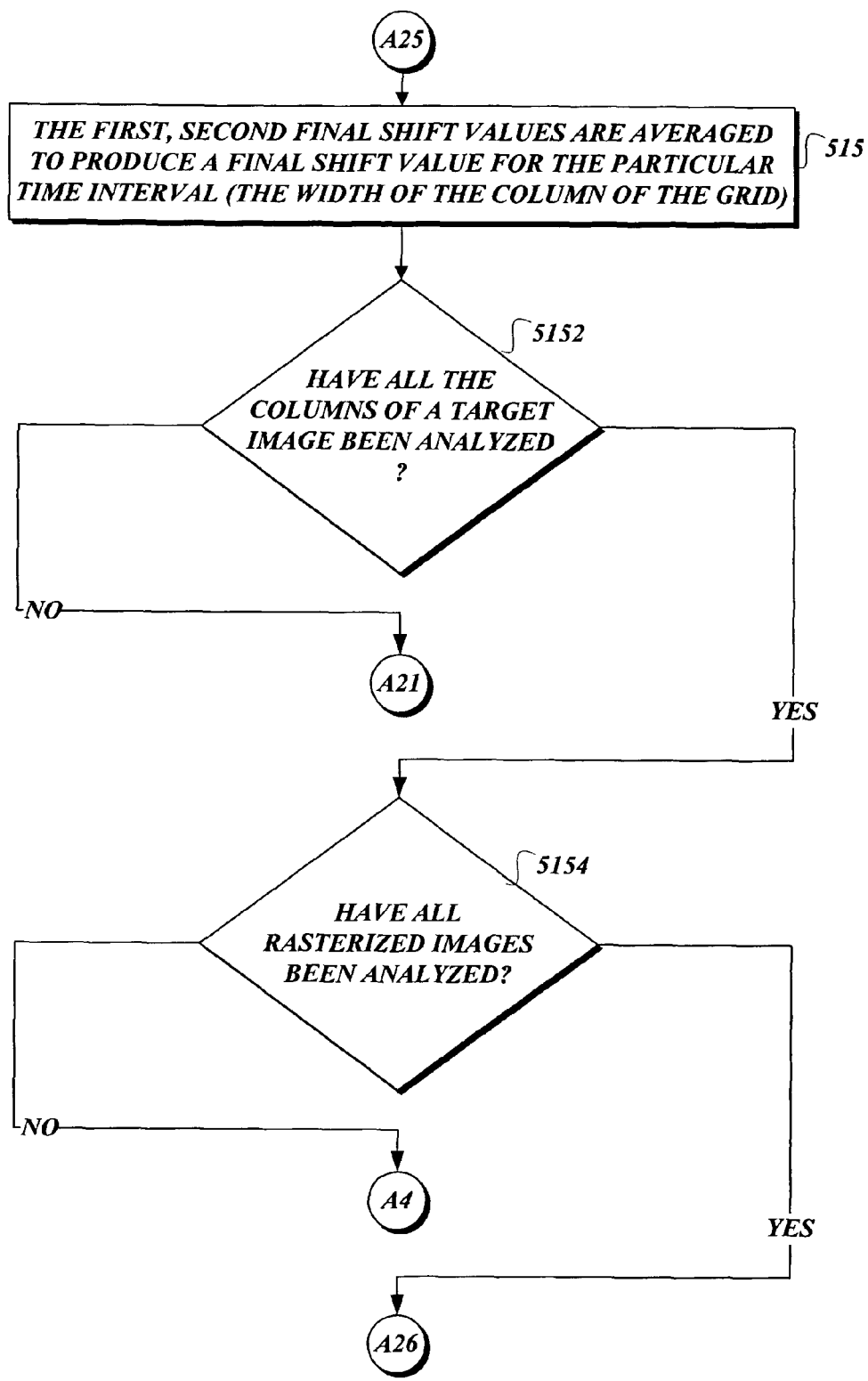
Figure 5R:
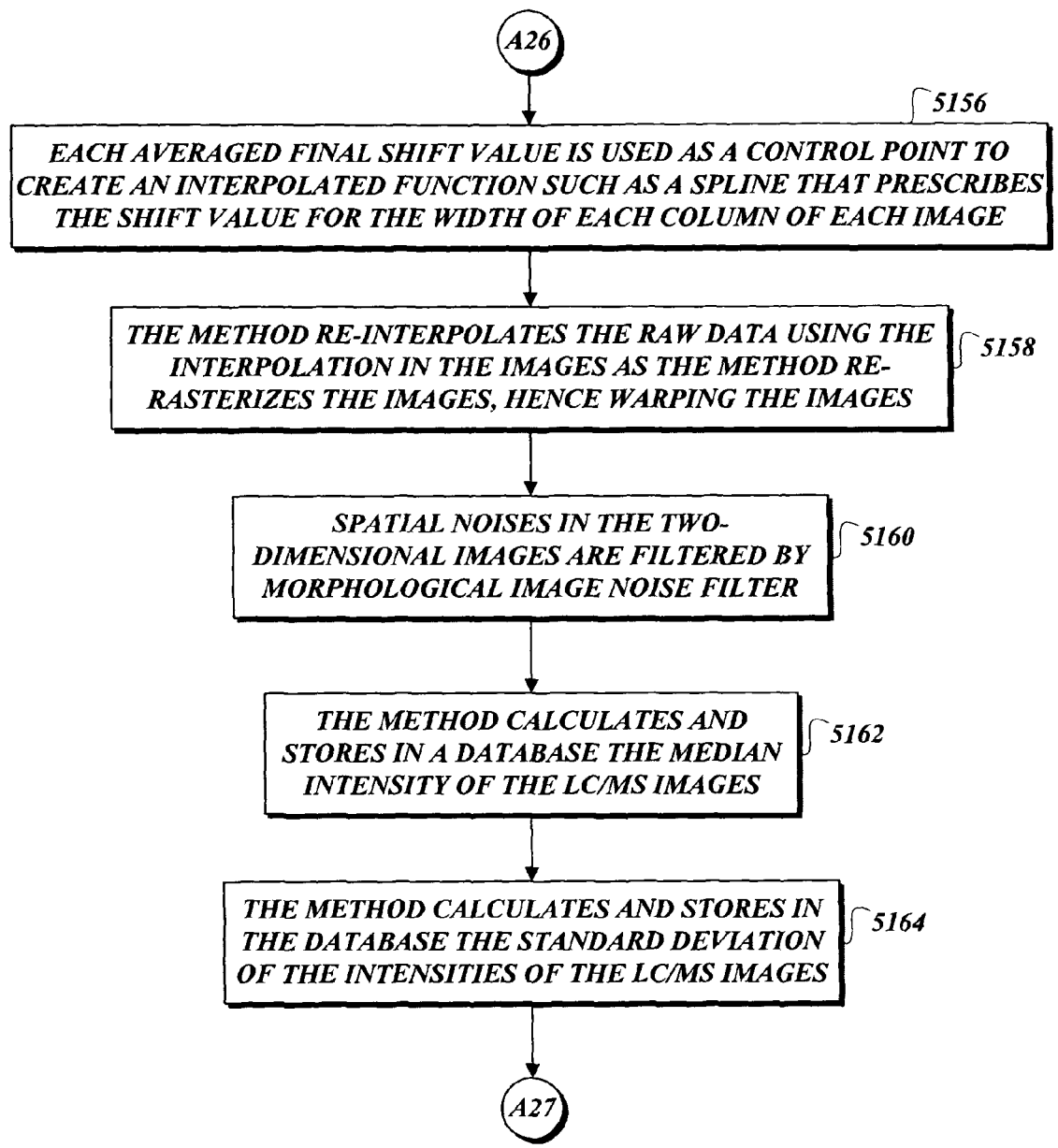
Figure 5S:
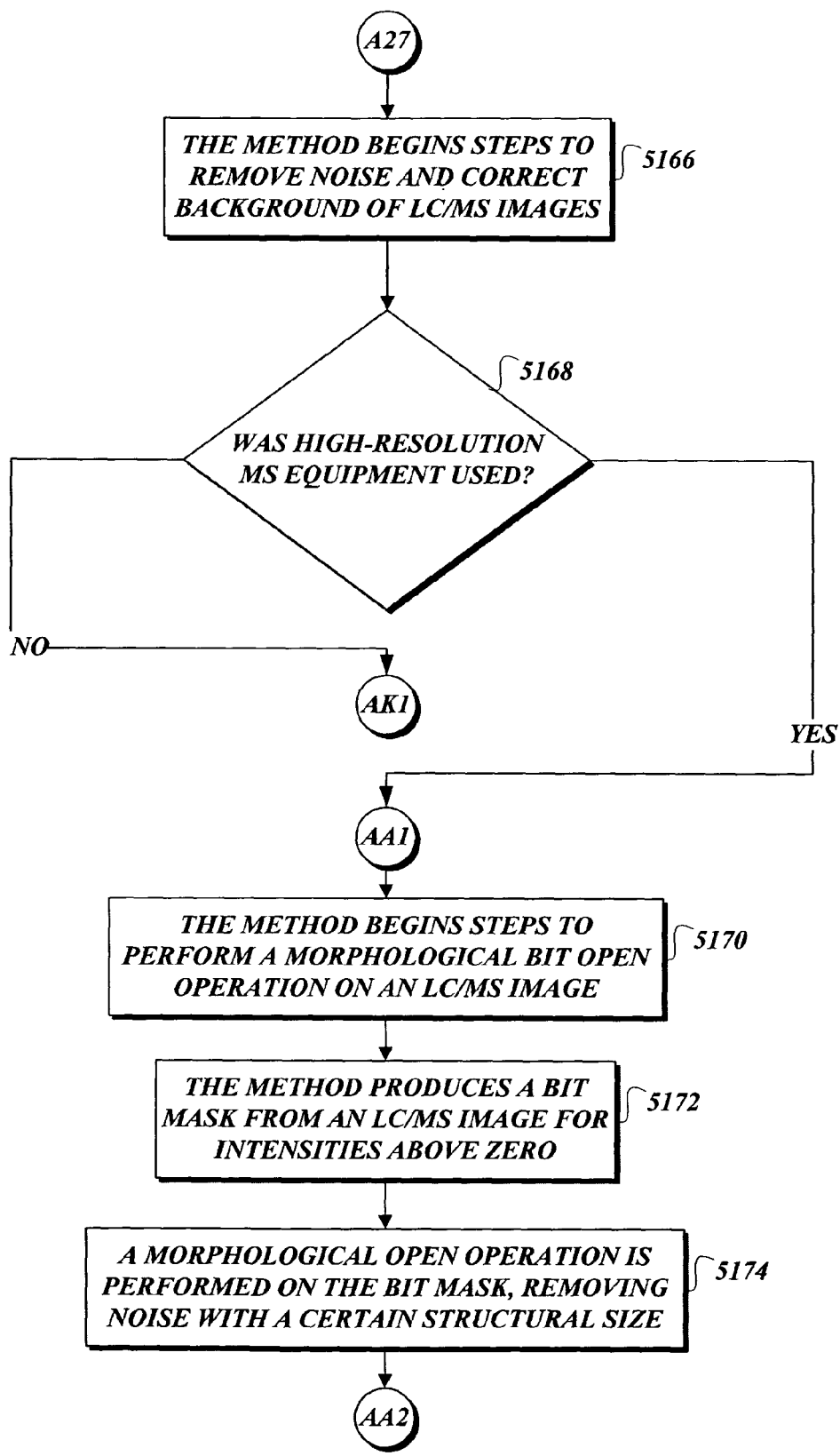
Figure 5S:
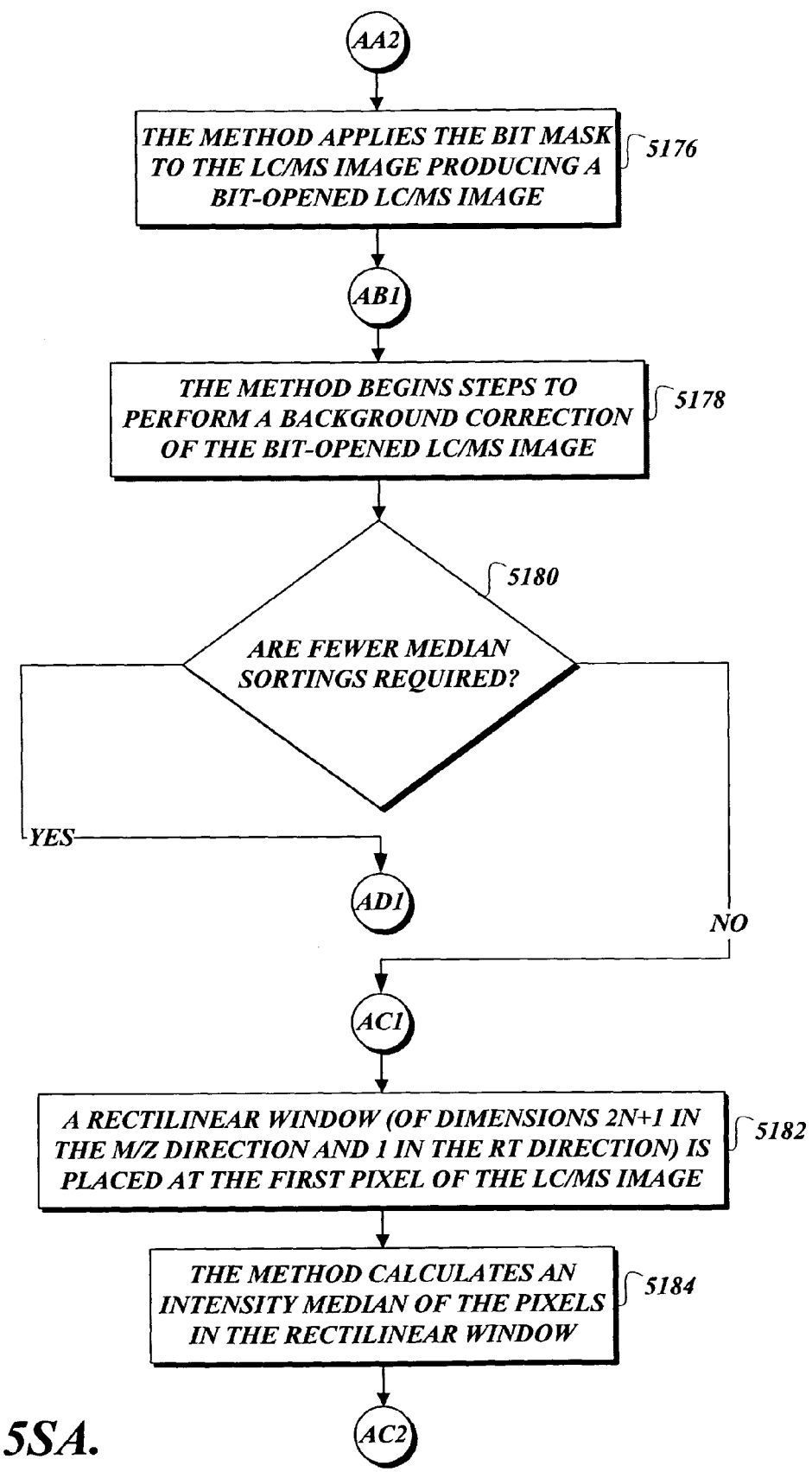
Figure 5S:
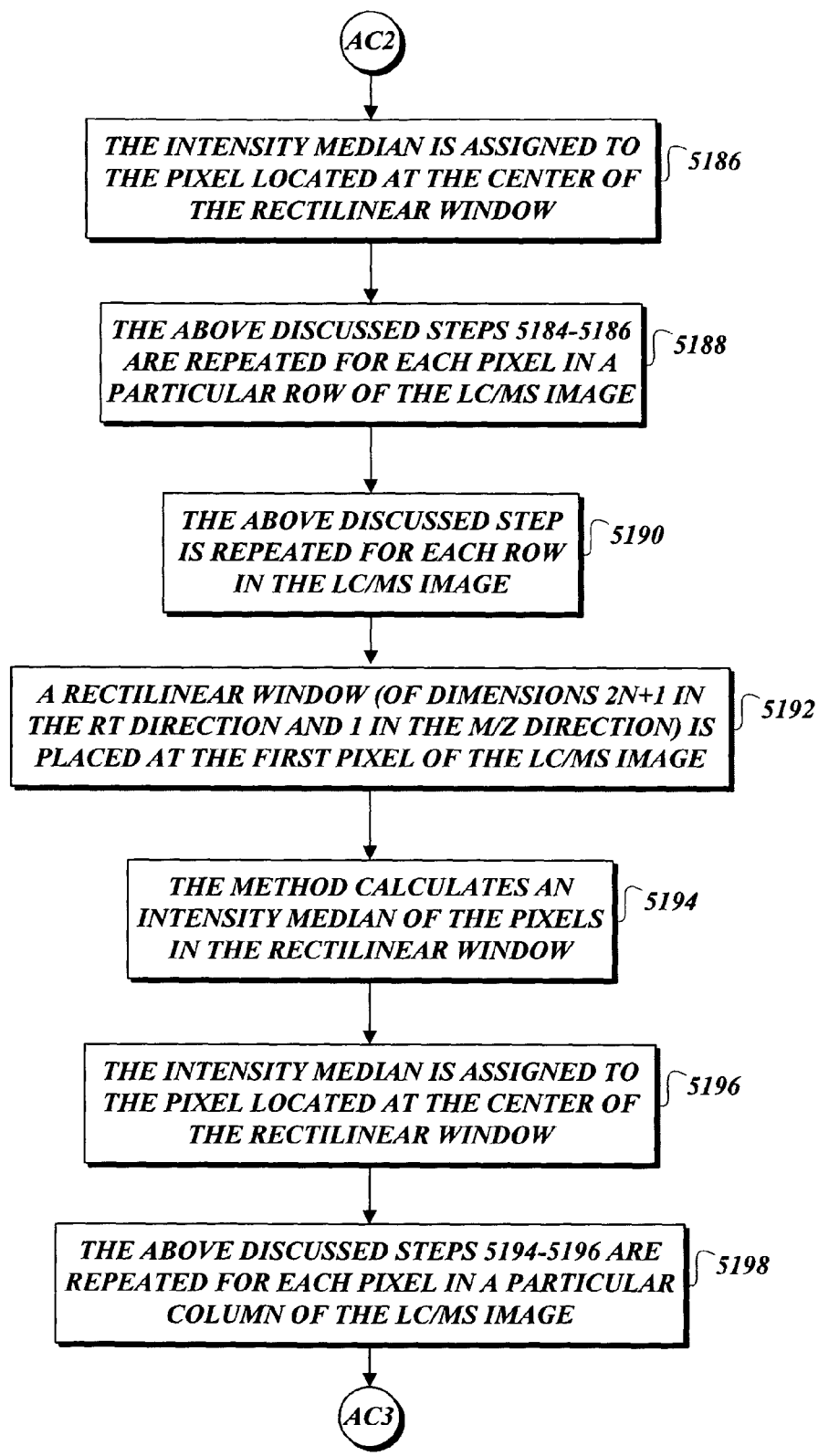
Figure 5S:
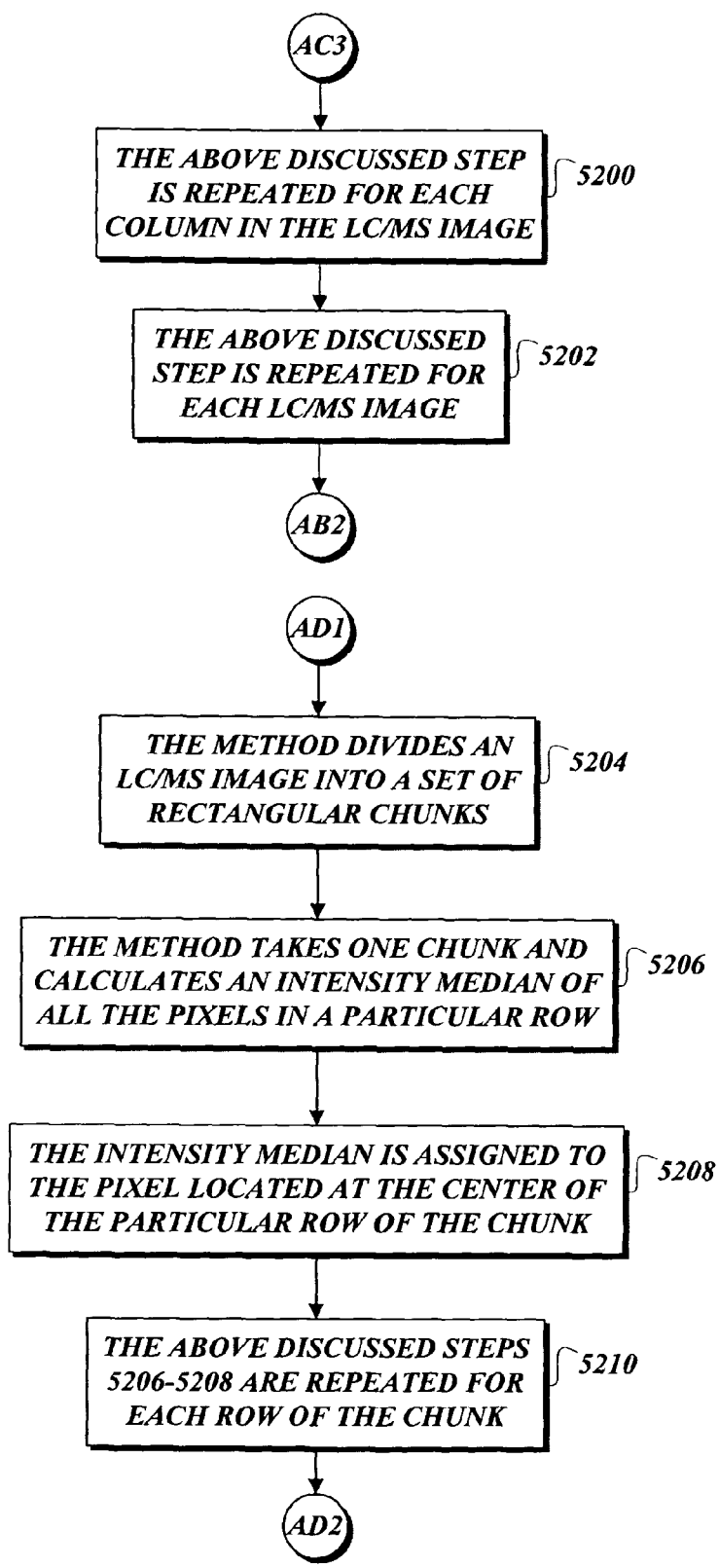
Figure 5S:
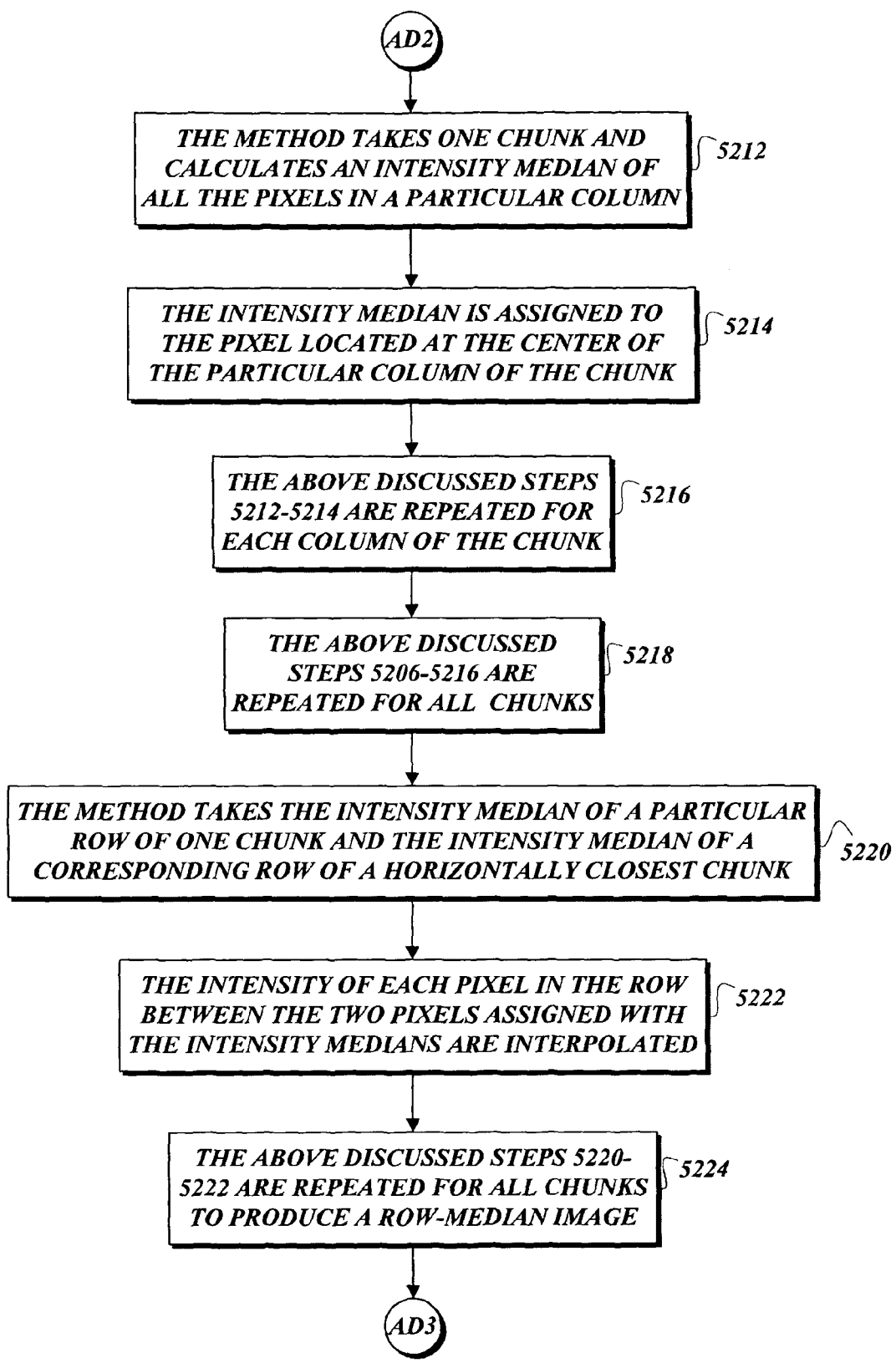
Figure 5S:
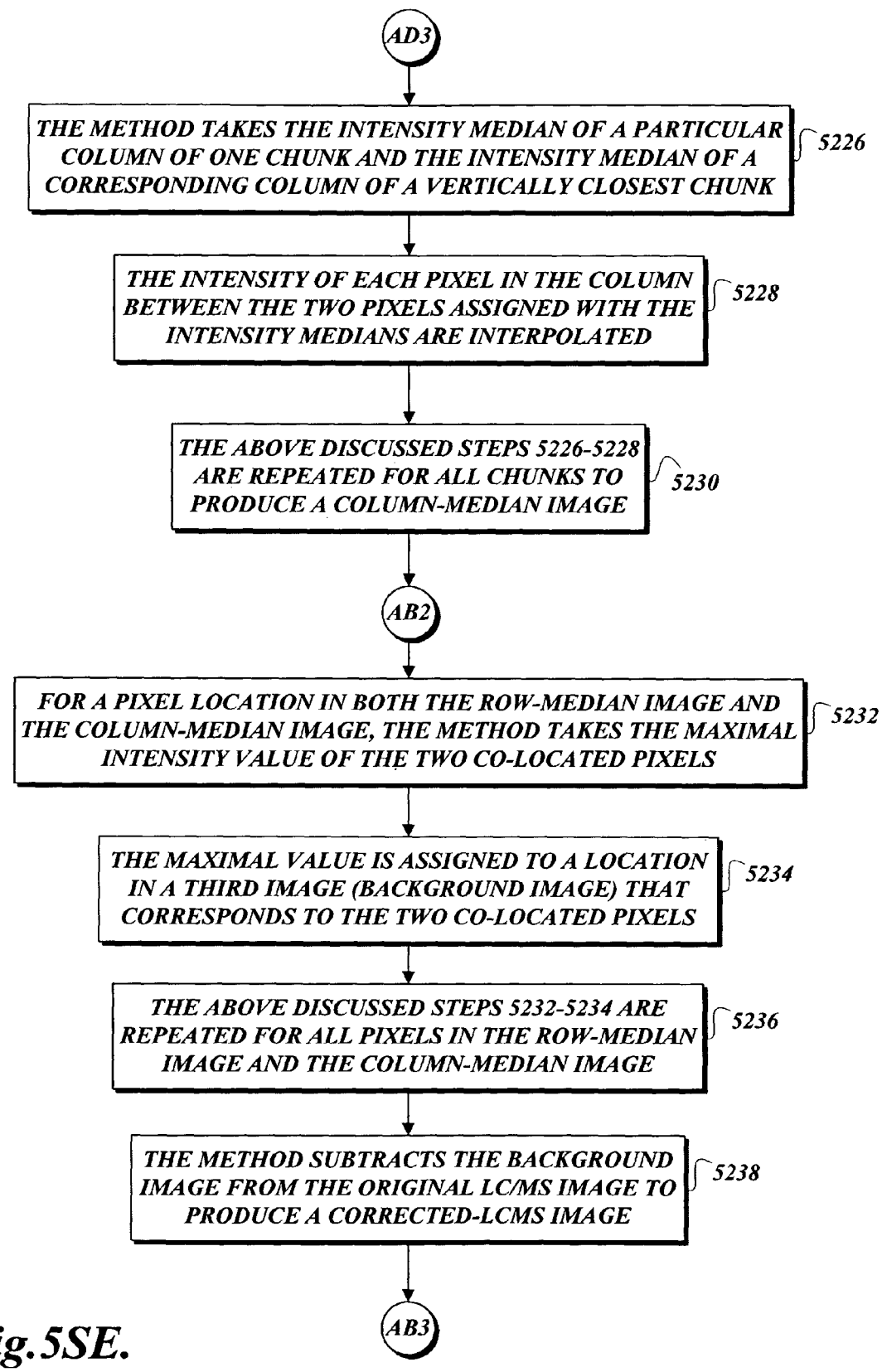
Figure 5S:
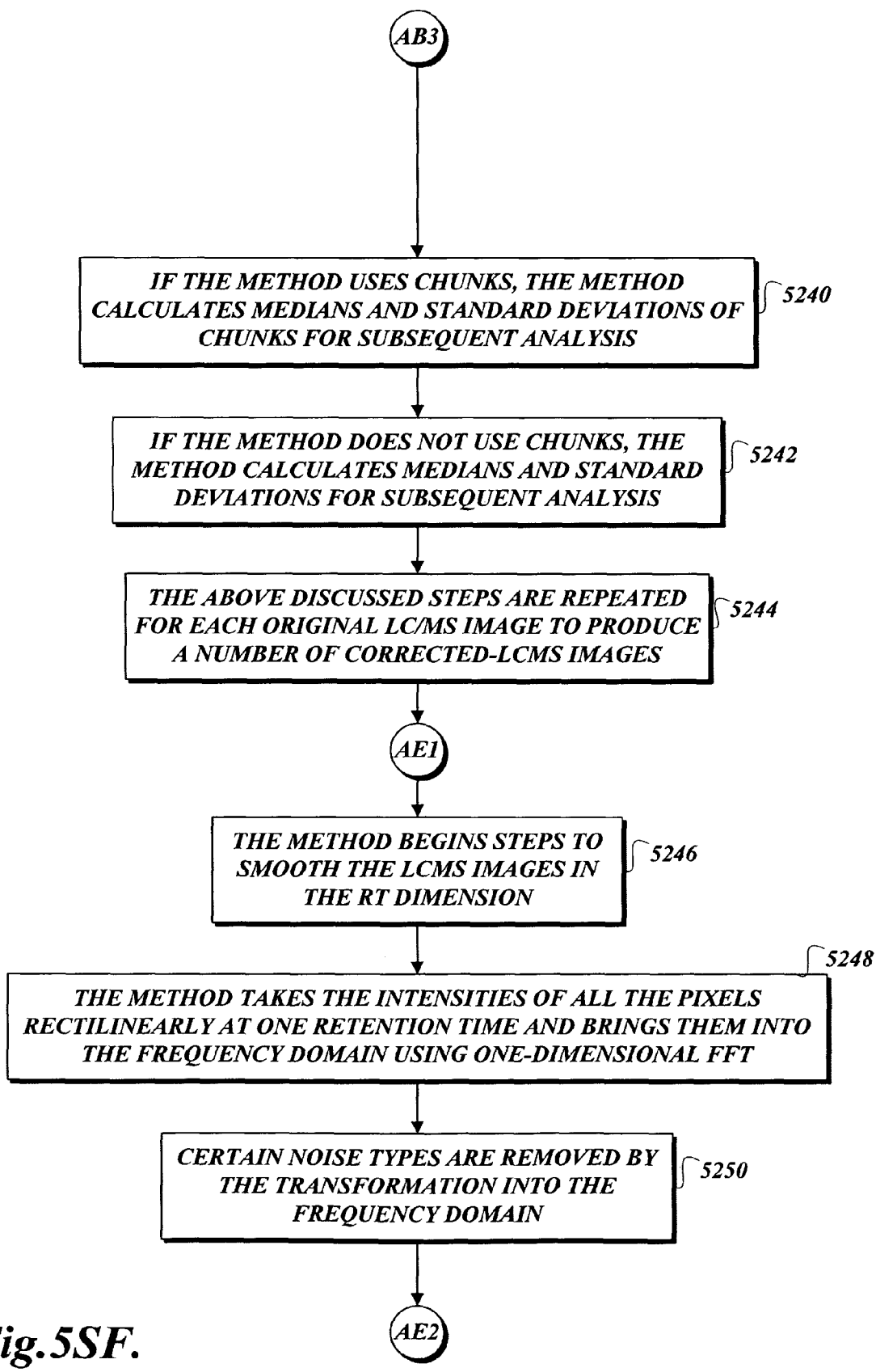
Figure 5S:
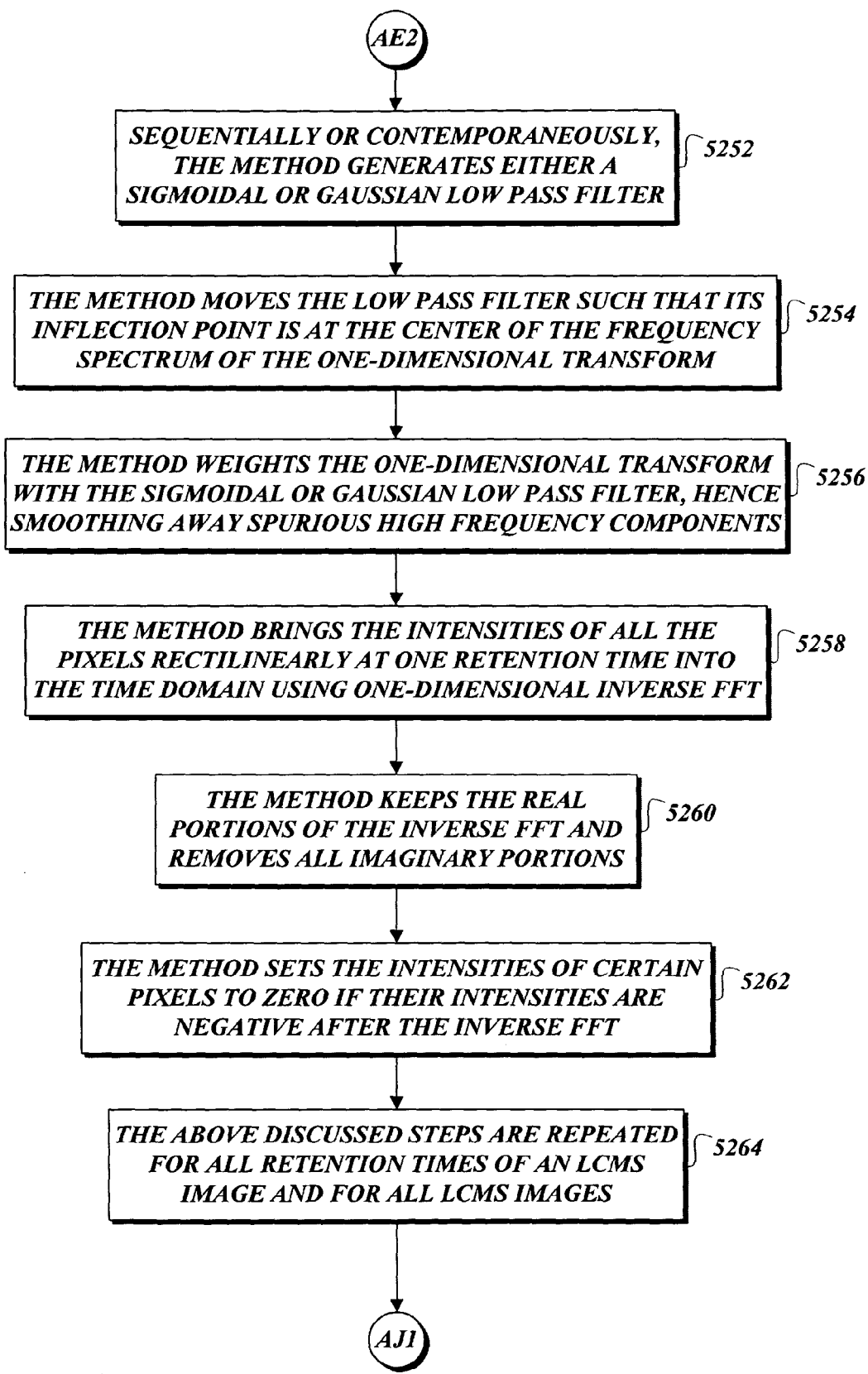
Figure 5S:
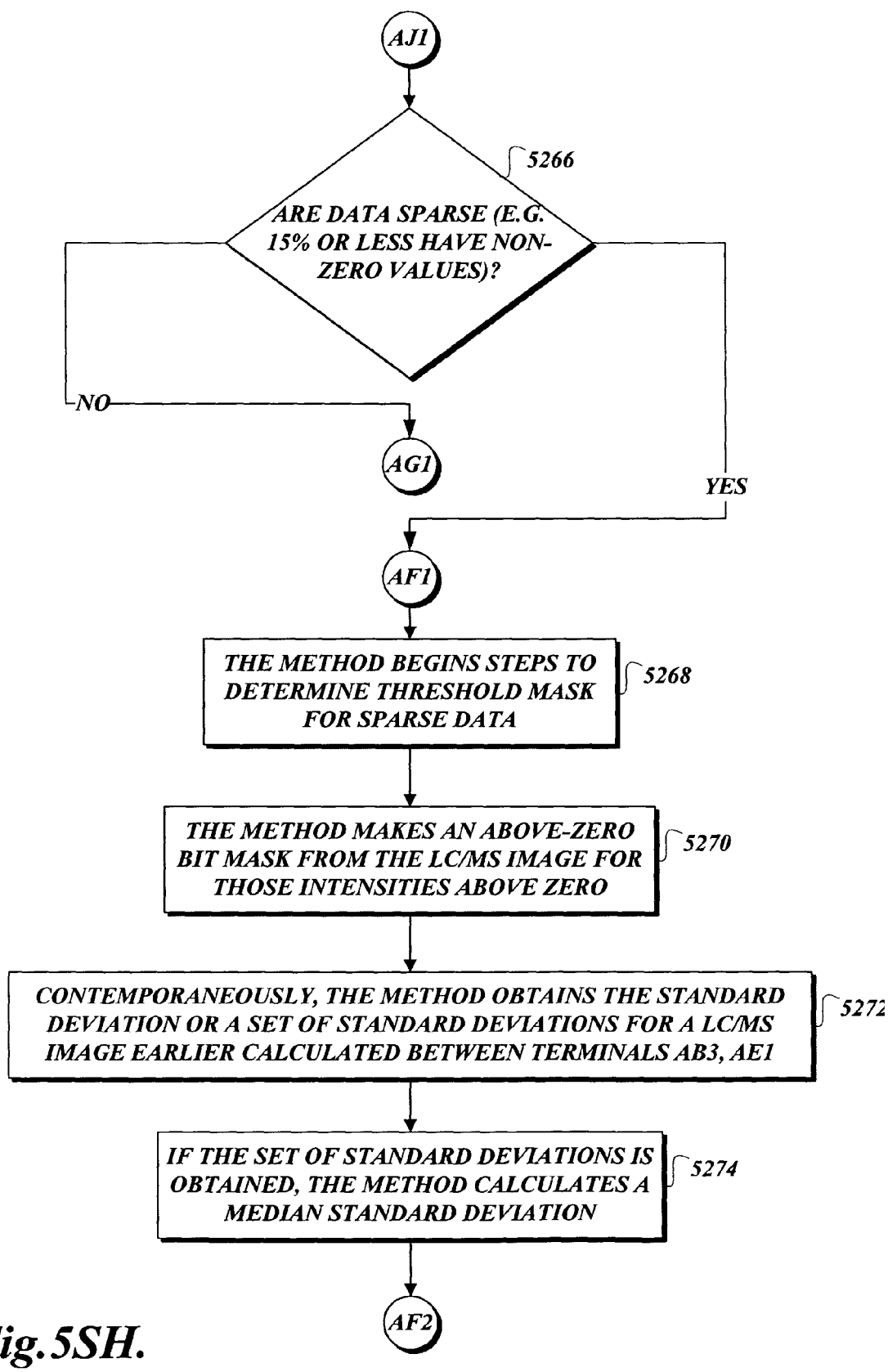
Figure 5S:
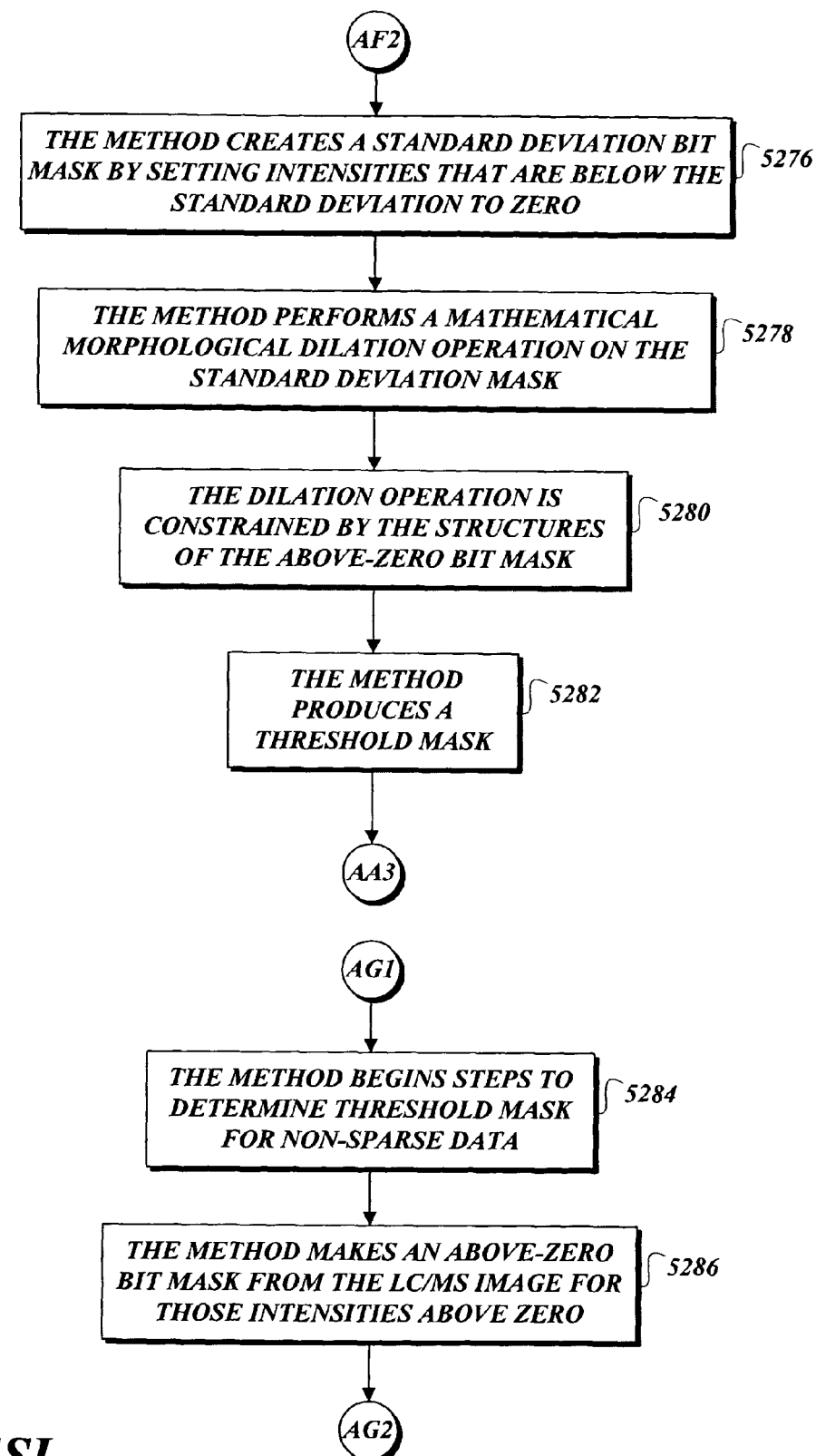
Figure 5S:
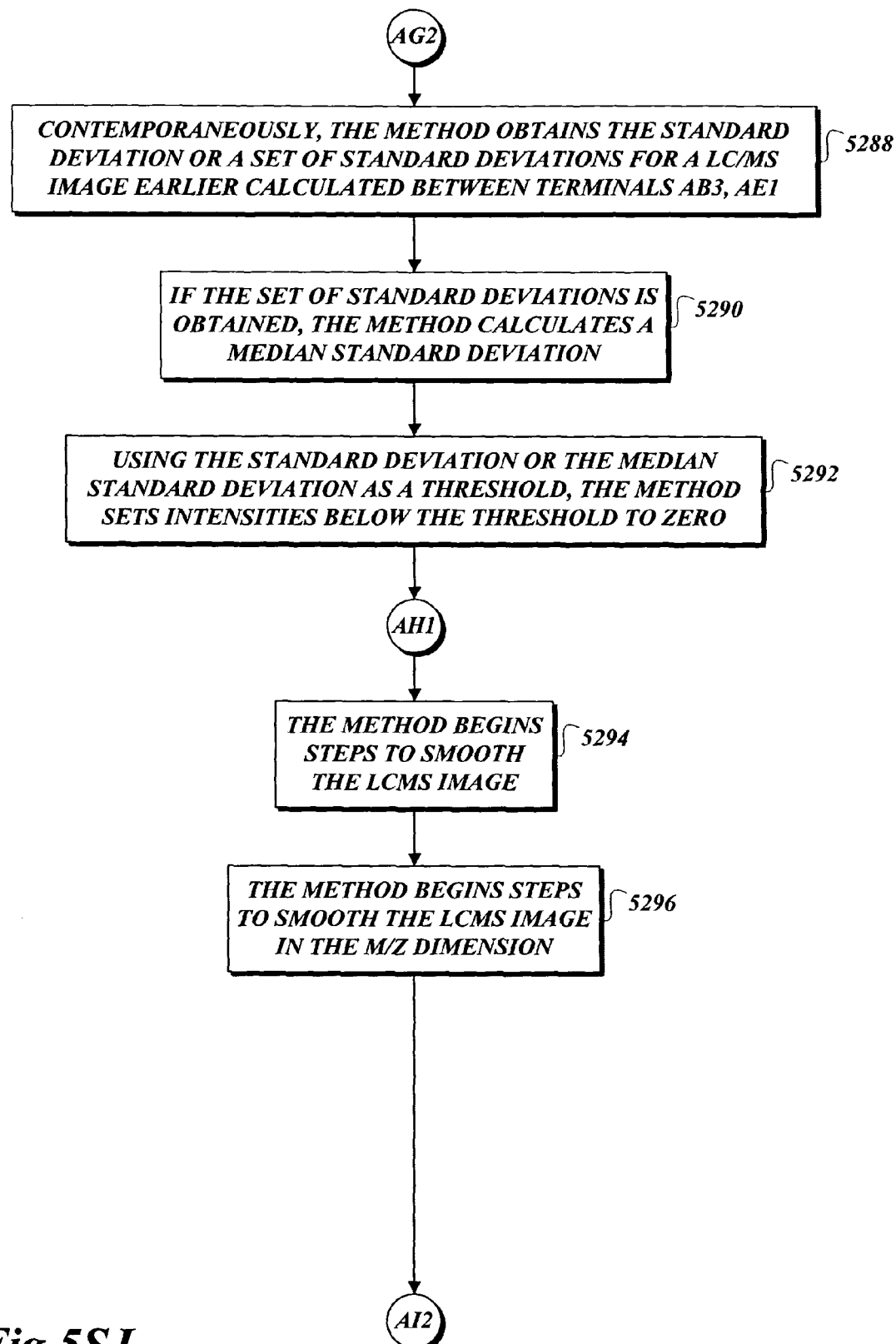
Figure 5S:
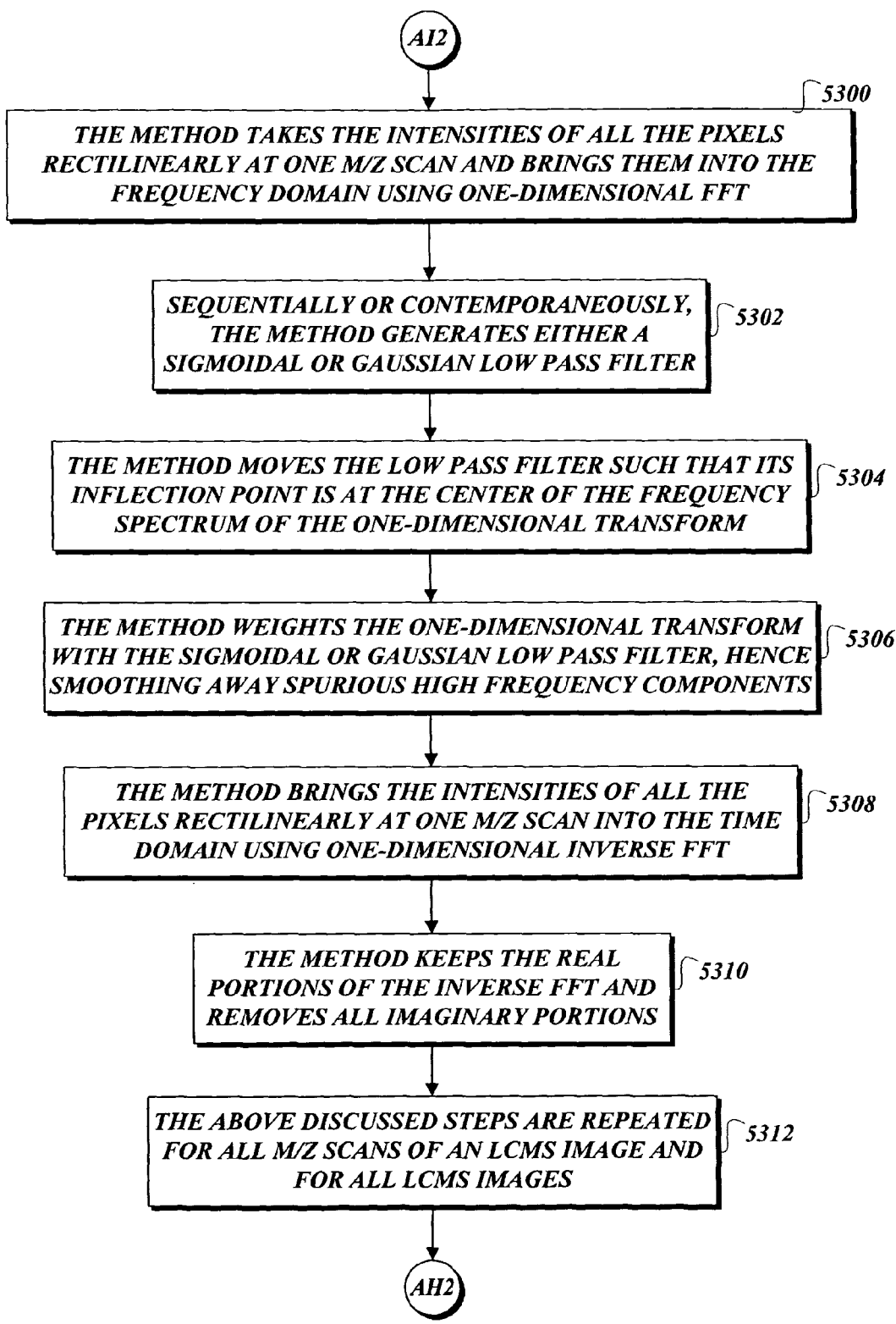
Figure 5S:
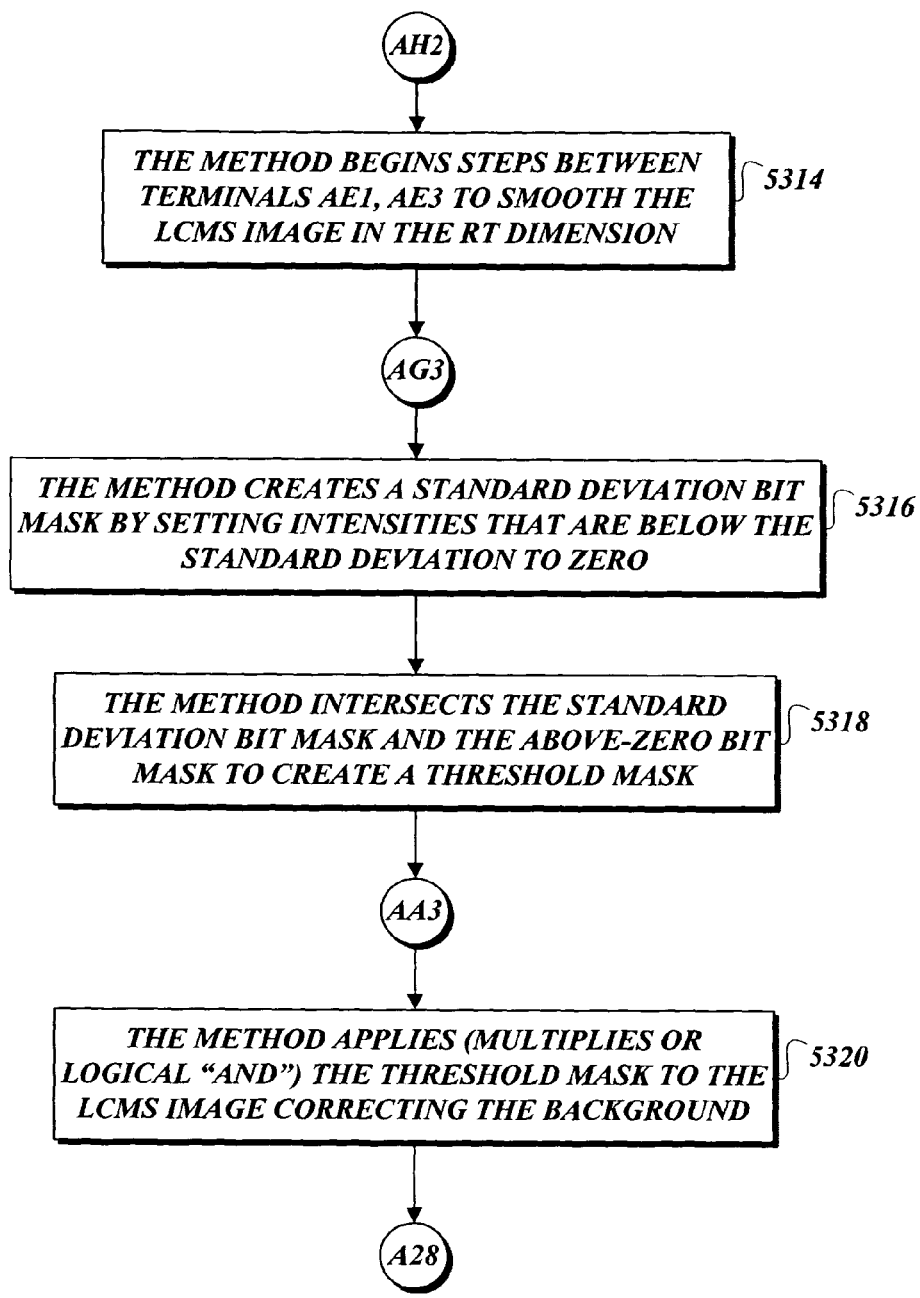
Figure 5S:
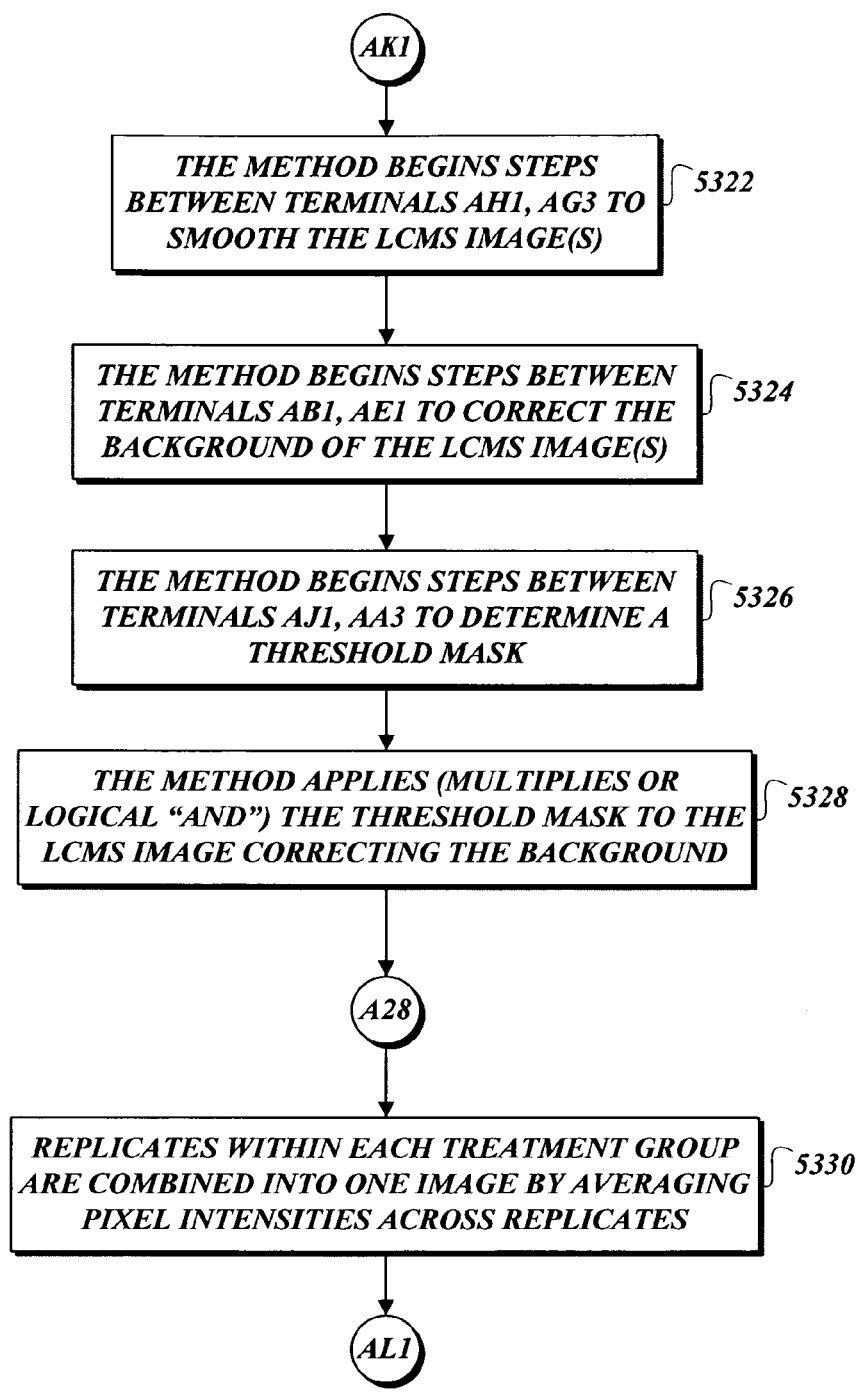
Figure 5S:
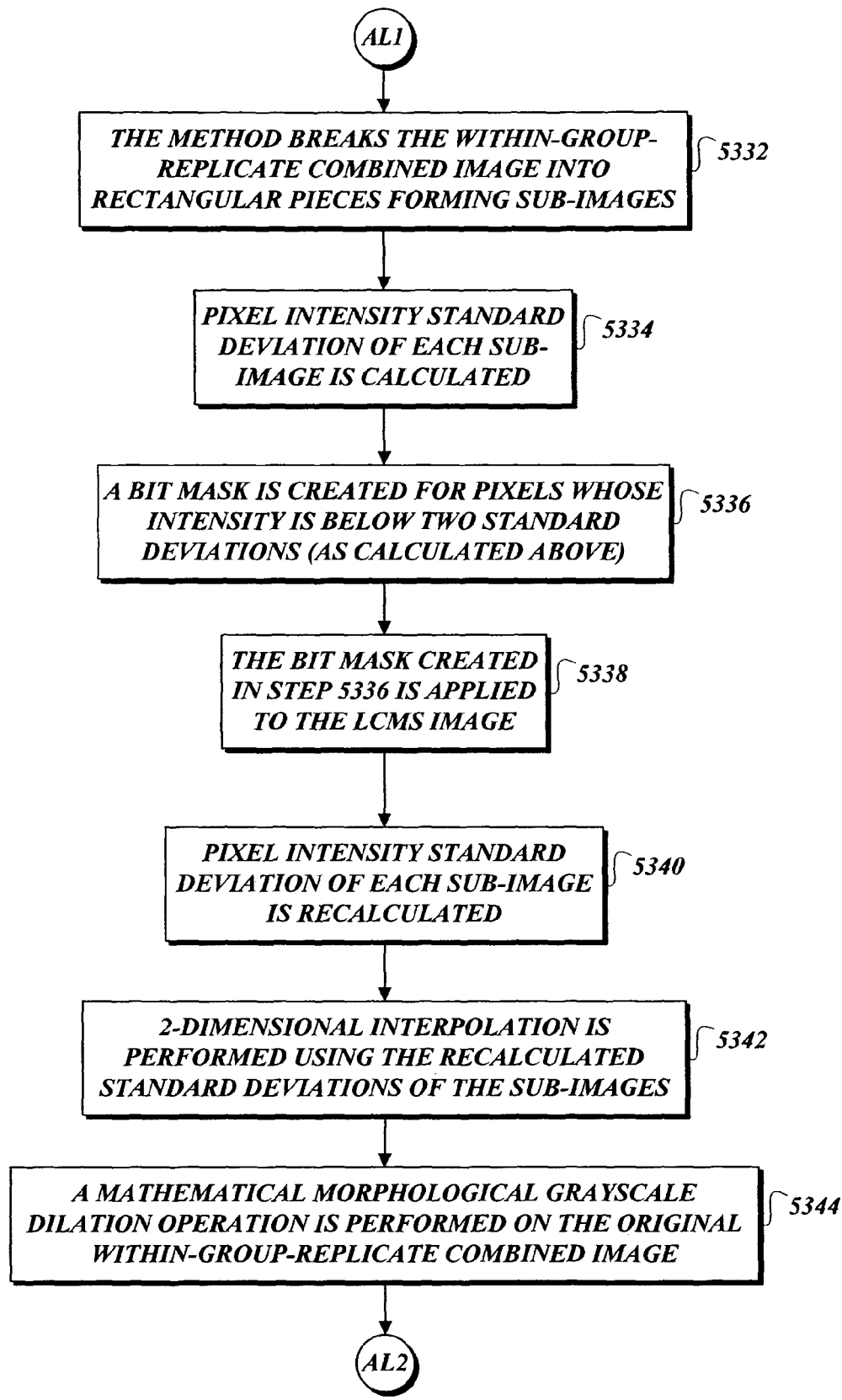
Figure 5S:
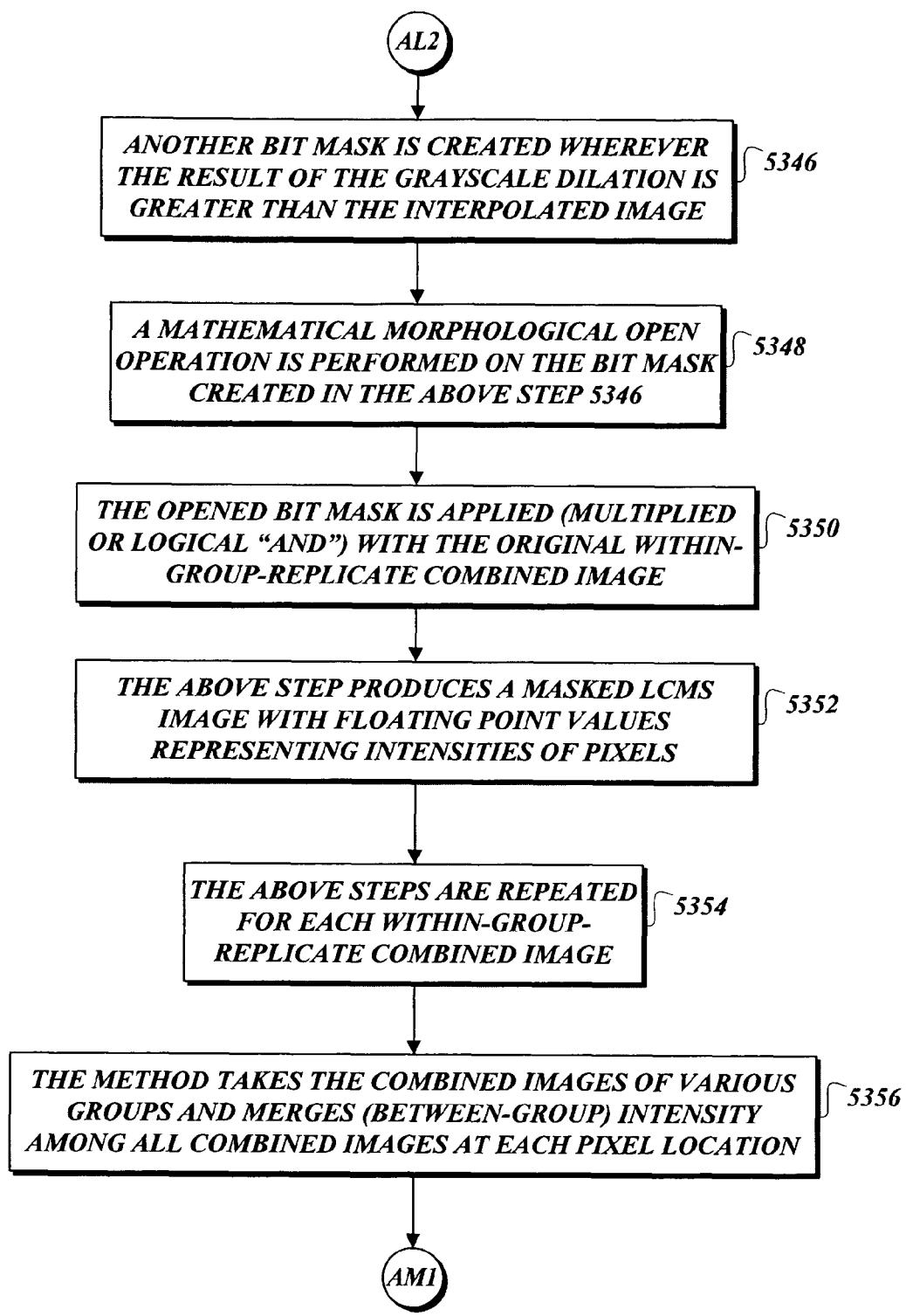
Figure 5S:
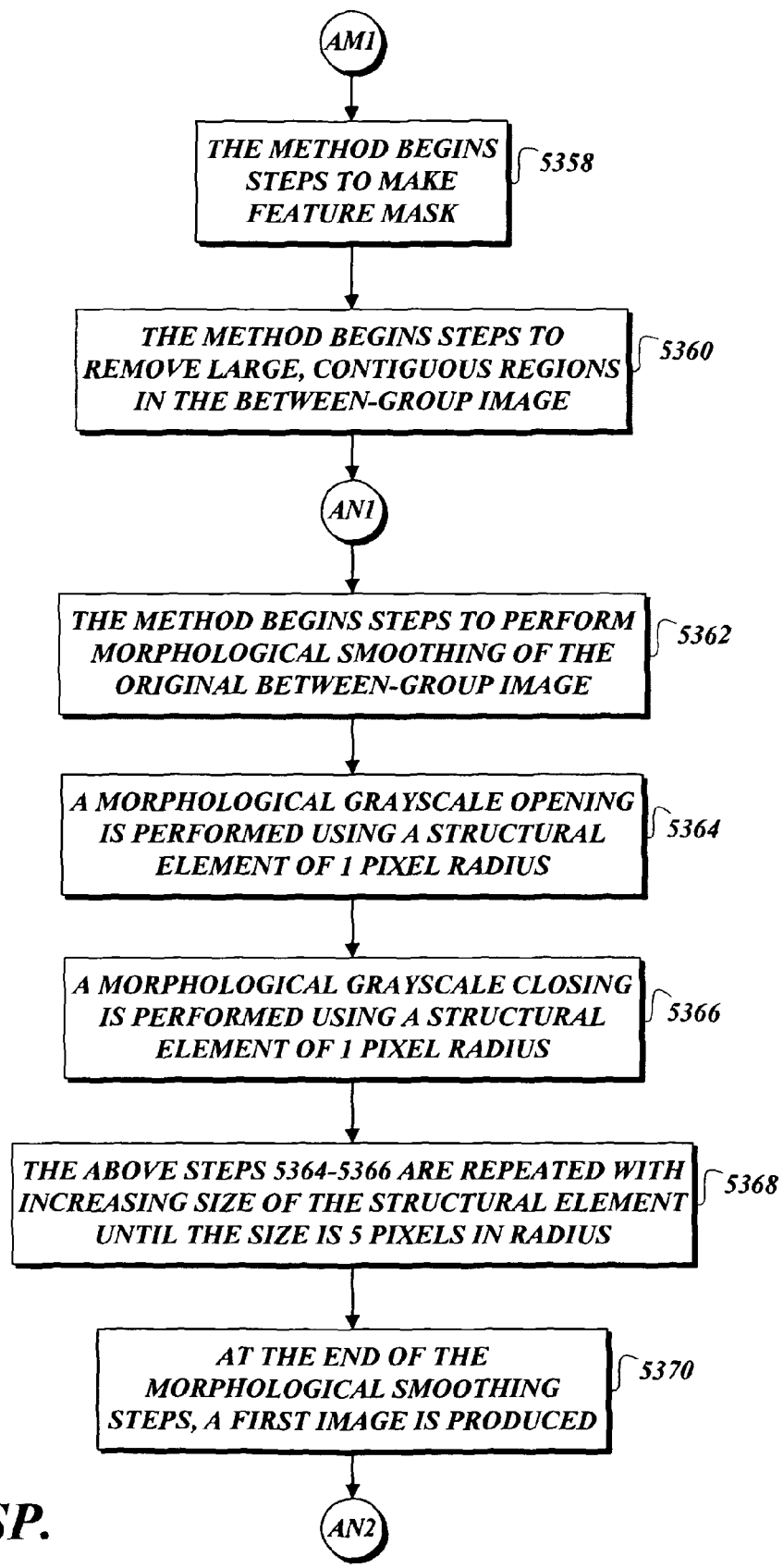
Figure 5S:
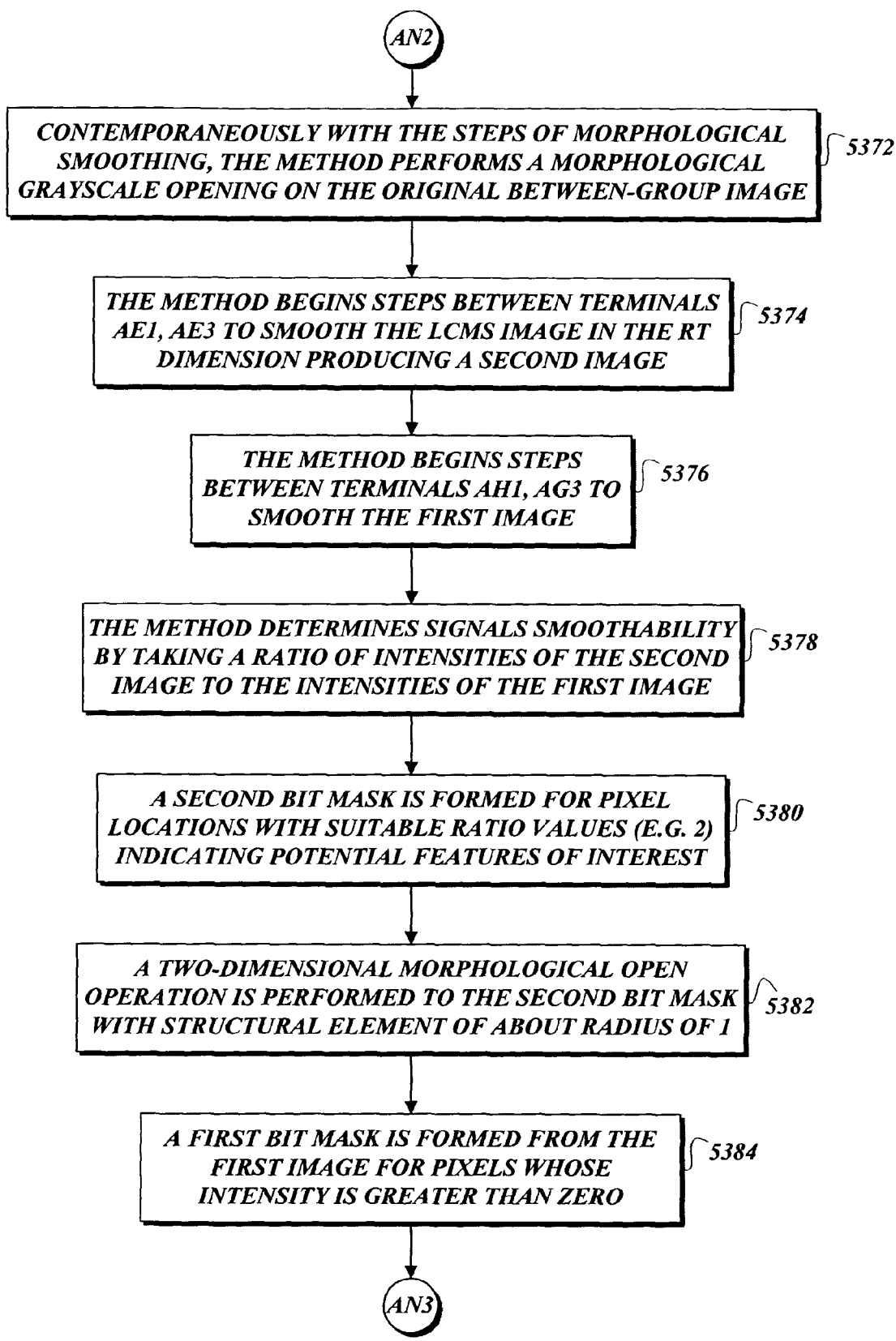
Figure 5S:
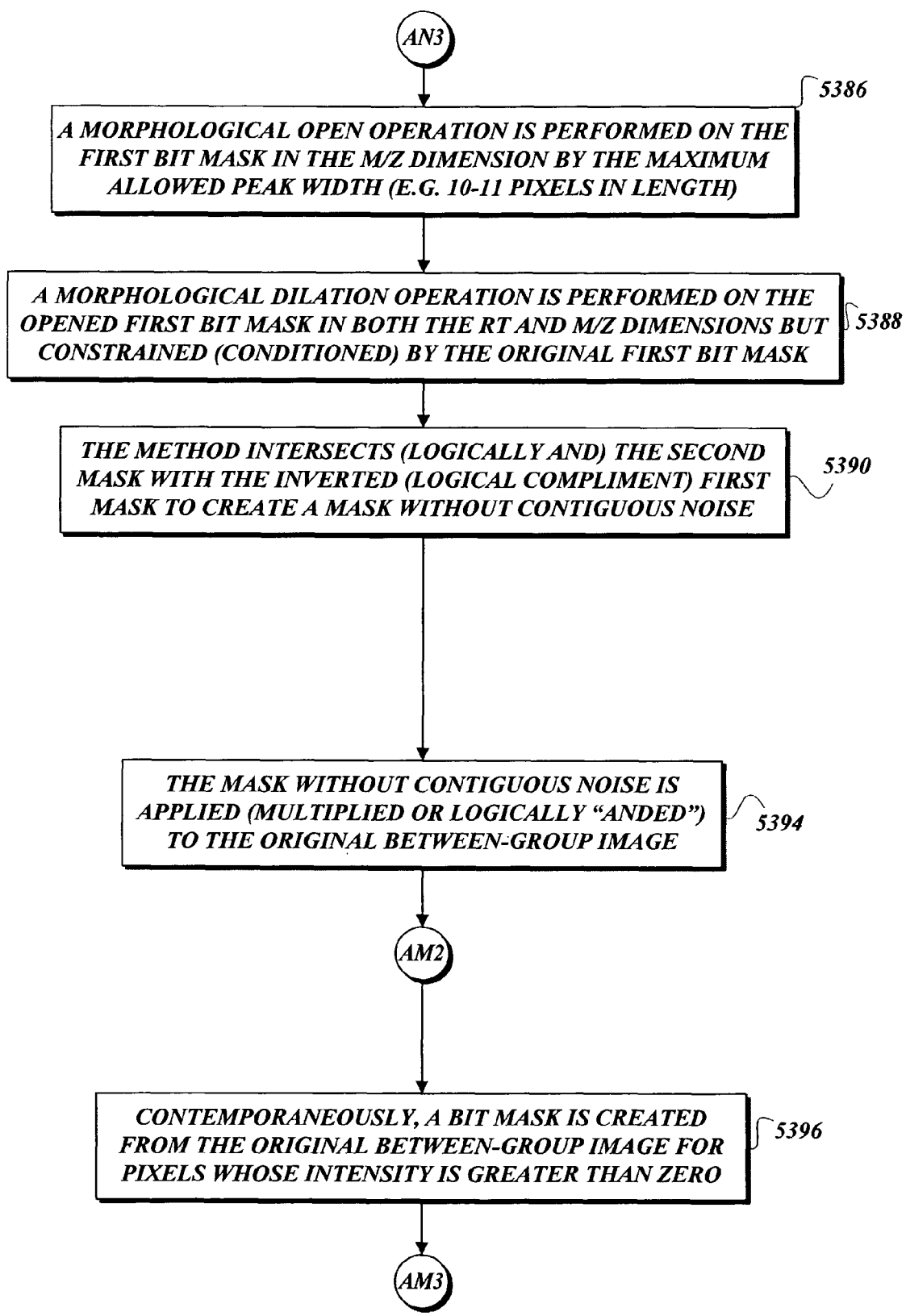
Figure 5S:
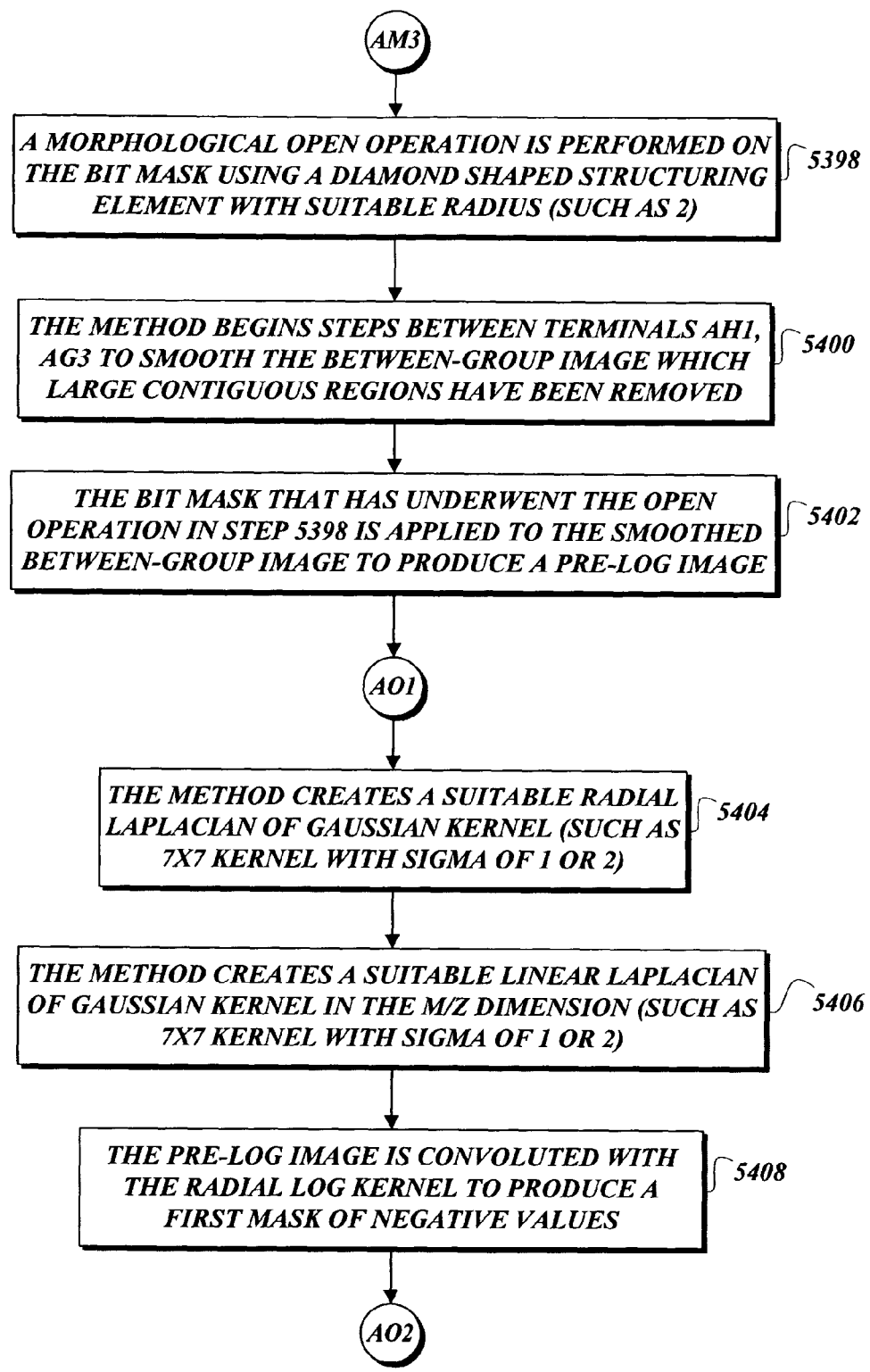
Figure 5S:
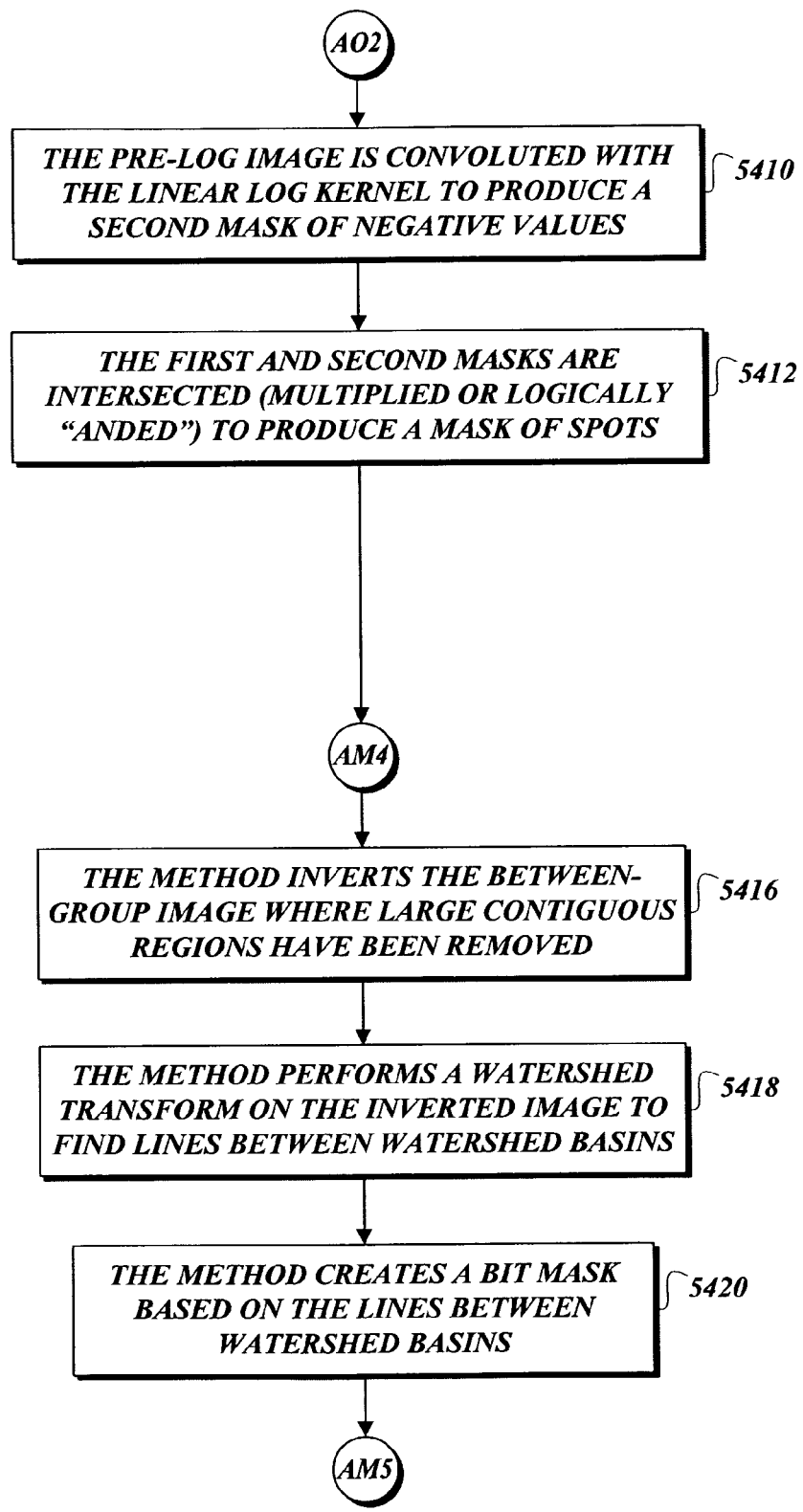
Figure 5S:
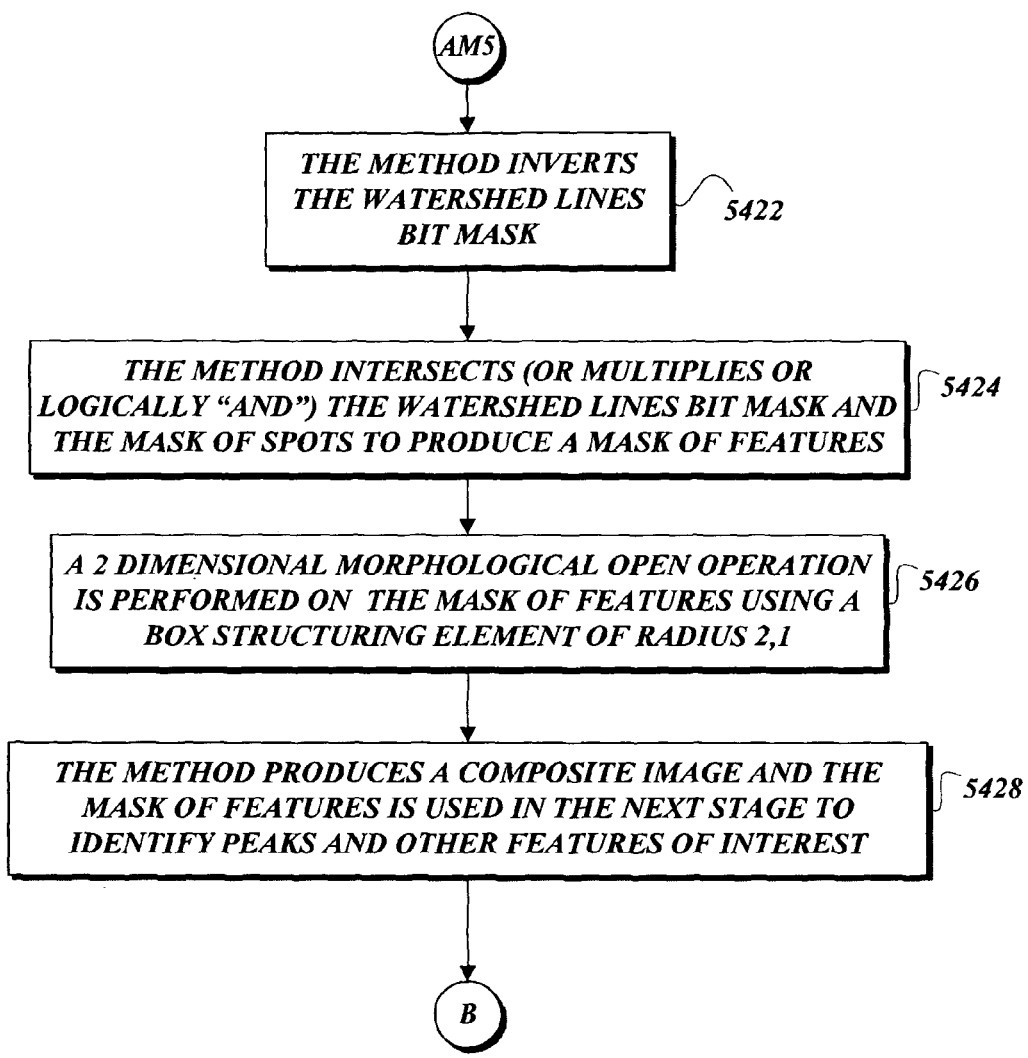
Figure 5T:
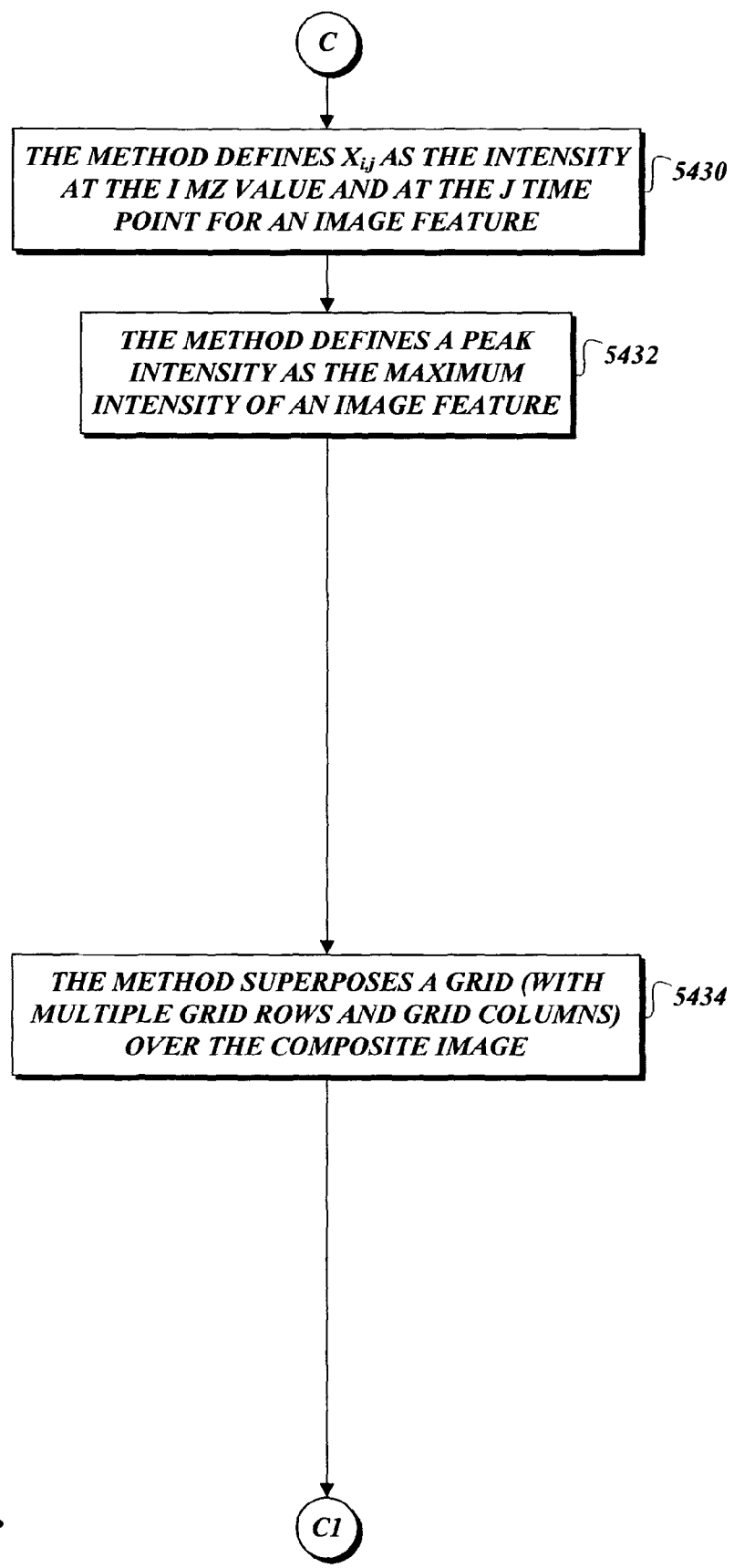
Figure 5U:
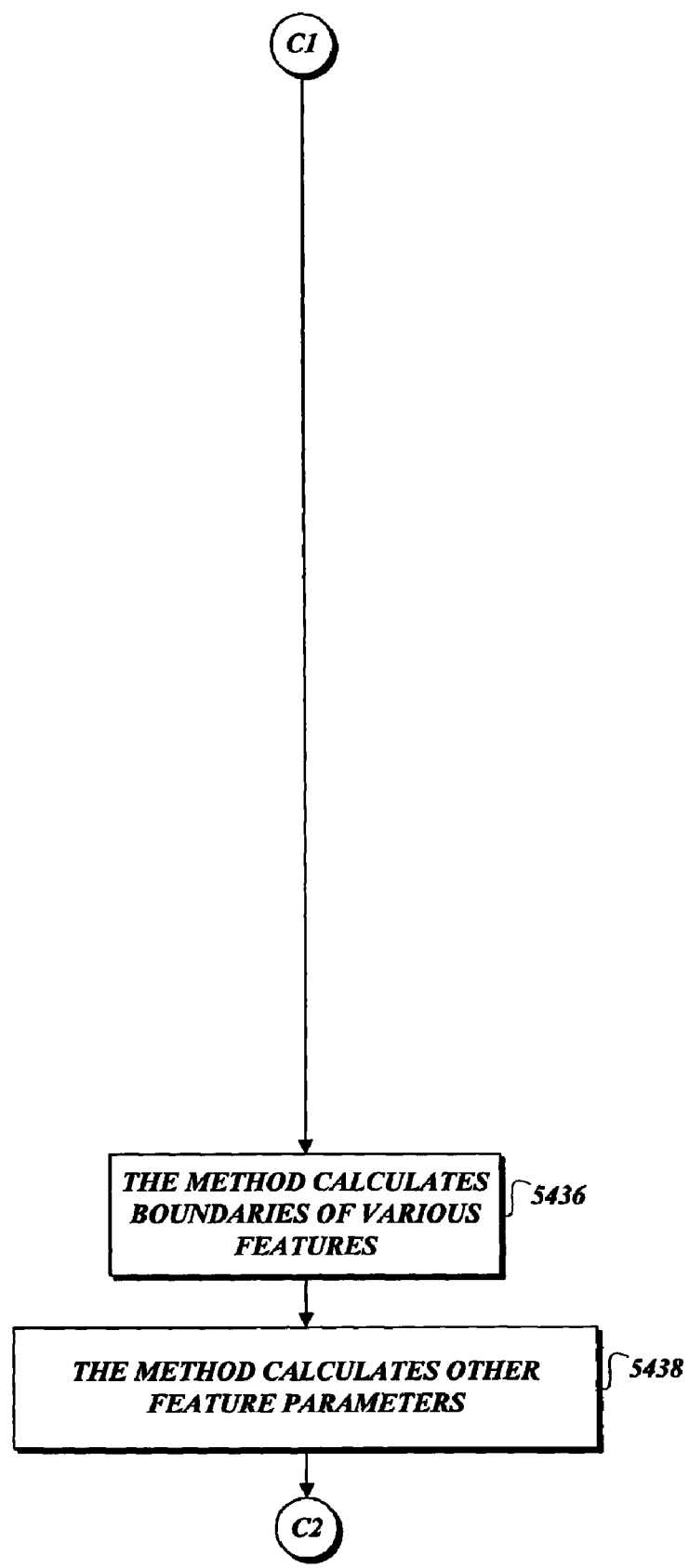
Figure 5V:
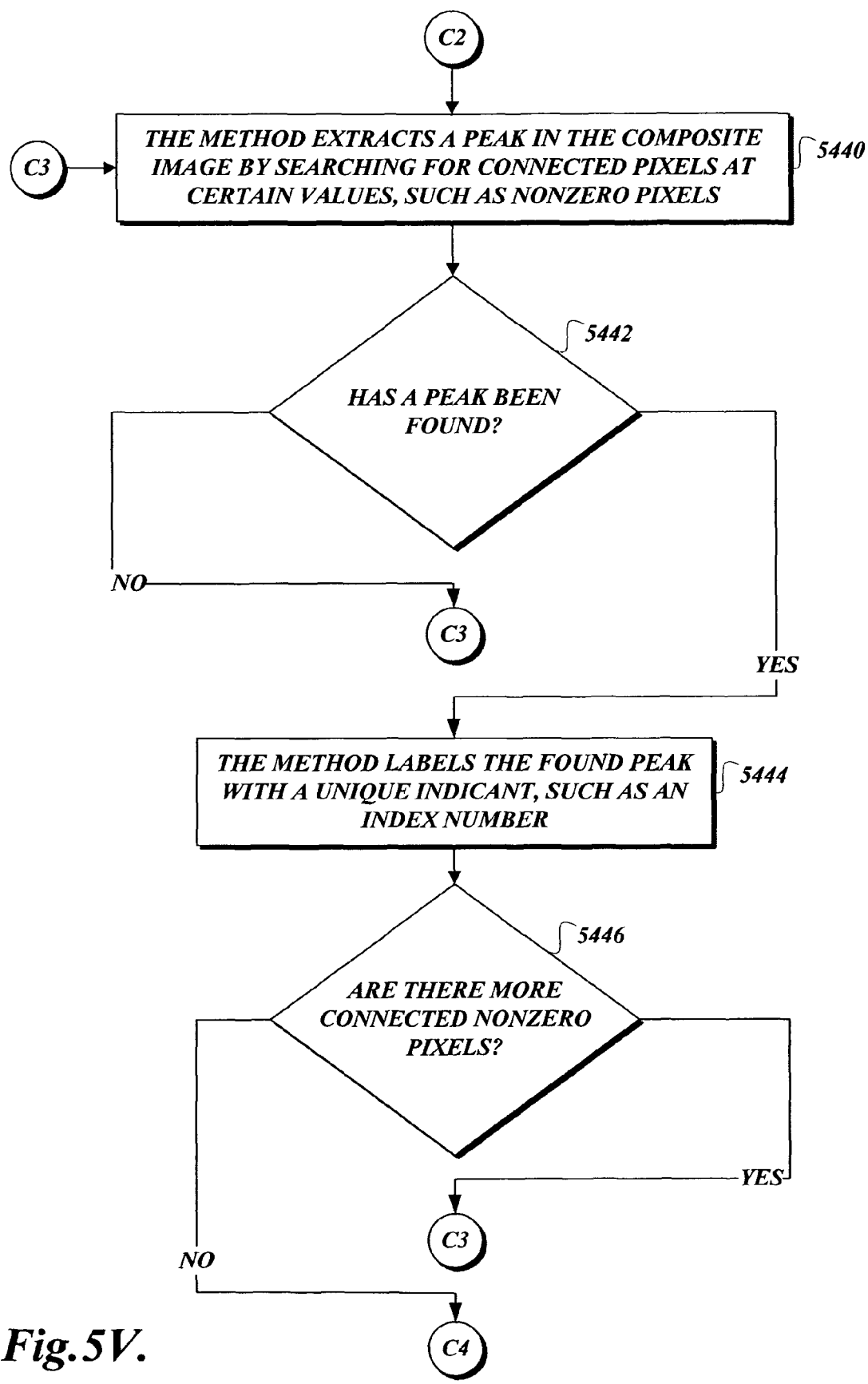

Generally, FIGS. 5V-5AT illustrate a method implemented by an exemplary image feature extractor using image processing techniques to extract biological features from LC/MS rasterized images. Firstly, peaks and isotope groups are identified and labeled regardless of whether or not they are differentially or non-differentially expressed.

The differential or non-differentially detection relies on the extracted peak intensity information. Various method steps in FIGS. 5V-5AT measure relative expression abundance, such as peptide/proteins, and to detect differential or non-differential expression. The abundance measurement quantity has high signal-to-noise ratio. Various embodiments of the present invention combine multiple pixel intensity measurements first to achieve high signal-to-noise ratio instead of combining probability p-values later. Isotope group intensity from combined intensities of isotopic peaks ordinarily has higher signal-to-noise ratio than the intensity from an individual peak. Various embodiments of the present invention not only identify individual peak but also isotope groups and charge groups.

The method steps of FIGS. 5V-5AU in some embodiments extract peaks and isotope groups first and then perform expression analysis, such as measuring differential expression. This peak-based approach reduces the requirement of precise retention time alignment. As long as peaks are properly extracted, small variations in peak shapes and peak locations have little adverse effect to the subsequent analysis.

The two-dimensional image processing technique of various embodiments of the present invention leverages information from large number of rasterized LC/MS images. Because biological peaks and isotope groups have certain shapes, image processing filters can be used to improve the signal-to-noise ratio and image pattern recognition methods can be used to detect those peaks, isotope groups and their characteristics, such as charges. The image processing steps in FIGS. 5V-5AT leverage information from multiple experiment replicates in a study to further improve the signal-to-noise ratio in feature extraction. Multiple images from replicates can be combined (averaged) together to reduce the measurement noise. Higher signal-to-noise ratio images make feature extraction more accurate and reliable.

Method steps as illustrated at FIGS. 5B-5U in various embodiments use morphological filters for LC/MS image noise reduction. LC/MS data typically have measurement noise. The noise can make peak extraction difficult in method steps illustrated at FIGS. 5V-5AT. Conventional filters affect peaks of real signal and peaks of noise. Morphological filter belongs to a set of image filtering methods that alter the image based on the special shape of contents in the image. For example, binary morphological erosion filter can shrink the white features in a binary image. Features less than certain sizes will be removed. For another example, binary morphological dilation filter will enlarge the white features. In the exemplary image processing pipeline, erosion and dilation filters are applied in various places to reduce the LC/MS image noise.

Method steps as illustrated at FIGS. 5B-5U estimate LC/MS image background information including noise. Image background noise is a low level random readings from MS instruments even when information signals are absent. Estimating the level of the background noise is desired for extracting signal peaks from the noise. The background information is also desirable for building error models for the LC/MS intensity measurements. Background noise estimation is accomplished in the exemplary image processing pipeline by estimating, in one embodiment, the statistical properties of the background noise. For example, non-zero data points can be removed by various morphological filter are considered as background noise. The background mean and standard deviation can be directly estimated from these pixels in segmented regions of the LC/MS image. In different regions of the image, the mean and standard deviation are different. Because the selection of pixels for background estimation need not based on arbitrary intensity threshold but in some embodiments based on the spatial difference between signal and noise in the image, the background estimation method of various embodiments of the present invention facilitates better LC/MS image feature extraction as discussed in connection with method steps illustrated at FIGS. 5V-5AT.

Now, the specific steps in the method 500 as illustrated by FIGS. 5A-5AU are described so that the flow of the method can be discerned. FIGS. 5A-5AU illustrate a method 5000 for identifying features of interest in biological samples. From a start block, the method 5000 proceeds to a set of method steps 5002, defined between a continuation terminal ("Terminal A") and an exit terminal ("Terminal B"). The set of method steps 5002 describes pre-processing of images of prepared biological samples obtained from biological experiments.

From Terminal A (FIG. 5B), the method 5000 proceeds to block 5008 where expression experiments of different phenotypical or treatment conditions are performed. Prepared biological samples obtained from various biological experiments are collected at block 5010. At block 5012, the prepared biological samples are ionized and undergo a liquid chromatography (LC) process to produce eluted samples. The eluted samples from the liquid chromatography process are provided to mass spectrometers (MS) at block 5014. At block 5016, MS spectra are collected repeatedly at a particular retention time and at a fixed or varying sampling rate. Raw LC/MS data, in the form of a collection of MS spectra from an image where m/z is the y-axis and retention time is the x-axis. The method then proceeds to another continuation terminal ("Terminal A1").

From Terminal A1 (FIG. 5C), the method optionally performs retention time pre-alignment by removing global time misalignment among different LC/MS runs of replicates. See block 5020. At block 5022, the method performs data rasterization by interpolating the raw LC/MS data to create an LC/MS image. The method then removes pixels whose intensities rank in the lower 90% of the image at block 5024. At block 5026, an original bit mask is created from the LC/MS image for pixels with intensity greater than zero. A mathematical morphological open operation is performed on the bit mask using pre-aligned maximum peak width. See block 5028. At block 5030, the open operation in the RT dimension removes many small features of the bit mask, reconstituting features that are defined as RT streaks. At block 5032, a conditional dilation operation follows in which RT streaks are dilated in the RT and m/z dimensions back to their size. The method then continues to another continuation terminal ("Terminal AA1").

From Terminal AA1 (FIG. 5CA), the method 5000 proceeds to block 5034 where the method inverts the bit mask. The inverted bit mask is multiplied (logical "end" operation) with the LC/MS image, causing the RT streaks to be removed. The method then optionally performs novelization at block 5038. The above steps are repeated for each LC/MS image generated by the system 100. The method then proceeds to another continuation terminal ("Terminal A2").

From Terminal A2 (FIG. 5D), the method 5000 proceeds to block 5040 where a candidate image is selected among the rasterized images. At block 5042, the base peak in intensity of the candidate image is measured, which determines the highest intensity value for each time point in the candidate image. The method calculates the standard deviation for the base peak intensity measurement at block 5044. At block 5046, a test is performed to determine whether there are more images to measure. If the answer to the test at decision block 5046 is YES, the method 5000 proceeds to another continuation terminal ("Terminal A3") and skips back to block 5040, where the above-identified processing steps are repeated. Otherwise, if the answer to the test at decision block 5046 is NO, the method 5000 proceeds to block 5048 where the image with the highest standard deviation in the base peak intensity is chosen to be the master image because it is likely to have many distinct image features in high contrast for analysis. The method 5000 then proceeds to another continuation terminal ("Terminal A4").

Figure 2C:
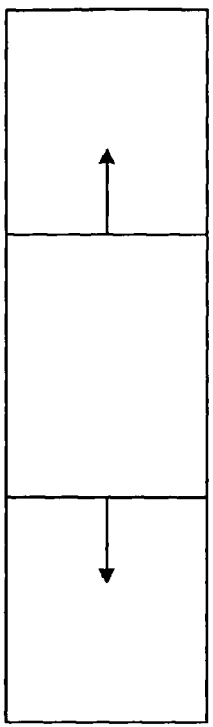
FIG. 2C is a pictorial diagram illustrating a target sub-region slidable over a master sub-region for various calculations to quantify alignment.
Figure 2D:
FIG. 2D is a pictorial diagram illustrating apices of coefficient values, which are indicative of locations of potential alignment.
Figure 2B:
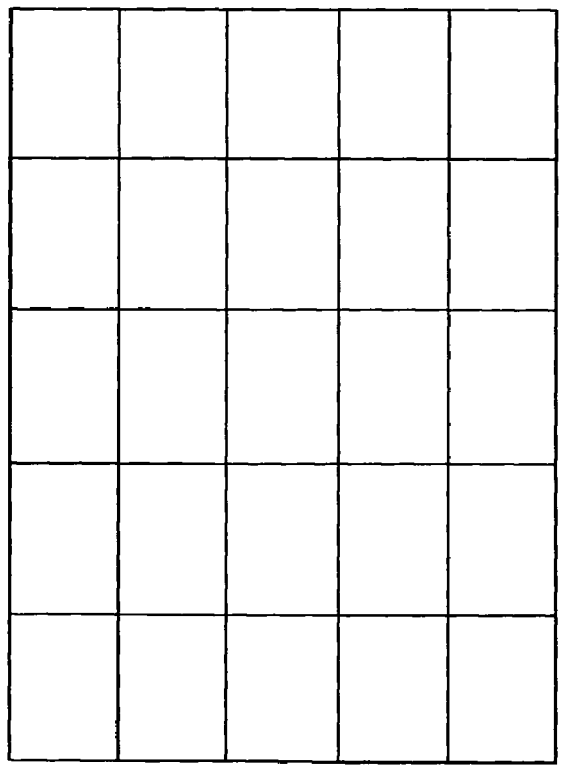
FIG. 2B is a pictorial diagram illustrating a rasterized image that is superposed with a grid formed from uniformly spaced horizontal and perpendicular lines.

From Terminal A4 (FIG. 5E), the method 5000 proceeds to block 5050 where an image is divided up into time columns of a particular width (e.g., 1.5 minutes) depending on the density of the data in the images. See also diagram 220 of FIG. 2B. At block 5052, each column is further divided into m/z subregions of various rows of a certain height (for example, 20 m/z), depending on the density of the data in the images. See also diagram 220 of FIG. 2B. At block 5054, a sub-region of the master image at a certain row in a certain column is selected for alignment analysis. The method then continues to another continuation terminal ("Terminal A5").

From Terminal A5 (FIG. 5E), the method 5000 proceeds to block 5056, where a sub-region of a target image is shifted or slid a step (incrementally, such as one or more pixels per shift step) over the master sub-region to create an overlap. See diagram 222 of FIG. 2C. At block 5058, the method begins a calculation of a correlation coefficient (step shift value) for quantifying how well the step is aligned. A minimum intensity value for the sub-region of the target image is found (where the intensity is greater than zero) at block 5060. The intensity of pixels in various sub-regions (the target image and the master image) is subtracted by the minimum intensity value. See block 5062. The method then proceeds to another continuation terminal ("Terminal A6").

From Terminal A6 (FIG. 5F), the method proceeds to block 5064 where the method looks at a target's pixel and a master's pixel at an overlapped pixel location. A test is performed at decision block 5066 to determine whether either the target's or the master's pixel intensity is greater than zero. If the answer to the test at decision block 5066 is NO, the method continues to another continuation terminal ("Terminal A8"). Otherwise, if the answer to the test at decision block 5066 is YES, the method proceeds to another decision block 5068, where a test is performed to determine whether either the target's or the master's pixel intensity is zero. If the answer to the test at decision block 5068 is YES, the method proceeds to block 5070, where the zero value is incremented by one for the particular pixel location. The method then continues to another continuation terminal ("Terminal A7"). Otherwise, the answer to the test at decision block 5068 is NO, and the method proceeds to Terminal A7.

From Terminal A7 (FIG. 5G), the method 5000 proceeds to block 5072 where calculations are made to allow both high and low intensity pixels to have an impact on the correlation coefficient (e.g., $\log_{10}$ of the target's and $\log_{10}$ of the master's pixel intensity are taken). The target's and master's pixel intensity calculations are placed in the target array and the master array, respectively, for the particular pixel location at block 5074. The method then proceeds to Terminal A8 (FIG. 5G), where it further proceeds to decision block 5076, where a test is performed to determine whether all pixels in the overlap have been analyzed. If the answer to the test at decision block 5076 is NO, the method proceeds to Terminal A6 and skips back to block 5064 where the above-identified processing steps are repeated. Otherwise, the answer to the test at decision block 5076 is YES, and the method 5000 proceeds to block 5078 where a correlation coefficient is calculated from intensity calculations stored in the target array and the master array. At block 5080, the correlation coefficient is stored to an array of correlation coefficients for the particular step. The method then continues to another continuation terminal ("Terminal A9").

From Terminal A9 (FIG. 5H), the method 5000 proceeds to block 5082 where the method begins a calculation of an overlap fit value (another step shift value) for quantifying how well the step is aligned. The method then looks at a target's pixel and a master's pixel at an overlapped pixel location at block 5084. Next, at decision block 5086, a test is performed to determine whether the master's pixel intensity is greater than zero. If the answer to the test at decision block 5086 is NO, the method continues to another continuation terminal ("Terminal A12"). Otherwise, the answer to the test at decision block 5086 is YES, and the method proceeds to decision block 5088 where another test is performed to determine whether the target's pixel intensity is equal to zero. If the answer to the test at decision block 5088 is YES, the method proceeds to another continuation terminal ("Terminal A10"). Otherwise, the answer to the test at decision block 5088 is NO, and the method 5000 proceeds to another continuation terminal ("Terminal A13").

From Terminal A10 (FIG. 5I), the method 5000 proceeds to block 5090 where a first counter (indicating that the master's pixel intensity is greater than zero and that the target's pixel intensity is zero) is incremented. The method 5000 proceeds to another continuation terminal ("Terminal A13"). From Terminal A12 (FIG. 5I), the method 5000 proceeds to decision block 5092 where a test is performed to determine whether the master's pixel intensity is equal to zero. If the answer to the test at decision block 5092 is NO, the method proceeds to Terminal A13. Otherwise, the answer to the test at decision block 5092 is YES, and the method proceeds to decision block 5094, where another test is performed to determine whether the target's pixel intensity is greater than zero. If the answer to the test at decision block 5094 is YES, the method proceeds to another continuation terminal ("Terminal A11"). Otherwise, the answer to the test at decision block 5094 is NO, and the method proceeds to Terminal A13.

From Terminal A11 (FIG. 5J), the method 5000 proceeds to block 5096, where a second counter (indicating that the master's pixel intensity is equal to zero and that the target's pixel intensity is greater than zero) is incremented. The method 5000 then proceeds to Terminal A13 (FIG. 5J), where it continues on to decision block 5098, where a test is performed to determine whether all pixels in the overlap have been analyzed. If the answer to the test at decision block 5098 is NO, the method 5000 proceeds to another continuation terminal ("Terminal A14"), where it skips back to block 5084 and the above-identified processing steps are repeated. Otherwise, the answer to the test at decision block 5098 is YES, and the method proceeds to block 5100 where an overlap fit value is calculated by taking a negative of a sum of the first and second counters. At block 5102, the overlap fit value is also stored to the array of step shifts for the particular step (in essence, the array is an array of two fields, correlation coefficient and overlap fit value). The method 5000 proceeds to another continuation terminal ("Terminal A15").

From Terminal A15 (FIG. 5K), the method 5000 proceeds to decision block 5104 where a test is performed to determine whether the target's sub-region has slid across the entire master sub-region. If the answer to the test at decision block 5104 is NO, the method proceeds to Terminal A5 (FIG. 5E), where it skips back to block 5056 and the above-identified processing steps are repeated. Otherwise, the answer to the test at decision block 5104 is YES, and the method proceeds to block 5106 where for each step shift (indicating a location where the target sub-region is led over a location of the master sub-region), an apex is calculated using the arrays of step shifts. At block 5108, the apices are sorted into a list of descending order based on the height of each apex. The method then selects an apex from the top of the list at block 5110. The method 5000 then proceeds to another continuation terminal ("Terminal A16").

From Terminal A16 (FIG. 5L), the method 5000 proceeds to decision block 5112, where a test is performed to determine whether the apex has a minimum number of points between the inflections. If the answer to the test at decision block 5112 is YES, the method proceeds to another continuation terminal ("Terminal A18"). Otherwise, the answer to the test at decision block 5112 is NO, and the method proceeds to block 5114 where the apex is removed from the list. The method then proceeds to decision block 5116 where another test is performed to determine whether there are more apices to consider. If the answer to the test at decision block 5116 is NO, the method proceeds to another continuation terminal ("Terminal A20"). Otherwise, the answer to the test at decision block 5116 is YES, and the method proceeds to another continuation terminal ("Terminal A17").

From Terminal A18 (FIG. 5M), the method 5000 proceeds to decision block 5118, where a test is performed to determine whether the second highest apex is lower than the highest apex by a suitable threshold. If the answer to the test at decision block 5118 is NO, the method proceeds to another continuation terminal ("Terminal A19"). From Terminal A19 (FIG. 5L), the method skips back to block 5114, where the above-identified processing steps are repeated. Otherwise, the answer to the test at decision block 5118 is YES, and the method proceeds to block 5120 where the method stores the apex in an apex array, which indicates high correlation between master, target sub-regions, and signifying a location of potential alignment. The method 5000 then proceeds to Terminal A20 (FIG. 5M), where it further proceeds to decision block 5122 where a test is performed to determine whether there are more target sub-regions in different rows to consider. If the answer to the test at decision block 5122 is YES, the method continues to Terminal A21 (FIG. 5E), where the above-identified processing steps are repeated. Otherwise, the answer to the test at decision block 5122 is NO, and the method 5000 proceeds to another continuation terminal ("Terminal A22").

From Terminal A22 (FIG. 5N), the method 5000 proceeds to block 5124 where the method begins final analysis of the correlation coefficient technique. At block 5126, a histogram is created for the shift values stored in the array of step shift using a suitable bin size, such as 0.20. The histogram is sorted in descending order, based on the number of members that belong to each bin in the histogram at block 5128. At block 5130, all of the values in the highest ranked bin are averaged to determine a final shift value for the technique. At decision block 5132, a test is performed to determine whether the highest ranked bin has a minimum number of members. If the answer to the test at decision block 5132 is YES, the method proceeds to another continuation terminal ("Terminal A23"). Otherwise, the answer to the test at decision block 5132 is NO, and the method proceeds to another continuation terminal ("Terminal A24").

From Terminal A23 (FIG. 5O), the method 5000 proceeds to decision block 5134 where a test is performed to determine whether the second ranked bin has 90% of the members of the first ranked bin. If the answer to the test at decision block 5134 is NO, the method proceeds to another continuation terminal ("Terminal A24"). If the answer to the test at decision block 5134 is YES, the method proceeds to block 5136 where members of the first and second ranked bins are averaged together to produce a final shift value. At decision block 5138, another test is performed to determine whether the final shift value is calculated from correlation coefficients. If the answer to the test at decision block 5138 is NO, the method proceeds to Terminal A24. Otherwise, the answer to the test at decision block 5138 is YES, and the method proceeds to block 5140 where the final shift value is stored as the first final shift value (for correlation-coefficient analysis). The method proceeds to Terminal A24 after the execution of block 5140.

From Terminal A24 (FIG. 5P), the method 5000 proceeds to decision block 5142 where a test is performed to determine whether the final analysis of the overlap fit value technique has occurred. If the answer to the test at decision block 5142 is NO, the method 5000 proceeds to Terminal A22 where it loops back to block 5124 (FIG. 5N), and the above-identified processing steps are repeated. Otherwise, the answer to the test at decision block 5142 is YES, and the method proceeds to block 5144 where the second final shift value is stored as the first final shift value (for overlap-fit analysis). The method then proceeds to decision block 5146 where another test is performed to determine whether the first, second final shift values are within proximity of each other. If the answer to the test at decision block 5146 is NO, the method 5000 proceeds to block 5148 where the final shift values are discarded because there lacks an agreement on the degree of alignment needed and the process is restarted using another column. The method 5000 proceeds to another continuation terminal ("Terminal A26"). If the answer to the test at decision block 5146 is YES, the method proceeds to another continuation terminal ("Terminal A25").

From Terminal A25 (FIG. 5Q), the method 5000 proceeds to block 5150 where the first, second final shift values are averaged to produce a final shift value for the particular time interval (the width of the column of the grid). A test is performed at decision block 5152 to determine whether all of the columns of a target image have been analyzed. If the answer to the test at decision block 5152 is NO, the method 5000 proceeds to Terminal A21 where it skips back to block 5054 (FIG. 5E) and the above-identified processing steps are repeated. Otherwise, the answer to the test at decision block 5152 is YES, an the method proceeds to decision block 5154 where another test is performed to determine whether all of the rasterized images have been analyzed. If the answer to the test at decision block 5154 is NO, the method proceeds to Terminal A4 (FIG. 5E) where it loops back to block 5050 and the above-identified processing steps are repeated. Otherwise, the answer to the test at decision block 5144 is YES, and the method 5000 proceeds to Terminal A26.

From Terminal A26 (FIG. 5R), each averaged final shift value is used as a control point to create an interpolated function such as a spline that prescribes the shift value for the width of each column of each image. See block 5156. At block 5158, the method re-interpolates the raw data using the interpolation in the images as the method re-rasterizes the images, hence warping the images. At block 5160, spatial noises in the two-dimensional images are filtered by a morphological image noise filter. The method calculates and stores in a database the median intensity of the LC/MS images at block 5162. At block 5164, the method calculates and stores in the database the standard deviation of the intensities of the LC/MS images. The method 5000 then proceeds to another continuation terminal ("Terminal A27").

From Terminal A27 (FIG. 5S), the method 5000 begins steps to remove noise and correct background of LC/MS images at block 5166. A test is performed to determine, at block 5168, whether high-resolution MS equipment was used. If the answer to the test at decision block 5168 is NO, the method 5000 proceeds to another continuation terminal ("Terminal AK1"). Otherwise, the answer to the test at decision block 5168 is YES, and the method proceeds to another continuation terminal ("Terminal AA1") and the method further proceeds to block 5170 where the method begins steps to perform a morphological bit open operation on an LC/MS image. The method produces a bit mask from an LC/MS image for intensities above zero at block 5172. At block 5174, a morphological open operation is performed on the bit mask, removing noise with a certain structural size. The method 500 then proceeds to another continuation terminal ("Terminal AA2").

From Terminal AA2 (FIG. 5SA), the method 5000 proceeds to block 5176 where it applies the bit mask to the LC/MS image, producing a bit-opened LC/MS image. The method then proceeds to another continuation terminal ("Terminal AB1") and it then further proceeds to block 5178 where the method begins steps to perform a background correction of the bit-opened LC/MS image. At decision block 5180, a test is performed to determine whether fewer median sortings are required. If the answer to the test at decision block 5180 is YES, the method 5000 proceeds to another continuation terminal ("Terminal AD1"). Otherwise, the answer to the test at decision block 5180 is NO, and the method proceeds to another continuation terminal ("Terminal AC1") and it then proceeds to block 5182 where a rectilinear window (of dimensions 2n+1 in the m/z direction and 1 in the RT direction) is placed at the first pixel of the LC/MS image. The method then calculates an intensity median of the pixels in the rectilinear window at block 5184. The method proceeds to another continuation terminal ("Terminal AC2").

From Terminal AC2 (FIG. 5SB), the method 5000 proceeds to block 5186 where the intensity median is assigned to the pixel located at the center of the rectilinear window. At block 5188, the above-discussed steps 5184-5186 are repeated for each pixel in a particular row of the LC/MS image. The above-discussed steps are also repeated for each row in the LC/MS image at block 5190. At block 5192, a rectilinear window (of dimensions 2m+1 in the RT direction and 1 in the m/z direction) is placed at the first pixel of the LC/MS image. At block 5194, the method calculates an intensity median of the pixels in the rectilinear window. The intensity median is assigned to the pixel located at the center of the rectilinear window at block 5196. At block 5198, the above-discussed steps 5194-5196 are repeated for each pixel in a particular column of the LC/MS image. The method then continues to another continuation terminal ("Terminal AC3").

From Terminal AC3 (FIG. 5SC), the above-discussed step is repeated for each column in the LC/MS image at block 5200. At block 5202, the above-discussed step is repeated for each LC/MS image. The method then continues to another continuation terminal ("Terminal AB2"). From Terminal AB1 (FIG. 5SC), the method 5000 proceeds to block 5204 where the method divides an LC/MS image into a set of rectangular chunks. At block 5206, the method takes one chunk and calculates an intensity median of all the pixels in a particular row. The intensity median is assigned to the pixel located at the center of the particular row of the chunk at block 5208. At block 5210, the above-discussed steps 5206-5208 are repeated for each row of the chunk. The method then continues to another continuation terminal ("Terminal AD2").

From Terminal AD2 (FIG. 5SD), the method 5000 proceeds to block 5212 where the method takes one chunk and calculates an intensity median of all the pixels in a particular column. At block 5214, the intensity median is assigned to the pixel located at the center of the particular column of the chunk. The above-discussed steps 5212-5214 are repeated for each column of the chunk at block 5216. The above-discussed steps 5206-5216 are also repeated for all chunks. See block 5218. At block 5220, the method takes the intensity median of a particular row of one chunk and the intensity median of a corresponding row in a horizontally closest chunk. The intensity of each pixel in the row between the two pixels assigned with the intensity medians are interpolated at block 5222. At block 5224, the above-discussed steps 5220-5222 are repeated for all chunks to produce a row-median image. The method then proceeds to another continuation terminal ("Terminal AD3").

From Terminal AD3 (FIG. 5SE), the method 5000 takes the intensity median of a particular column of one chunk and the intensity median of a corresponding column in a vertically closest chunk at block 5226. At block 5228, the intensity of each pixel in the column between the two pixels assigned with the intensity medians are interpolated. At block 5230, the above-discussed steps 5226-5228 are repeated for all chunks to produce a column-median image. The method 5000 then proceeds to another continuation terminal ("Terminal AB2"). From Terminal AB2 (FIG. 5SE), the method 5000 proceeds to block 5232 where for a pixel location in both the row-median image and the column-median image, the method takes the maximal intensity value of the two co-located pixels. The maximal value is assigned to a location in a third image (background image) that corresponds to the two co-located pixels at block 5234. The above-discussed steps 5232-5234 are repeated for all pixels in the row-median image and the column-median image at block 5236. At block 5238, the method subtracts the background image from the original LC/MS image to produce a corrected LC/MS image. The method then continues to another continuation terminal ("Terminal AB3").

From Terminal AB3 (FIG. 5SF), the method 5000 proceeds to block 5240 where if the method uses chunks, the method calculates medians and standard deviations of chunks for subsequent analysis. At block 5242, if the method does not use chunks, the method calculates medians and standard deviations for subsequent analysis. The above-discussed steps are repeated for each original LC/MS image to produce a number of corrected-LC/MS images. The method 5000 then proceeds to another continuation terminal ("Terminal AE1"). From Terminal AE1 (FIG. 5SF), the method 5000 proceeds to block 5246 where it begins steps to smooth the LC/MS images in the RT dimension. At block 5248, the method takes the intensities of all the pixels rectilinearly at one retention time and brings them into the frequency domain using a one-dimensional Fast Fourier Transform. At block 5250, certain noise types are removed by the transformation into the frequency domain. The method 5000 proceeds to another continuation terminal ("Terminal AE2").

From Terminal AE2 (FIG. 5SG), the method 5000 proceeds to block 5252 where sequentially or contemporaneously, the method generates either a sigmoidal or Gaussian low-pass filter. At block 5254, the method moves the low pass filter such that its inflection point is at the center of the frequency spectrum of the one-dimensional Fast Fourier Transform. The method weights the one-dimensional Fast Fourier Transform with the sigmoidal or Gaussian low pass filter, hence smoothing away spurious high frequency components at block 5256. At block 5258, the method brings the intensities of all the pixels rectilinearly at one retention time into the time domain using the one-dimensional inverse Fast Fourier Transform. The method keeps the real portions of the inverse Fast Fourier Transform and removes all imaginary portions at block 5260. At block 5262, the method sets the intensities of certain pixels to zero if their intensities are negative after the application of the inverse Fast Fourier Transform. The above-discussed steps are repeated for all retention times of an LC/MS image and for all LC/MS images at block 5264. The method 5000 proceeds to another continuation terminal ("Terminal AJ1").

From Terminal AJ1 (FIG. 5SH), the method 5000 proceeds to decision block 5266 where a test is performed to determine whether the data are sparse (such as 15% or less of the data have non-zero values). If the answer to the test at decision block 5266 is NO, the method 5000 proceeds to another continuation terminal ("Terminal AG1"). Otherwise, the answer to the test at decision block 5266 is YES, and the method proceeds to another continuation terminal ("Terminal AF1") and further proceeds to block 5268 where the method begins steps to determine threshold masks for sparse data. At block 5270, the method makes an above-zero bit mask from the LC/MS image for those intensities above zero. Contemporaneously, the method obtains the standard deviation or a set of standard deviations for an LC/MS image earlier calculated between Terminals AB3, AE1 at block 5272. If the set of standard deviations is obtained, the method calculates a median standard deviation at block 5274. The method 5000 proceeds to another continuation terminal ("Terminal AF2").

From Terminal AF2 (FIG. 5SI), the method 5000 proceeds to block 5276 where the method creates a standard deviation bit mask by setting intensities that are below the standard deviation to zero. At block 5278, the method performs a mathematical morphological dilation operation on the standard deviation mask. The dilation operation is constrained by the structures of the above-zero bit mask at block 5280. The method then produces a threshold mask at block 5282. The method 5000 proceeds then to another continuation terminal ("Terminal AA3"). From Terminal AG1 (FIG. 5SI), the method 5000 proceeds to block 5284 where the method begins steps to determine threshold mask for non-sparse data. At block 5286, the method makes an above-zero bit mask from the LC/MS image for those intensities above zero. The method continues to another continuation terminal ("Terminal AG2").

From Terminal AG2 (FIG. 5SJ), the method 5000 proceeds to block 5288 where contemporaneously, the method obtains the standard deviation or a set of standard deviations for an LC/MS image earlier calculated between Terminals AB3, AE1. If the set of standard deviation is obtained, the method calculates a median standard deviation at block 5290. At block 5292, using the standard deviation or the median standard deviation as a threshold, the method sets intensities below the threshold to zero. The method 5000 proceeds to another continuation terminal ("Terminal HH1"). The method continues to block 5294 where the method begins steps to smooth the LC/MS image. At block 5296, the method begins steps to smooth the LC/MS image in the m/z dimension. The method continues to another continuation terminal ("Terminal AI2").

From Terminal AI2 (FIG. 5SK), the method 5000 takes the intensities of all the pixels rectilinearly at one m/z scan and brings them into the frequency domain using one-dimensional Fast Fourier Transform at block 5300. At block 5302, sequentially or contemporaneously, the method generates either a sigmoidal or Gaussian low pass filter. At block 5304, the method moves the low pass filter such that its inflection point is at the center of the frequency spectrum of the one-dimensional Fast Fourier Transform. The method weights the one-dimensional Fast Fourier Transform with a Sigmoidal or Gaussian low pass filter, hence smoothing away spurious high frequency components at block 5306. Next, at block 5308, the method brings the intensities of all the pixels rectilinearly at one m/z scan into the time domain using one-dimensional inverse Fast Fourier Transform. The method keeps the real portions of the inverse Fast Fourier Transform, and removes all imaginary portions at block 5310. At block 5312, the above-discussed steps are repeated for all m/z scans of an LC/MS image and for all LC/MS images. The method proceeds to another continuation terminal ("Terminal AH2").

From Terminal AH2 (FIG. 5SL), the method 5000 begins steps between Terminals AE1, AE3 to smooth the LC/MS image in the RT dimension. See block 5314. The method then continues to another continuation terminal ("Terminal AG3"). The method further proceeds to block 5316 where the method creates a standard deviation bit mask by setting intensities that are below the standard deviation to zero. At block 5318, the method intersects the standard deviation bit mask and the above-zero bit mask to create a threshold mask. The method proceeds to another continuation terminal ("Terminal AA3") and further proceeds to block 5320 where the method applies (multiplies or logical "end") the threshold mask to the LC/MS image correcting the background. The method proceeds to another continuation terminal ("Terminal A28").

From Terminal AK1 (FIG. 5SM), the method 5000 begins steps between Terminals AH1, AG3 to smooth the LC/MS images at block 5322. At block 5324, the method begins steps between Terminals AB1, AE1 to correct the background of the LC/MS images. The method begins steps between Terminals AJ1, AA3 to determine a threshold mask at block 5326. Next, at block 5328, the method 5000 applies (multiplies or logical "end") the threshold mask to the LC/MS image correcting the background. The method 5000 proceeds to Terminal A28 and further proceeds to block 5330 where replicates within each treatment group are combined into one image by averaging pixel intensities across replicates. The method 5000 proceeds to another continuation terminal ("Terminal AL1").

From Terminal AL1 (FIG. 5SN), at block 5332, the method 5000 breaks the within-group-replicate combined image into rectangular pieces, forming sub-images. At block 5334, pixel intensity standard deviation of each sub-image is calculated. A bit mask is created for pixels whose intensity is below two standard deviation (as calculated above) at block 5336. At block 5338, the bit mask created in step 5336 is applied to the LC/MS image. At block 5340, pixel intensity standard deviation of each sub-image is recalculated. At block 5342, two-dimensional interpolation is performed using the recalculated standard deviations of the sub-images. At block 5344, a mathematical morphological grayscale dilation operation is performed on the original within-group-replicate combined image. The method then continues to another continuation terminal ("Terminal AL2").

From Terminal AL2 (FIG. 5SO), at block 5346, another bit mask is created wherever the result of the grayscale dilation is greater than the interpolated image. At block 5348, a mathematical morphological open operation is performed on the bit mask created in the above step 5346. At block 5350, the open bit mask is applied (multiplied or logical "end") with the original-within-group replicate combined image. At block 5352, the above step produces a masked LC/MS image with floating point values representing intensities of pixels. The above steps are repeated for each within-group-replicate combined image at block 5354. The method takes the combined images of various groups and merges (between-group) intensity among all combined images at each pixel location at block 5356. The method 5000 then proceeds to another continuation terminal ("Terminal AM1").

From Terminal AM1 (FIG. 5SP), the method 5000 begins steps to make feature masks at block 5358. The method begins steps to remove large, contiguous regions in the between-group image at block 5360. These large, contiguous regions may be caused by noise and background from the elution of a large number of unrelated contaminants. The method proceeds to another continuation terminal ("Terminal AN1"). The method further proceeds to block 5362 where the method begins steps to begin morphological smoothing of the original between-group image. At block 5364, a morphological grayscale opening is performed using a structural element of one pixel radius. At block 5366, a morphological grayscale closing is performed using a structural element of one pixel radius. The above steps 5364-5366 are repeated with increasing size of the structural element from one until the size is five pixels in diameter at block 5368. The pixels that survive are considered to contain pertinent signal to the discovery of biological features of interest. At block 5370, at the end of these morphological smoothing steps, a first image is produced. The method 5000 then proceeds to another continuation terminals ("Terminal AN2").

From Terminal AN2 (FIG. 5SQ), contemporaneously with the steps of morphological smoothing, the method performs a morphological grayscale opening on the original between-group-image at block 5372. At block 5374, the method begins steps between Terminals AE1, AE3 to smooth the LC/MS image in the RT dimension, producing a second image. The method begins steps between Terminals AH1, AG3 to smooth the first image at block 5376. At block 5378, the method determines signal smoothability by taking a ratio of intensities of the second image to the intensities of this first image. At block 5380, a second bit mask is performed for pixel locations with suitable ratio values (e.g., such as too close) indicating potential features of interest. At block 5382, a two-dimensional morphological open operation is performed to the second bit mask with a structural element of about radius of 1. A first bit mask is formed from the first image for pixels whose intensity is greater than zero at block 5384. The method 5000 proceeds to another continuation terminal ("Terminal AN3").

From Terminal AN3 (FIG. 5SR), a morphological open operation is performed on the first bit mask in the m/z dimension by the maximum allowed peak width (e.g., 10-11 pixels in length) at block 5386. At block 5388, a morphological dilation operation is performed on the opened first bit mask in both the RT and m/Z dimensions but constrained (also conditioned) by the original first bit mask. At block 5390, the method intersects (logically AND) the second mask with the inverted (logical compliment) first mask to create a mask without contiguous noise. The mask without contiguous noise is applied (multiplied or logically "ANDed") to the original between-group image of block 5394. The method then continues to another continuation terminal ("Terminal AM2") and further proceeds to block 5396 where contemporaneously, a bit mask is created from the original between-group-image for pixels whose intensity is greater than zero. The method then continues to another continuation terminal ("Terminal AM3").

From Terminal AM3 (FIG. 5SS), a morphological open operation is performed on the bit mask using a diamond shaped structuring element with suitable radius, such as 2, at block 5398. At block 5400, the method begins steps between Terminals AH1, AG3 to smooth the between-group image which large contiguous regions have been removed. The following technique uses a Laplacian transformation to obtain artifacts that are represented as negative values between the edges detected by the Laplacian transformation. These artifacts are used to locate areas of potential biological features of interest, including peaks. The Laplacian transformation is used in combination with the Gaussian transformation to avoid noise near the apices of the peaks that may obscure the ability to locate potential biological features of interest. The bit mask that has undergone the open operation in step 5398 is applied to the smoothed between-group image to produce a pre-LoG (Laplacian of a Gaussian) image. See block 5402. The method 5000 proceeds to another continuation terminal ("Terminal AO1") and further proceeds to block 5404 where the method creates a suitable radial Laplacian of Gaussian kernel (such as a 7×7 kernel with sigma of one or two). At block 5406, the method also creates a suitable linear Laplacian of Gaussian kernel in the m/z dimension (such as a 7×7 with sigma of one or two). At block 5408, the pre-LoG image is convoluted with the radial LoG kernel to produce a first mask of negative values. The method then continues to another continuation terminal ("Terminal AO2").

From Terminal AO2 (FIG. 5ST), the pre-LoG image is convoluted with the linear LoG kernel to produce a second mask of negative values at block 5410. At block 5412, the first and second masks are intersected (multiplied or logically "ANDed") to produce a mask of spots. The method then continues to another continuation terminal ("Terminal AM4") and further proceeds to block 5416 at which the method inverts the between-group image from where large contiguous regions have been removed. At block 5418, the method performs a watershed transform on the inverted image to find lines between a watershed basins. The watershed transform helps split apart merged biological features, such as peaks, that were not earlier separated by the Laplacian of Gaussian transformation. The method creates a bit mask based on the lines between the watershed basins at block 5420. The method proceeds to another continuation terminal ("Terminal AM5").

From Terminal AM5 (FIG. 5SU), the method 5000 inverts the watershed lines bit mask at block 5422. At block 5424, the method intersects (or multiplies or logically "end") the watershed lines bit mask and the mask of spots to produce a mask of features. At block 5426, a two-dimensional morphological open operation is performed on the mask of features using a box structuring element of radius 2, 1. At block 5428, the method produces a composite image and a mask of features is used in the next stage to identify peaks and other features of interest. The method then proceeds to Terminal B.

From Terminal B (FIG. 5A), the method 5000 proceeds to a set of method steps 5004, defined between a continuation terminal ("Terminal C") and another continuation terminal ("Terminal D"). The set of method steps 5004 extracts image features, including peaks, isotope groups, and charge groups.

From Terminal C (FIG. 5T), the method 5000 defines $x_{i,j}$ as the intensity of the i m/z value and at the j time point for an image feature. See block 5430. At block 5432, the method defines a peak intensity as the maximum intensity of an image feature. At block 5434, the method superposes a grid (with multiple grid rows and grid columns) over the composite image. The method then continues to another continuation terminal ("Terminal C1").

From Terminal C1 (FIG. 5U), the method 5000 calculates boundaries of various features at block 5436. At block 5438, the method calculates other feature parameters. The method then continues to another continuation terminal ("Terminal C2").

From Terminal C2 (FIG. 5V), the method 5000 extracts a peak in a composite image by searching for connected pixels of certain values, such as non-zero pixels. See block 5440. At decision block 5442, a test is performed to determine whether a peak has been found. If the answer to the test at decision block 5442 is NO, the method continues to another continuation terminal ("Terminal C3") and skips back to block 5440 where the above-identified processing steps are repeated. If the answer to the test at decision block 5442 is YES, the method continues to block 5444 where the method labels the found peak with a unique indicant, such as an index number. The method proceeds to decision block 5446 where another test is performed to determine whether there are more connected non-zero pixels. If the answer to the test at decision block 5446 is YES, the method proceeds to Terminal C3 where it skips to block 5440 and the above-identified processing steps are repeated. Otherwise, the answer to the test at decision block 5446 is NO, and the method proceeds to another continuation terminal ("Terminal C4").

From Terminal C4 (FIG. 5W), the method 5000 begins analysis of overlapping peaks in the m/z direction at block 5448. At block 5450, the method computes a median peak intensity of all peaks in a grid row (m/z direction). At block 5452, the method computes high grid row peaks which are peaks in the grid row that have peak intensity higher than the median peak intensity. The method computes a width threshold (that delimits overlapping peaks) based on a median m/z width of a high grid row peaks and its deviation at block 5454. At block 5456, the method computes a peak m/z centroid width. A test is performed at decision block 5458 to determine whether the peak centroid width is greater than or equal to the width threshold. If the answer to the test at decision block 5458 is NO, the method proceeds to another continuation terminal ("Terminal C5"). Otherwise, the answer to the test at decision block 5458 is YES, and the method proceeds to another continuation terminal ("Terminal C15").

From Terminal C5 (FIG. 5X), the method 5000 proceeds to decision block 5460 where a test is performed to determine whether all peaks in the grid row have been analyzed. If the answer to the test at decision block 5460 is NO, the method 5000 proceeds to block 5462 where the method selects another peak within the grid row for overlapping analysis. The method then continues to another continuation terminal ("Terminal C6") and loops back to block 5456 (FIG. 5W) where the above-identified processing steps are repeated. Otherwise, the answer to the test at decision block 5460 is YES, and the method proceeds to decision block 5464 where another test is performed to determine whether all grid rows have been analyzed. If the answer to the test at decision block 5464 is NO, the method proceeds to block 5468 where it selects another grid row for overlapping analysis. the method then proceeds to another continuation terminal ("Terminal C7") and skips back to block 5450 where the above-identified processing steps are repeated. Otherwise, the answer to the test at decision block 5464 is YES, and the method proceeds to another continuation terminal ("Terminal C11").

From Terminal C15 (FIG. 5Y), the method 5000 proceeds to decision block 5470 where a test is performed to determine whether the method is performing high-contrast splitting. If the answer to the test at decision block 5470 is YES, the method proceeds to another continuation terminal ("Terminal C8"). Otherwise, the answer to the test at decision block 5470 is NO, and the method proceeds to block 5472 where the method begins performing low-contrast splitting. The method then continues to another continuation terminal ("Terminal C17").

From Terminal C8 (FIG. 5Z), the method 5000 proceeds to block 5474 where the method begins high-contrast splitting of overlapping peaks. At block 5476, the method obtains a sequence of points (x1, x2, . . . , xn) that describe the overlapping peaks, each point with a corresponding intensity. A test is performed at decision block 5478 where it is determined whether there are a sufficient number of points (e.g., 4) to split. If the answer to the test at decision block 5478 is NO, the method 5000 proceeds to another continuation terminal ("Terminal C10"). Otherwise, the answer to the test at decision block 5478 is YES, and the method proceeds to block 5480 where the method finds dips in the sequence, which are points with intensity lower than 2 immediate point neighbors. At block 5482, the method calculates a contrast threshold (e.g., a product of a contrast level, such as 0.1, and the maximum intensity of the sequence). The method then continues to another continuation terminal ("Terminal C9").

From Terminal C9 (FIG. 5AA), the method 5000 proceeds to decision block 5484 where a test is performed to determine whether one of the dips has intensity less than the contrast threshold. If the answer to the test at decision block 5484 is NO, the method proceeds to Terminal C10. Otherwise, if the answer to the test at decision block 5484 is YES, the method proceeds to block 5486 where the overlapping peaks are high-contrast and are splittable. At block 5488, the method finds all connected sets of points with an intensity that is less than a threshold (e.g., a product of a standard deviation and the maximum value of the sequence). The method finds a minimum dip in the connected sets of points (or the first minimum dip if there are many) at block 5490. At block 5492, the method splits the overlapping peaks at the point of the minimum dip. At block 5494, the method labels the split peaks with unique indicants, the original unique indicant being reused for one of the peaks. The method proceeds to Terminal C10.

From Terminal C10 (FIG. 5AB), the method 5000 proceeds to decision block 5496 where a test is performed to determine whether the method is analyzing in the m/z direction. If the answer to the test at decision block 5496 is YES, the method proceeds to Terminal C5 where it skips back to decision block 5460 and the above-identified processing steps are repeated. Otherwise, if the answer to the test at decision block 5496 is NO, the method proceeds to another continuation terminal ("Terminal C14"). From Terminal C11 (FIG. 5AB), the method 5000 proceeds to block 5498 where the method begins analysis of overlapping peaks in the retention time direction. At block 5500 the method computes a median peak intensity of all peaks in the composite image. The method computes high peaks, which are peaks that have peak intensity higher than the median peak intensity at block 5502. The method then continues to another continuation terminal ("Terminal C12").

From Terminal C12 (FIG. 5AC), the method 5000 computes a width threshold (that delimits overlapping peaks) based on a median time width of all high peaks in its deviation period. See block 5504. At block 5506, the method computes a peak time centroid width for a high peak. The method proceeds to decision block 5508 where a test is performed to determine whether the peak centroid width is greater than or equal to the width threshold. If the answer to the test at decision block 5508 is YES, the method proceeds to Terminal C15 where the method skips back to decision block 5470 and the above-identified processing steps are repeated. Otherwise, the answer to the tests at decision block 5508 is NO, and the method proceeds to another continuation terminal ("Terminal C14").

From Terminal C14 (FIG. 5AD), the method 5000 proceeds to decision block 5510 where a test is performed to determine whether all high peaks have been analyzed. If the answer to the test at decision block 5510 is NO, the method 5000 proceeds to another continuation terminal ("Terminal C13") and skips back to block 5506 where the above-identified processing steps are repeated. Otherwise, the answer to the test at decision block 5510 is YES, and the method proceeds to decision block 5512 where another test is performed to determine whether the overlapping analysis should be repeated. If the answer to the test at decision block 5512 is YES, the method proceeds to Terminal C4 and skips back to block 5448 (FIG. 5W), where the above-identified processing steps are repeated. Otherwise, the answer to the test at decision block 5512 is NO, and the method proceeds to another continuation terminal ("Terminal C20").

From Terminal C17 (FIG. 5AE), the method 5000 models overlapped peaks using a Gaussian function at block 5514. At block 5516, an optimization process is applied to find the best fit of the multiple Gaussian functions to the overlapped peaks. A no-hypothesis is constructed for the supposition where all peaks are completely overlapped and not splittable at block 5518. A p-value is provided to measure whether the probability of the no-hypothesis is true at block 5520. A test is performed at decision block 5522 to determine whether the p-value is smaller than a threshold. If the answer to the test at decision block 5522 is NO, the method proceeds to block 5524 where the no-hypothesis is true and the peaks are not splittable. The method 5000 continues to Terminal C10 where is loops back to decision block 5496 and the above-identified processing steps are repeated. Otherwise, the answer to the test at decision block 5522 is YES, and the method proceeds to another continuation terminal ("Terminal C18").

From Terminal C18 (FIG. 5AF), the method 5000 proceeds to block 5526 where the no-hypothesis is rejected and the peaks are splittable. At block 5528, the method uses the Gaussian functions to determine the location of the overlap or connection. The method also determines the intensity contribution from each individual peak to the overlap or connected peak at block 5530. A test is performed at block 5532 to determine whether the splitting should occur at the location of the overlap. If the answer to the test at decision block 5532 is NO, the method proceeds to another continuation terminal ("Terminal C19"). Otherwise, the answer to the test at decision block 5532 is YES, and the method splits the peaks using the locations determined by the Gaussian functions at block 5534. At block 5536, the method labels the splitted peaks with unique indicants, the original unique indicant being reused for one of the peaks. The method then continues to Terminal C10 where it loops back to decision block 5496 and the above-identified processing steps are repeated.

From Terminal C19 (FIG. 5AG), the method 5000 measures the total intensity using area under the curve of the peak with exceptionally wide width or its volume under the surface at block 5538. At block 5540, the method computes the intensity fraction of each peak within the peak with exceptionally wide width. The method splits the peaks using the fractional intensity based on the proportion of the areas under the peaks at block 5542. At block 5544, the method labels the splitted peaks with unique indicants, the original unique indicant being reused for one of the peaks. The method then continues to Terminal C10 and loops back to decision block 5496 where the above-identified processing steps are repeated. From Terminal C20 (FIG. 5AG) the method proceeds to block 5546 where the method trims over-wide time peaks. The method then proceeds to another continuation terminal ("Terminal C21").

From Terminal C21 (FIG. 5AH), the method 5000 uses a model, such as a modified Maxwell distribution function, to create a chromatogram model for an ideal peak at block 5548. At block 5550, the method adjusts the model parameters so as to obtain an approximate match to a peak from the composite image. The method produces a peak time score that measures how good the match is for the peak (for a perfect match, the score is 1, and for a noisy peak the score tends toward 0) at block 5552. At block 5554 the method computes various other time feature characteristics. A test is performed at decision block 5556 where it is determined whether all peaks have been characterized. If the answer to the test at decision block 5556 is YES, the method proceeds to another continuation terminal ("Terminal C22"). If the answer to the test at decision block 5556 is NO, the method proceeds to Terminal C21 where it skips back to block 5548 and the above-identified processing steps are repeated.

From Terminal C22 (FIG. 5AI), the method 5000 creates a model to measure characteristics of peaks in the m/z direction using a model, such as a Gaussian distribution function at block 5558. At block 5560, the method adjusts the model parameters, modifying the model so as to obtain an approximate match to a peak from the composite image. The method produces an m/z peak score that measures the quality of a spectral peak (when the peak is clean, the score is 1, and for a contaminated peak, the score tends toward 0) at block 5562. The method computes various other m/z feature characteristics at block 5564. A test is performed at block 5566 to determine whether all peaks have been characterized. If the answer to the test at decision block 5566 is YES, the method continues to another continuation terminal ("Terminal C23").

If the answer to the test at decision block 5566 is NO, the method proceeds to Terminal C22, where it skips back to block 5558 and the above-identified processing steps are repeated. From Terminal C23 (FIG. 5AJ), the method 5000 proceeds to block 5568 where the method ranks all peaks by their intensity in the retention time direction ($R_T$) intensity in the m/z direction ($R_M$), and time score ($R_S$). At block 5570, the method computes a combined rank using a suitable formula, such as $R=R_S+(R_T+R_M)/2$. The method reorders the combined rank at block 5572 so that the feature with the largest R score is listed first and the second largest R score is listed second, and so on. At block 5574, the method selects a seed peak, which is a peak listed first in the combined rank to find an isotope group. The method at block 5576 attempts to find the charge of the seed peak by calculating charge scores using a peak model and selecting a charge with the highest charge score. At block 5578, the method looks for an isotope peak towards the lower m/z direction. The method then proceeds to another continuation terminal ("Terminal C24").

From Terminal C24 (FIG. 5AK), the method 5000 proceeds to decision block 5580 where a test is performed to determine whether the method should switch the m/z direction of the search. If the answer to the test at decision block 5580 is YES, the method looks for an isotope peak at block 5582 by iterating a positive isotope number (K) to search an m/z level higher than the m/z position of the seed peak. The method then continues to another continuation terminal ("Terminal C25"). Otherwise, the answer to the test at decision block 5580 is NO, and the method proceeds to block 5584 where the method looks for an isotope peak by iterating a negative isotope number (K) to search an m/z level lower than the m/z position of the seed peak. The method continues to terminal 25 and further proceeds to block 5586 where the method equates the width of an isotope area to search for an isotope peak to the time width of the seed peak. The method defines the center of the isotope area at block 5588 based on the centroid width of the seed peak, an isotope number (K), the neutron mass, and the charge. The method defines the height of the isotope area based on a constant and a grid-adjusted m/z width of the seed peak at block 5590. The method proceeds to another continuation terminal ("Terminal C26").

From Terminal C26 (FIG. 5AL), the method 5000 proceeds to decision block 5592 where a test is performed to determine whether the method has searched for isotope peaks in all directions. If the answer to the test at decision block 5592 is YES, the method proceeds to another continuation terminal ("Terminal C30"). If the answer to the test at decision block 5592 is NO, the method proceeds to block 5594 where the method finds a candidate peak at the isotope position identified by the isotope number (K) within the isotope area. The method calculates a quotient at block 5596 based on the isotope intensity, the seed isotope intensity, the maximum isotope intensity computed so far, and the isotope intensity of a previous isotope. A test is performed at decision block 5598 where it is determined whether the quotient indicates that the intensity of the candidate peak is acceptable. If the answer to the test at decision block 5598 is NO, the method proceeds to Terminal C24, where it loops back to decision block 5580 and the above-identified processing steps are repeated. Otherwise, the answer to the test at decision block 5598 is YES, and the method proceeds to another continuation terminal ("Terminal C27").

From Terminal C27 (FIG. 5AM), a no-hypothesis is constructed for the simple position that the candidate peak completely matches with an isotope m/z intensity/shape model and an isotope time intensity/shape model at block 5560. P-values in both the m/z direction and the time direction at block 5602 are provided to gauge whether the candidate peak can be accepted or rejected as part of the isotope group. The time direction is the retention time direction. At block 5604, the method compares the candidate peak to the isotope models using a Gaussian function. A test is performed at decision block 5606 to determine whether the p-values of the candidate peak are greater than an acceptance threshold. If the answer to the test at decision block 5606 is YES, the method proceeds to block 5608 where the candidate peak is labeled with a unique indicant identifying it with a particular isotope group. The method then continues to another continuation terminal ("Terminal C28"). Otherwise, the answer to the test at decision block 5606 is NO, and the method proceeds to another continuation terminal ("Terminal C29").

From Terminal C28 (FIG. 5AN), the method 5000 proceeds to block 5610 where the no-hypothesis is TRUE and the candidate peak belongs to an isotope group, a member of which is a seed peak. The candidate peak at block 5612 is removed from the ranking. The method then continues to Terminal C24 and loops back to decision block 5580 where the method proceeds to execute the above-discussed processing steps. From terminal C29 (FIG. 5AN), a decision block 5614 is executed where a test is performed to determine whether p-values are less than a rejection threshold. If the answer to the test at decision block 5614 is NO, the method continues to block 5616 where the candidate peak is placed on hold by the method in case other isotope groups may claim the found peak later. The method then continues to Terminal C24 and skips back to decision block 5580 where the above-identified processing steps are repeated. Otherwise, the answer to the test at decision block 5614 is YES, and the method proceeds to block 5618 where the found peak is not a member of the isotope group. The method then continues to Terminal C24 and skips back to decision block 5580 where the above-identified processing steps are repeated.

From Terminal C30 (FIG. 5AO), the method 5000 labels the isotope group with a unique indicant at block 5620. At block 5622, the method removes the seed peak from the ranking so that it does not interfere with finding peaks and charges of other isotope groups. A test is performed at decision block 5624 where it is determined whether there are more seed peaks to be analyzed. If the answer to the test at block 5624 is YES, the method 5000 proceeds to another continuation terminal ("Terminal C31"). Otherwise, the answer to the test at decision block 5624 is NO, and the method proceeds to block 5626 where the method removes isotope groups that have peaks belonging to multiple isotope groups. The method then continues to another continuation terminal ("Terminal C32").

From Terminal C32 (FIG. 5AP), the method 5000 proceeds to decision block 5628 where a test is performed to determine whether the method detects the mono-isotope. If the answer to the test at decision block 5628 is NO, the method proceeds to another continuation terminal ("Terminal C33"). Otherwise, the answer to the test at decision block 5628 is YES, and the method proceeds to block 5630 where the method begins to compute the mass of the isotope group. The mass of the isotope group is a product based on the charge (G), the proton mass, and the m/z intensity centroid of the first peak in the lowest detected isotope. See block 5632. The method then continues to another continuation terminal ("Terminal C39").

From Terminal C33 (FIG. 5AQ), the method 5000 estimates the mass initially by using the lowest m/z intensity centroid of the peak in the lowest isotope position. See block 5634. At block 5636, the method computes an observed distribution by using the maximum model RT intensity of the peaks in each isotope. The method compares the theoretical isotope distribution at block 5638 with the observed isotope distribution and shifts them until the best match is found, resulting in an integer offset. The mass of the isotope group is recomputed using the integer offset. See block 5640. The method then continues to Terminal C39 and further proceeds to decision block 5642 where a test is performed to determine whether there are more isotope groups to be analyzed. If the answer to the test at decision block 5642 is NO, the method proceeds to another continuation terminal ("Terminal C34"). Otherwise, the answer to the test at decision block 5642 is YES, and the method proceeds to Terminal C32 where it skips back to decision block 5628 and the above-identified processing steps are repeated.

From Terminal C33 (FIG. 5AR), the method 5000 begins finding charge groups, which are sets of isotope groups that have the same mass and retention times but different charge states. See block 5644. At block 5646, the method removes isotope groups with a single isotopic peak from the finding process. The method calculates a combined rank (R) at block 5648, which is the sum of a rank of average RT scores for all peaks in an isotope group and the rank of maximum peak intensity of all peaks in an isotope group. At block 5650, the combined rank is generated for each isotope group and is ordered, with isotope groups having the higher score ranked first. At block 5652, a seed isotope group (seed) is selected. Boundaries are defined at block 5654 within which are candidate isotope groups based on units of mass from the seed and within certain units of time from the RT centroid of the seed. At block 5656, a candidate isotope group is selected for examination. The method then continues to another continuation terminal ("Terminal C34").

From Terminal C34 (FIG. 5AS), a no-hypothesis is constructed for the supposition that two isotope groups belong to the same group based on an isotope group centroid model, an isotope group RT intensity centroid model, at block 5658. At block 5660, p-values are provided to gauge whether the isotope groups can be accepted or rejected as part of a charge group. The method compares, at block 5662, the candidate isotope groups to the models using a Gaussian function. A test is performed at decision block 5664 to determine whether the p-values of the candidate isotope groups are greater than a threshold. If the answer to the test at decision block 5664 is NO, the method proceeds to another continuation terminal ("Terminal C35"). Otherwise, the answer to the test at decision block 5664 is YES, and the method proceeds to block 5666 where the no-hypothesis is true and the candidate isotope groups belong to a charge group, a member of which is the seed isotope group. The method proceeds to block 5668 where the candidate isotope group is removed from the ranking. The method 5000 then proceeds to Terminal C35.

From Terminal C35 (FIG. 5AT), the method 5000 proceeds to decision block 5670 where a test is performed to determine whether there are more candidate isotope groups to consider. If the answer to the test at decision block 5670 is YES, the method proceeds to another continuation terminal ("Terminal C37") and skips back to block 5656 where the above-identified processing steps are repeated. Otherwise, the answer to the test at decision block 5670 is NO, and the method proceeds to block 5672 where the seed is removed from the ranking. Another test is performed at decision block 5674 where it is determined whether there is another seed isotope group to consider. If the answer to the test at decision block 5674 is YES, the method proceeds to another continuation terminal ("Terminal C36") and skips back to block 5652 where the above-identified processing steps are repeated. Otherwise, the answer to the test at decision block 5674 is NO, and the method proceeds to Terminal D.

From Terminal D (FIG. 5A), the method 5000 proceeds to a set of method steps 5006, defined between a continuation terminal ("Terminal E") and another terminal ("Terminal F"). The set of method steps 5006 describe the analysis of expression statistics to produce a list of instances of interest in biological samples.

From Terminal E (FIG. 5AU), the method 5000 proceeds to block 5676 where the method computes expression characteristics. The method produces expression profiles at block 5678 of all replicates in all conditions at three summarization levels (peak, isotope group, and charge group). The method calculates at block 5680 error models. At block 5682, the method performs peak squeeze. The method produces a list of all instances' features and their characteristics at block 5684. At block 5686, the method performs sequencing using parallel mass spectrometer processes. The method then continues to Terminal F and terminates execution.

Now, the mathematical basis into various techniques for identifying features of interest in biological samples is discussed. FIGS. 5B-5U illustrates method steps regarding image-registration based retention time alignment and time warping. For an image feature, such as a peak, the retention time of the peak in the LC/MS image often slightly varies in repeated runs. In order to quantitatively compare biological feature measurements among different treatments, the retention time variation in various embodiments should be corrected so that peaks from the same biological feature are aligned properly across multiple runs.

The time alignment and bias correction method in various embodiments of the present invention need not rely on peak extraction. It may be based on image registration. Image registration methods match and align images based on similarities in image contents, which are not necessarily extracted. The method steps illustrated at FIGS. 5B-5U apply image registration to correct retention time biases. Each LC/MS image is cut into small grids. By shifting the small rectangle image segment in each grid in the retention time direction or other directions, the method steps illustrated at FIGS. 5B-5U search and find a match of the segment to a selected master image. The shift from the original location to the best match location provides one bias estimation for the given retention time region. The method steps continue to derive a more reliable bias estimation for the time by considering all bias estimations from grids at the time. The method steps then construct a smooth time bias estimation curve using multiple bias estimations.

While the method steps illustrated at FIGS. 5B-5U discuss various embodiments using different correlation coefficient techniques to estimate misalignments or biases across replicates within a group or condition and the misalignments connected with combined group images across groups or conditions, some embodiments estimate misalignments or biases using the minimum of the absolute difference technique between two sub-windows as follows. Minor wobbling or drift in the retention times can limit the number of molecular ions that can be identified between samples. The method steps of various embodiments apply the alignment to rasterized LC/MS filtered image data as discussed below.

Image-registration based retention time alignment is performed as herein described: In LC/MS measurements, both the accuracy and reproducibility of the mass over charge measurements (m/z) as measured with modern MS instruments are much better than those in retention time from only LC instruments. For a given biological feature, such as a peptide, the retention time of its representative peak in the LC/MS image often will vary slightly in repeated runs (replications). In order to compare peptide measurements across different treatments, it is desirable to identify and correct potential retention time shifts so that peaks from the same peptide can align properly across multiple runs. Time alignment and shift correction in some embodiments need not rely on peak extraction but instead on image registration. Image registration methods match and align images based on similarities in the images themselves. These image characteristics need not be extracted. Various embodiments look at all the pixels in a window and matching in two dimensions to get a better sense of time alignment that can be used later to aid peak extraction and identification.

Thus, image registration is used to correct the retention time biases. The method steps in various embodiments cut each LC/MS image into small windows defining a rectangular grid. By shifting a small rectangular image segment of the grid in the retention time direction, the method steps search and find the best match of the segment to a selected master image. The shift from the original location to the location that gives the best match provides an estimate for the bias of the given retention time. The method steps derive shift estimate by considering bias estimates from mass/charge windows at a particular time range and up and down the column of all available mass/charge values. A smooth time bias estimation curve is calculated by regressing multiple bias estimates for the different contiguous time regions. Image rasterization and interpolation methods as discussed below are used to regenerate each of the LC/MS images (starting from the raw data) after taking the estimated biases into consideration. This process is warping. The warped images are likely to be properly aligned.

More specifically, the computation of the bias occurs as follows. The method steps select a master among all the slides. The master slide is the slide to align against. It is desirable to have this slide have a lot of distinct features, that is, to have a high contrast. This reference slide is selected by first computing the Base Peak Intensity (BPI) for the slide and then the standard deviation for this measure. The slide with the highest standard deviation in BPI, becomes the master slide for the group. Base Peak Intensity refers to the highest intensity value for each time point. In essence, it provides a two-dimensional summary of all the mass/charge measurements against retention time and thus, it is a chromatogram.

Next, the method steps grid the images. Each slide to be aligned against the master is divided up into (non-overlapping) time columns of a given width first. Then each column is further divided up into non-overlapping mass/charge sub-windows. By having several to many sub-windows for each time column, the method steps can estimate the final alignment for the column by combining the individual estimates for each of the component sub-windows in the mass/charge direction, that is, all estimates for one column are considered replicate estimates of the shift for that column.

Next, the method steps attempt to match sub-windows. The method steps slide each sub-window of the query image (the master) against a target image (the slide to be aligned against the master). The method steps do this one pixel at a time left and right from their actual sampling time alignment to determine where the best shift might be. The sliding does not have to be one pixel at a time; it could be done also in a manner similar to that of a coarse search. The total number of pixels that the method steps will slide in each direction will depend on the perceived accuracy of the data. The larger the search interval, the more computationally demanding the alignment will be. Sliding as many pixels as to cover a search window within a suitable time frame, such as from −3 minutes to +3 minutes from the sampling time of alignment suffices for most cases. If this is not the case a pre-shifting alignment based on BPI could be done to bring the slides closer to a match. To determine the sliding point that provides the best matching between the two sub-images being compared, the method steps compute the mean of the absolute differences between the pixel intensities for the pixels in the query sub-window. It is important to restrict computation to these pixels only because the number of pixels influences a metric of similarity and a varying number of pixels for the computations would introduce additional biases into the calculations. The distance between the two sub-windows is thus computed as follows for each shift j that translates into times between $t_0-3$ and $t_0+3$ or any other width we decide our search window to be, we compute the mean of the pixel by pixel absolute difference $$\bar{d}_j = \underset{i \in Q}{mean}\{|I_i^Q - I_i^T|\},$$

where is the intensity at the ith pixel of the query image sub-window (Q), and is the corresponding pixel after shifting the image j pixels to the left and to the right of current sample alignment (at time $t_0$). The resulting sequence of differences will reach a minimum where the best match is for the sub-images being compared. Prior application of the morphological filter, which removed noise, may enhance chances of finding this minimum. It may be that the minimum does not exist there is not a reliable estimate for the sub-window, various embodiments calculate an estimate of error for the absolute differences using an error model as discussed below. By making the master and therefore the query window to have high contrast, the differences are likely to appear as a downwards or valley like shape. However, on occasion, the target sub-image will have stronger features than the query one and taking the mean of the absolute differences may cause an upwards rise that obscures the determination of its minimum using the low-frequency method described below. In these few cases, the computation of the differences is flipped and the method steps look to minimize instead a distance defined in the same way but with the query pixels subtracted from the target ones.

Next, the method steps calculate an estimate for error for each of the pixel absolute differences. This standard error approximation is computed as follows:

$$\sigma_d = \frac{1}{N_Q}\sqrt{\sum_{i \in Q}\left(\sigma_{I_i^Q}^2 + \sigma_{I_i^T}^2\right)},$$

where $(\sigma_{I_i^Q}^2 + \sigma_{I_i^T}^2)$ is the sum of the variances for each of the pixels in the query sub-image (Q) and the target sub-image (T) for the pixels in the query, $N_Q$ is the number of pixels in the query sub-window. Next, the method steps bootstraps the estimates. For each sub-window that the method steps are aligning, the method steps have estimates for differences against the master plus an estimate of the standard error of these differences. The method steps now take the minimum of the one curve of differences $\{\bar{d}_t\}_{t \in [-3,3]}$ and call it a match. However, it is desirable to have a measurement of how good this estimate is. The method steps use a bootstrapping technique to refine the estimate of time shift that provides the match and bring in the error information. Namely, the standard error is used around the mean absolute differences to generate a random sample of differences and for each of these samples the method steps find the shift that leads to a match, that is, the shift that minimizes the differences between the sub-windows.

Next, the method steps attempt to fit an inverted Gaussian. To find a match signaled by the minimum of the absolute differences between two sub-windows, the method steps consider low-frequency changes within the window. Therefore, to find the minimum difference, the method steps fit a valley-like function shaped as an inverted Gaussian to each of the random samples generated and find the minimum of the Gaussian fit. The estimate of the ideal shift for the sub-window is then computed as the median of all bootstrap estimates. A corresponding weight is calculated as the median absolute deviation (MAD) of all bootstrap estimates, that is, the median of the deviations from the median. Here is the mathematics $$\text{MAD} = \underset{i}{median}\{|Y_i - \underset{j}{median}(Y_j)|\}.$$

Next, the method steps compute weighted mean for the column. An unbiased minimum variance estimate (UMVE) of the column shift, $shift_{col}$, can now be computed using the sub-windows shift and weight pairs $(Y_k, w_k)$ as follows:

$$shift_{col} = \left(\frac{1}{\sum_{k=1}^{n} w_k}\right)\sum_{k=1}^{n} w_k Y_k.$$

To assure that this is unbiased and minimum variance, the weights $w_k$ are defined as the inverse of the variance estimates for each window, that is $$w_k = \frac{1}{\sigma_{Y_k}^2} \approx \frac{1}{(1.4826\text{MAD})^2}.$$

Next, the method steps smooth out outlier column estimates. To avoid cases where a column shift might be very different from neighboring shifts, the method steps pass the final column shifts through a Tukey Bi-weight 3-point running mean. In other words, the method steps take each shift and look at its neighboring column shifts and adjust its values in a way that is proportional to the median deviation between them. Next, the method steps interpolate using a cubic spline. A cubic spline if fitted to the discrete shift column estimates to calculate the smoothly varying transformation that will be applied to the raw data to align it. Once a smooth transformation has been determined to align in the time direction, the method steps can implement the transformation and thus synchronize all the samples.

The method steps attempt to align between conditions. The same image registration method described above is applied between conditions. After warping and re-rasterizing (described below) takes place for the within-group replicate images, these are combined by taking the mean of all replicates in the group for each pixel. These combined images are then put through the same image registration process described above and a between-shift is computed for each of the conditions. The final shift, to be applied to the raw image data, will be the aggregate of a pre-shift (if any), the within time shift, and the between time shift.

Next, the method steps perform image warping and re-rasterization. Having derived a smooth time indexing transformation trough the steps described above, the method steps now go back to the raw images and re-interpolate the raw data as it re-rasterizes it. A new rasterization is needed to base feature extraction and other downstream analyses upon. This time the data will be indexed by correcting their original sampling times through shifting them with the aggregation of the three components determined by the image registration based time alignment algorithm (pre-shift, within and between-groups corrections). The new (rasterized) data is obtained by linear interpolation using the corrected time indexes for the data points. Data for each grid point is interpolated using the neighboring points to the right and to the left using the new adjusted time indexes in deciding adjacencies. The resulting rasterized images are warped to its best alignment, that is, stretched out or shrunken in places depending on what the time alignment calculation results dictated. Any inconsistencies in their retention time have been removed and the method steps are ready to proceed with the analysis of the features.

After the misalignments or biases are estimated by the techniques discussed hereinbefore or hereinafter, image rasterization and interpolation can be used to regenerate each of the LC/MS images from raw data after taking the estimated biases calculated by the time alignment process into consideration. These new images are warped and aligned for feature extraction as explained hereinabove in some embodiments and hereinbelow in other embodiments. The method steps illustrated at FIGS. 5B-5U may use various interpolation techniques. In some embodiments, the interpolation techniques are based on linear interpolation in two-dimensional space. Interpolated values are intensities of image points in two-dimensional space that comprises retention time in one dimension and mass-over-charge (or mass/charge) in another dimension.

In various embodiments, a mass/charge interpolation process is used at the beginning of image processing to convert input raw data based on different raw mass/charge coordinates to the same mass/charge grid for one technology based group of replicates. The mass/charge interpolation process assumes that the mass/charge grid is not regular. The input data into this mass/charge interpolation process includes one-dimensional array of raw retention time data, two-dimensional array of raw mass/charge data, two-dimensional array of raw intensity data, one-dimensional array representing result mass/charge grid points. The process produces a two-dimensional array of grid intensities for raw retention time and mass/charge grid points. More specifically, the mass/charge interpolation process includes the following steps: Linear interpolation is performed for left and right neighbors for each mass/charge grid point. Retention time coordinates are maintained without any changes. No distance threshold is used. The mass/charge interpolation process refrains from interpolation where both grid point neighbors are the same.

In some embodiments, a fast retention time interpolation process is used before alignment image processing step when bright peak information is important in the analysis and isolated points should be eliminated. The fast retention time interpolation process assumes that the retention time grid is regular with fixed retention step. The input data into the fast retention time interpolation process includes one-dimensional array of raw retention time information, two-dimensional array of mass/charge information belonging to the previously created grid, two-dimensional array of intensity information, retention time grid step, and interpolation distance threshold. The fast retention time interpolation process produces a two-dimensional array of grid intensities for retention time and mass/charge grid points. More specifically, the various steps of the fast retention time interpolation process include using distance-based linear interpolation of left and right neighbors for each retention time grid point. Mass/charge coordinates are maintained without any changes. If a grid point does not have left and right neighbors inside a particular interpolation distance, then the process produces resultant intensity at zero.

In various embodiments, an adaptive retention time interpolation process is used for precise interpolation in the retention time direction. Mass/charge coordinates are maintained without any changes. Resultant grid points are based on shifted input raw retention coordinates. Resultant intensity information is scaled based on an input scale vector. The input data into the adaptive retention time interpolation process includes a one-dimensional array of raw retention time information, a two-dimensional array of mass/charge information belonging to a previously created grid, a two-dimensional array of intensity information, retention time grid step, one main interpolation distance threshold, a solid interpolation distance threshold, a small interpolation distance threshold, a one-dimensional array of retention time shifts, and a one-dimensional array of intensity scale coefficients. The adaptive retention time interpolation process produces a two-dimensional array of grid intensities for retention time and mass/charge grid points. The steps of the adaptive retention time interpolation process can be summarized by an interpolation decision tree, which begins with a first test to determine whether a point has direct neighbors. If the answer to the first test is no, the grid value is zero. If the answer to the first test is yes, a second test is performed to determine whether the point has neighbors on both sides. If the answer to the second test is yes, the process applies linear interpolation to get grid value. Otherwise, if the answer to the second test is no, a third test is performed to determine whether the point is solid on one side. If the answer to the third test is yes, the process applies linear interpolation with zero substitution. If the answer to the third test is no, the process performs a fourth test which determines whether the point is an isolated point. If the answer to the fourth test is yes, the process uses isolated point value. Otherwise, the answer to the fourth test is no, and the grid value is determined to be zero. More specifically, the steps of the adaptive retention time interpolation process is a distance-based linear interpolation of left and right neighbors for each retention time grid point. Neighbors (direct neighbors) are found inside main interpolation distance with retention time shifts applied to each raw retention time coordinate. If there is only one direct neighbor on one side of grid point, then the process tries to find what kind of point it is. If there is more points on the one side in the distance of solid distance threshold (in some embodiments, about two times the main interpolation distance), then the resultant intensity is calculated based on special rules. First, the process creates a new virtual raw point with zero intensity and position symmetrically to a direct neighbor with the distance equal to the distance to the closest solid point. If the new virtual point is on another side from current retention grid point then the grid intensity value is the linear interpolation of direct neighbor and new virtual point otherwise result intensity is zero. This part of the process helps to make image peak boundaries smoother. If direct neighbor is not solid, then the process refrains from interpolating (or make bigger) isolated points. In this case, the process is checking to see if the direct neighbor is in a small interpolation distance (half of main interpolation distance). If the retention time grid and raw points are in the small distance, then grid intensity is set equal to the raw intensity. Otherwise, it is set to zero. All result intensities are scaled in some embodiments using input scale coefficient.

In some embodiments, a sift filtering operation is performed to eliminate very long image stripes in the retention time direction. The operation is bitwise and can be made to work with the whole image at a time. Input data into the sift filtering operation includes a two-dimensional bit array of image intensities, retention time peak length threshold, retention time gap length, and mass/charge gap length. The sift filtering operation produces a sifted two-dimensional bit array of image intensities. More specifically, the steps of the sift filtering operation includes the elimination of gaps in the retention time direction and the mass/charge direction. The operation is based on retention gap length that is equal to four retention grid steps and mass/charge gap length that is equal to two mass/charge grid steps. The elimination is performed by standard morphological dilate filter. After elimination of gaps, the new image is filtered in the retention time direction to eliminate (e.g., by setting intensity to zero) mass/charge stripes with retention time length bigger then the retention time peak length threshold.

The method steps illustrated at FIGS. 5B-5U also help to form a composite image for peak feature extraction. An exemplary method for feature extraction is executed after image alignment. See FIGS. 5V-5AT. The method first combines replicates (if available) within each treatment group by averaging pixel intensities across replicates. The combined image in each treatment group has higher signal-to-noise ratio than that in images of individual replicates. Then, the method merges the combined images from all treatment groups into one composite image by various suitable techniques, such as taking the maximum intensity among all combined images at each pixel location.

As long as biological features are present in any one of those treatment conditions, their peaks are likely to appear in the composite image. A peak can be found by looking at connected pixels that have intensity above a background noise parameter, such as the mean, median, maximum, minimum, or the standard deviation at a particular location. Peaks extracted from the composite image should match all peaks in all individual images before combination. The peak contour boundaries extracted from the composite image may be used in some embodiments to estimate peak expression intensities (volume under surface) in each image of individual LC/MS run. Thus, various embodiments of the present invention perform image matching first and peak extraction second.

In various embodiments of the present invention, when experiment conditions are similar between an existing experiment and a new experiment, all LC/MS images in both experiments can be combined together, aligned, and form one composite image for feature extraction. Because it should not be difficult to find previously identified isotope groups in the new composite image, the method in some embodiments uses previously available peptide information to annotate the new experiment. The remaining peaks are those that have not been annotated in the previous experiment.

Various embodiments of the present invention include parametric models for LC/MS peak and peak-isotope-group characterization. Peaks extracted from a composite image can still be noise. Experiment artifacts shown in the image can also be extracted as peak features. Various embodiments of the present invention allow a method for characterizing these peaks so that scores can be assigned which is based on how close the peaks look like real peaks, and not peaks formed from artifacts or noises. Peak characterization and scoring are helpful to filter out false positives in various analyses later.

At least two parametric models for peak characterization are made available by various embodiments of the present invention. The first is a chromatogram model for an ideal LC retention time peak using a suitable distribution function, such as a modified Maxwell distribution function or any other suitable function that describes the physical characteristics of elusion. During peak characterization, the model parameters are optimized to find a model that matches the extracted peak from the composite image. The time peak score measures how good the match is. For a perfect match, the score is one. When the peak is noisy or is artifact, the score decreases towards zero. The second model is for the m/z peak in the MS continuum using a suitable distribution function, such as a Gaussian distribution function or any other suitable function that describes the mass continuum resolution characteristics. The m/z peak score characterizes the quality of peak in the m/z direction. When the m/z peak is clean and well defined, the score is close to one. When the extracted peak is contaminated or is a combination of two overlapping peaks, the m/z peak score drops.

Several other parameters are available to score the goodness of a isotope group. (1) Average-time-peak-score is the mean of time peak scores of all peaks in the isotope group; (2) Average-m/z-peak-score is the mean of m/z peak scores of all peaks in the isotope group; (3) Time-peak-misalignment-score measures the relative deviation of centroids of PC time peaks in the isotope group from the mean centroid. A good isotope group where all peak centered at the same retention time gives a score close to zero; (4) M/z-distribution-score measures how well the measured MS spectral isotopic peak intensity distribution in the isotope group matches to a theoretical isotopic intensity distribution. A well matched isotope group has the score near one. Poorly matched isotope group has the score close to zero. (5) P-value for the m/z-distribution-score provides a confidence measure on how reliable the m/z-distribution-score is. When the number of isotopic peaks detected in the isotope group is very small, such as 2 or 3, even though the match may seem perfect, the probability of matching by random chance is high. In this case the p-value is closer to one. When the found match is less likely a random event, the p-value is small and closer to zero.

Method steps illustrated in FIGS. 5V-5AT detect and split overlapping peaks. During initial peak extraction, inevitably several overlapped peaks may be mistakenly detected as one large peak. These overlapped peaks should in various embodiments be detected and split. The exemplary image processing pipeline detects and splits overlapped peaks in the time and the m/z directions separately. In each direction, peaks that have exceptionally wide width comparing to the overall width distribution of other peaks are detected. Then, these wide peaks are split if possible. The method steps for detecting and the splitting may be repeated several times to ensure splittable peaks are split. After splitting, the method steps check peaks again and erase long tails in the retention time of some long lasting peaks.

To detect the overly wide peaks, in one embodiment, a distribution (histogram) of peak width for all peaks are computed. There are many suitable ways to define peak width. One suitable way is to use the peak centroid width, which in one embodiment is defined as 4 times the square-root of the intensity-weighted difference square between each time point and the centroid of the peak. A statistical model based approach is developed to help split overlapped peaks. In some embodiments, each peak is modeled with a Gaussian function. An overlapped peak includes multiple mixed Gaussian shaped peaks. An optimization process is applied to find the best fit of the multi-Gaussian model to the measured peak. A null-hypothesis is constructed for the case where all peaks are completely overlapped and not splittable. P-value of the hypothesis test measures the probability of the null is true. When the p-value is small, the method rejects the null-hypothesis. In other words, the peaks are splittable. By setting the p-value threshold to a desired level, confidence in correctly identifying overlapped peaks can be selectively managed. This statistical approach is much more objective and robust than overlapping detection methods that are based on arbitrary rules and cut-offs. The optimized multi-Gaussian model can also be used to define the method of splitting. In an example of a two-peak model, the two Gaussian functions allow us to determine the location of overlap and the intensity contribution from each individual peak to the overlapped peak. With this information, we can either split the two peaks at the location of the overlap or compute the intensity fraction of each peak in the measured total intensity (area under curve or volume under surface) based on the proportion of the areas under the two modeled peaks.

Method steps as illustrated at FIGS. 5V-5AT provide statistical-pattern-recognition approach to estimate charge state, identification of isotope groups, and charge groups. The method steps provide a statistical pattern recognition technique to associate peaks into isotope groups. There is no need to use arbitrary time and m/z range thresholds in this method. Users in various embodiments define acceptable sensitivity and specificity probabilities. These probability thresholds need not be arbitrary. They in some embodiments are based on a user's risk tolerance. In accordance with one embodiment, the method steps first rank detected peaks in the descending order of the peak intensity, the time peak score and the m/z peak score. Isotope group identification is started from highly expressed and best looking peaks at the beginning of the rank list. After a isotope group is identified, all peaks that belong to the isotope group are removed from the rank list. Then, the method steps go down the list and work on the next best peak remaining in the list.

The peak association process in the method steps illustrated at FIGS. 5V-5AT depends on estimation of the isotope charge state. In various embodiments of the present invention, a charge estimation method works with data even those coming from complex samples. The method steps, in one embodiment, initially construct an MS continuum by the weighted sum of individual continua around the retention time centroid of the main peak from the top of the rank list. The weighing is larger for continua that have their retention time near the centroid than those far away from the centroid. This weighted average method increases the signal-to-noise ratio and decreases the influence of peaks from adjacent isotope groups. Then ideal models are created at different charges states. Each model is matched to the weighted sum continuum and the method steps find the one that has the best match. The charge state of the best matched model is the charge that the method steps apply in the peak association for finding one or more isotope groups.

For the given top ranked peak and its charge state, the method steps search for isotopic peaks that belong to the same isotope group. These isotopic peaks can have m/z lower or higher than the top rank peak. For each possible isotope, the method steps compare detected peaks to a theoretical model. The method steps construct a null-hypothesis that the detected peak completely matches with the model. The method steps use p-values of the hypothesis test in both m/z and retention time directions to gauge whether the detected peak as the expected isotope can be accepted or rejected. Acceptance p-value (e.g., >0.6) can be used to control the detection sensitivity and the rejection p-value (e.g., <0.1) can be used to control the detection specificity. For the p-value in between, a watch list is maintained to see whether some other isotope groups will claim a detected peak as an accepted isotope or overlapped isotope. In one embodiment, the method steps allow one peak to be claimed by two isotope groups when the p-values in both isotope groups are lower than the acceptance level and higher than the rejection level. Users can control their risk tolerance in detection sensitivity and specificity by properly setting the p-value threshold. The objective detection sensitivity and specificity acceptance criteria remain consistent in different m/z, expression abundance, signal-to-noise conditions. Furthermore, the use of theoretical isotope intensity distribution of the given mass and charge to match with the detect peak intensity enhances the computation.

As previously discussed, error models for LC/MS data analysis are provided. LC/MS intensity measurements are likely to have to deal with noise. An error model in the exemplary image processing pipeline specifies the noise in the pixel intensity measurement. In one embodiment the LC/MS error model has three error components: additive error, Poisson error, and fractional error. The error model provides intensity error estimation for pixel intensity measurements. The method steps 5AU estimate errors of peak intensity (sum of pixel intensities within the peak) and isotope group intensity by properly propagating pixel intensity errors to the peak level and the isotope group level. The error models help to reduce false positives during analysis when the number of replicates is small. Error-model based intensity transformation method can also be used to stabilize intensity variance during ANOVA or other statistical tests for differential expression.

More specifically, the variance of the modeled error is estimated as $\sigma_{mod\ eled}^2(i,j) = \sigma_{add}^2(i,j) + POISSON \cdot I(i,j) + FRACTION^2 \cdot I^2(i,j)$, where i and j iterate over the retention time and mass/charge directions, and I is the intensity measurement. The variance can be viewed as the Taylor-series expansion of the intensity-dependent variance. The equipment-dependent parameters POISSON and FRACTION are estimated for a given equipment technology type, such as specific mass spectrometer, during error model development. They are fixed as long as the technology remains unchanged. Poisson and fraction noises can be slightly different in different equipment, but they are usually stable over time for a given piece of equipment. There are many possible methods to model the additive component. Feature extraction process as described hereinabove and hereinbelow provides some background estimations based on pixels that surround an image feature. Regardless of what background measurement method being used, for a given feature, some embodiments use the averaged information from a surrounding region much larger than one spot to model the additive term in the above error model. When developing the error model, the values for parameters POISSON and FRACTION are estimated.

The discussion hereinabove generally describes method steps illustrated at FIGS. 5A-5AU. The discussion hereinbelow more describes the method steps in more details. To summarize, the method applies morphological filters and estimate background noise; combines replicates; merges the combined and filtered images to form one composite image; labels image features; splits overlapped peaks; computes feature parameters; groups isotopic peaks; aggregates isotope groups; computes peak statistics; computes charge group statistics; performs peak-level analysis, such as differential analysis or non-differential analysis; performs isotope-group level analysis, such as differential analysis or non-differential analysis; and performs charge group level analysis, such as differential analysis or non-differential analysis.

FIGS. 5D-5R illustrate method steps for aligning LC/MS images. FIG. 5D illustrates method steps for determining the master image. The master or reference image is used to align all other images representing replicates in an experiment. The image with the highest standard deviation of the interpolated base peak intensity data is used as the master.

FIGS. 5E-5R illustrate method steps for aligning images representing replicates. A typical image representing a replicate (a replicate image) has a retention time of about forty to seventy minutes. Usually, although not always, a replicate image is mismatched from the master image in a non-linear fashion in the time direction. To address this problem, the method calculates alignment shift values at suitable time intervals, such as 1.5 minutes. Points at a given retention time (for a suitable mass/charge range) are shifted to correct the mismatch problem when the shift values are determined. More specifically, these shift values are in some embodiments used as control points to create an interpolated function, such as a spline or a piece wise linear function, that dictates the shift value for each time point in the replicate image. In various embodiments, the replicate image or target image is logically divided into suitable sub regions, such as 1.5 minutes by 20 mass/charge levels. The size of the sub region can vary based on the density of the LC/MS data. In some embodiments, a target image has from 60-80 sub regions in a column. Although the shift values will vary within a single time interval, redundant measurements of shift values allow the method to choose the best shift value for each column of time interval. To increase accuracy, the method in various embodiments uses, but are not limited to, two measurement techniques for each sub region or cell. This allows the method to determine the final shift value for each time interval for both techniques, but also allows the method to discard the entire shift value for the time interval if all techniques do not agree within some delta. The actual shift values for each sub region of the target image are determined by averaging the final shift values calculated by the measurement techniques.

To actually determine the shift values per cell, the sub region of the replicate is shifted over a larger sub region of the master. In some embodiments, a suitable number of pixels (n number) per shift step is shifted, such as one pixel. At each shift step, two step shift values are calculated in various embodiments. The step shift values are put into an array of step shifts which represent how well the target image matches the underlying master image. Each step shift value is calculated from a different measurement technique. The step shift values quantify how well the current step is aligned. Although any number of techniques can be used to calculate step correlation values, the method uses correlation coefficient technique and overlap fit value technique.

Regarding the correlation coefficient technique, the method first finds the minimum target intensity value for the sub region where the intensity is greater than zero. Next, all target pixels in the sub regions have the minimum value subtracted from their intensity. The same is repeated for the master sub region. Next, all points in the sub region are iterated over. During this iteration over the data, if either the target pixel intensity is greater than zero or the master pixel intensity greater than zero, the common logarithm is applied to both intensity values unless one of the values is zero; in which case, zero is simply used instead of applying the common logarithm. The master and target common logarithm intensity values are added to corresponding master and target arrays. A correlation coefficient is calculated from these two arrays. The common logarithm intensity is used to allow both high and low intensity pixels to have an impact on the step shift value.

Another measurement technique is called overlap fit value technique and is based on the following mathematics: −(zero-MasterNonZeroReplicateCount+zeroReplicateNonZero-MasterCount), where the zeroMasterNonZeroReplicate-Count and the zeroReplicateNonZeroMasterCount are counters. In executing the overlap fit value technique, the method looks at the amount of overlap between the target and master sub regions. Intensity values are not used in some embodiments in the calculations, giving very low intensity parts of the image and very high intensity parts of the image the same impact on the overlap fit value. When the two sub regions are in alignment, the overlap fit value should approach zero, indicating that for every pixel in the target that has a non zero intensity, there is a corresponding non zero intensity pixel in the master. This technique emphasized a more holistic view of overlap to determine the best overlap fit value. A negative sign is factored into the above equation so that the best match becomes the highest value in the collection of overlap fit values for this technique.

Two arrays of measurement values are generated in executing the two techniques (one array describing correlation coefficients and the other overlap fit values). These arrays are then searched by the method to find the highest peak, indicating the best correlation between target and master sub regions at the max of the highest peak. The arrays of measurement values have a running mean applied (obtained using 3 points in some embodiments but in other embodiments other suitable number of points can be used). The method finds the highest peak for each of these arrays of alignment values. The ideal case is a graph with a single steep peak, indicating the most accurate shift location. See FIG. 2E. When the peaks of the graph are located and sorted in descending order based on peak height, the max peak will be used by the method if the following criteria are met. First, the peak should have at least some number of points. Ten points are detected in some embodiments, but could be any number depending on how vigorous the outlier rejection needs to be in various embodiments. Outliers are features that are not of interest. More specifically, the number of points between the two inflection points that make the peak should be greater than or equal to ten. Second, the second highest peak cannot be higher than some percentage of the highest peak, such as forty-five percent, although the percentage could vary depending on how many replicate sub regions are used per column and how vigorous the outlier rejection needs to be. With many small replicate sub regions, the method can be more aggressive in outlier rejection because of the potentially high number of redundant correlation values. With fewer larger replicate sub regions, aggressive outlier rejection could dismiss too much data.

When shift values have been determined for each target sub region, using multiple techniques, all of the shift values for each technique are examined to determine a final column shift value per technique. Each technique is in some embodiments handled independently. All of the shift values in a time interval column for a single technique are binned into a histogram, using a suitable bin size, such as 0.20, although the bin size can change depending on how exact the alignment needs to be. A larger bin size will increase the chances of finding a viable shift value for the time interval, but will decrease the exactness of the final shift value. Once the shift values for a technique are put into a histogram, the histogram is sorted in descending order, based on the number of members that belong to each bin of the histogram. All of the values in the highest bin are then averaged to determine a final shift value for the technique. The following criteria is in various embodiments used by the method to determine the final shift value: The bin with the most members should in some embodiments have at least four members although this number could differ depending on how vigorous the outlier rejection needs to be. If the bin with the second most members has within 90% of the number of members of the largest bin, then the members of both bins are averaged together to produce a final shift value.

After a number of final shift values have been calculated for a time interval column, (using different measurement techniques) the final shift values are combined into a single shift value based on the following criteria: The shift values for all techniques should in various embodiments should be within some suitable time of each other, such as 0.15 minutes, but this could differ based on how exact alignment needs to be. The shift values from the techniques are averaged together to produce a final shift value per time interval. These individual shift values are then used as control points to interpolate exact retention time shift values for each retention time.

One purpose of the method at FIGS. 5T-5AT is to extract image features from the composite image. The method at FIG. 5T discusses steps for superposing a grid (with multiple grid rows and grid columns) over the composite image to facilitate feature extraction. The grid lines are equally spaced, but the method need not be constrained by this. The grid allows features to be classified in a grid row, a grid column, or a grid cell. The grid has several parameters that may be used in computation. For example, the "median mass/charge peak width" grid parameter is the median of all feature mass/charge centroid widths in a grid row whose features have feature peak intensity greater than the median peak intensity.

The method at FIG. 5U discusses steps for computing feature boundary and feature parameters. Many suitable parameters can be calculated. A feature volume is defined as the sum of all intensities of the feature $$\left(\sum_i \sum_j x_{ij}\right).$$

If $x_{i,j}$ represents the intensity of the i'th mass/charge value and j'th time point for a peak, the mass/charge intensity is the sum of the intensities for a particular mass/charge value $$\left(\sum_j x_{ij}\right)$$

and retention time intensity is the sum of the intensities for retention time value $$\left(\sum_i x_{ij}\right).$$

The "feature sum intensity square" parameter is the sum of all intensity squares of the feature $$\left(\sum_i \sum_j x_{ij}^2\right).$$

The "feature pixels" parameter is the number of data points with intensity greater than zero. The "feature mass/charge base start" parameter is the mass/charge value before the first mass/charge value of the feature, if it exists; otherwise it is the first mass/charge value of the feature. The "feature mass/charge base end" parameter is the mass/charge value after the last mass/charge value of the feature, if it exists; otherwise, it is the last mass/charge value of the feature. The "feature mass/charge peak intensity" parameter is the maximum mass/charge intensity $$\left(\max_i \left(\sum_j x_{ij}\right)\right).$$

The "feature mass/charge centroid" parameter is the centroid of the mass/charge values for the feature, weighted by the mass/charge intensities. The centroid is defined as $$\left(\frac{\sum_i w_i x_i}{\sum_i x_i}\right),$$

where w is a vector of retention time or mass/charge and x is a vector of intensity weights. A "feature mass/charge centroid width" parameter is defined as the centroid width of the mass/charge values for the feature, weighted by the mass/charge intensities. The "centroid width" is in some embodiments defined as four times a centroid standard deviation, which is defined as $$\left(\sqrt{\frac{\sum_i (w_i - c)^2 x_i}{\sum_i x_i}}\right),$$

where c is the centroid, w is a vector of retention time or mass/charge, and x is a vector of intensity weights. The "feature mass/charge centroid skew" parameter is the centroid skew of the mass/charge values for the feature, weighted by the mass/charge intensities. The centroid skew is defined as $$\left(2\frac{\sum_i (w_i - c)^3 x_i}{\sum_i x_i}\right),$$

where c is the centroid, w is a vector of retention time or mass/charge, and x is a vector of intensity weights. The "feature mass/charge peak" parameter is the mass/charge value that has the maximum mass/charge intensity; if there are multiple mass/charge values that have the same maximum mass/charge intensity, the method in various embodiments chooses the mass/charge value of the middle one identified by a middle index; the middle index is computed by rounding up; for example, if the mass/charge values are indexed by indexes n1, n2, . . . , nk, the peak mass/charge value is the one indexed by nk/2, the term "k/2" being rounded up to the next integer. The "feature time peak" parameter is the time value that has the maximum time-intensity. The "feature time centroid" parameter is the centroid of the retention time values for the feature, weighted by the retention time intensities. The "feature time centroid width" parameter is the centroid width of the retention time values for the feature, weighted by the retention time intensities. The "feature time centroid skew" parameter is the centroid skew of the retention time values for the feature, weighted by the retention time intensities. The "feature time base start" parameter is the time point before the first time point of the feature, if it exists; otherwise, it is the first time point of the feature. The "feature time base end" parameter is the time point after the last time point of the feature, if it exists; otherwise, it is the last time point of the feature. The "feature time peak intensity" parameter is the maximum retention time intensity.

The method at FIG. 5V discusses steps for extracting peaks, a type of feature, by looking for islands of connected pixels above a range of values, such as non-zero. An image feature corresponds to a biological feature that may be of interest, such as a peptide, which appears as a peak in the composite image. The image feature is an area of two-dimensional space of mass/charge dimension and the retention time dimension where one more intensities form a peak. Each image feature has a boundary which includes the smallest rectangle that completely encloses the feature in the mass/charge and retention time coordinates.

Figure 5W:
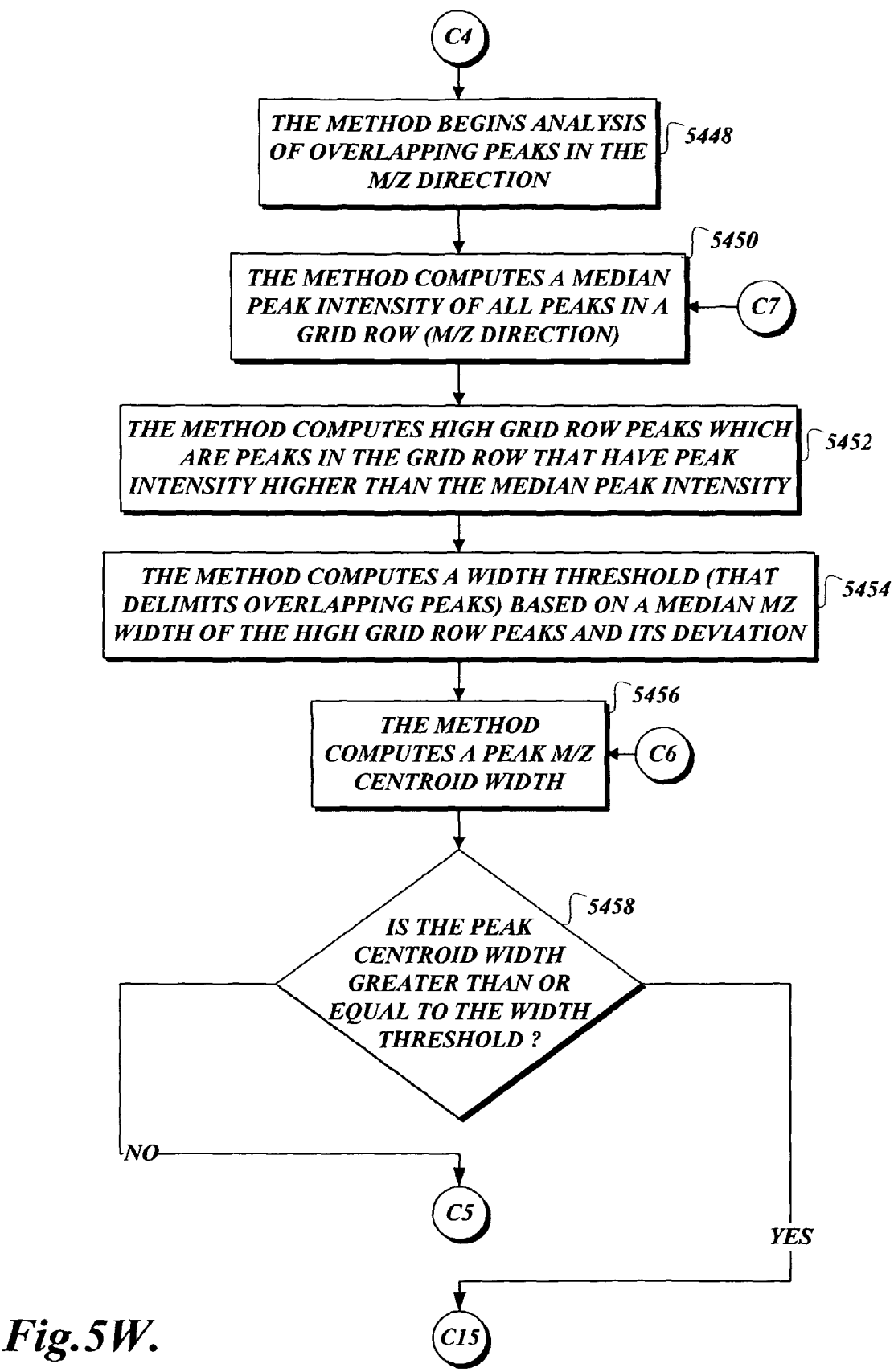

The method at FIGS. 5W-5AG discusses steps for finding features that represent multiple features (e.g., multiple peaks), and splits them into separate features. As a general overview, in some embodiments, features are split if they are overlapped in the mass/charge direction or retention time direction. Once a feature is determined to be overlapped, it is split using one of two procedures. If there is a large enough difference between the peaks and the intermediate valley (high contrast feature), the splitting is done at the valley, without the need for any model fitting. Otherwise, the valley is more precisely determined by fitting a two-peak Gaussian model to the wide feature. More specifically, first, high-contrast wide features are split. Splitting is done alternately in the mass/charge and the retention time direction, for several iterations, such as three. In other words, the following steps are repeated multiple times: find mass/charge overlapped features, and split the high-contrast ones; and find retention time overlapped features, and split the high-contrast ones. Afterwards, The low-contrast overlapped features are split. As before, splitting is done alternately in the mass/charge and the retention time direction several times, such as three. Whenever a feature is split or trimmed, the feature boundary and other feature parameters are in some embodiments recalculated. In various embodiments, the median mass/charge and retention time width and deviation are computed on the features before any splitting.

Figure 5X:
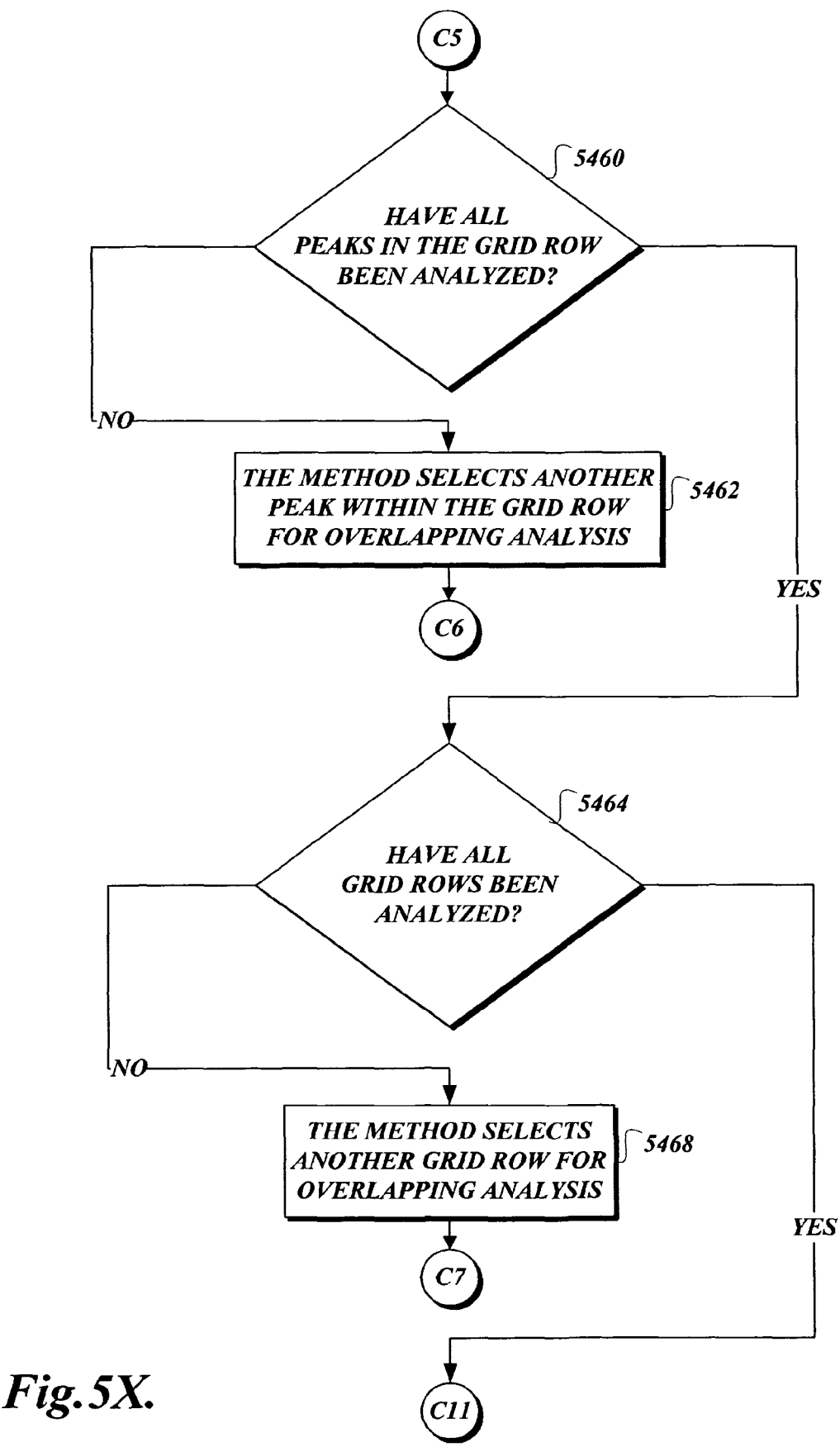
Figure 5Y:
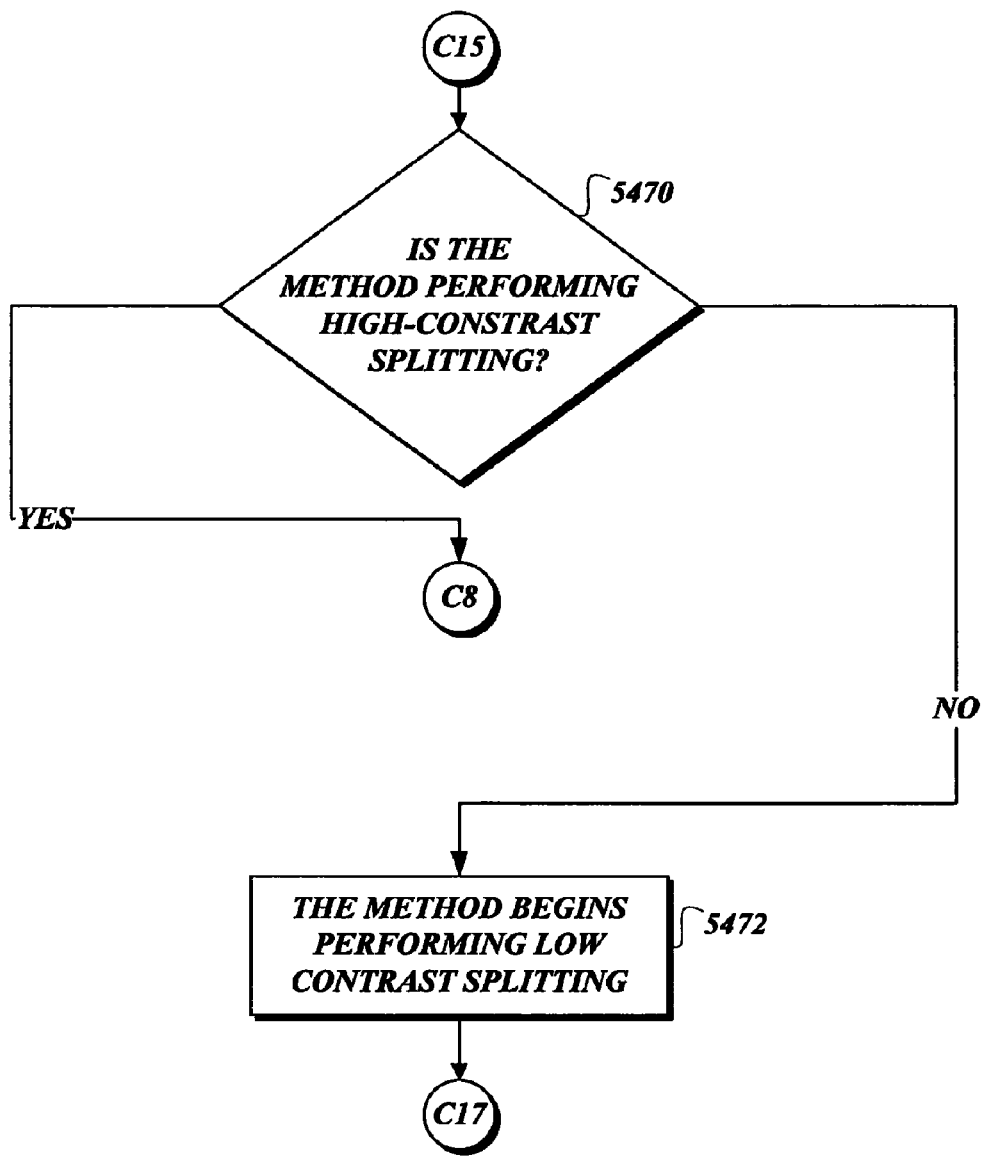

FIGS. 5W-5Y illustrate method steps for finding overlapped peaks in the mass/charge direction. The method find features that are unusually wide in the mass/charge direction as compared to the average feature within the same mass/charge grid row as follows: The method defines high grid row features to be a subset of the features in a given grid row that have peak intensity greater than the median peak intensity. The median peak intensity is computed among all features.

The median mass/charge width w is the median of the mass/charge widths of the high grid row features. The median mass/charge width standard deviation is calculated as $s_w=1.483*\text{median}(|w_i-w|)$. The method marks a feature as an overlapped mass/charge feature, if its centroid mass/charge width $w_i$ is greater than or equal to a product of a constant and $(w+s_w)$, where the constant is in some embodiments set at two.

FIGS. 5Y, 5AB-5AD illustrate method steps for finding overlapped peaks in the retention time direction. The method defines high features to be a subset of all features that have peak intensity greater than the median peak intensity. The median peak intensity is computed among all features. The median retention time width w is the median of the time-widths of all high features. The median retention time width standard deviation is: $s_w=1.483*\text{median}(|w_i-w|)$. The method marks a feature as an overlapped retention time feature, if its centroid retention time width $w_i$ is greater than or equal to a product of a constant and $(w+s_w)$, where the constant is in various embodiments set at five.

Figure 5Z:
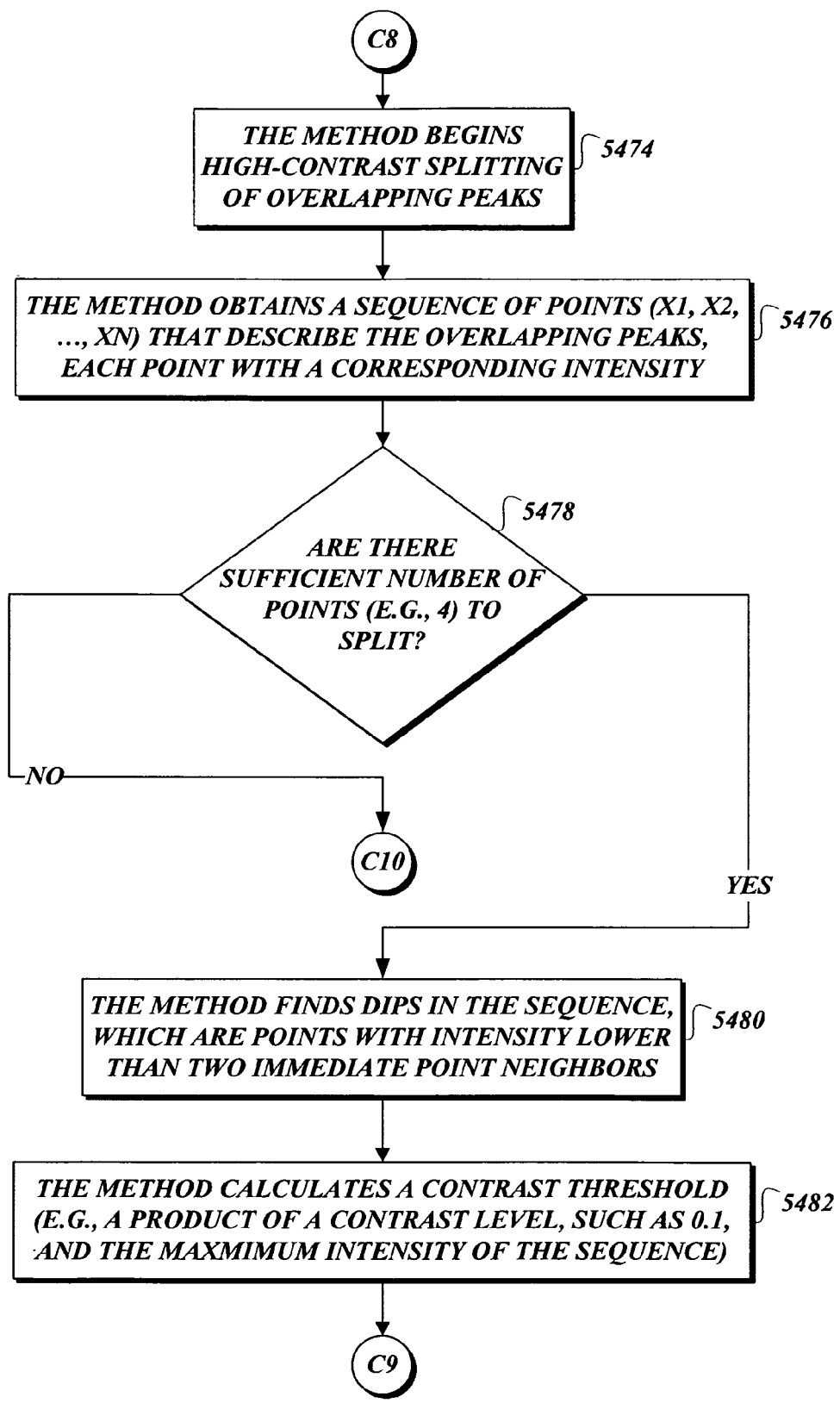
Figure 5A:
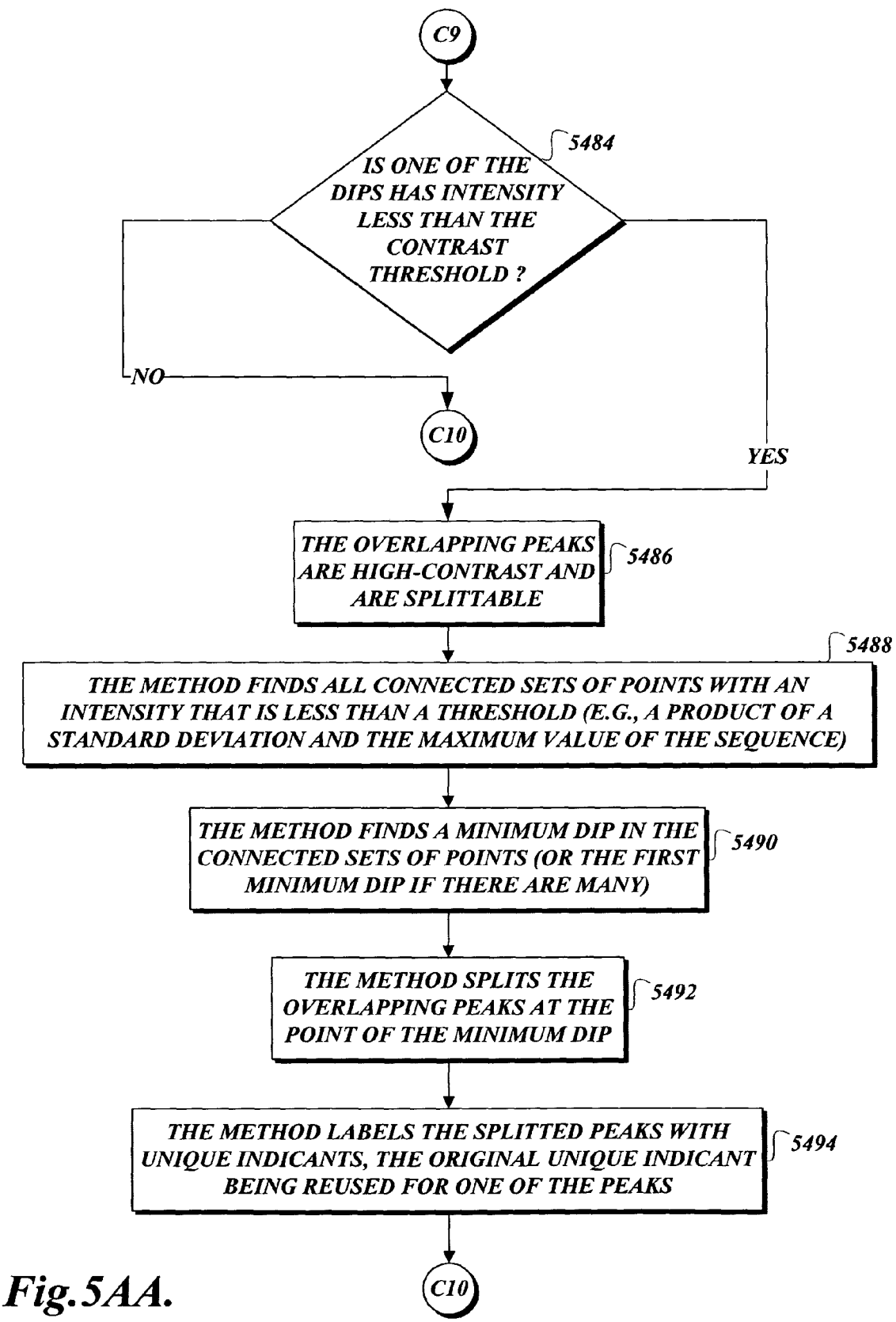
Figure 5A:
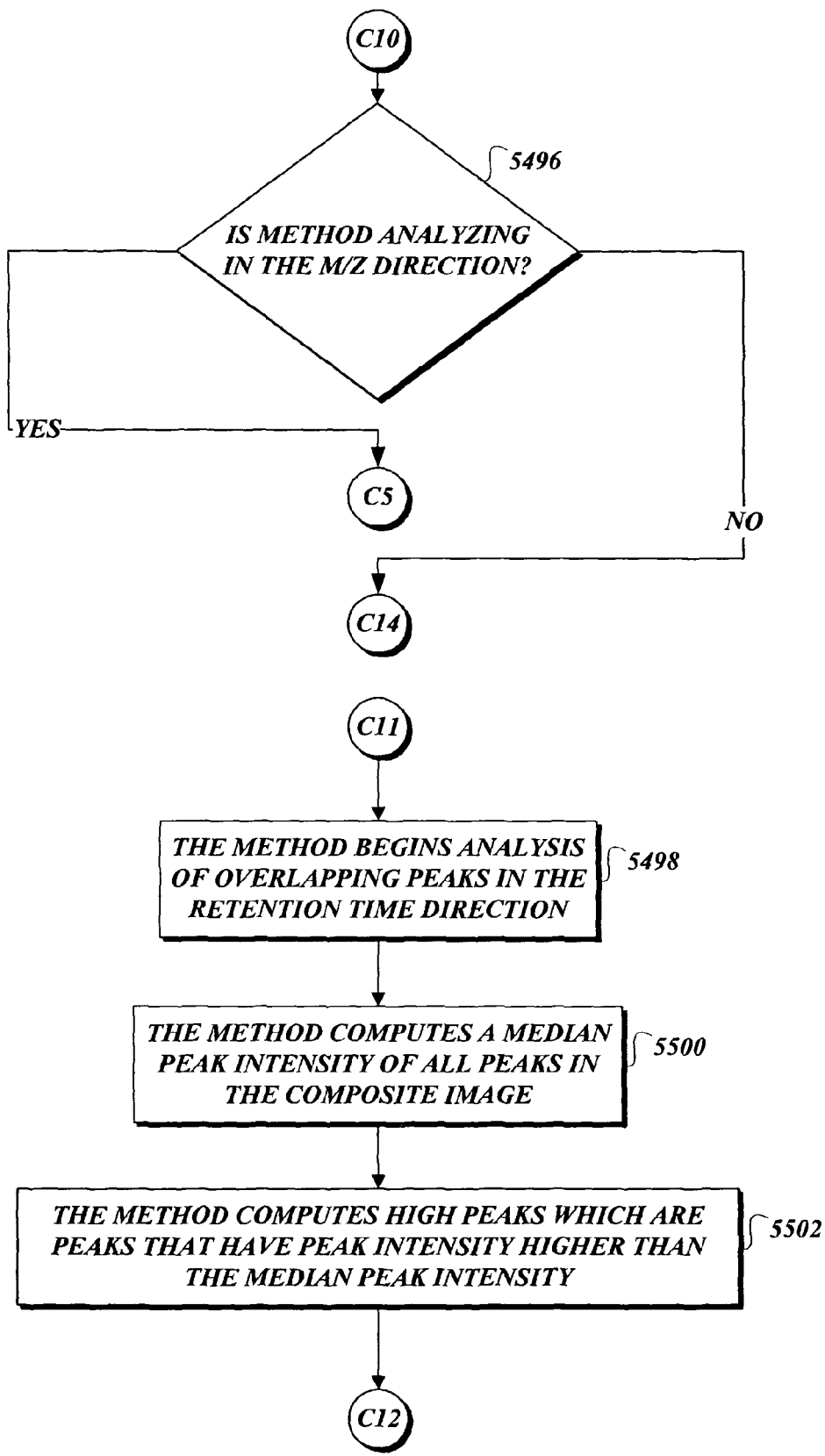
Figure 5A:
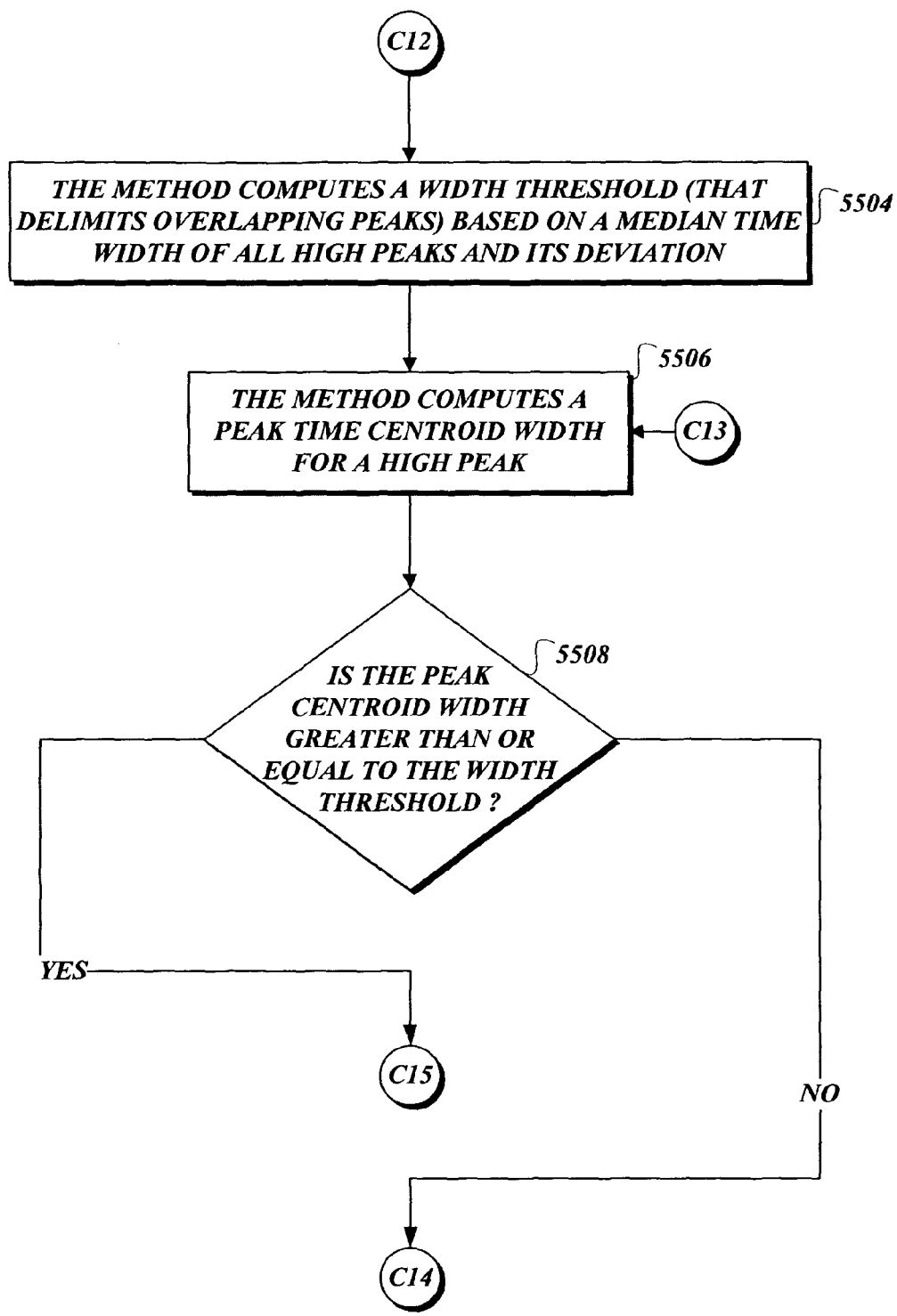
Figure 5A:
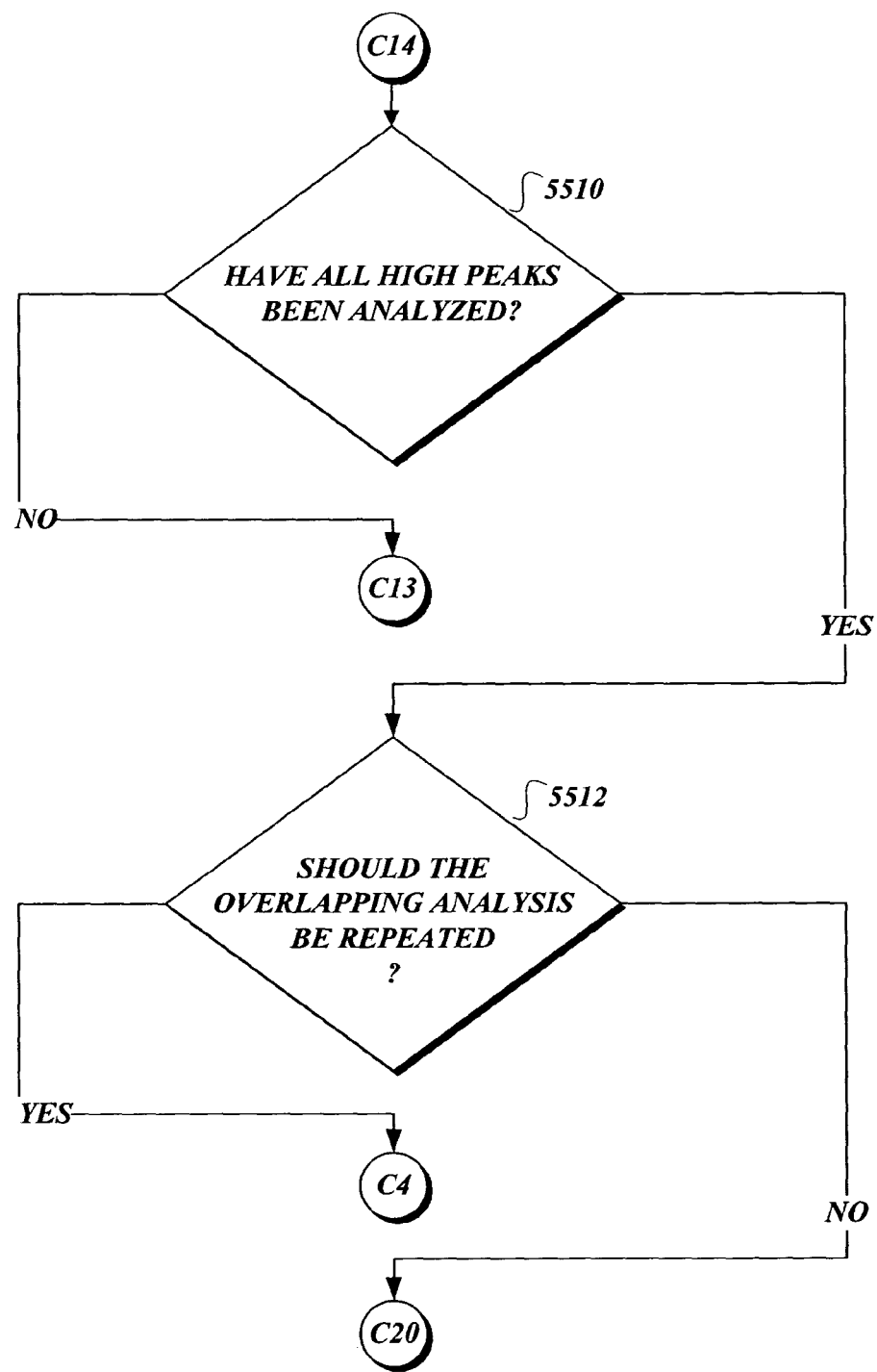
Figure 5A:
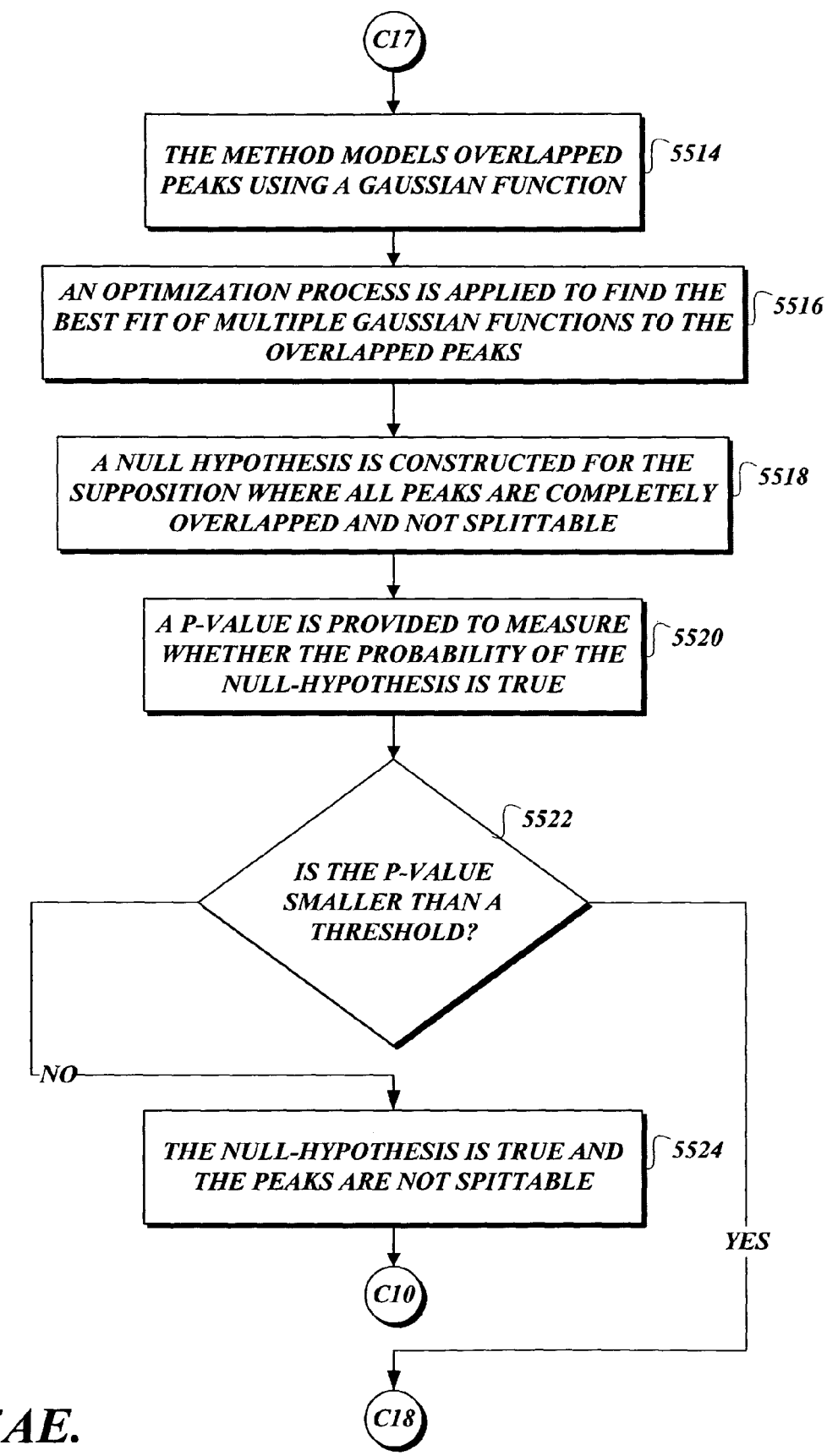
Figure 5A:
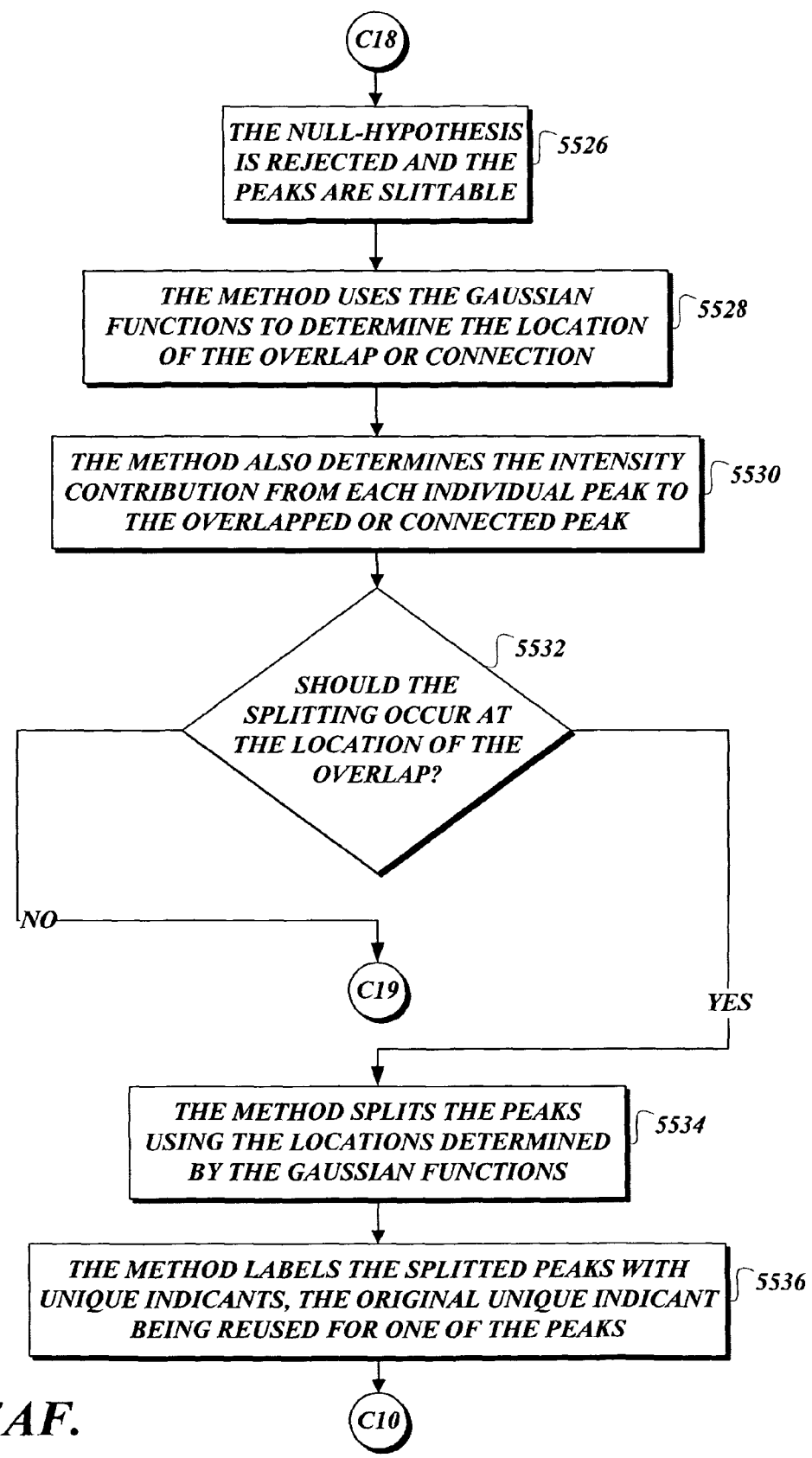
Figure 5A:
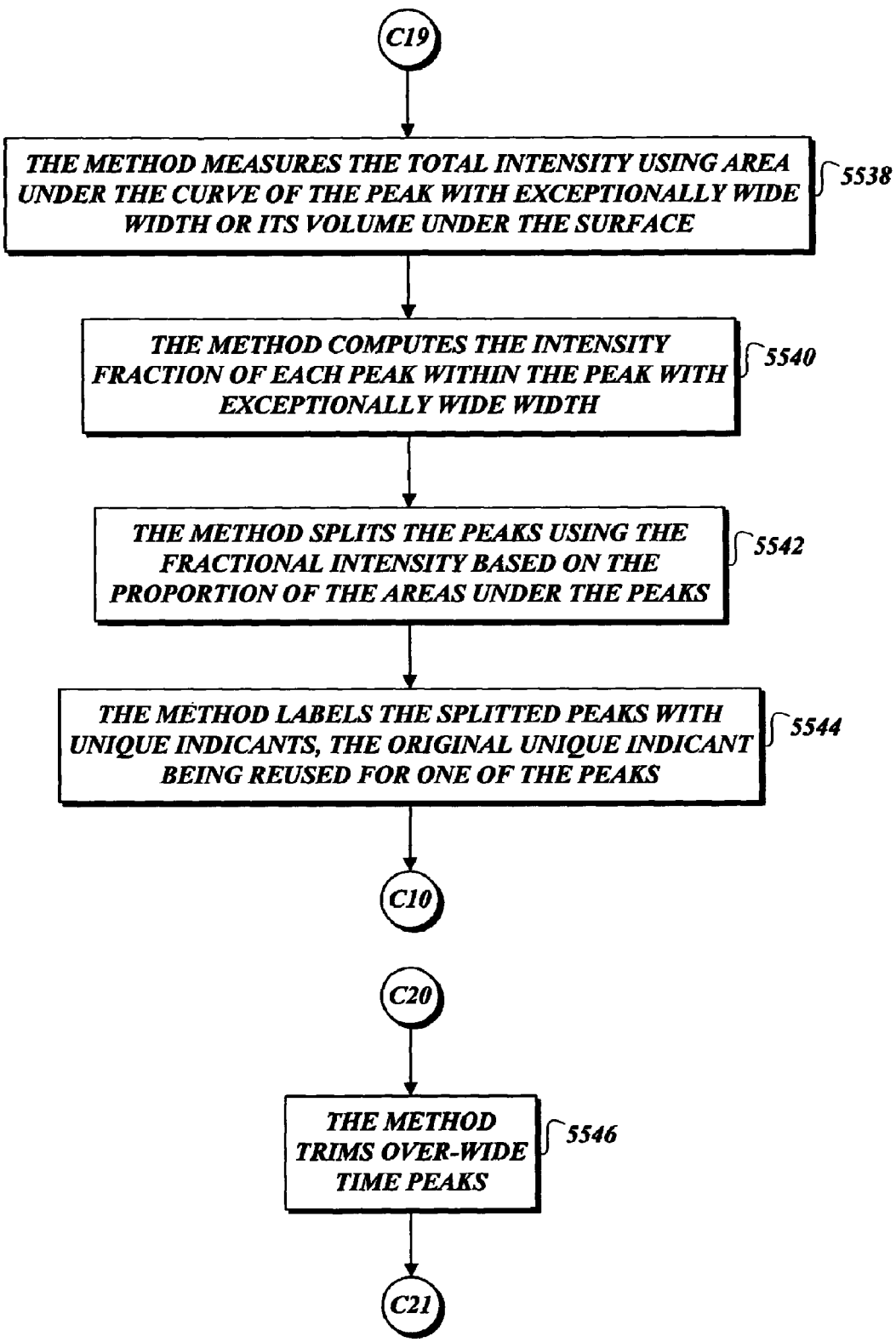
Figure 5A:
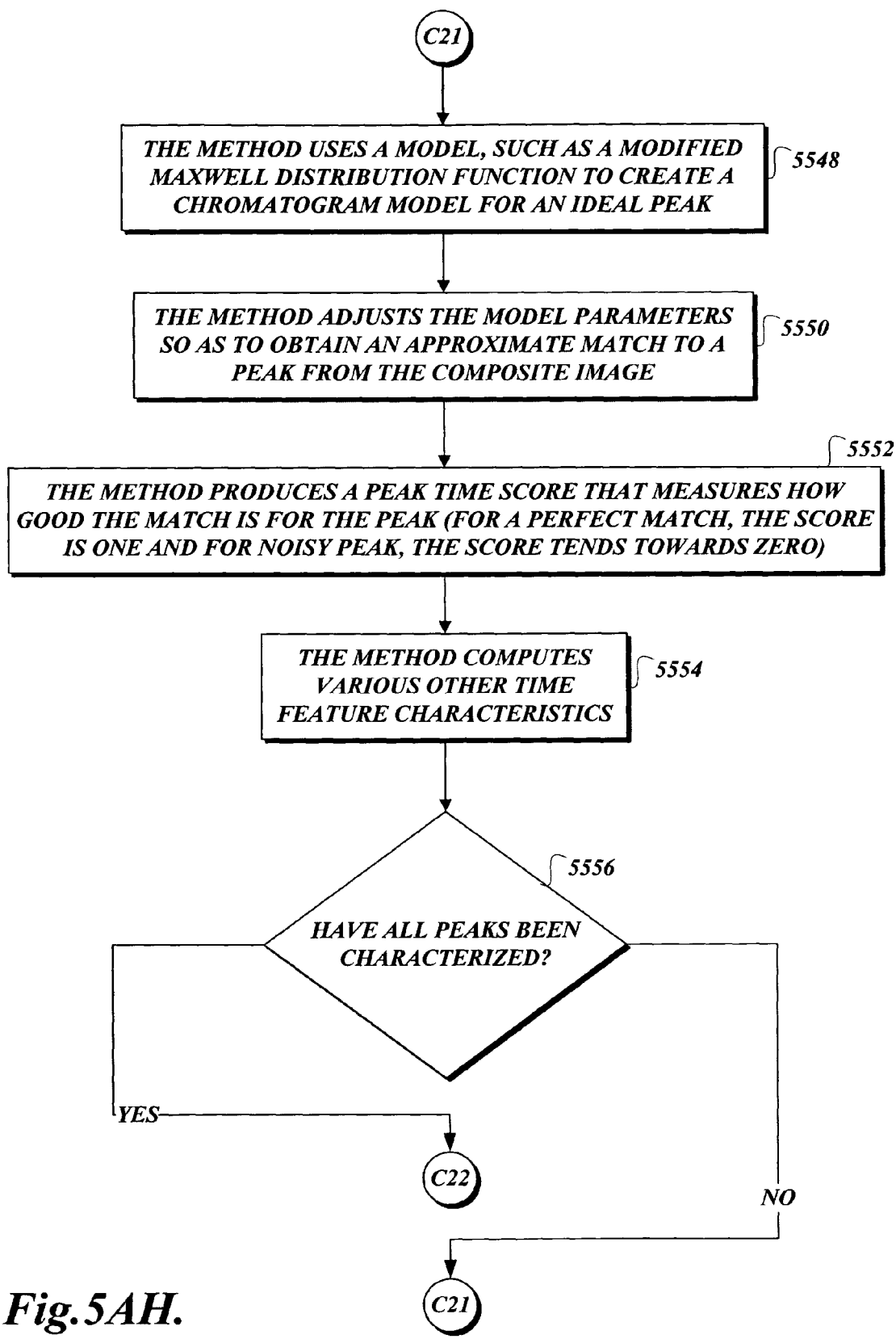
Figure 5A:
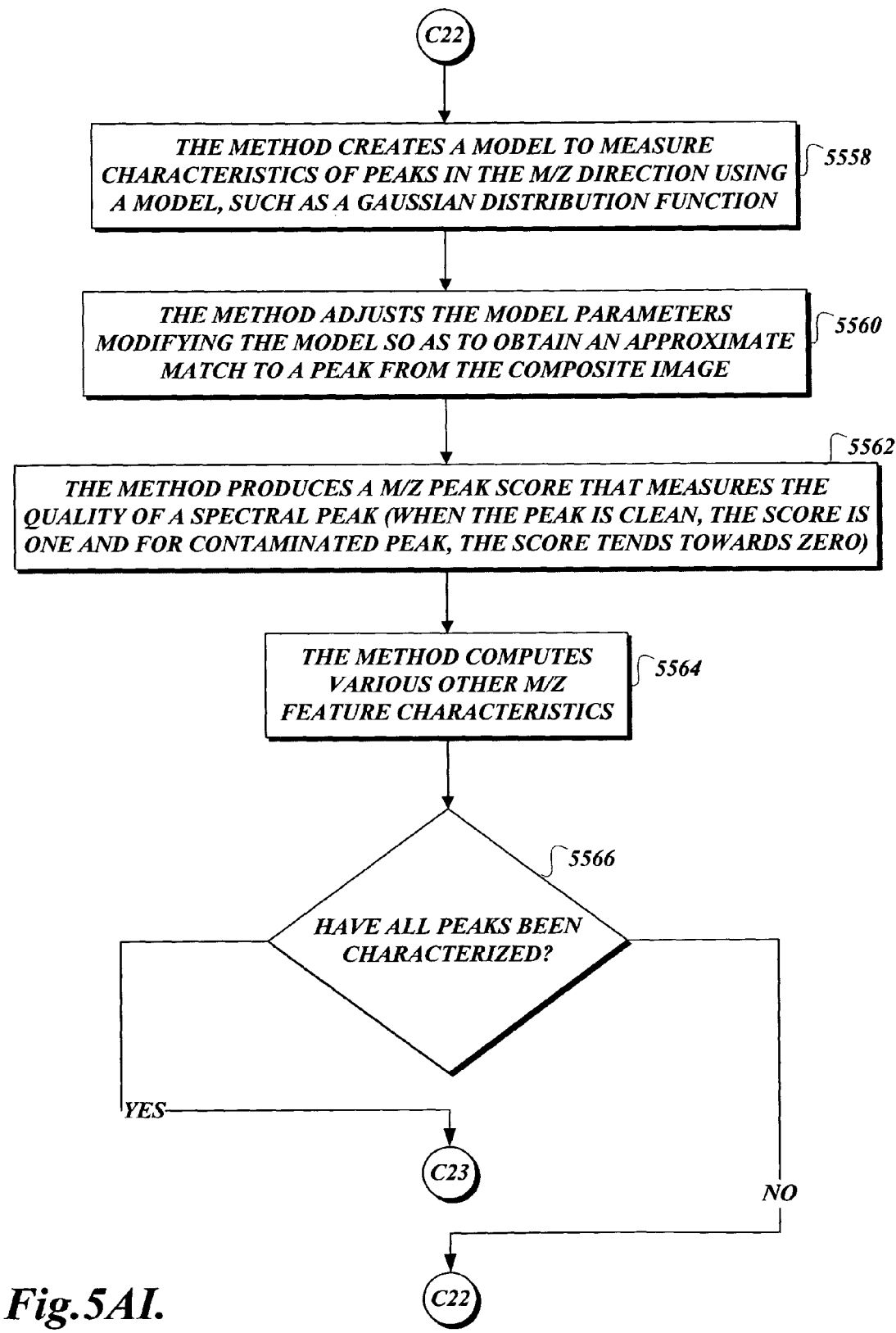
Figure 5A:
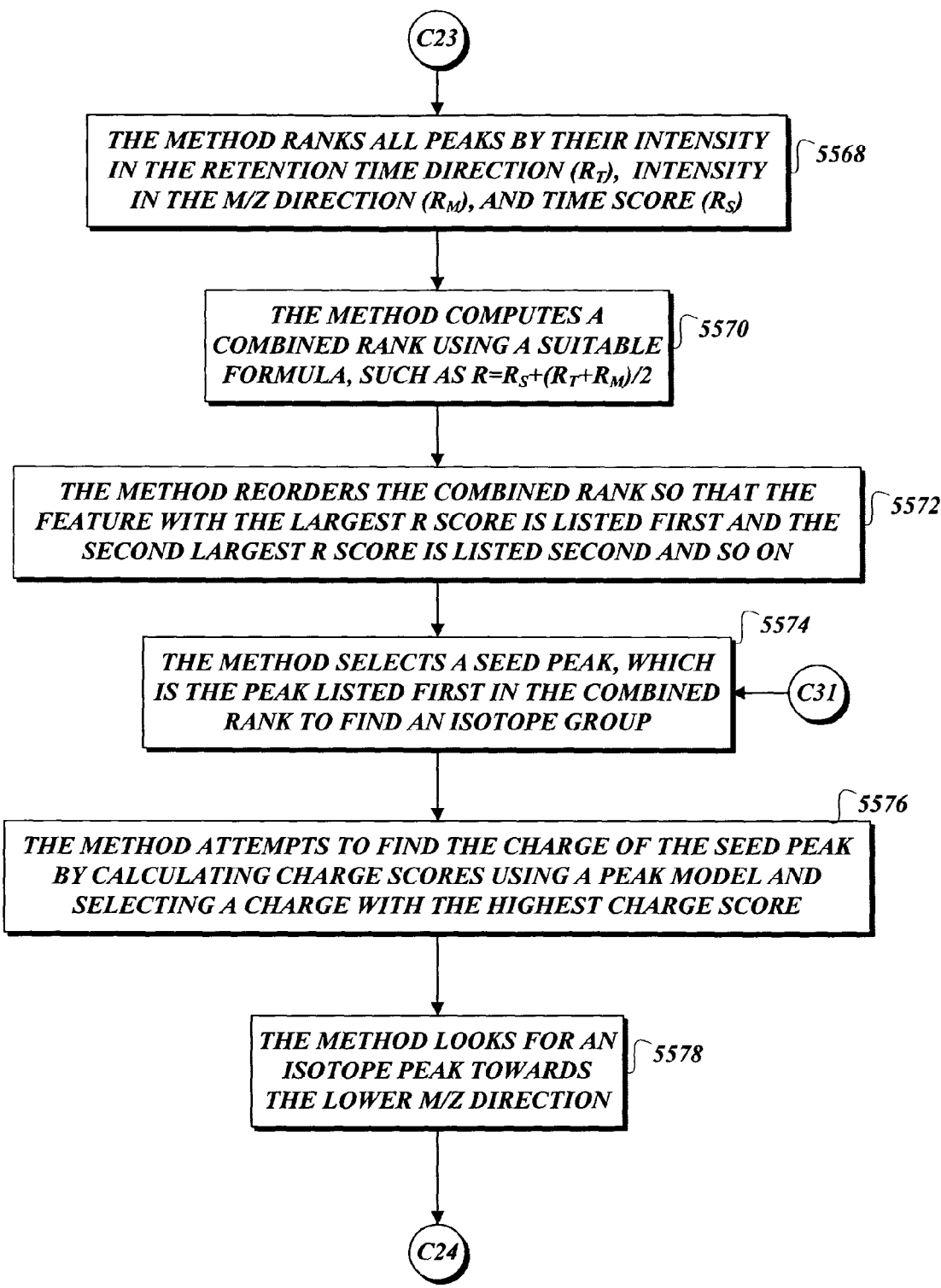
Figure 5A:
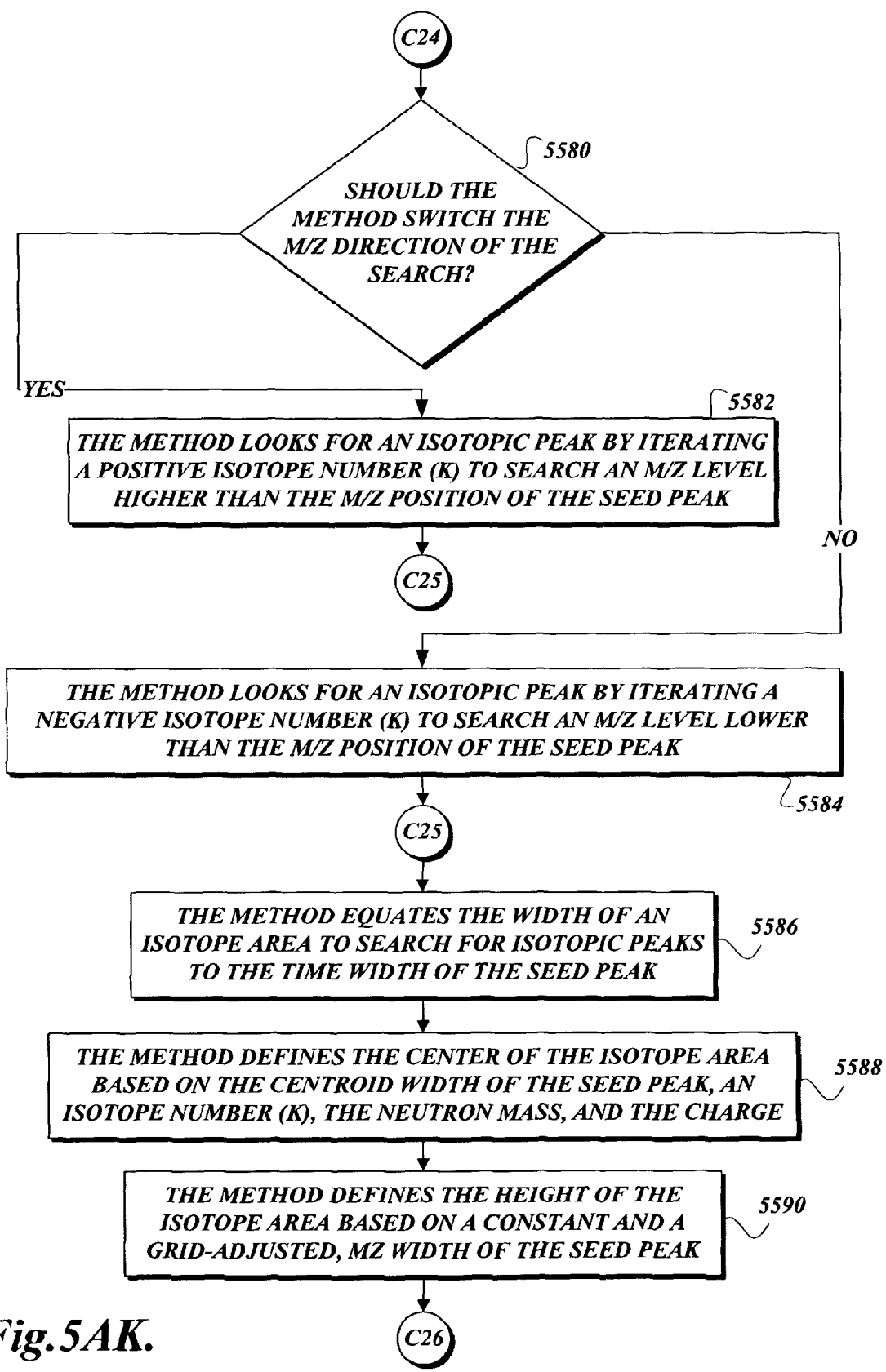
Figure 5A:
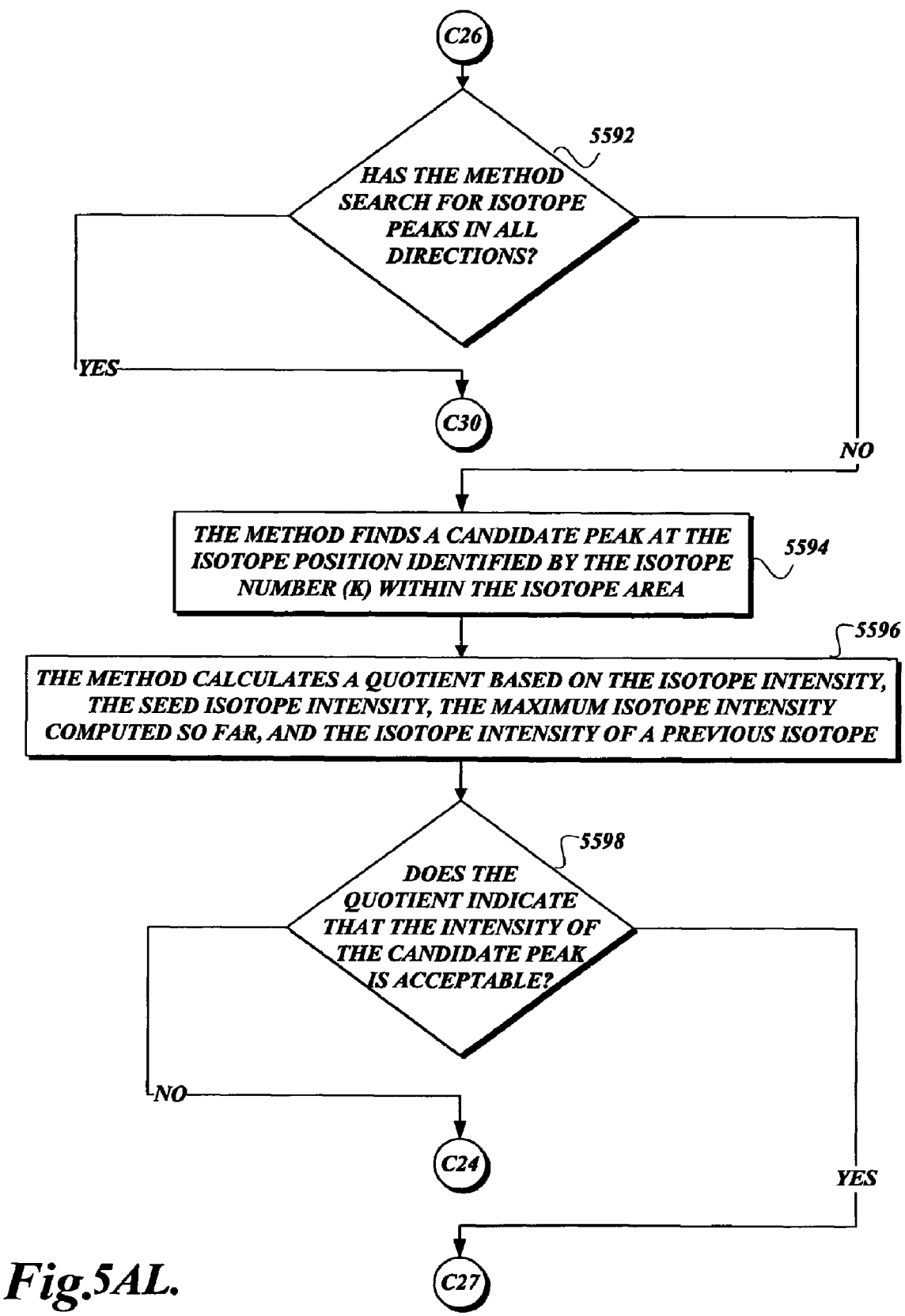
Figure 5A:
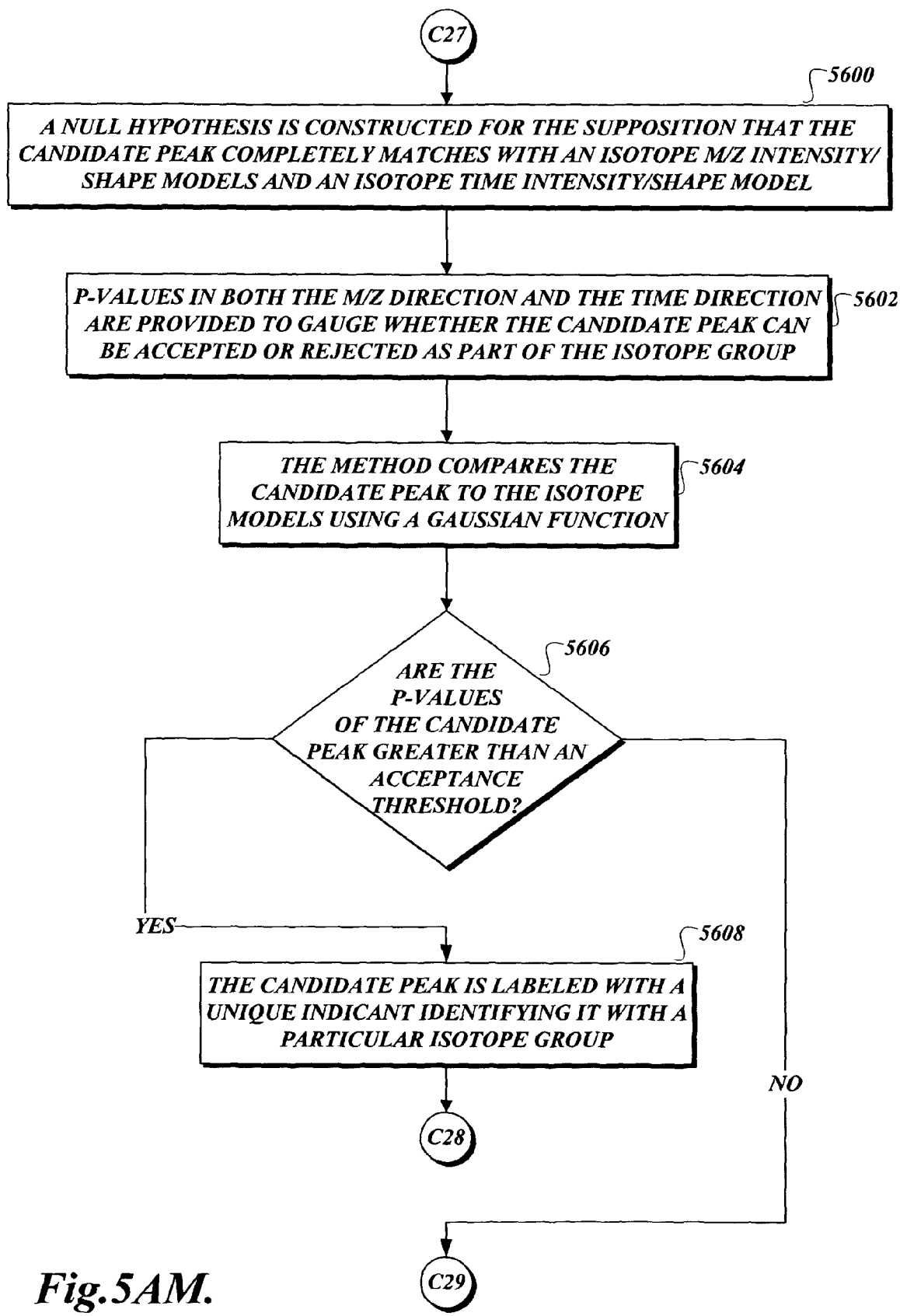
Figure 5A:
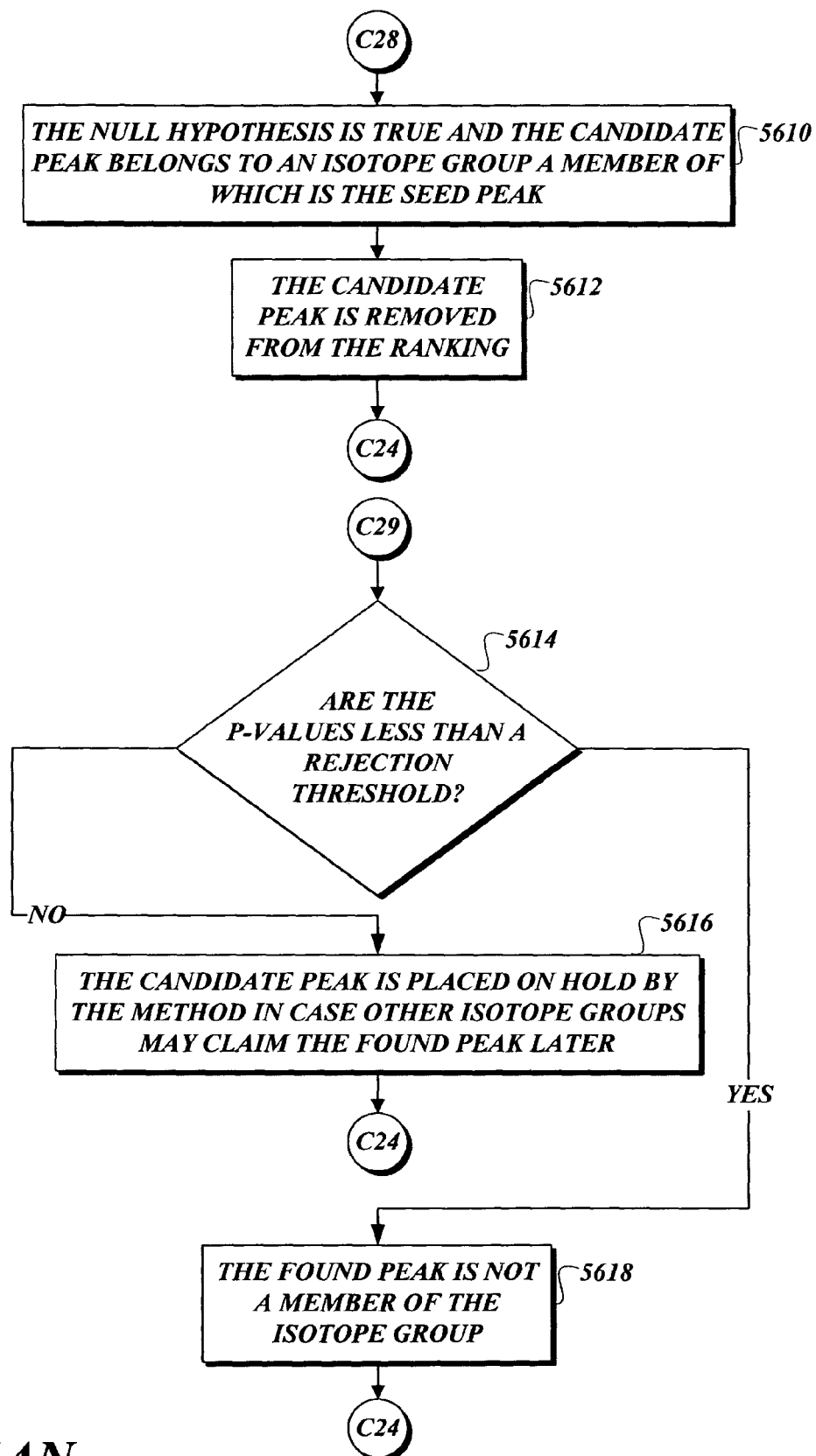
Figure 5A:
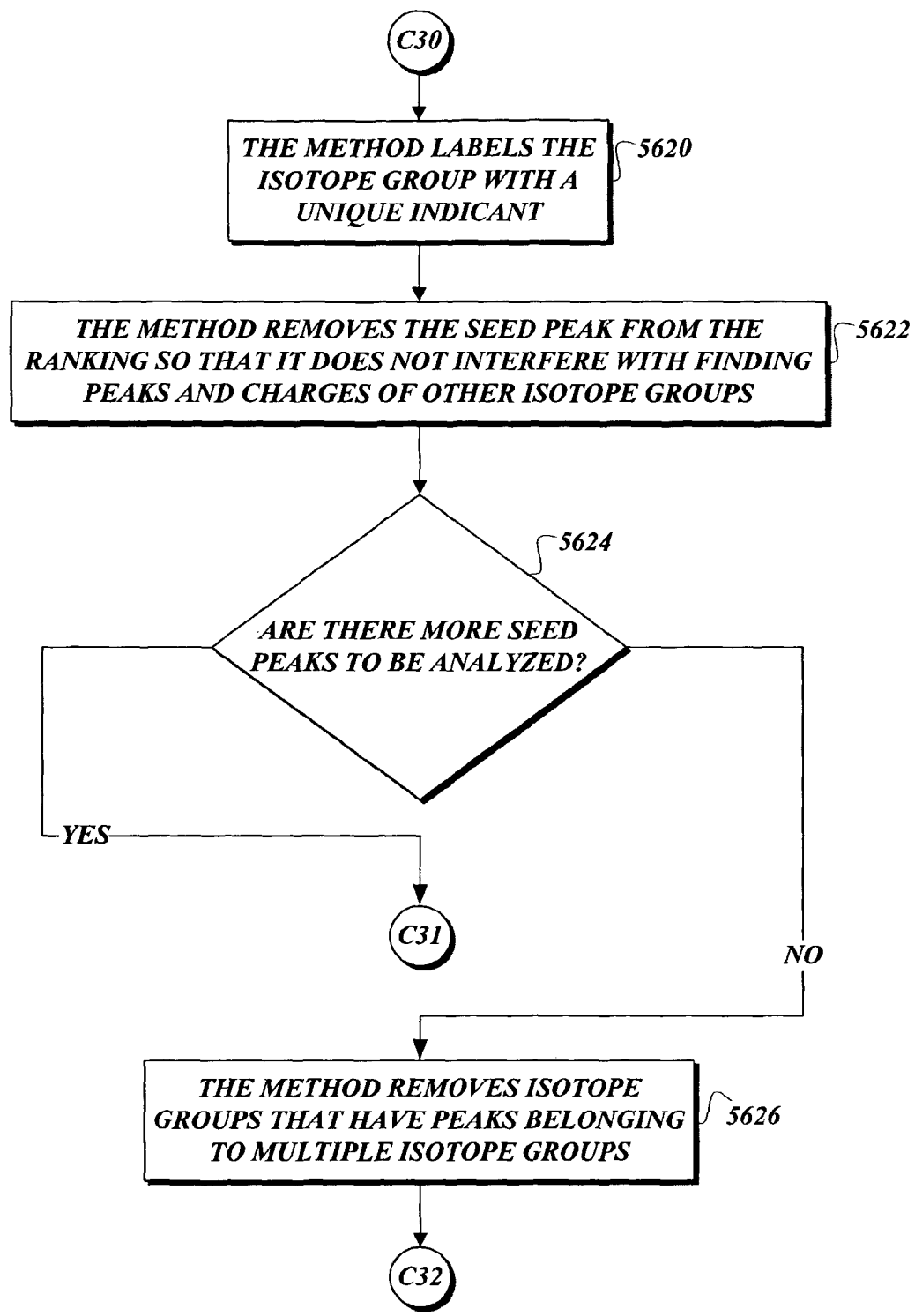
Figure 5A:
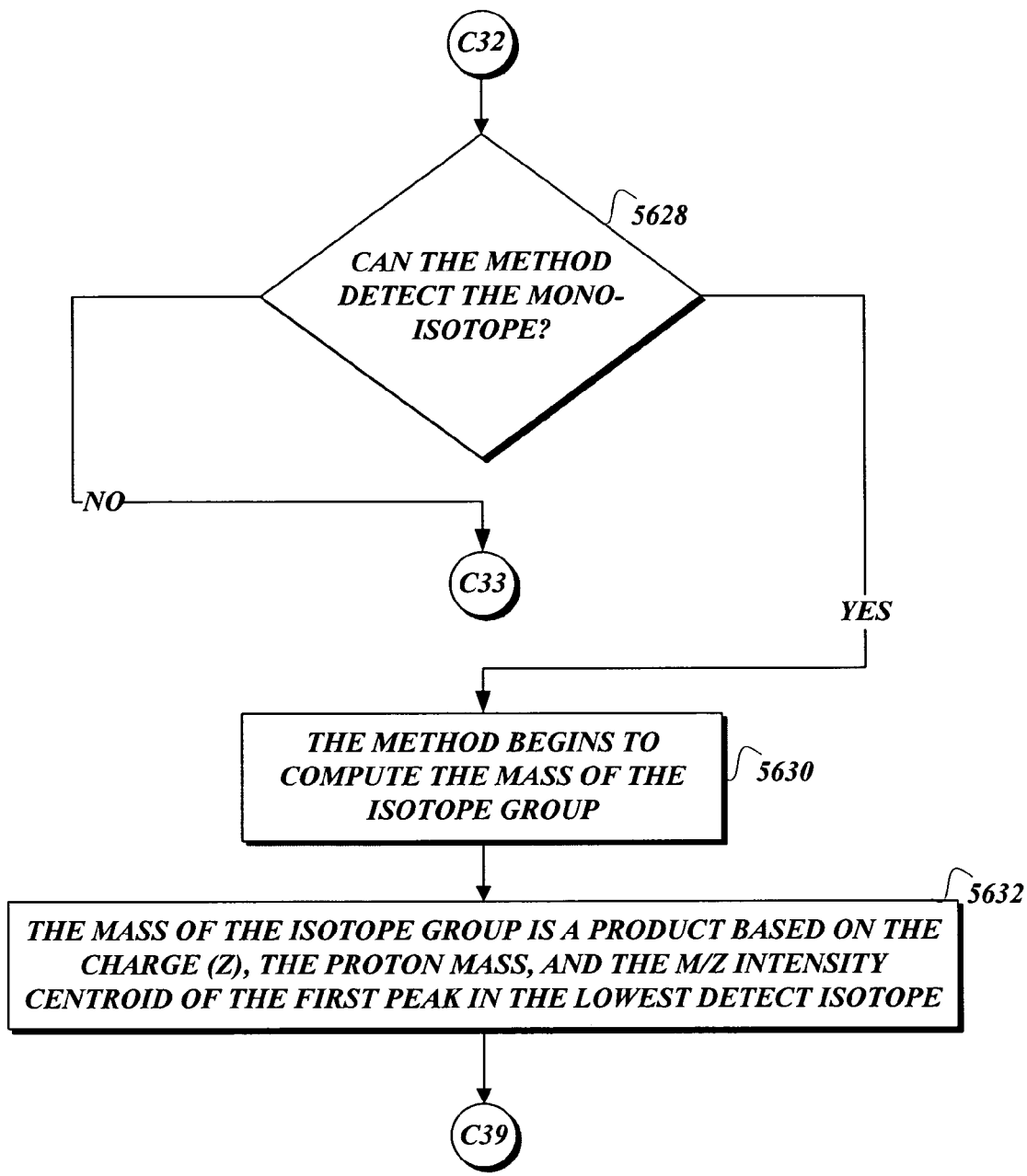
Figure 5A:
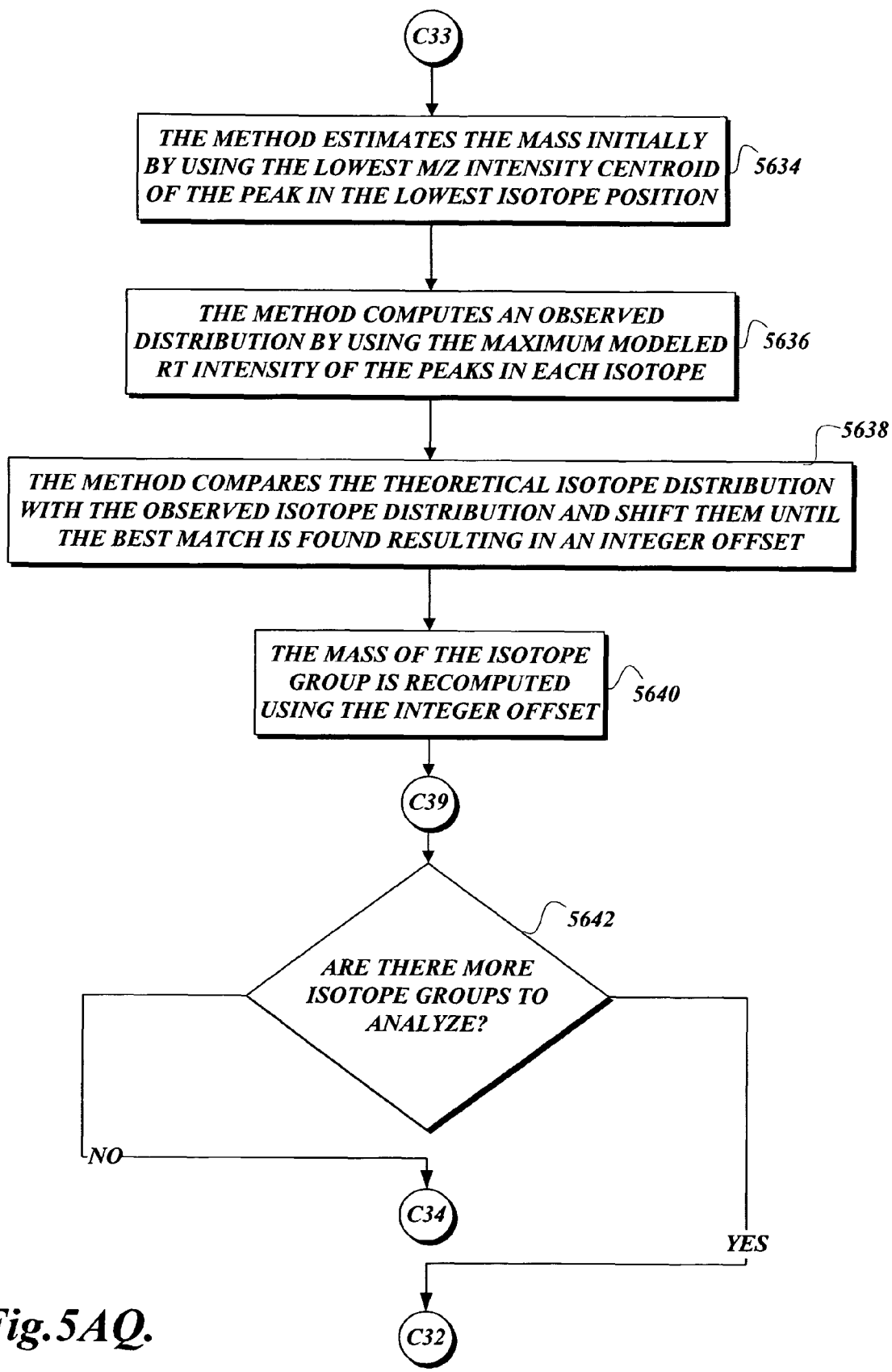
Figure 5A:
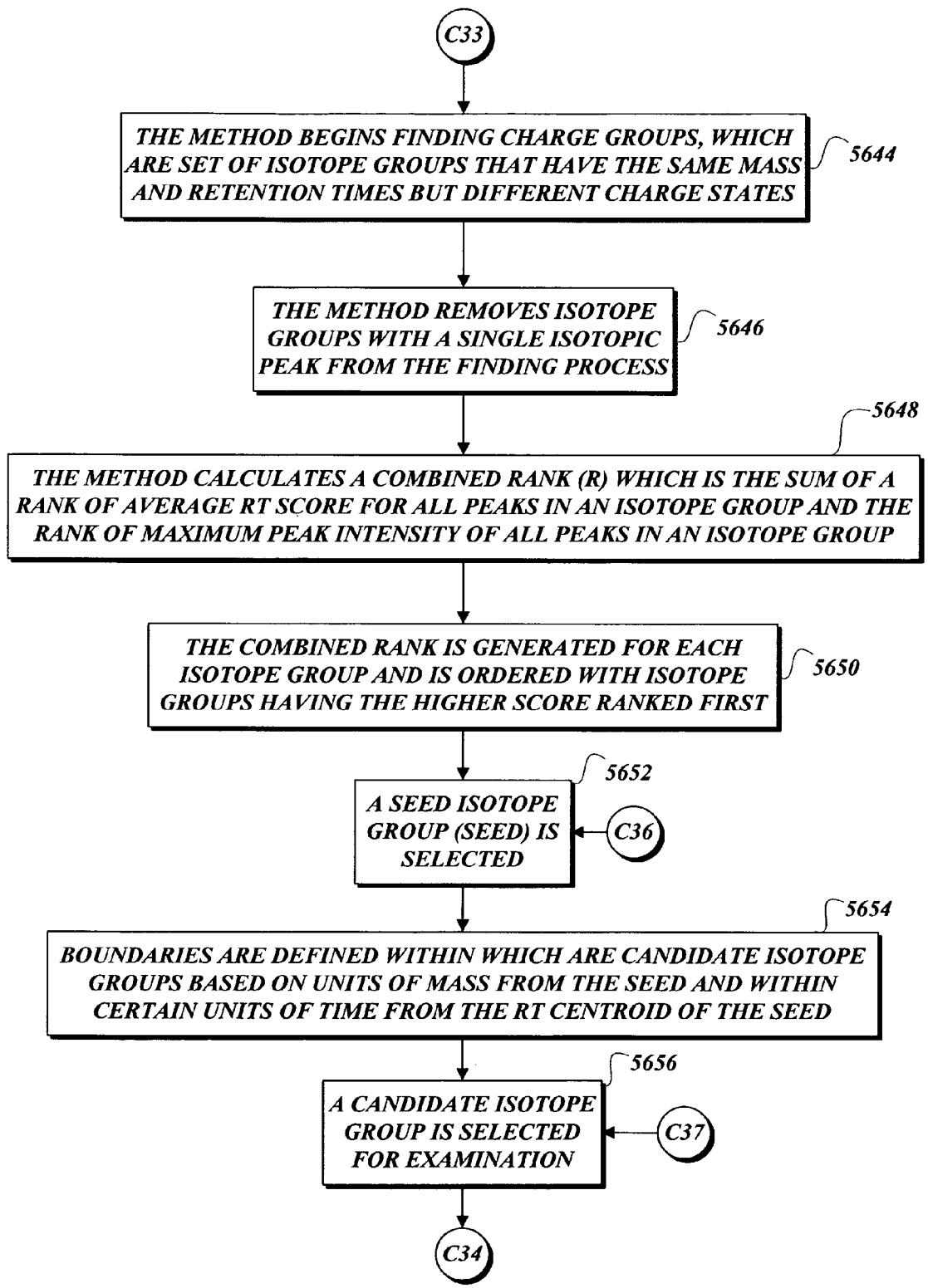
Figure 5A:
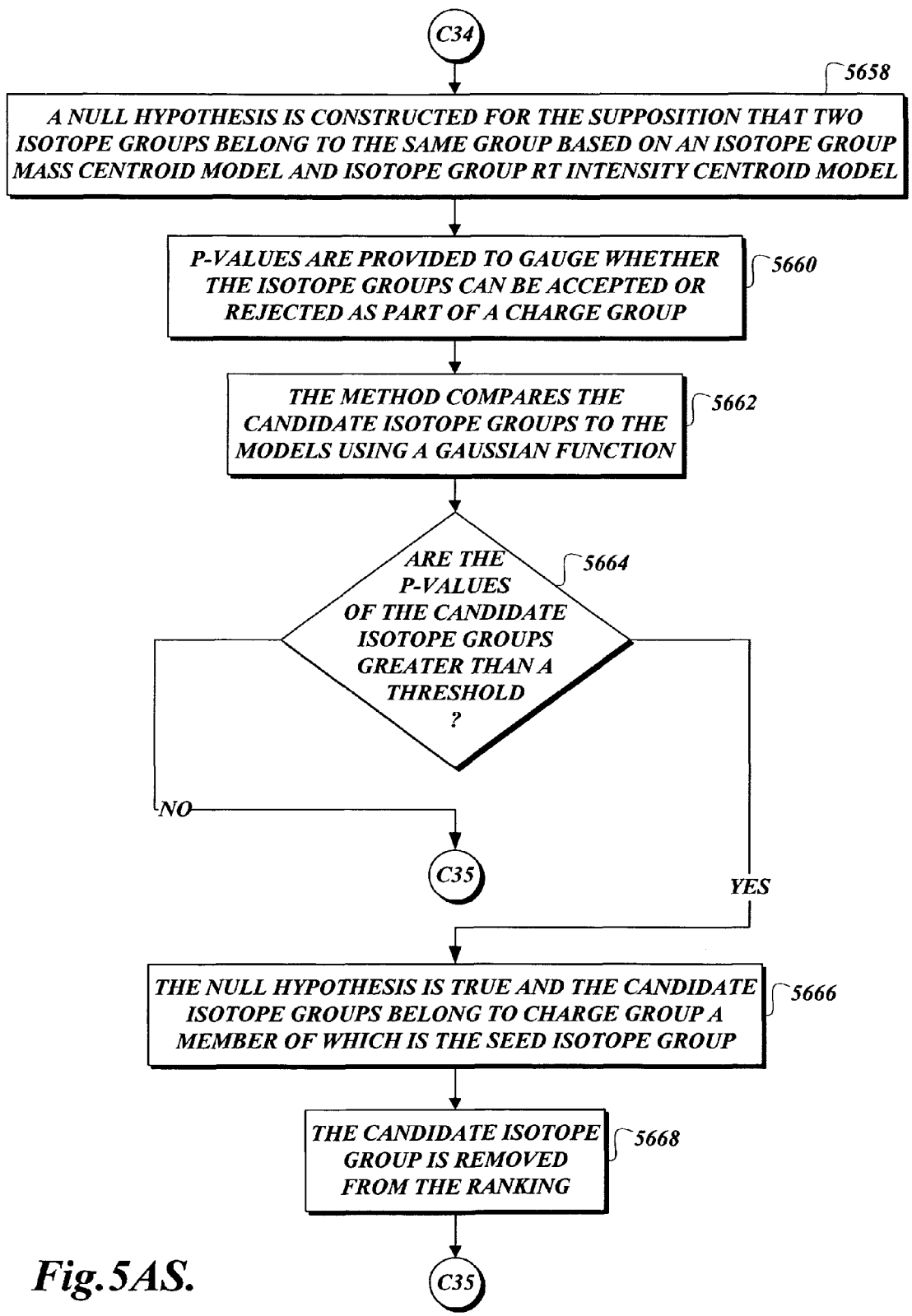
Figure 5A:
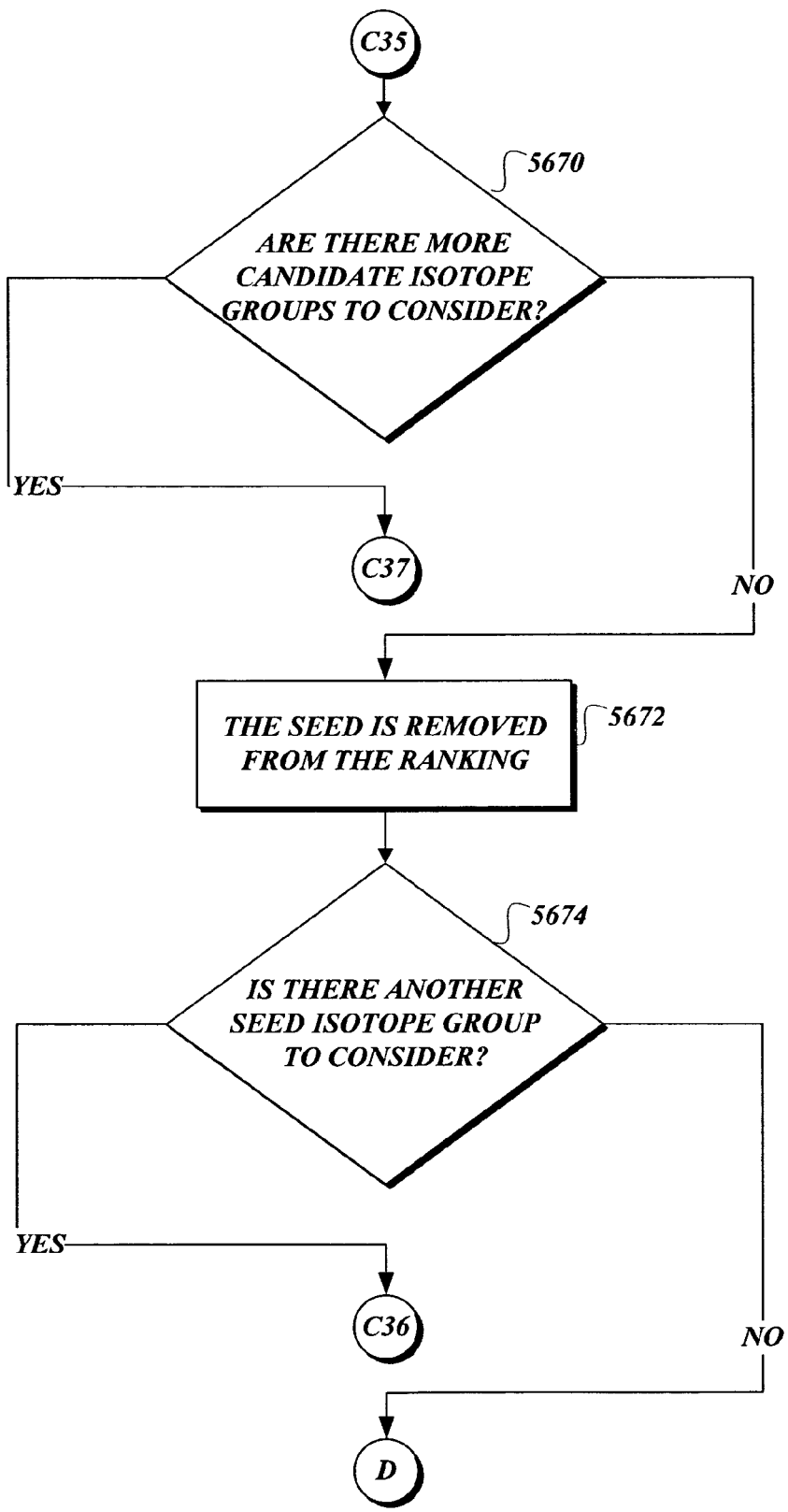
Figure 5A:
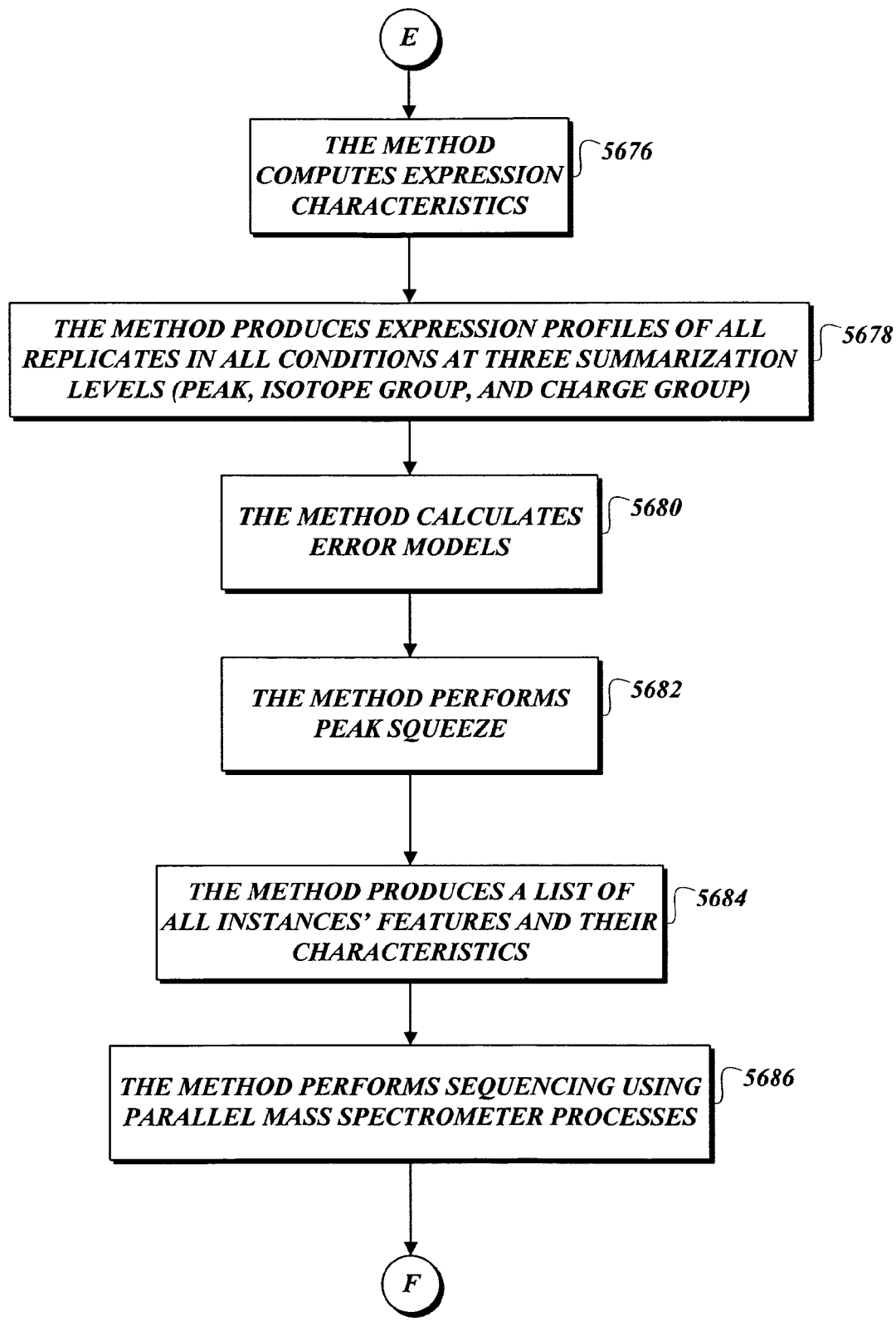

FIGS. 5Z-5AB illustrate method steps for performing high-contrast splitting of overlapped peaks and can be repeated as desired. The method steps are reusable for splitting overlapped peaks in either the mass/charge direction or the overlapped peaks in the retention time direction. Overlapped peaks and their valleys are described by a sequence of values, x1, x2, . . . , xn, which are presentable on a graph. High-contrast splitting attempts to split the sequence into two pieces at the lowest valley of a corresponding graph. If the sequence has at least 4 points, the method steps illustrated at FIGS. 5Z-5AB for performing high-contrast splitting are executed. The method defines M to be the maximum value of the sequence. The method then finds dips, which are points with a value lower than the two immediate neighbors. If one of the dips has value less than a product formed from a constant representing a contrast level and M, the maximum value of the sequence, the method has found a high-contrast sequence for which high-contrast splitting may be performed. The constant may be set at any suitable level; one suitable level is 0.1. The method finds all connected sets of points of the feature whose peak amplitude is less than a product of the standard deviation and M, the maximum value of the sequence. A set of points is connected if it consists of adjacent elements. In other words, all points $x_k$ where a is less than or equal to k and where k is less than or equal to b for certain integers a, b. The method in some embodiments ignores the sets that are at the edge of the feature (e.g. where a is 1 or b is n). For each such set of points, the method finds the minimum dip in it. If there are more than one minima, the method in various embodiments selects the first one. The point of the minimum dip in becomes a splitting point.

FIGS. 5Y, 5AE-5AG illustrate method steps for performing low-contrast splitting of overlapped peaks and can be repeated as desired. The method uses a least-squares non-linear fitting to fit a two-peak Gaussian model to a feature. The method then selects a point at which to split. The method is reusable in either the mass/charge direction or retention time direction, except for different input parameters as the initial estimates of the model parameters. Mathematically, the two-peak intensity model consists of the addition of two single-peak Gaussian models, that share the same deviation $$\left(y = Y_1 \exp\left(-\left(\frac{(x-c_1)}{w}\right)^2\right) + Y_2 \exp\left(-\left(\frac{(x-c_2)}{w}\right)^2\right)\right),$$

where $Y_1$, $Y_2$ are the peak amplitude of the two overlapped peaks; $c_1$, $c_2$ are peak centers; and w is the common width.

Figure 2E:
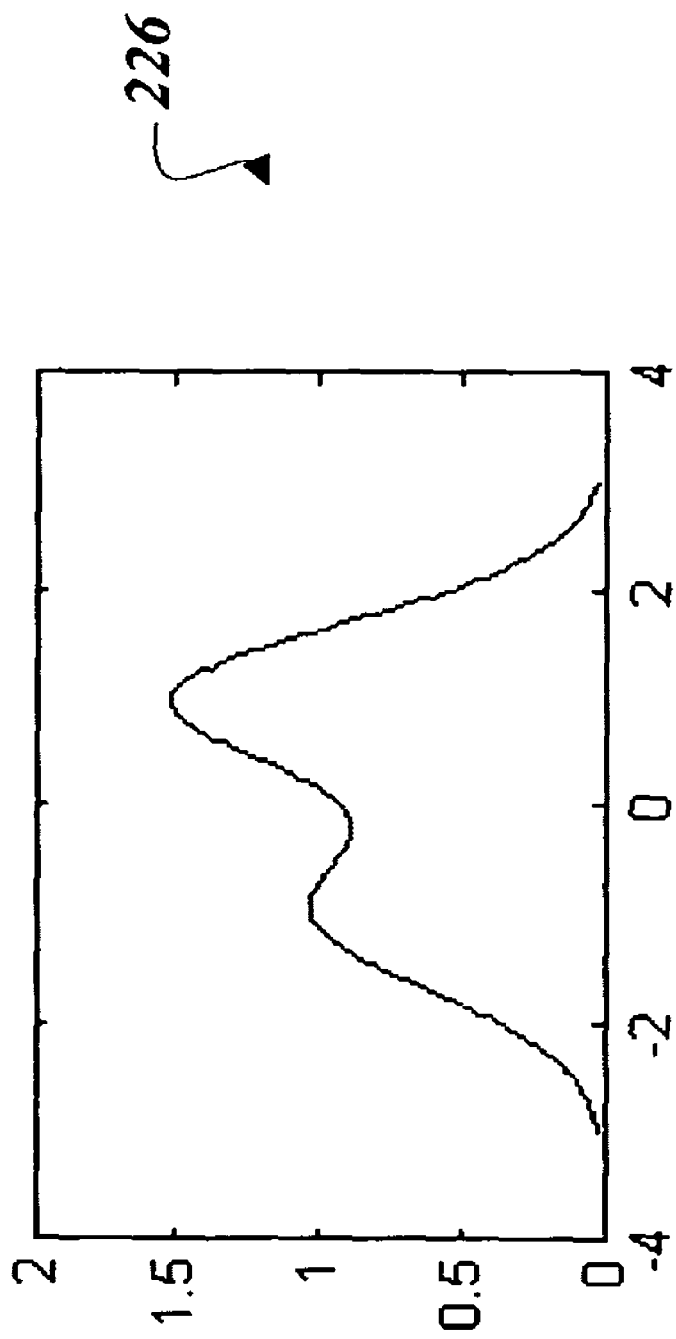
FIG. 2E illustrates mathematically how the two-peak model may look.

FIG. 2E illustrates how the two-peak model may look graphically from the mathematics above for various parameters. Given two peak centers (c1, c2) and a common width, a p-value can be computed as follows to test the supposition where all peaks are completely overlapped and not splittable:

$$\left(xdev = \frac{c_1 - c_2}{\sqrt{2w^2}}\right), \left(pvalue = erfc\left(\left|\frac{xdev}{\sqrt{2}}\right|\right)\right).$$

The method selects initial estimates peak centers ($c_1$, $c_2$) and peak magnitudes ($Y_1$, $Y_2$), and width w for the model parameters. The selection can be different for the mass/charge and the retention time direction. The method uses least-squares non-linear fitting to select parameters peak centers ($c_1$, $c_2$) and peak magnitudes ($Y_1$, $Y_2$). The method then defines the valley point as the point between the two centers where the two Gaussian models have the same amplitude. The method discards the split if the data point closest to the valley is one of the first two or last two data points, or if the p-value is above a certain threshold, such as 0.1. When the method splits the overlapped peaks, the method in some embodiments puts the valley point at a location of a feature that has the fewest points.

For low-contrast splitting in the mass/charge direction, the method estimates the initial parameters for the two-peak Gaussian model as follows: The method find peaks in the mass/charge direction. In other words, the method finds points $x_k$ whose values are greater than points $x_{k-1}$ and $x_{k+1}$. If there are fewer than two peaks, the method in various embodiments refrains from splitting the overlapped peaks. Otherwise, the method splits the overlapped peaks using the two highest peaks. For initial parameters, the method in some embodiments uses the positions and intensities of the two peaks. For the standard deviation, w, of both Gaussian models, the method in various embodiments uses a product of a constant, such as 1.5, and a quotient (median mass/charge width divided by another constant, such as 4).

For low-contrast splitting in the retention time direction, the method, as indicated above, also uses a two-peak Gaussian model, even though the single-peak time-intensity model is not necessarily Gaussian. The method finds the peaks and dips using a sliding window size of k time points, where k is odd. The size of the sliding window as represented by k is in some embodiments a quotient of a product (3m) and a product (2d), where m is the median time width of all features, and d is the time interval between measurements. The method in various embodiments rounds k to the nearest integer. If k is even, the method increments k by 1 to make it odd.

The method applies the sliding window to all sequences of contiguous k points. If the center of the window is a minimum or a maximum for the window, the method marks it as a dip or peak accordingly. If there are two or more peaks, the method selects the two largest peaks. If there is one peak and at least one dip, the method simulates a second peak by finding the maximum value on the side of the dip opposite the peak. If this is not possible, the method refrains from splitting the overlapped peaks. For initial parameters, the method in some embodiments uses the positions and intensities of the two selected peaks. For the standard deviation, of both Gaussian models, the method in various embodiments uses a product of a constant, such as 1.5, and a quotient (the median retention time width divided by another constant, such as 4).

After overlapped peaks are split, the method attempts to trim over-wide peaks in the retention time direction. See FIG. 5AG. The method first finds time peaks that satisfied the following condition: the quotient (the time range divided by the centroid width) is greater than a constant, such as two. If the condition is true, The method has likely found over-wide peaks. The method proceeds to clip the minimum and maximum sides of these peaks to one centroid width from the centroid center.

FIGS. 5AH-AI illustrate method steps to characterize peaks found in the above-discussed method steps. FIG. 5AH illustrates method steps to characterize peaks in the retention time direction. The "feature modeled time peak" parameter is the model-axis value where the modeled time-intensity is maximum. The "feature modeled time centroid width" parameter is the width of the centroid of the model axis values, weighted by the modeled time-intensities. The "feature modeled time peak intensity" parameter is the maximum value of the intensity computed by the time-intensity model. The retention time intensity model in the retention time direction is modeled by a modified Maxwell distribution function. Given parameters Y (amplitude), $t_s$ (shift), w (width), and d (offset), the time-intensity for a feature is modeled mathematically as follows:

$$\left(y = Y\left(\left(\frac{x-t_s}{w}\right)^2 \exp\left(1-\left(\frac{x-t_s}{w}\right)^2\right)-d\right)\right).$$

If x is less than $t_s$, the method sets y to zero. If y is less than zero, the method sets y to zero. The constant d is greater than or equal to zero and is less than or equal to one. The function ($y=x^2 \exp(1-x^2)$) has maximum of one when x equals to one, so that the time-intensity is maximum when x is equivalent to the sum of $t_s$ and w. The parameters Y, $t_s$, and w are fitted using least-squares non-linear fit. Initial values are set using the centroid of the times weighted by the time-intensities as follows: The amplitude Y is equated to the quotient formed from dividing the maximum time-intensity by the remainder of (1−d). The width w is equated to the quotient of a remainder (the time centroid center subtracts by the start time) and another remainder (1−d). The shift $t_s$ is equated to the remainder of (time centroid center subtracts by the width w). The parameter d is, in some embodiments, not fitted using a least-squares fit and its initial value is the model offset, as specified hereinbelow.

The model offset, as calculated by the method of various embodiments of the present invention, is a number between zero and one that is used in the time intensity model discussed hereinabove. In various embodiments, the model offset is initially computed after the features are split as follows: The method defines m and M be the common logarithm of the minimum and maximum peak intensities of all features, respectively. The method defines U to be the sum of m and a product of a constant, such as 0.8, and a remainder (M−m); in other words, U=m+0.8(M−m). The method defines L to be the sum of m and a product of a constant, such as 0.1, and a remainder (M−m); in other words, L=m+0.1 (M−m). The method further defines p to be the common logarithm of a feature's peak intensity. The method clamps p to be within L and U as follows: if p is greater than U, the method sets p to equal to U. Otherwise, if p is less than L, the method sets p to equal to L. The model offset for a particular feature is set to (c*(U−p)/(U−L)), which is a product of a constant c and the remainder (U−p) divided by another remainder (U−L). The constant can be of a suitable value, such as 0.8. In some embodiments, the model offset is rounded to the nearest multiple of 0.1. Also in various embodiments, the model offset is adjusted by computing the retention time peak score, which is described hereinbelow. In one embodiment, the offset is set to the maximum value between zero and the initial offset that produces a valid score. In other embodiments, the offset can be set to other values.

The retention time peak score is a correlation coefficient, such as the Pearson correlation coefficient, between the actual retention time intensities and those modeled by the retention time intensity model. The actual data is extended one data point beyond each end of the retention time range, as is done for the mass/charge intensities. The retention time peak score computation is used to adjust the model offset (the parameter d in the time intensity model). If the score is undefined, d is decremented by a constant, such as 0.1, and the computation is redone by the method of various embodiments of the present invention, until the score is a number or d reaches zero. The Pearson correlation p-value for a Pearson correlation value r computed using n pairs of points is given by $$\left(t = r\sqrt{\frac{n-2}{1-r^2}}\right).$$

If the method were to define the following conditions: k is equivalent to (n−2); t is distributed like a t-distribution with k degrees of freedom; and p is defined as $$\left(p = I_{\frac{k}{k+t^2}}\left(\frac{k}{2}, \frac{1}{2}\right)\right),$$

where I is the incomplete beta function. The mathematics resolves to $$\left(p = I_{1-r^2}\left(\frac{n-2}{2}, \frac{1}{2}\right)\right).$$

The Pearson correlation score is the product of r and the remainder of (1−p), where r is the Pearson correlation and p is the corresponding p-value. If there is only one data point, the score is, in various embodiments, set to zero by the method.

FIG. 5AI illustrates method steps to characterize peaks in the mass/charge direction. Given a peak amplitude Y, center (c), and width (w), the mass/charge intensity for a feature is modeled as a Gaussian with the following mathematics $$\left(y = Y\exp\left(-\left(\frac{(x-c)}{s}\right)^2\right)\right).$$

The center c, and standard deviation s, are computed through the centroid computation. The feature mass/charge intensity score is also calculated by the method. If the mass/charge intensity peak and the centroid standard deviation are positive, the peak score is the Pearson correlation score between the data and the model for mass/charge intensities, using the model (extended) mass/charge axis.

FIGS. 5AJ-5AO illustrate method steps for finding isotope groups, which are groupings of isotopic peaks. There are often several peaks at the same retention time point with mass/charge values that are close together. This is caused by isotopes. (If the biological feature were a peptide, the isotopes are members of the same peptide having atoms with different number of neutrons.) The method steps at FIGS. 5AJ-5AO find groups of neighboring isotopic peaks by first sorting all features so that the bigger and best shaped features are, in some embodiments, considered first. The method then takes each feature in order, the taken feature being the seed feature, and finds other features that should be clustered with the seed feature.

In some embodiments, the method ranks all the features by combining at least the following three ranks, in one embodiment: $r_t$=rank by the peak intensity, such as the peak retention time intensity or the peak pixel intensity; $r_m$=rank by peak mass/charge score; and $r_s$=rank by the retention time score. The method computes a combined rank r which is the sum of $r_s$ and a quotient of the sum of $r_t$ and $r_m$ divided by a constant, such as two. The method reverses the rank, so that features with higher score/intensities are, in various embodiments, listed first. The method processes the features in the ranked order. In other words, the biggest feature is examined first.

FIG. 5AN illustrates method steps to keep certain features for later classification into other isotope groups instead of discarding them. As features are grouped into isotope groups, they are classified as accepted, rejected, or placed on hold. At the end of the method for grouping isotopic peaks into isotope groups, each peak belongs to one or more isotope groups. If a peak belongs to more than one isotope group, the peak is placed on hold for further analysis. Otherwise, the peak is accepted in a single isotope group. If a peak is classified as placed on hold in a isotope group, and it is accepted in another isotope group, the second classification is changed to also be placed on hold. This also applies to the seed feature.

The method steps illustrated by FIGS. 5AJ-5AO, in various embodiments, uses a time-weighted intensity instead of the original intensity of the peak. The time-weighted intensity relative to a seed feature, at a point i,j, is defined mathematically as $$\left(I'_{ij} = I_{ij} \frac{T_j}{\max_m(T_m)}\right)$$

where $I_{ij}$ is the unweighted intensity, and $T_j$ is the time-intensity of the seed feature (i.e. the sum of the intensities over all rows of the seed feature for that column). In some embodiments, the index j is iterated to start at a certain time and to end at a specific time. The time-weighted intensity is defined for any mass/charge point (row), but only for those time points (columns) that are within the starting feature boundaries. The time-weighted mass/charge intensity is the sum of the time-weighted intensities over all time points within the seed feature boundaries.

In some embodiments, the method adjusts the mass/charge intensity width of a feature to be more in line with the median feature in the grid row of the seed feature of the isotope group. The adjustment is done as follows: the method finds the grid time point to which the seed feature belongs; the method defines $w_g$ as the median grid mass/charge centroid width; $Sw_g$ as the standard deviation of the grid mass/charge centroid widths; and $w_f$ as the current feature mass/charge centroid width. The method calculates the adjusted width as $w_g$ if $w_f$ is greater than the sum of $w_g$ and the product of a constant, such as 5, and $Sw_g$. Otherwise, the adjusted width is equal to the result of the following mathematics max($w_g$, $w_f$). The grid-adjusted mass/charge width uses unweighted mass/charge intensities.

FIG. 5AJ illustrates method steps to find charge scores to help the exemplary image processing pipeline better understand the charge states to cluster isotopic peaks together. The charge score for an integer charge z, is computed by applying a peak model, shifted by a combination of charge amount and mass difference, and computing the inner product of the modeled mass/charge intensities with the observed time-weighted mass/charge intensities. The inputs into the computation of the charge scores include x, which is the mass/charge values for a section (a vector); y, which is the time-weighted mass/charge intensities of the section; $c_0$, which is the peak center to use in the model; $w_0$, which is the peak width to use in the model; z, which is an integer charge count. The method calculates the charge score by applying the mass/charge intensity model to the x values according to the following mathematics $$\left(y' = Y\exp\left(-\left(\frac{(x-c)}{s}\right)^2\right)\right).$$

In one embodiment, the method uses Y with the value of 1; s with the value of the quotient of $w_0$ divided by a constant, such as 4; and c with the value of the sum of $c_0$ and a product of a constant k and neutron mass divided by z. The method iterates k over the following set of elements (−2, −1, 1, 2). The method obtains four vectors, y'(k). And the charge score is, in some embodiments, defined mathematically as (y·[y'(−2)+2y'(−1)+2y'(1)+y'(2)]).

FIG. 5AJ continues to illustrate method steps for finding the charge states. Given a seed feature, the method attempts to find its charge by looking at a section of the original image with mass/charge center situated at the feature mass/charge centroid. The mass/charge width is, in various embodiments, set by the product of a standard deviation and a constant, such as 2.2. The time coordinates of this section are, in some embodiments, the same as the time coordinates of the starting feature. While in the section of interest, the method zeroes the feature intensities of the seed feature. Next, the method computes the weighted mass/charge intensities of the section by summing the time-weighted intensities along the retention time axis. The method further defines $w_0$ as the grid-adjusted mass/charge width of the feature; $c_f$ as the starting feature mass/charge centroid; $p_f$ as the starting feature mass/charge peak; and $c_0$ as $c_f$ if $p_f$ is greater than or equal to the remainder of $c_f$ and the product of a constant, such as ¼, and $w_0$ or if $p_f$ is less than or equal to the sum of $c_f$ and the product of a constant, such as ¼, and $w_0$ or otherwise, $c_0$ is equated to $p_f$. The method then computes the charge score for z of a certain range, such as 1, 2, ... 15, and so on, using the parameters $c_0$, $w_0$ as calculated above. The method then selects a charge z that has the highest charge score. The isotope group parameter mass/charge delta is defined as the remainder of ($c_0$−$c_f$).

FIGS. 5AJ-5AO illustrates the execution of method steps for finding peaks for an isotope group. The method looks for isotopic peaks by moving a peak model down (towards lower mass/charge levels) and then moving the peak model up (towards higher mass/charge levels) from the seed peak. At each down or up step the method defines a rectangular isotope area that has bounds in the retention time direction the same as those of the seed feature; a center in the mass/charge direction that is equivalent to a sum of ($c_0$+k*$M_n$/z) where $M_n$ is the neutron mass and k is the isotope number, which is a positive integer when method looks for isotopic peaks by moving up and a negative integer when the method looks for isotopic peaks by moving down; a height in the mass/charge direction that is equivalent to a product of a constant, such as 4, and $w_0$ where $w_0$ is the grid-adjusted mass/charge width of the seed feature.

The candidate peaks for this isotope (at a particular k) are the peaks whose boundaries intersect the above-defined isotope area. If there are no candidate peaks for this isotope, the method stops looking in a particular direction. In each direction (downward or upward), the method, in various embodiments, looks for at most a certain number of isotope locations, such as ten. There are several different criteria, in some embodiments, used by the method of various embodiments of the present invention to classify a candidate peak to a isotope group, such as isotope intensity; mass/charge intensity and shape; and time intensity and shape. Each of the criteria classifies a candidate peak as accepted, rejected, or placed on hold. Various criteria are combinable into one classification.

In various embodiments, the isotope intensity criterion need not use any characterizations of candidate features except for the peak intensity of the isotope area. The isotope intensity $p_k$ is the maximum of the time-weighted intensities in the isotope area. The seed isotope intensity $p_0$ is the maximum of the time-weighted intensities in the seed feature. Let $p_{max}$ be the maximum isotope intensity of all isotope intensities computed so far (in downward and upward directions), including $p_0$. Let p' be the isotope intensity of the previous isotope. If k, the isotope position, is positive, the method defines p' to be equivalent to $p_k-1$. Otherwise, the method defines p' to be equivalent to $p_k+1$. The candidate feature for isotope position k is accepted if the absolute value of a quotient is less than a constant, such as 0.6. The dividend of the quotient is the remainder of the isotope intensity $p_k$ and the isotope intensity of the previous isotope p'. The divisor of the quotient is the maximum of the maximum isotope intensity $p_{max}$ and the isotope intensity $p_k$. Otherwise, if the quotient is not less than the constant, the feature is rejected. Instead of using the isotope intensity criterion as described hereinabove, in some embodiments, the feature is accepted or rejected by comparing the intensities to a theoretical distribution function.

Regarding the mass/charge and time intensity criteria, the method computes a p-value of the candidate peak that measures whether the candidate peak and the expected theoretical peak differ by chance. The method then classifies the candidate peak as accepted, rejected, or placed on hold by using, in some embodiments, two thresholds $p_{low}$ and $p_{high}$. If p-value is greater than or equal to $p_{high}$, the candidate peak is accepted. If $p_{low}$ is less than the p-value and the p-value is less than $p_{high}$, the candidate peak is placed on hold to see if another isotope group may claim the candidate peak as a member of its isotope group. If the p-value is less than or equal to $p_{low}$, the candidate peak is rejected. Any suitable threshold values can be used for $p_{low}$ and $p_{high}$. For example, one pair of suitable threshold values for mass/charge intensity includes $p_{high}$ being equated to 0.4 and $p_{low}$ being equated to 0.05. As another example, one pair of suitable threshold values for time intensity includes $p_{high}$ being equated to 0.6 and $p_{low}$ being equated to 0.2.

The mass/charge intensity p-value is computed, in one embodiment, by the method as follows. The method defines $w_0$ as the grid-adjusted mass/charge width of the seed feature and w as the grid-adjusted mass/charge width of the candidate feature. (Both widths are grid-adjusted using the grid row of the seed feature.) Additionally, the method defines c as the mass/charge centroid of the candidate feature. The p-value for the mass/charge intensity is mathematically calculated as follows, in one embodiment $$\left( p = \text{erfc}\left( \left| \frac{c - \left(c_0 + \frac{k * M_n}{q}\right)}{\sqrt{2}\sqrt{2\left(\frac{\max(w_0, w)}{4}\right)^2}} \right| \right) = \text{erfc}\left( \left| 2\frac{c - \left(c_0 + \frac{k * M_n}{q}\right)}{\max(w_0, w)} \right| \right) \right).$$

The constants in the mathematics may be different in other embodiments.

The time-intensity p-value is computed as follows by the method, in one embodiment. The method defines $t_0$, $S_{t0}$ be the time-intensity centroid and standard deviation of the seed feature and t, $S_t$ be the time-intensity centroid and standard deviations of the candidate feature. The method defines the p-value mathematically as follows, in one embodiment $$\left( p = \text{erfc}\left( \left| \frac{t - t_0}{\sqrt{2}\sqrt{S_t^2 + S_{t_0}^2}} \right| \right) \right).$$

The constants in the mathematics may be different in other embodiments.

The method defines the candidate peak as accepted in the isotope group if the candidate peak is accepted by all three criteria. The candidate peak is placed on hold if accepted according to the time intensity criterion, and is accepted by one of the other two criteria, and also the candidate peak is not placed on hold in more than one other isotope group already. Otherwise, the candidate peak is rejected. After each candidate peak is classified as accepted for the isotope group, the method removes it from the ranking, so that the candidate peak is not considered for other isotope groups. Also, the method, in various embodiments, removes candidate peaks that have been classified as placed on hold in two isotope groups.

As indicated above, after the method finds features that belong in a isotope group, the method removes the features that have been classified as accepted from the ranking, so that these features do not interfere with finding features and charges of other isotope groups. In some embodiments, the method also removes features that have been classified as placed on hold in two isotope groups. If an isotope group has only placed-on-hold features, the method removes the isotope group, and makes the features accepted in other isotope groups. See FIG. 5AO. After each isotope is determined, in various embodiments, the following isotope parameters are calculated. The "primary isotope feature" parameter is the feature with the maximum modeled peak retention time intensity; the "isotope intensity" parameter is the modeled peak retention time intensity; the "isotope mass/charge centroid" parameter is the mass/charge centroid of the primary isotope feature; and the "isotope mass/charge centroid width" parameter is the mass/charge centroid width of the primary isotope feature.

FIGS. 5AP-5AQ illustrate method steps for calculating the mass of the isotope group. There is a relationship between the mass of the isotope group and the mono-isotope of the isotope group. The mono-isotope is the lowest isotope for a particular isotope group which has the lowest mass/charge. The mass of the biological feature of a charge group is computed from the mono-isotope (the image feature with the lowest mass/charge) by the following mathematics $$\left(I_{mz} = \frac{m + zM_p}{z}\right),$$

where z is the charge (an integer), $M_p$ is the proton mass, m is the mass of the biological feature to be computed, and $I_{mz}$ is the mono-isotope mass/charge. Initially, the method estimates the mono-isotope mass/charge as the mass/charge intensity centroid of the first feature in the lowest detected isotope. With this estimation, the mass of the isotope group is mathematically derived as follows ($m=z(I_{mz}-M_p)$).

To find the mono-isotope so as to calculate the mass of the isotope group, the method estimates the location of the mono-isotope by extrapolating where the mono-isotope should be located based on several observed isotopes. For a given biological feature mass, such as peptide mass, there is a theoretical distribution of isotopic peaks. In some embodiments, the method refrains from computing this theoretical distribution, but instead uses a tabulated version of the theoretical distribution, for certain masses, such as m1, m2, and so on. Once the method has a mass estimate m, the method selects a tabulated mass $m_k$ to use for the distribution table, such that the mass is greater than or equal to $m_k$ and less than or equal to the sum of a constant and $m_k$. In various embodiments, the theoretical distribution is scaled so that the theoretical distribution has maximum of one. The method estimates the mass initially by using the lowest mass/charge intensity centroid of the features in the first isotope position. If there are features that are accepted in the isotope, the method, in some embodiments, uses those for the estimation. Next, the method computes an observed distribution by using the maximum-modeled retention time intensity of the peaks in each isotope. The method scales the observed distribution so that the observed distribution has a maximum of one. Then, the method compares the theoretical isotope distribution with the observed isotope distribution, and shifts these two distributions against each other until the method finds the best match. A score is generated and is used to compare the two distributions as the sum of the absolute differences between the theoretical distribution and observed distribution. In some embodiments, the method considers offsets such that one of the two distributions is completely overlapped in the other. The resulting integer offset is what we add to the observed isotope numbers to correct them so that they match the theoretical isotope numbers. (The offset may be positive, negative, or zero.) When the method has found the best offset, the method computes a correlation coefficient and p-value of the theoretical distribution as compared to the shifted observed distribution.

FIG. 5AQ illustrates method steps for recomputing the mass of the isotope group. When the offset between the theoretical and observed isotope distributions is known, the method recomputes the isotope group mass using the isotope mass/charge centroids for all isotopes in the isotope group as follows. The mono-isotope Mass/charge $I_{mz}$ is mathematically defined as $$\left(mz(k) - \frac{k*M_n}{z}\right),$$

where k is the (corrected) isotope number, mz(k) is the isotope mass/charge centroid for the isotope k, $M_n$ is the neutron mass, and z is the isotope group charge state. The isotope group mass is mathematically defined as before ($m=z(I_{mz}-M_p)$). The mass width is defined as the mean of the isotope mass/charge centroid widths multiplied by z as follows (z*mzwidth(k)).

The method also, in various embodiments, determines whether a isotope group has only placed-on-hold features that are also placed on hold in other isotope groups. If so, the method, in some embodiments, removes the isotope group and checks to see whether the features can be accepted in other isotope groups. In various embodiments, several isotope group parameters are calculated. For example, the isotope group mass is defined as the corrected mass (as computed before). The isotope group mass width is as defined above. The isotope group feature is the feature with the maximum peak intensity. The isotope group retention time intensity centroid is the retention time intensity centroid of the isotope group feature.

FIGS. 5AR-5AT illustrate method steps for finding charge groups which are aggregation of isotope groups depending on their charge. A charge group is a set of isotope groups that have the same mass and retention times, but different charge states. The method aggregates isotope groups together into charge groups so that each isotope group, in one embodiment, is in one and only one charge group. Other isotope group configurations are possible in other embodiments. The method, in some embodiments, aggregates isotope groups that have non-zero charge. In various embodiments, the method refrains from considering isotope groups with a single peak. Initially, the method ranks isotope groups by forming a rank $r_t$ comprising isotope groups that are ranked by average retention time score for all the image features in an isotope group. The method also forms another rank $r_I$ comprising isotope groups that are ranked by maximum peak intensity of all the features in an isotope group. The method then produces a combined rank r (which is the sum $r_t+r_I$) and re-orders the isotope groups by the combined rank so that features with higher score/intensities are listed first.

From the combined rank, the method chooses a seed isotope group to begin the processing of forming a charge group by looking for other isotope groups with different charge states as follows. The method first looks for incrementally smaller charge states (down to charge 1). The method then looks for isotope groups that are in the desired charge state and are within a certain units of mass (such as 10) from the seed isotope group mass centroid, and within $t_w$ units of time from the starting isotope group retention time centroid. The method defines $t_w$ is defined as the retention time centroid width of the peak feature of the seed isotope group, but no less than a certain retention time period, such as 2 minutes. Isotope groups within these boundaries are candidate isotope groups for grouping. The method uses at least two criteria for classifying the candidate isotope groups and these criteria include isotope group mass centroid and isotope group retention time intensity centroid. Each criterion uses a p-value cutoff to accept or reject two isotope groups as being in the same charge group. Two isotope groups belong in the same charge group if they pass both criteria.

For each candidate isotope group, the method determines the mass p-value and retention time p-value between the candidate isotope group and the seed isotope group, as follows. Given mass centroids c1, c2 and corresponding centroid deviations s1, s2, the mass p-value ($p_{mass}$) is mathematically defined as $$\left( \text{erfc}\left( \left| \frac{c_1 - c_2}{\sqrt{2}\sqrt{s_1^2 + s_2^2}} \right| \right) \right).$$

Given retention time centroids c1, c2 and corresponding centroid deviations s1, s2, the retention time p-value ($p_{rt}$) is mathematically defined as $$\left( \text{erfc}\left( \left| \frac{c_1 - c_2}{\sqrt{2}\sqrt{s_1^2 + s_2^2}} \right| \right) \right).$$

The overall p-value is p which is the product of $p_{mass}$ and $p_{rt}$. The method then selects candidate isotope groups that have $p_{mass}$ greater than $p_{cutoff}$ and $p_{rt}$ greater than $p_{cutoff}$. The method defines $p_{cutoff}$ to be a constant of a suitable threshold, such as 0.6. If there are more than one candidate isotope groups that pass these criteria, the method selects the one candidate isotope group that has the highest overall p-value for inclusion in the charge group. Once a isotope group is included in a charge group, the method refrains from considering it again for another charge group.

The method calculates several isotope group parameters. For example, the "primary isotope feature" parameter is the isotope feature with the maximum feature modeled time peak intensity. The "accepted feature count" parameter is the number of features that accepted (unique) in the isotope group. The "overlapped feature count" parameter is the number of features that are overlapped in the isotope group (i.e. they are also in other isotope groups). The "total isotope cnt" parameter is the number of isotopes detected. The "group charge state" parameter is the charge state of the isotope group, as an integer. The "mass/charge delta" parameter is the difference between the seed feature's mass/charge centroid and the mass/charge used for finding isotopes for the isotope group. The "mass centroid width" parameter is the average mass/charge centroid of the primary feature in each isotope, multiplied by the charge state. The "monoisotopic mass/charge" parameter is the average of the mono mass/charge computed for each isotope; for one isotope, the mono mass/charge is computed by the following mathematics (mz–k*$M_n$/z), where mz is the mass/charge centroid of the primary isotope feature, k is the isotope number (adjusted by the distribution offset), $M_n$ is the neutron mass, and z is the charge state. The "mass centroid" parameter is the mass of the isotope group; it is equivalent to (mz–$M_p$)*z, where mz is the monoisotopic mz, z is the charge state, and $M_p$ is the proton mass. The "monoisotopic location offset" parameter is the isotope number of the first detected isotope; the offset is detected by aligning the detected and theoretical isotope distributions. The "average time peak score" parameter is the average feature time peak score over all features in the isotope group. The "average mass/charge peak score" parameter is the average feature mass/charge peak score over all features in the isotope group. The "time peak misalignment score" parameter is computed as ($S_c$/w), where $S_c$ is the standard deviation of the retention time centroids of all features, and w is the average retention time centroid width of all features in the isotope group. The "mass/charge peak distribution score" parameter is the Pearson correlation between theoretical and observed isotope distributions. The "mass/charge peak distribution score p-value" parameter is the p-value associated with the mass/charge peak distribution score. The "max isotope num" parameter is the isotope number of the peak isotope; the peak isotope is the isotope that has the feature with the highest feature peak intensity in the isotope group. The "max isotope peak intensity" parameter is the feature peak intensity of the peak isotope. The "max isotope mass/charge centroid" parameter is the feature mass/charge centroid parameter of the peak isotope. The "max isotope mass/charge centroid width" parameter is the feature mass/charge centroid width parameter of the peak isotope. The "max isotope time centroid" parameter is the feature time centroid parameter of the peak isotope. The "max isotope time centroid width" parameter is the feature time centroid width parameter of the peak isotope. The "max isotope time base start" parameter is the feature time base start parameter of the peak isotope. The "max isotope time base end" parameter is the feature time base end parameter of the peak isotope. The "max isotope mz base start" parameter is the feature mass/charge base start parameter of the peak isotope. The "max isotope mass/charge base end" parameter is the feature mass/charge base end parameter of the peak isotope. The "isotope time base start" parameter is the minimum feature time base start of all features in the isotope group. The "isotope time base end" parameter is the maximum feature time base end of all features in the isotope group. The "isotope mass/charge base start" parameter is the minimum feature mass/charge base start of all features in the isotope group. The "isotope mass/charge base end" parameter is the maximum feature mass/charge base end of all features in the isotope group.

While illustrative embodiments have been illustrated and described, it will be appreciated that various changes can be made therein without departing from the spirit and scope of the invention.

The invention claimed is:

1. A system for discovering biological features, comprising:
   a data collector configured to receive a set of images formed with chromatography instrument data and mass spectrometer data;
   an image processor for processing a composite image, which is produced from the set of images, the image processing pipeline producing feature characteristics, expression profiles, and a candidate feature list; and
   an image feature extractor is configured to identify isotope peaks from connected non-zero pixels on a composite image; and split identified isotope peaks that are composed of two or more isotope peaks in a mass/charge direction, a retention time direction, or both.

2. The system of claim 1, wherein the feature characteristics provide information about a biological feature at three levels including peak, isotope group, and charge group.

3. The system of claim 2, wherein the peak is an isotopic peak defined by its contour at a specific retention time range and mass/charge range, wherein the isotope group is a group of isotopic peaks at the same charge state, and wherein the charge group is a collection of isotope groups.

4. The system of claim 3, wherein feature characteristics are selected from a group consisting of peak retention time start and end, peak mass/charge start and end, mass/charge centroid, charge state, and mass.

5. The system of claim 1, wherein expression profiles include a profile on peak intensity, which is a summation of intensity measurements of all non-zero pixels within a boundary contour of a peak.

6. The system of claim 1, wherein the candidate feature list is a set of peaks or isotope groups selected for protein identification.

7. A computer-implementable image processing pipeline, comprising:
- a collector for collecting data from a process in which prepared biological samples are obtained from expression experiments under different treatment conditions;
- an image processor for processing the data from the collector and forming a composite image; and
- an image feature extractor for extracting feature characteristics from the composite image, which include peaks, isotope groups, and charge groups, wherein the image feature extractor is configured to identify isotope peaks from connected non-zero pixels on a composite image; and split identified isotope peaks that are composed of two or more isotope peaks in a mass/charge direction, a retention time direction, or both.

8. The computer-implementable image processing pipeline of claim 7, wherein the image processor includes a retention time streak remover, a data interpolator, an image aligner, noise remover, and a background corrector.

9. The computer-implementable image processing pipeline of claim 7, further comprising an expression statistics processor for processing feature characteristics to produce expression profiles of replicates in all conditions at three summarization levels, which is selected from a group consisting of peak, isotope group, and charge group.

10. The computer-implementable image processing pipeline of claim 9, further comprising an expression analysis processor for processing expression profiles to produce a candidate list regarding differential and nondifferentially expressed features for biological target identifications.

11. The computer-implementable image processing pipeline of claim 7, wherein the image feature extractor is configured to compute isotope peak characteristics that are selected from a group consisting of peak mass/charge centroid, peak mass/charge width, peak time centroid, and peak time width.

12. The computer-implementable image processing pipeline of claim 7, wherein the image feature extractor is configured to identify isotope peaks that belong to an isotope group and labeling the isotope group with a unique isotope group index number.

13. The computer-implementable image processing pipeline of claim 12, wherein the image feature extractor is configured to compute isotope group characteristics that are selected from a group consisting of charge state, mono-isotopic mass/charge, and peptide mass.

14. The computer-implementable image processing pipeline of claim 13, wherein the image feature extractor is configured to process images of different treatment conditions to form a composite image; and
    find isotope peaks from connected pixels in the composite image that have intensity above a background noise parameter which is selected from a group consisting of the mean, median, maximum, minimum, and the standard deviation at a particular location in the composite image.

15. A computer-implementable image processing pipeline, comprising:
- a collector for collecting data from a process in which prepared biological samples are obtained from expression experiments of different treatment conditions;
- an image processor for processing the data from the collector and forming a composite image; and
- an image feature extractor for extracting feature characteristics from the composite image, which include peaks, isotope groups, and charge groups, wherein the image feature extractor is configured to compute isotope group characteristics that are selected from a group consisting of charge state, mono-isotopic mass/charge, and peptide mass, and further wherein the image feature extractor is configured to identify an isotope group with only one isotope peak as belonging to a charge group with an unknown charge.

16. The computer-implementable image processing pipeline of claim 15, wherein the image feature extractor is configured to assign isotope groups having different charge states as belonging to one charge group if they have similar retention time and peptide mass.

17. A computer-implementable image processing pipeline, comprising:
- a collector for collecting data from a process in which prepared biological samples are obtained from expression experiments of different treatment conditions;
- an image processor for processing the data from the collector and forming a composite image; and
- an image feature extractor for extracting feature characteristics from the composite image, which include peaks, isotope groups, and charge groups, wherein the image feature extractor is configured to remove streaks in a retention time direction by:
- setting pixels, whose intensities rank in the lower ninety percentile, of a rasterized LC/MS image to zero to create a threshold LC/MS image;
- creating an original bit mask;
- performing a morphological open operation in the retention time direction on the original bit mask using a maximum peak width to reveal retention time streaks;
- executing a conditional dilation operation to dilate the retention time streaks back to their original sizes in the retention time direction and in the mass/charge direction;
- inverting the original bit mask to form an inverted bit mask; and
- multiplying the inverted bit mask with the rasterized LC/MS image to remove the retention time streaks.

* * * * *